(12) United States Patent
McKernan et al.

(10) Patent No.: US 10,323,277 B2
(45) Date of Patent: *Jun. 18, 2019

(54) REAGENTS, METHODS, AND LIBRARIES FOR BEAD-BASED SEQUENCING

(71) Applicant: APPLIED BIOSYSTEMS, LLC, Carlsbad, CA (US)

(72) Inventors: Kevin McKernan, Woburn, MA (US); Alan Blanchard, Middleton, MA (US); Lev Kotler, Allston, MA (US); Gina Costa, Carlsbad, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 15/291,982

(22) Filed: Oct. 12, 2016

(65) Prior Publication Data

US 2017/0081717 A1 Mar. 23, 2017

Related U.S. Application Data

(63) Continuation of application No. 14/057,055, filed on Oct. 18, 2013, now Pat. No. 9,493,830, which is a continuation of application No. 13/737,534, filed on Jan. 9, 2013, now Pat. No. 9,217,177, which is a continuation of application No. 12/628,209, filed on Nov. 30, 2009, now abandoned, which is a continuation of application No. 12/220,201, filed on Jul. 21, 2008, now abandoned, which is a continuation of application No. 11/345,979, filed on Feb. 1, 2006, now abandoned.

(60) Provisional application No. 60/722,526, filed on Sep. 30, 2005, provisional application No. 60/699,541, filed on Jul. 15, 2005, provisional application No. 60/673,749, filed on Apr. 21, 2005, provisional application No. 60/656,599, filed on Feb. 25, 2005, provisional application No. 60/649,294, filed on Feb. 1, 2005.

(51) Int. Cl.

| | |
|---|---|
| *C12P 19/34* | (2006.01) |
| *C12Q 1/6874* | (2018.01) |
| *C12Q 1/68* | (2018.01) |
| *B82Y 15/00* | (2011.01) |
| *B82Y 30/00* | (2011.01) |
| *C12Q 1/6837* | (2018.01) |
| *C12Q 1/6844* | (2018.01) |
| *C12Q 1/6869* | (2018.01) |

(52) U.S. Cl.
CPC ............ *C12Q 1/6874* (2013.01); *B82Y 15/00* (2013.01); *B82Y 30/00* (2013.01); *C12Q 1/68* (2013.01); *C12Q 1/6837* (2013.01); *C12Q 1/6844* (2013.01); *C12Q 1/6869* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,855,225 A | 8/1989 | Fung et al. |
| 4,863,849 A | 9/1989 | Melamede |
| 4,888,750 A | 12/1989 | Kryder et al. |
| 4,965,188 A | 10/1990 | Mullis et al. |
| 4,988,617 A | 1/1991 | Landegren et al. |
| 5,002,867 A | 3/1991 | Macevicz |
| 5,011,769 A | 4/1991 | Duck et al. |
| 5,188,934 A | 2/1993 | Menchen et al. |
| 5,202,231 A | 4/1993 | Drmanac et al. |
| 5,302,509 A | 4/1994 | Cheeseman |
| 5,380,833 A | 1/1995 | Urdea |

(Continued)

FOREIGN PATENT DOCUMENTS

| | | |
|---|---|---|
| DE | 19527155 | 1/1997 |
| EP | 2236628 | 10/2010 |

(Continued)

OTHER PUBLICATIONS 08006533.7, , "Extended European Search Report dated May 15, 2009".

(Continued)

*Primary Examiner* — Kenneth R Horlick
(74) *Attorney, Agent, or Firm* — Applied Biosystems, LLC; Karen R. Zachow

(57) ABSTRACT

The present invention provides methods for determining a nucleic acid sequence by performing successive cycles of duplex extension along a single stranded template. The cycles comprise steps of extension, ligation, and, preferably, cleavage. In certain embodiments the methods make use of extension probes containing phosphorothiolate linkages and employ agents appropriate to cleave such linkages. The invention provides methods of determining information about a sequence using at least two distinguishably labeled probe families. In certain embodiments the methods acquire less than 2 bits of information from each of a plurality of nucleotides in the template in each cycle. In certain embodiments the sequencing reactions are performed on templates attached to immobilized beads. The invention further provides sets of labeled extension probes containing phosphorothiolate linkages In addition, the invention includes performing multiple sequencing reactions on a single template by removing initializing oligonucleotides and extended strands and performing subsequent reactions using different initializing oligonucleotides.

31 Claims, 56 Drawing Sheets

Specification includes a Sequence Listing.

(56) References Cited

U.S. PATENT DOCUMENTS

| | | | |
|---|---|---|---|
| 5,403,708 A | 4/1995 | Brennan et al. | |
| 5,430,708 A | 7/1995 | Fukuda et al. | |
| 5,503,980 A | 4/1996 | Cantor | |
| 5,510,270 A | 4/1996 | Fodor et al. | |
| 5,552,278 A | 9/1996 | Brenner | |
| 5,578,458 A | 11/1996 | Caskey et al. | |
| 5,604,097 A | 2/1997 | Brenner | |
| 5,627,032 A | 5/1997 | Ulanovsky | |
| 5,641,658 A | 6/1997 | Adams et al. | |
| 5,659,025 A | 8/1997 | Engels | |
| 5,665,572 A | 9/1997 | Ikeda et al. | |
| 5,705,628 A | 1/1998 | Hawkins | |
| 5,714,330 A | 2/1998 | Brenner et al. | |
| 5,740,341 A | 4/1998 | Oota et al. | |
| 5,744,305 A | 4/1998 | Fodor et al. | |
| 5,750,341 A | 5/1998 | Macevicz | |
| 5,770,367 A | 6/1998 | Southern et al. | |
| 5,798,210 A | 8/1998 | Canard et al. | |
| 5,800,992 A | 9/1998 | Fodor et al. | |
| 5,830,663 A | 11/1998 | Embleton et al. | |
| 5,880,994 A | 3/1999 | Miyamoto et al. | |
| 5,888,737 A | 3/1999 | DuBridge et al. | |
| 5,898,071 A | 4/1999 | Hawkins | |
| 5,969,119 A | 10/1999 | Macevicz | |
| 6,007,987 A | 12/1999 | Cantor et al. | |
| 6,013,445 A | 1/2000 | Albrecht et al. | |
| 6,023,540 A | 2/2000 | Walt et al. | |
| 6,140,489 A | 10/2000 | Brenner | |
| 6,150,516 A | 11/2000 | Brenner et al. | |
| 6,172,214 B1 | 1/2001 | Brenner | |
| 6,172,218 B1 | 1/2001 | Brenner | |
| 6,175,002 B1 | 1/2001 | DuBridge et al. | |
| 6,210,891 B1 | 4/2001 | Nyren et al. | |
| 6,235,475 B1 | 5/2001 | Brenner et al. | |
| 6,235,480 B1 | 5/2001 | Shultz et al. | |
| 6,255,475 B1 | 7/2001 | Kwiatkowski | |
| 6,258,568 B1 | 7/2001 | Nyren | |
| 6,268,490 B1 | 7/2001 | Imanishi et al. | |
| 6,306,597 B1 | 10/2001 | Macevicz et al. | |
| 6,309,836 B1 | 10/2001 | Kwiatkowski | |
| 6,348,313 B1 | 2/2002 | Sibson | |
| 6,352,828 B1 | 3/2002 | Brenner | |
| 6,376,184 B1 | 4/2002 | Hosoi et al. | |
| 6,406,848 B1 | 6/2002 | Bridgham et al. | |
| 6,429,027 B1 | 8/2002 | Chee et al. | |
| 6,440,671 B1 | 8/2002 | Mirzabekov et al. | |
| 6,489,103 B1 | 12/2002 | Griffiths et al. | |
| 6,511,803 B1 | 1/2003 | Church et al. | |
| 6,534,262 B1 | 3/2003 | McKernan et al. | |
| 6,613,513 B1 | 9/2003 | Parce et al. | |
| 6,632,609 B2 | 10/2003 | Lizardi | |
| 6,632,655 B1 | 10/2003 | Mehta et al. | |
| 6,646,243 B2 | 11/2003 | Pirrung et al. | |
| 6,654,505 B2 | 11/2003 | Bridgham et al. | |
| 6,664,079 B2 | 12/2003 | Ju et al. | |
| 6,806,052 B2 | 10/2004 | Bridgham et al. | |
| 6,831,994 B2 | 12/2004 | Bridgham et al. | |
| 6,844,028 B2 | 1/2005 | Mao et al. | |
| 7,011,971 B2 | 3/2006 | Qiao et al. | |
| 7,057,026 B2 | 6/2006 | Barnes et al. | |
| 7,070,927 B2 | 7/2006 | Drmanac | |
| 7,108,891 B2 | 9/2006 | Chari et al. | |
| 7,429,467 B2 | 9/2008 | Hollinger et al. | |
| 7,612,020 B2 | 11/2009 | Stuelpnagel et al. | |
| 8,329,404 B2 | 12/2012 | McKernan et al. | |
| 8,431,691 B2 | 4/2013 | McKernan et al. | |
| 2002/0048753 A1 | 4/2002 | Hosoi et al. | |
| 2002/0160360 A1 | 10/2002 | Chenchik et al. | |
| 2002/0177141 A1 | 11/2002 | Chee et al. | |
| 2003/0068609 A1 | 4/2003 | Chari et al. | |
| 2003/0068629 A1 | 4/2003 | Rothberg et al. | |
| 2003/0170392 A1 | 9/2003 | Chari et al. | |
| 2005/0019745 A1 | 1/2005 | Chari et al. | |
| 2005/0019804 A1 | 1/2005 | Chari et al. | |
| 2005/0079510 A1 | 4/2005 | Berka et al. | |
| 2006/0019267 A1 | 1/2006 | Quake | |
| 2006/0024681 A1 | 2/2006 | Smith et al. | |
| 2006/0228720 A1 | 10/2006 | Kaplan et al. | |
| 2006/0229819 A1 | 10/2006 | Kaplan et al. | |
| 2008/0003571 A1 | 1/2008 | McKernan et al. | |
| 2009/0062129 A1 | 3/2009 | McKernan et al. | |
| 2009/0181385 A1 | 7/2009 | McKernan et al. | |
| 2009/0181860 A1 | 7/2009 | McKernan et al. | |
| 2010/0297626 A1 | 11/2010 | McKernan et al. | |
| 2011/0077169 A1 | 3/2011 | McKernan et al. | |

FOREIGN PATENT DOCUMENTS

| | | |
|---|---|---|
| EP | 2239342 | 10/2010 |
| EP | 2272983 | 1/2011 |
| EP | 2003214 | 4/2013 |
| GB | 2236852 | 4/1991 |
| WO | WO-1990/04652 | 5/1990 |
| WO | WO-1991/06678 | 5/1991 |
| WO | WO-1992/02528 | 2/1992 |
| WO | WO-1992/10587 | 6/1992 |
| WO | WO-1993/21340 | 10/1993 |
| WO | WO-1994/011530 | 5/1994 |
| WO | WO-1994/23064 | 10/1994 |
| WO | WO-1995/04160 | 2/1995 |
| WO | WO-1995/09248 | 4/1995 |
| WO | WO-1995/20053 | 7/1995 |
| WO | WO-95/027080 | 10/1995 |
| WO | WO-1995/27080 | 10/1995 |
| WO | WO-1996/12014 | 4/1996 |
| WO | WO-96/33205 | 10/1996 |
| WO | WO-1996/33205 | 10/1996 |
| WO | WO-1997/46704 | 12/1997 |
| WO | WO-1998/31831 | 7/1998 |
| WO | WO-1998/31836 | 7/1998 |
| WO | WO-1998031836 | 7/1998 |
| WO | WO-1998/40726 | 9/1998 |
| WO | WO-1998/50782 | 11/1998 |
| WO | WO-1998/53300 | 11/1998 |
| WO | WO-1999/02671 | 1/1999 |
| WO | WO-1999/60170 | 11/1999 |
| WO | WO-00/11223 | 3/2000 |
| WO | WO-2000/18957 | 4/2000 |
| WO | WO-2000/39587 | 7/2000 |
| WO | WO-2000/40712 | 7/2000 |
| WO | WO-2000/56937 | 9/2000 |
| WO | WO-2001/46675 | 6/2001 |
| WO | WO-2003/040410 | 5/2003 |
| WO | WO-2003/048387 | 6/2003 |
| WO | WO-2003/065038 | 8/2003 |
| WO | WO-2004/018497 | 3/2004 |
| WO | WO-2004/027093 | 4/2004 |
| WO | WO-2004/029586 | 4/2004 |
| WO | WO-2004/069849 | 8/2004 |
| WO | WO-2004/070005 | 8/2004 |
| WO | WO-2004/070007 | 8/2004 |
| WO | WO-2005/010145 | 2/2005 |
| WO | WO-2005/021786 | 3/2005 |
| WO | WO-2005/040425 | 5/2005 |
| WO | WO-2005/042781 | 5/2005 |
| WO | WO-2005/082098 | 9/2005 |
| WO | WO-2006/073504 | 7/2006 |
| WO | WO-2006/084132 | 8/2006 |

OTHER PUBLICATIONS

101588671, , "Extended European Search Report dated Oct. 1, 2010".

10158872.1, , "Extended European Search Report dated Nov. 25, 2010".

101588754, , "Extended European Search Report dated Sep. 9, 2010", 8.

10158877.5, , "Extended European Search Report dated Aug. 16, 2010", 8.

10158879.6, , "Extended European Search Report dated Aug. 17, 2010", 8.

10158883.8, , "Extended European Search Report dated Sep. 6, 2010", 7.

(56) References Cited

OTHER PUBLICATIONS 10158887.9, , "Extended European search report dated Aug. 17, 2010", 8.
10158888.7, , "Extended European Search Report dated Aug. 17, 2010".
10158891.1, , "Extended European Search Report dated Aug. 17, 20100", 8.
10183294.7, , "Extended European Search Report dated Mar. 1, 2011", 5.
Amasova, P et al., "Effect of the 1-(2'deoxy-B-D-ribofuranosyl)-3-nitropyrrole residue on the stability of DNA duplexes and triplexes", Nuc Acids Res, vol. 25(10), 1997, pp. 1930-1934.
Anker, H S. , "A Solubilizable Acrylamide Gel for Electrophoresis", FEBS Letters, vol. 7(3), 1970, pp. 293.
Applera Corporation, , "v Illumina "Exhibit D" (List of References)".
Attan, J et al., "Sorted (cDNA) Restriction Fragments", International Symposium—Large Scale DNA Sequencing, Tokyo, JP, Mar. 18, 1994.
Bannwarth, W , "Solid-Hase Synthesis of Oligodeoxynucleotides Containing Phosphoramidate Internucleotide Linkages and their Specific Chemical Cleavage", Helvetica Chimica Acta, vol. 71, 1988, pp. 1517-1527.
Berger, et al., "Universal bases for hybridization, replication and chain termination" Nucleic Acids Research, vol. 28, Issue 15,, Aug. 1, 2000, 2911-2914.
Blanchard, A , "Sequence Specific Effects on the Incorporation of Dideoxynucleotides by a Modified T7 Polymerase", Thesis, California Institute of Technology, 1993, pp. 1-117.
Bogdanov, V et al., "Multicolor instrumentation for direct fluorescent detection of nucleic acids microchip", SPIE vol. 3259, 1998, pp. 156-164.
Boiteux, S et al., "Formamidopyrimidine-DNA glycosylase Escherichia coli: cloning and sequencing of the fpg structural gene and over-production of the protein", EMBO Journal, vol. 6(10), 1987, pp. 3177-3183.
Brown, et al., ""Synthesis and Duplex Stability of Oligonucleotides Containing Adenine-Guanine Analogues,"", Carbohydrate Research. vol. 216, 1991, 129-139.
Canard, et al., "DNA Sequencing Using Fluorescent Chain Terminators Reversibly Tagged in 3", Genome Mapping & Sequencing Abstracts, May 11 -15, 1994, 1994, pp. 295.
Canard, B. et al., "DNA polymerase fluorescent substrates with reversible 3'-tags", Gene, vol. 148, No. 1, 1994, 1-6.
Chladek, S et al., "Nucleophilic Reactions of Some Nucleoside Phosphorothioates", J Am Chem. Soc, vol. 96(4), 1972, pp. 2079-2084.
Choules, G et al., "An Acrylamide Gel Soluble in Scintillation Fluid: Its Application to Electrophoresis at Neutral and Low pH1", Analytical Biochem, vol. 13, 1965, pp. 336-344.
Cook, A , "Nucleoside S-Alkyl Phosphorothioates. IV. Synthesis of Nucleoside Phosphorothioate Monoesters", J Am Chem Soc, vol. 92(1), 1970, pp. 190-195.
Cosstick, R et al., "Solid Phase Synthesis of Oligonucleotides", Tetrahedron Letters, vol. 30(35), 1989, pp. 4693-4696.
Cosstick, R et al., "Synthesis and Phosphorus-Sulphur Bond cleavage of 3'-Thiothymidylyl(3'-5')thymidine", J. Chem. Soc., Chem. Commun., 1988, pp. 992-993.
Cosstick, R et al., "Synthesis and properties of dithymidine phosphate analogues containing 3'-thiothymidine", Nuc Acids Res, vol. 18(4), 1990, pp. 829-835.
Crkvenjakov, R et al., "Miniaturization of sequencing by Hybridization (SBH): A Novel Method for Genome Sequencing", Human Genome Contractors/Grantee Workshop Abstracts, Santa Fe, New Mexico Nov. 3-4, 1989, 1989,
Dizdaroglu, M et al., "Substrate Specificity of the Esherichia coli Endonuclease III: Excision of Thymine- and Cytosine-Derived Lesions in DNA produced by Radiation-Generated free Radicals", Biochem, vol. 32, 1993, pp. 12105-12111.
Doublie, S et al., "The crystal structure of human endonulease VIII—like 1 (NEIL 1) reveals a zincless finger motif required for glycosylase activity", PNAS, vol. 101(28), 2004, pp. 10284-10289.
Dressman, D et al., "Transforming single DNA molecules into fluorescent magnetic particles for detection and enumeration of genertic vari", PNAS, vol. (15), 2003, pp. 8817-8822.
Drmanac, R et al., "Sequencing by Hybridization (SBH): Advantages, Achievements, and Opportunities", Advances in Biochemical Engineering/Biotechnology, vol. 77, 2002, pp. 75-101.
Drmanc, R et al., "Prospects for a Miniaturized, Simplified and Frugal Human Genome Project", Sci. Yugosl.. 16(1-2), 1990, pp. 97-107.
EP 08006533, , "Partial ESR", Jan. 23, 2009.
Franca, L et al., "A review of DNA sequencing techniques", Quarterly Reviews of Biophysics, vol. 35(2), 2002, pp. 169-200.
Frederico, L et al., "A Sensitive Genetic Assay for the Detection of Cytosine Deamination: Determination of Rate constants and the Activation Energy", Biochem, vol. 29, 1990, pp. 2532-2537.
GB9315847.5, , "Tag Reagent and Assay Method", PCT/GB94/01675, Jul. 30, 1993.
GB9401200, , "Sequencing of Nucleic Acids", Jan. 21, 1994.
Gryaznov, S et al., "Oligodeoxyribonucleotid N3'-P5' Phosphoramidates: Synthesis and Hybridization Properties", JACS, 116, 1994, pp. 3143-3144.
Gryaznov, S et al., "Synthesis and properties of oligonucleotides containing aminodeoxythymidine units", Nuc. Acids Res., vol. 20(13), 1992, pp. 3403-3409.
Gryaznov, S et al., "Template controlled coupling and recombination of oligonucleotide blocks containing thiophosphoryl groups", Nucl. Acids Res., vol. 21(6), 1993, pp. 1403-1408.
Gryaznov, S. et al., "Enhancement of selectivity in recognition of nucleic acids via chemical autoligation", Nucleic Acid Res., vol. 22(12), 1994, pp. 2366-2369.
Haltiwanger, B et al., "Characterization of class II apurinic/apyrimidinic endonuclease activities in the human malaria parasit, Plasmodium falciparum", Biochem J, vol. 345, 2000, pp. 85-89.
Hatahet, Z et al., "New Substrates for Old Enzymes", J Biol Chem, vol. 269, 1994, pp. 18814-18820.
He, B et al., "Deoxyxanthosine in DNA is repaired by Escherichia coli endonuclease V", Mutation Resolution, vol. 459, 2000, pp. 109-114.
Herman, T et al., "Chemically Cleavable Biotin-Labeled Nucleotide Analogs", Meth Enzymol, vol. 184, 1990, pp. 584-588.
Hitchcock, T et al., "Cleavage of deoxyoxanosine—containing oligodeoxyribonucleotides by bacterial endonuclease V", Nuc Acids Res, vol. 32(13), 2004, pp. 4071-4080.
Jiang, D et al., "Characterization of Escherichia coli Endonuclease VIII", J Biologial Chem, vol. 272(51), 1997, pp. 32230-32239.
Jiang, D et al., "Escherichia coli Endonuclease VII: Cloning, Sequencing, and Overexpression of the nei Structural Gene and characterization of nei and nei nth Mutants", J Bacteriology, vol. 1997, pp. 3773-3782.
Kane, et al., "Assessment of the sensitivity and specificity of oligonucleotide (50mer) microarrays", Nucleic Acids Research,28(22), 2000, 4552-4557.
Koshkin, et al., "LNA (Locked Nucleic Acids): synthesis of the adenine, cytosine, guanine, 5-methylcytosine, thymine and uracil bicyclonucleoside monomers, oligomerisation, and unprecedented nucleic acid recognition", Tetrahedron, vol. 54, 1998, 3607-3630.
Krokan, H et al., "DNA glycosylases in the base excision repair of DNA", Biochem. J, vol. 325 (Pt. 1), 1997, pp. 1-16.
Lander, E et al., "Initial sequencing and analysis of the human genome", Nature, vol. 409, 2001, pp. 860-921.
Lee, et al., ""DNA sequencing with dye-labeled terminators and T7 DNA polymerase: effect of C48 dyes and dNTPs on incorporation od dye-terminators and probability analysis of termination fragments,"", Nucleic Acids Research, vol. 20, No. 10, 1992, 2471-2483.
Lehman, J , "DNA Ligase: Structure, Mechanism, and Function", Science, vol. 186, 1974, pp. 790-797.
Levin, J et al., "Analysis of class ** (hydrolytic) and class I (B-lyase) apurinic/apyrimidinic endonucleases with a synthetic DNA substrate", Nuc acids Res, vol. 18(17), 1990, pp. 5069-5075.

(56) References Cited

OTHER PUBLICATIONS

Levina, A et al., "Photomodification of RNA and DNA fragments by oligonucleotide reagents bearing arylazide groups", *Biochemie*, 75, 1993, pp. 25-27.
Li, X et al., "Application of the Michaelis-Arbusov Reaction to the Synthesis of Internucleoside 3'-S-Phosophorothiolate linkages", *J. Chem. Soc. Perkin Trans*, 1994, pp. 2123-2129.
Li, X et al., "Synthesis of a Dinucleoside 3'-S-Phosphorothiolate Containing 2'-Deoxy-3'Thioadenosine", *Tetrahedron*, vol. 48(13), 1992, pp. 2729-2738.
Lin, Paul K. et al., "Synthesis and duplex stability of oligonucleotides containing cytosine-thymine analogues", *Nuc Acids Res*, vol. 17(24), 1989, 10373-10383.
Lin, Paul K. et al., "Synthesis of oligodeoxyriboncleotides containing degenerate bases and their use as primers in the polymerase chain reaction", *Nuc Acids Res*, vol. 20(19), 1992, pp. 5149-5152.
Liu, X et al., "3'-Thiouridylyl-(3'-5')-uridine", *Tetrahedron Letters*, vol. 37(6), 1996, pp. 925-928.
Loakes, et al., "5-Nitroindole as an universal base analogue", *Nucleic Acids Research*, vol. 22, Issue 20,, Oct. 11, 1994, 4039-4043.
Loakes, , "Survey and Summary: The applications of universal DNA base analogues", *Nucleic Acids Research*, vol. 29, Issue 12, Jun. 2001, 2437-2447.
Luo, J et al., "Improving the Fidelity of Thermus thermophilus DNA Ligase", *Nuc Acids Res*, vol. 24( 14), 1996, pp. 3071-3078.
Mag, M et al., "Synthesis and selective cleavage of an oligodeoxynucleotide containing a bridged internucleotide 5'-phosphorothioate linkage", *Nuc Acids Res*, vol. 19(7) 1991, pp. 1437-1441.
Mag, M et al., "Synthesis and Selective Cleavage of an Oligodeoxynucleotide Containing a Bridged Non-Chiral Internucleotide 3'-Phosphoramidate Linkage", *Tetrahedron Letters*, vol. 33(48), 1992, pp. 7319-7322.
Malier, B et al., "Replication by a single DNA polymerase of a stretched single-stranded DNA", *PNAS*, vol. 97(22), 2000, pp. 12002-12007.
Maxam, A. et al., "A new method for sequencing DNA", *Proc. Natl. Acad. Sci. USA*, vol. 74, No. 2,, 1977, pp. 560-564.
Metelev, V G. et al., "New Chemically reactive dsDNAs containing single internucleotide monophosphoryldithio links: Reactivity of 5-mercapto-oligodeoxyribonucleotides", *Nucleic Acids Research*; vol. 29(19), Oct. 1, 2001, 4062-4069.
Metzker, M et al., "Progress of BASS (Base addition Sequencing Scheme) as a Novel DNA Sequencing Approach", Genome Mapping & Sequencing Abstracts, May 12-16, 1993, 1993, pp. 164.
Metzker, M et al., "Stop-Start DNA Synthesis in the Base Addition Sequencing Scheme (BASS)", *Genome Mapping & Sequencing*, May 11-15, 1994, 1994, pp. 170.
Metzker, M. et al., "Termination of DNA synthesis by a novel 3'-modifies-deoxyribonucleoside 5'-triphosphates", Nucleic Acids Research, vol. 22, No. 20, Jan. 1994, 4259-4267.
Micklefield, J et al., "Backbone Modification of Nucleic Acids: Synthesis, Structure and Therapeutic Applications", *Cur. Med. Chem.*, vol. 8, 2001, pp. 1157-1179.
Mitra, R et al., "Fluorescent in Situ Sequencing on Polymerase Colonies", *Anal Biochem*, vol. 320, 2003, pp. 55-65.
Moe, A et al., "Incision at hyoxanthine residues in DNA by a mammalian homologue of the *Escherichia coli*antimutator enzyme endonuclease V", Nuc Acids Res, vol. 31(14), 2003, pp. 3893-3900.
Nauwelaerts, K et al., "Cleavage of dNA without loss of genetic information by incorporation of a disaccharide nucleoside", *Nuc Acids Res*, vol. 31(23), 2003, pp. 6758-6769.
Neff, J et al., "A novel method for surface modification to promote cell attachment to hydrophobic substrates", *J. Biomed. Mater. Res.*, vol. 40 1998, pp. 511-519.
Nichols, et al., "A universal nucleoside for use at ambiguous sites in DNA primers", *Nature*, vol. 369, No. 6480,, Jun. 9, 1994, 492-493.

Ohtsuka, E et al., "An Alternative Approach to Deoxyoligonucleotides as Hybridization Probes by Insertion of Deoxyinosine at Ambiguous Codon Positions", *J. Biol. Chem.*, vol. 260, No. 5, American Society of Biological Chemists, Inc., 1985, 2605-2608.
PCT/US2006/003845, , "International Preliminary Report on Patentability", dated Aug. 7, 2007.
PCT/US2006/003845, , "International Search Report", dated Feb. 27, 2007.
PCT/US2007/066931, , "International Search Report dated Aug. 1, 2008", Aug. 1, 2008.
Peelen, D et al., "Immobilization of Amine-Modified Oligonucleotides on Aldehyde-Terminated Alkanethiol Monolayers on Gold", *Langmuir*, vol. 21(1), 2005, pp. 266-271.
Prud'Homme, R et al., "Structure and Rheology Studies of Poly(oxyethylene-oxypropylene-oxyethylene) Aqueous Solution", *Lanquimuir*, vol. 12, 1996, pp. 4651-4659.
Radicella, J et al., "Cloning and characterization of hOGG1, a human homolog of the OGG1 gene of *Saccharomyces cerevisiae*", *PNAS*, vol. 94, 1997, pp. 8010-8015.
Rahman, M et al., "Nebularine (9-2'-deoxy-B-D-ribofuranosylpurine) has the template characteristics of adenine in vivo and in vitro", *Mutation Research*, vol. 377, 1997, pp. 263-268.
Ronaghi, M et al., "Real-time DNA Sequencing Using Detection of Pyrophosphate Release", *Anal Biochem*, vol. 242(1) 1996, pp. 84-89.
Rosenthal, A et al., "DNA Sequencing by sequential Addition to Tagged Nucleotides", *Genome Mapping and Sequencing*, May 12-May 16, 1993, 1993, pp. 222.
Rybakov, V et al., "Some substrate properties of analogues of oligothymidylates with a p-s-C5'bonds", *Nuc Acids Res,*, vol. 9(1), 1981, pp. 189-201.
Sabbagh, G et al., "Synthesis of phosphorothioamidites derived from 3'-thio-3'-deoxythymidine and 3'-thio-2', 3'-dideoxycytidine and the automated synthesis of oligodeoxynucleotides containing a 3'-S-phosphorothiolate linkage", *Nuc Acids Res*, vol. 32(2), 2004, pp. 495-501.
Sanger, F. et al., "DNA sequencing with chain-terminating inhibitors", *Proc. Natl. Acad. Sci. USA*, vol. 74(12), 1977, 5463-5467.
Shendure, J. et al., "Accurate multiplex polony sequencing of an evolved bacterial genome", *Science, American Association for the Advancement of Science*, US, Washington, DC,, vol. 309, No. 5741, Sep. 1, 2005, pp. 1728-1732.
Shimkus, M et al., "A chemically cleavable biotinylated nucleotide: Usefulness in the recovery of protein-DNA complexes from avidin affinity columns", *PNAS*, vol. 82, 1985, pp. 2593-2597.
Shimkus, M et al., "Laboratory Methods Synthesis and Characterizaiton of Biotin-Labeled Nucleotide Analogs", *DNA*, vol. 5(2) 1986, pp. 247-255.
Singh, S et al., "LNA (locked nucleic acids): synthesis and high-affinity nucleic acid recognition", *Chem. Commun.*, 1998, pp. 455-456.
Soukup, G et al., "Preparation of Oligonucleotide-Biotin Conjugates with Cleavable Linkers", *Bioconiuqate Chem*, vol. 6, 1995, pp. 135-138.
Speicher, M et al., "Karyotyping human chromosomes by combinatorial multi-fluor FISH", *Nature Genetics*, vol. 12, 1996, pp. 368-375.
Spurgeon, S et al., "Automated Referenced Fluorescent sequencing of DNA Templates and Its Application to Multiplex Sequencing", *Genome Mapping and Sequencing*, May 6-10, 1992, May 1992, 331.
Stephan, J et al., "Towards a general procedure for sequenciing single DNA molecules", *J Biotech*, vol. 86 2001, pp. 255-267.
Sun, S et al., "Synthesis of 3'-Thioribouridine, 3'-Thio-Ribocytidine, and Their Phosphoramidites", *Nucleosides & Nucleotides*, vol. 16, 1997, pp. 1543-1545.
Sun, S. et al., "Synthesis of 3'-thioribonucleosides and theirincorporation into oligoribonucleotides via phosphoramidite chemistry", *RNA*, vol. 3 (11), Jan. 1, 1997, pp. 1352-1363.
Tchou, J et al., "Substrate specificity of Fpg Protein", *J Biological Chem*, vol. 269(21), 1994, pp. 15318-15324.
Tillib, S. et al., "Integration of Multiple PCR Amplifications and DNA Mutation Analyses by Using Oligonucleotide Microchip", *Anal. Biochem*, , vol. 292(1), Jan. 5, 2001, pp. 155-160.

(56) References Cited

OTHER PUBLICATIONS

Venter, J C. et al., "The sequence of the human genome", *Science*, vol. 291, No. 5507, Feb. 16, 2001, 1304-1351.
Vyle, J et al., "New Methods for the Synthesis of 3'-S-Phosphorothiolate Internucleoside Linkages", *Tetrahedron Letters*, vol. 33(21), 1992, pp. 3017-3020.
Vyle, J. S. et al., "Sequence- and strand-specific cleavage in oligodeoxyribonucleotides and DNA containing 3'thiothymidine", *Biochem*, vol. 31(11), 1992, pp. 3012-3018.
Weinstein, L et al., "Synthesis and Characterization of an RNA Dinucleotide Containing a 3'-S-Phospho", *J Am Chem Soc*, vol. 118(43), 1996, pp. 10341-10350.
Xu, Y et al., "Chemical and enzymatic properties of bridging 5'-S-phosphorothioester linkages in DNA", *Nuc Acids Res*, vol. 26(13), 1998, pp. 3159-3164.
Yao, G et al., "Molecular-beacon-based array for sensitive DNA analysis", *Analytical Biochemistry*. vol. 331(2), 2004, pp. 216-223.
Yao, M et al., "Cleavage of Insertion/Deletion Mismatches, Flap and Pseudo-Y DNA Structures by Deoxyinosine 3'-Endonuclease from *Escherichia coli*", *Journal of Biological Chemistry*, vol. 271(48), 1996, pp. 30672-30676.
Yao, M et al., "Interaction of Deoxyinosine 3'-Endonuclease from *Escherichia coli* with DNA containing Deoxyinosine", *J Biological Chem*, vol. 270(48), 1995, pp. 28609-28616.
Yasuda, et al., "The ATP-waiting confimation of rotating F1-ATPase revealed by single-pair fluorescence resonance energy transfer.", *PNAS*,100(16), 2003, 9314-9318.

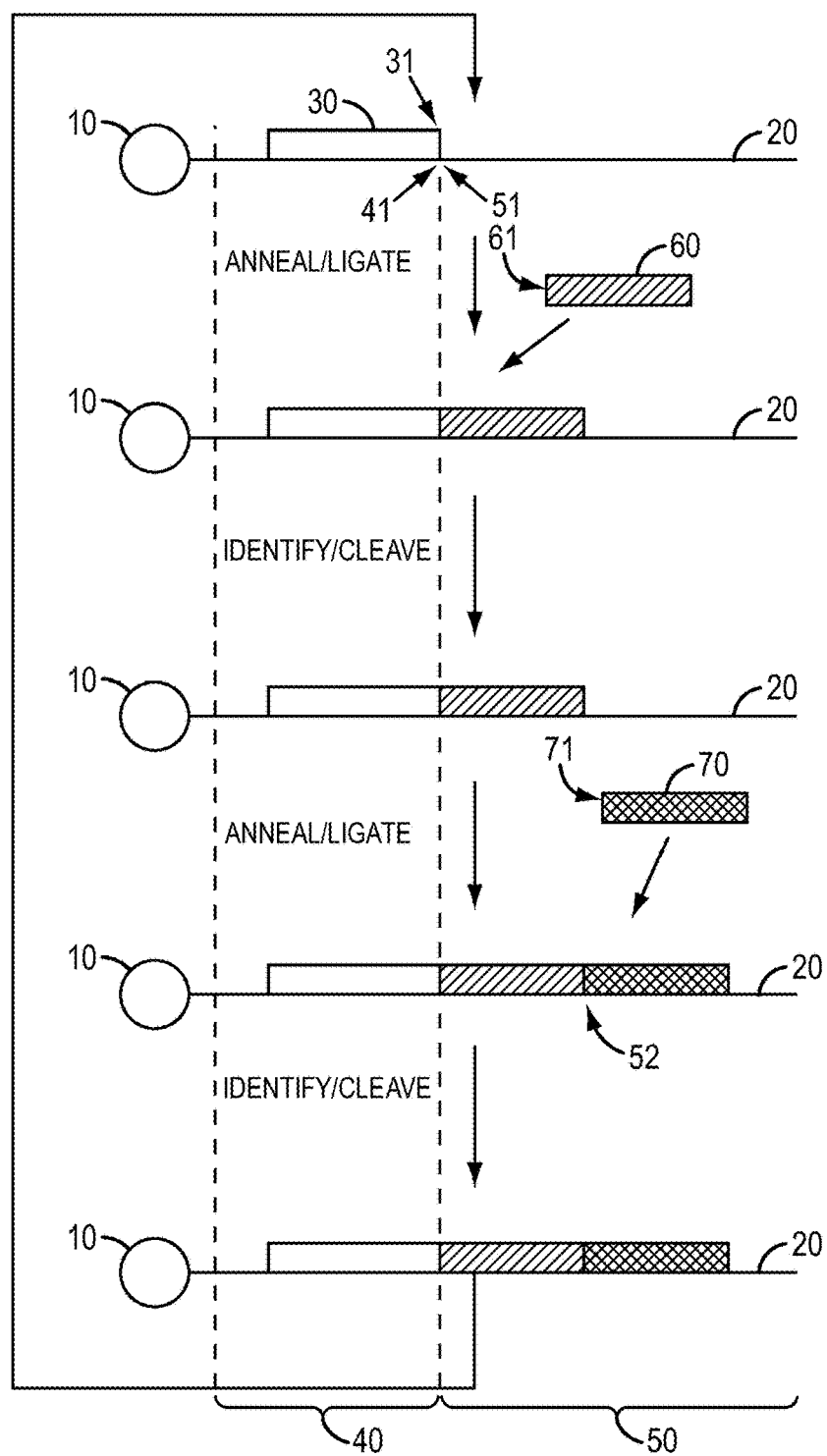

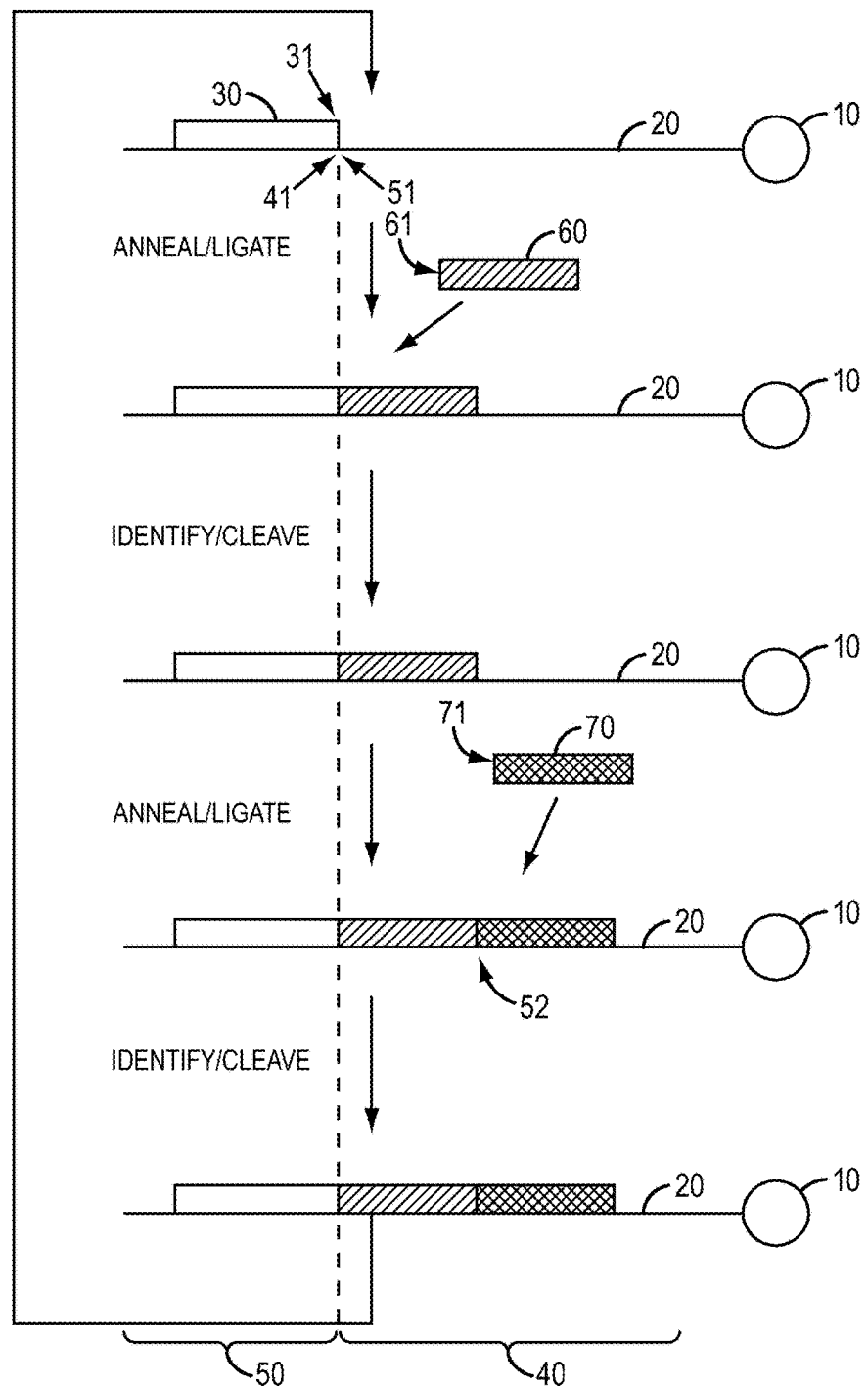

FIG. 2

| COLOR | 5' | | | | | 3' |
|---|---|---|---|---|---|---|
| RED | N | N | N | N | N | C |
| YELLOW | N | N | N | N | N | A |
| GREEN | N | N | N | N | N | G |
| BLUE | N | N | N | N | N | T |

```
TEMPLATE     ACCAAATGGCACCCAATTTTGCATCCCAGGGGCATTACCGAATGGAGCCGTATC
Primer 1                                                          C
Primer 2 (n-1)                                                  A T
Primer 3 (n-2)                                                A C
Primer 4 (n-3)                                              C G A
Primer 5 (n-4)                                            C T G C T
Primer 6 (n-5)                                          A C C A G
```

FIG. 3B

S-P bond cleaved by Ag+ under mild conditions

Sequencing by cycled oligonucleotide ligation and cleavage

FIG. 6A

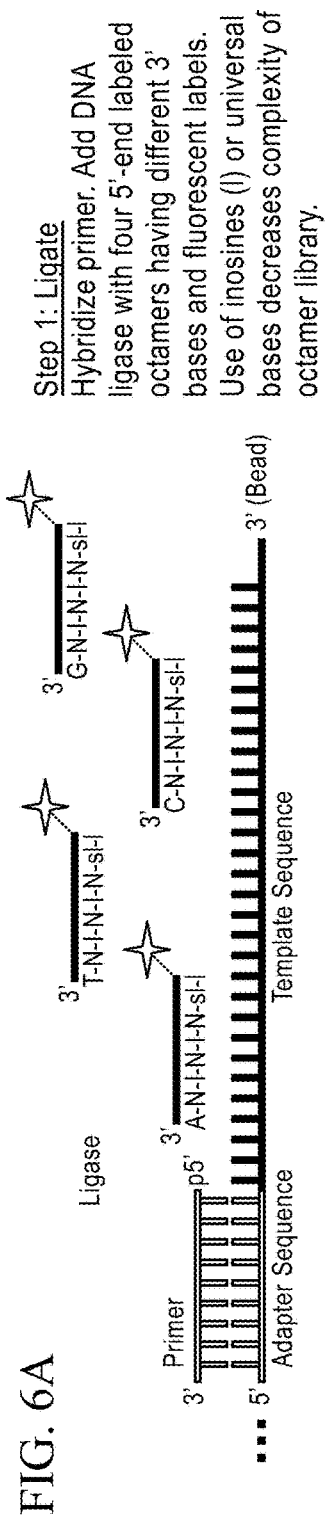

Step 1: Ligate
Hybridize primer. Add DNA ligase with four 5'-end labeled octamers having different 3' bases and fluorescent labels. Use of inosines (I) or universal bases decreases complexity of octamer library.

FIG. 6B

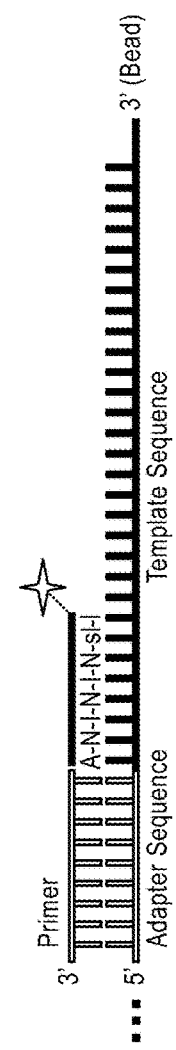

Step 2: Image
Image beads and record first base downstream of the primer after ligation of the correct octamer.

FIG. 6C

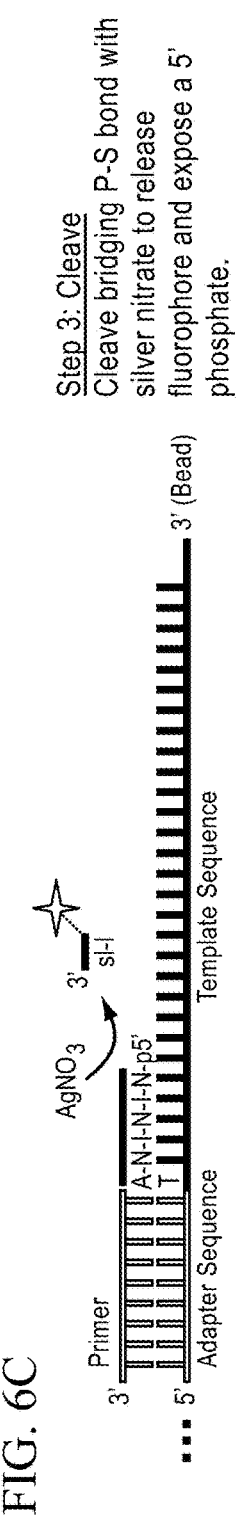

Step 3: Cleave
Cleave bridging P-S bond with silver nitrate to release fluorophore and expose a 5' phosphate.

Synthesis Scheme for 3'-Thiophosphoramidites of dA and dG

ATP-dependent DNA Ligase Mechanism:

E + pppA ⇌ EpA + PPi

EpA + pDNA ⇌ AppDNA + E

DNAoh + AppDNA ⇌ DNApDNA + pA

NAD⁺-dependent DNA Ligase Mechanism:

E + NAD⁺ ⇌ EpA + NMN⁺

EpA + pDNA ⇌ AppDNA + E

DNAoh + AppDNA ⇌ DNApDNA + pA

Common Phosphoramidate Intermediate

FIG. 11A

```
                              Degenerate
                              Oligo
                              3'ANNNNNNN5'
                                      ↙
Primer:   3'tctccttatccttgggccccgtcp5'
LST1:     5'agagaatgaggaacccggggcagTCACGAGTgtgtgcactgcgtacgtcgacg5'
Position:                         12345678
```

FIG. 11B

*Taq* DNA Ligase

|   | 1 | 2 | 3 | 4 | 5 | 6 | 7 | 8 |
|---|---|---|---|---|---|---|---|---|
|   | <u>T</u> | <u>C</u> | <u>A</u> | <u>C</u> | <u>G</u> | <u>A</u> | <u>G</u> | <u>T</u> |
| T | 100% (52) | 0 | 2% (1) | 0 | 0 | 0 | 0 | 92% (48) |
| C | 0 | 100% (52) | 2% (1) | 100% (52) | 0 | 6% (3) | 8% (4) | 2% (1) |
| A | 0 | 0 | 94% (49) | 0 | 2% (1) | 94% (49) | 0 | 6% (3) |
| G | 0 | 0 | 2% (1) | 0 | 98 (51%) | 0 | 92% (48) | 0 |

FIG. 11C

T4 DNA Ligase

|   | 1 | 2 | 3 | 4 | 5 | 6 | 7 | 8 |
|---|---|---|---|---|---|---|---|---|
|   | <u>T</u> | <u>C</u> | <u>A</u> | <u>C</u> | <u>G</u> | <u>A</u> | <u>G</u> | <u>T</u> |
| T | 100% (38) | 0 | 5% (2) | 0 | 0 | 13% (5) | 21% (8) | 76% (29) |
| C | 0 | 100% (38) | 5% (2) | 100% (38) | 0 | 2.5% (1) | 13% (5) | 8% (3) |
| A | 0 | 0 | 90% (34) | 0 | 2% (1) | 68% (26) | 8% (3) | 8% (3) |
| G | 0 | 0 | 0 | 0 | 100% (38) | 16% (6) | 58% (22) | 8% (3) |

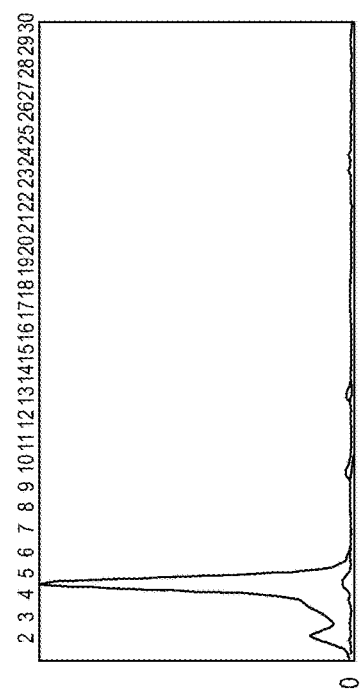
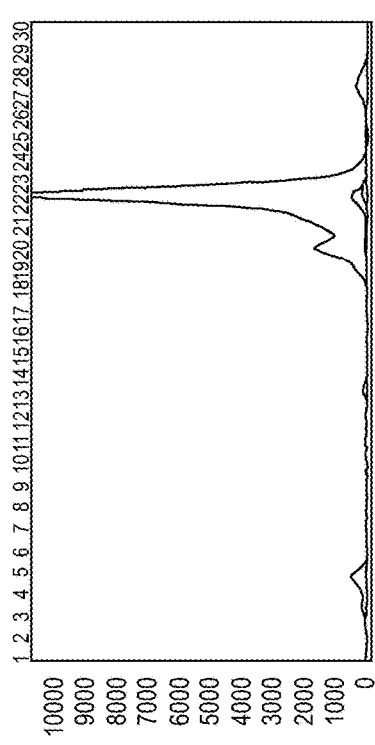
FIG. 13A
(BEAD)2Biotin-spacer-cgagccccctctgagtcaggacagagaatgaggaacccggggcagtcacgagtgtgtgcactgcgtacgtcgacg5' LST1
                   Seq Primer
FAM☆----3'TCTCTTACTCCTTGGGCCCGTCp5'
In-gel Oligo ligtion
3' AGTGCTCA5'
FIG. 13B
FIG. 13C FIG. 17A
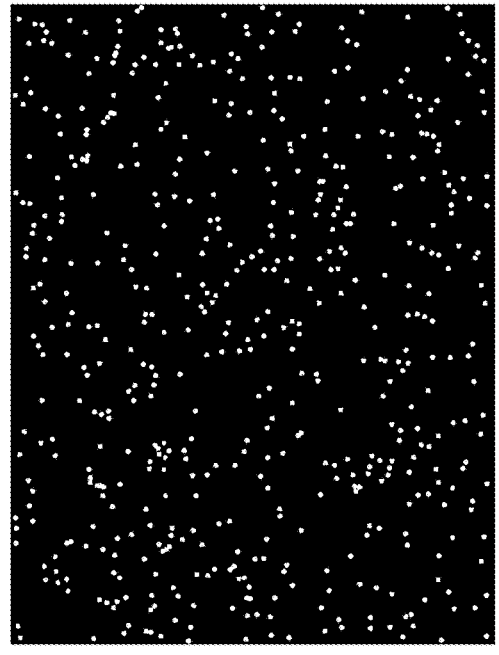
FIG. 17B
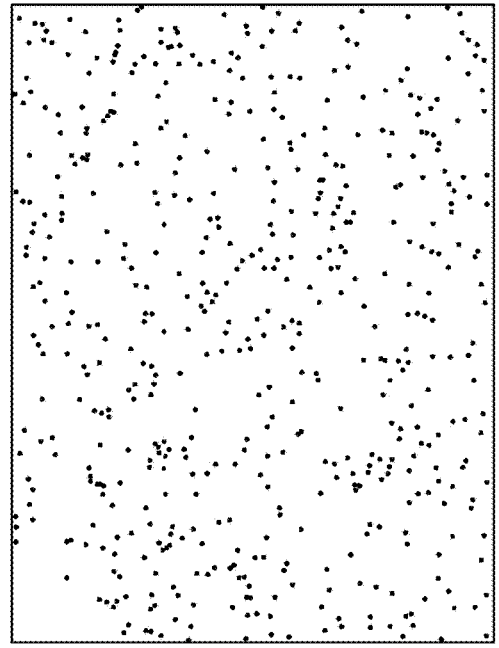
FIG. 17C

```
                                    Initializing Oligonucleotide
                              3'TCTCTTACTCCTTGGGCCCCGTCp5'
(BEAD)2Biotin-spacer-cgagcccctctgagtcaggacagagaatgaggaacccgggcagtcacgagtgtgcactgcgtacgtcgacg5' LST1

3'TCTCTTACTCCTTGGCCCCGTCTGTGCTCA5'
                                         Probe
(BEAD)2Biotin-spacer-cgagcccctctgagtcaggacagagaatgaggaacccgggcagtcacgagtgtgcactgcgtacgtcgacg5' LST1.A 3'TCTCTTACTCCTTGGGCCCCGTCCGTGCTCA5'
(BEAD)2Biotin-spacer-cgagcccctctgagtcaggacagagaatgaggaacccgggcagtcacgagtgtgcactgcgtacgtcgacg5' LST1.G 3'TCTCTTACTCCTTGGGCCCCGTCGGTGCTCA5'
(BEAD)2Biotin-spacer-cgagcccctctgagtcaggacagagaatgaggaacccgggcagtcacgagtgtgcactgcgtacgtcgacg5' LST1.C 3'TCTCTTACTCCTTGGGCCCCGTCAGTGCTCA5'
(BEAD)2Biotin-spacer-cgagcccctctgagtcaggacagagaatgaggaacccgggcagtcacgagtgtgcactgcgtacgtcgacg5' LST1.T
```

FIG. 18A

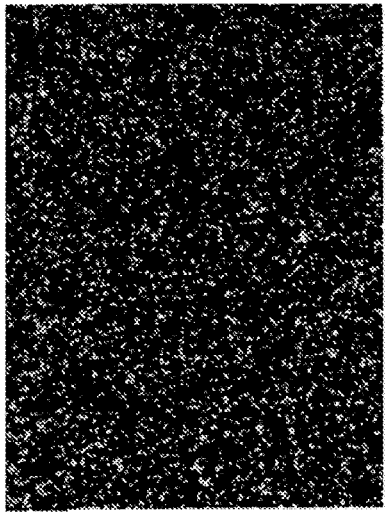
FIG. 18B
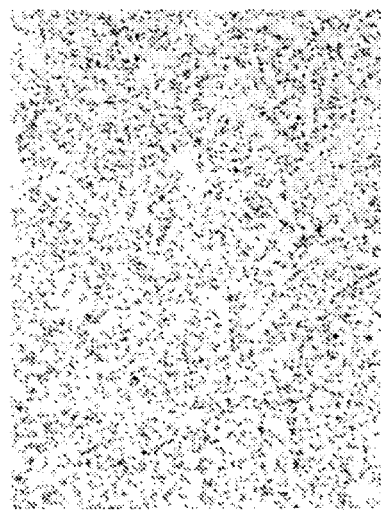
FIG. 18C
| Template | Probe | Exp | Obs | (#) |
|---|---|---|---|---|
| LST1.C | Cal560 (green) | 60% | 60% | (2066) |
| LST1.G | Cy5 (red) | 25% | 21% | (717) |
| LST1.A | FAM (blue) | 10% | 13% | (466) |
| LST1.T | Cal610 (orange) | 5% | 6% | (206) |
| Total beads per image: | | | | 3455 |
FIG. 18D

| Template | Probe | Exp | Obs | (#) |
|---|---|---|---|---|
| LST1.C | Cal560(green) | 60% | 52% | (1802) |
| LST1.G | Cy5(red) | 25% | 25% | (864) |
| LST1.A | FAM(blue) | 10% | 17% | (580) |
| LST1.T | Cal610(orange) | 5% | 6% | (188) |
| Total beads per image: | | | | 3434 |

A. CCD camera
B. Fluorescence microscope
C. Movable stage
D. Peltier flow cell
E. Temperature control
F. Fluid handling
G. Computer

FIG. 25A

| LABEL | 5' | | | | | 3' |
|---|---|---|---|---|---|---|
| | | | | | | |
| RED | N | N | N | N | T | C |
| RED | N | N | N | N | G | A |
| RED | N | N | N | N | A | G |
| RED | N | N | N | N | C | T |
| | | | | | | |
| YELLOW | N | N | N | N | C | C |
| YELLOW | N | N | N | N | T | A |
| YELLOW | N | N | N | N | G | G |
| YELLOW | N | N | N | N | A | T |
| | | | | | | |
| GREEN | N | N | N | N | A | C |
| GREEN | N | N | N | N | C | A |
| GREEN | N | N | N | N | T | G |
| GREEN | N | N | N | N | G | T |
| | | | | | | |
| BLUE | N | N | N | N | G | C |
| BLUE | N | N | N | N | A | A |
| BLUE | N | N | N | N | C | G |
| BLUE | N | N | N | N | T | T |

Sequencing Using Probe Families
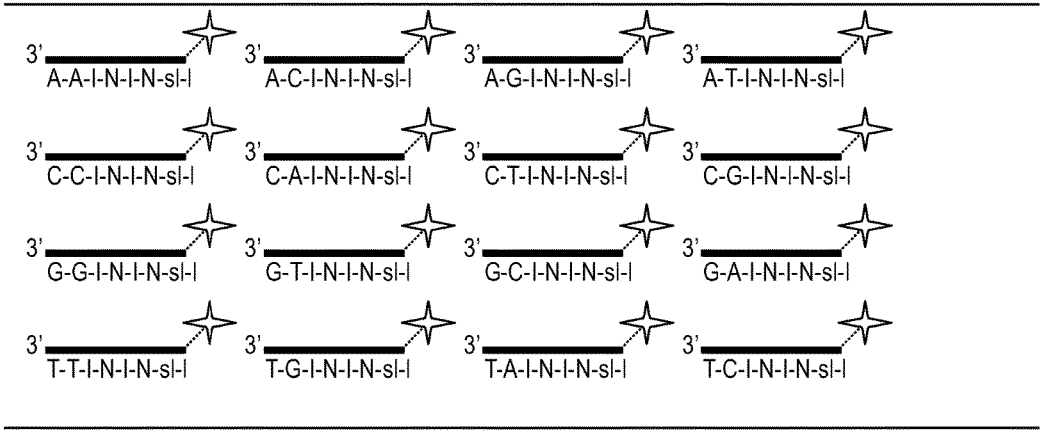
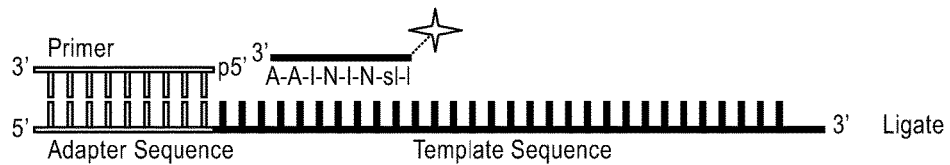 Ligate
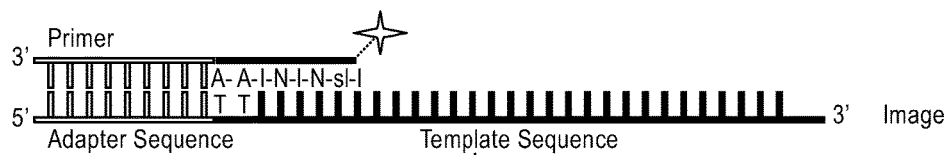 Image
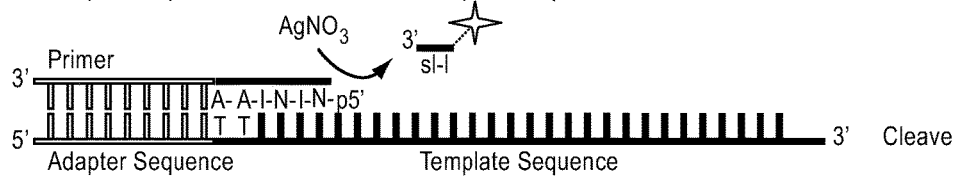 Cleave
Repeating the extensions and resetting the extensions are done as in Sequencing Methods AB, including the use of (n-1), (n-2), (n-3), (n-4) and (n-5) primers. The interpretation of the images is different because a color is no longer associated with a single base.
FIG. 25B

FIG. 26

| LABEL | 5' | | | | | 3' |
|---|---|---|---|---|---|---|
| | | | | | | |
| RED | N | N | N | N | A | A |
| RED | N | N | N | N | C | G |
| RED | N | N | N | N | G | T |
| RED | N | N | N | N | T | C |
| | | | | | | |
| YELLOW | N | N | N | N | A | C |
| YELLOW | N | N | N | N | C | A |
| YELLOW | N | N | N | N | G | G |
| YELLOW | N | N | N | N | T | T |
| | | | | | | |
| GREEN | N | N | N | N | A | T |
| GREEN | N | N | N | N | C | C |
| GREEN | N | N | N | N | G | A |
| GREEN | N | N | N | N | T | G |
| | | | | | | |
| BLUE | N | N | N | N | A | G |
| BLUE | N | N | N | N | C | T |
| BLUE | N | N | N | N | G | C |
| BLUE | N | N | N | N | A | T |

FIG. 27A

| FIRST BASE | SECOND BASE | | | |
|---|---|---|---|---|
| | LABEL 1 | LABEL 2 | LABEL 3 | LABEL 4 |
| A | A | C | G | T |
| C | C | A | T | G |
| G | G | T | C | A |
| T | T | G | A | C |

FIG. 27B

| FIRST BASE | SECOND BASE | LABEL |
|---|---|---|
| A | A | 1 |
| C | C | 1 |
| G | G | 1 |
| T | T | 1 |
| A | C | 2 |
| C | A | 2 |
| G | T | 2 |
| T | G | 2 |
| A | G | 3 |
| C | T | 3 |
| G | C | 3 |
| T | A | 3 |
| A | T | 4 |
| C | G | 4 |
| G | A | 4 |
| Y | C | 4 |

FIG. 27C

| A | A | C | G | T |
|---|---|---|---|---|
| C | C | A | T | G |
| G | G | T | C | A |
| T | T | G | A | C |

| A | A | C | G | T |
|---|---|---|---|---|
| C | C | G | T | A |
| G | G | T | A | C |
| T | T | A | C | G |

| A | A | C | G | T |
|---|---|---|---|---|
| C | C | T | A | G |
| G | G | A | T | C |
| T | T | G | C | A |

| A | A | C | G | T |
|---|---|---|---|---|
| C | C | A | T | G |
| G | G | T | A | C |
| T | T | G | C | A |

| A | A | C | G | T |
|---|---|---|---|---|
| C | C | A | T | G |
| G | T | G | A | C |
| T | G | T | C | A |

| A | A | C | G | T |
|---|---|---|---|---|
| C | C | G | T | A |
| G | T | A | C | G |
| T | G | T | A | G |

| A | A | C | G | T |
|---|---|---|---|---|
| C | C | T | A | G |
| G | T | G | C | A |
| T | G | A | T | C |

| A | A | C | G | T |
|---|---|---|---|---|
| C | C | A | T | G |
| G | T | G | C | A |
| T | G | T | A | C |

| A | A | C | G | T |
|---|---|---|---|---|
| C | G | A | T | C |
| G | C | T | A | G |
| T | T | G | C | A |

| A | A | C | G | T |
|---|---|---|---|---|
| C | G | T | A | C |
| G | C | A | T | G |
| T | T | G | C | A |

| A | A | C | G | T |
|---|---|---|---|---|
| C | G | T | C | A |
| G | C | A | T | G |
| T | T | G | A | C |

| A | A | C | G | T |
|---|---|---|---|---|
| C | G | T | A | C |
| G | C | G | T | A |
| T | T | A | C | G |

| A | A | C | G | T |
|---|---|---|---|---|
| C | G | A | T | C |
| G | T | G | C | A |
| T | C | T | A | G |

| A | A | C | G | T |
|---|---|---|---|---|
| C | G | T | A | C |
| G | T | A | C | G |
| T | C | G | T | A |

| A | A | C | G | T |
|---|---|---|---|---|
| C | G | T | A | C |
| G | T | G | C | A |
| T | C | A | T | G |

| A | A | C | G | T |
|---|---|---|---|---|
| C | C | A | T | G |
| G | G | T | A | C |
| T | T | G | C | A |

| A | A | C | G | T |
|---|---|---|---|---|
| C | C | A | T | G |
| G | G | T | C | A |
| T | T | G | A | C |

| A | A | C | G | T |
|---|---|---|---|---|
| C | C | G | T | A |
| G | G | T | A | C |
| T | T | A | C | G |

| A | A | C | G | T |
|---|---|---|---|---|
| C | T | G | C | A |
| G | C | T | A | G |
| T | G | A | T | C |

| A | A | C | G | T |
|---|---|---|---|---|
| C | T | G | C | A |
| G | C | A | T | G |
| T | G | T | A | C |

| A | A | C | G | T |
|---|---|---|---|---|
| C | T | A | C | G |
| G | G | T | A | C |
| T | C | G | T | A |

| A | A | C | G | T |
|---|---|---|---|---|
| C | T | G | C | A |
| G | G | A | T | C |
| T | C | T | A | G |

| A | A | C | G | T |
|---|---|---|---|---|
| C | T | G | A | C |
| G | G | T | C | A |
| T | C | A | T | G |

| A | A | C | G | T |
|---|---|---|---|---|
| C | T | G | C | A |
| G | G | T | A | C |
| T | C | A | T | G |

FIG. 28

| BASE 1 | BASE 2 | LABEL |
|--------|--------|-------|
| A | A | 1 |
| A | C | 1 |
| A | G | 3 |
| A | T | 3 |
| C | A | 2 |
| C | C | 2 |
| C | G | 4 |
| C | T | 4 |
| G | A | 1 |
| G | C | 1 |
| G | G | 3 |
| G | T | 3 |
| T | A | 2 |
| T | C | 2 |
| T | G | 4 |
| T | T | 4 |
|   |   |   |

FIG. 29A

|   | 1 | 2 | 3 | 4 |   |
|---|---|---|---|---|---|
| A | A | T | G | C | A |
| C | C | G | T | 4 | |
| G | G | C | A | T | |
| T | T | A | C | G | |
| A | C | A | T | G | C |
| C | A | C | G | T | |
| G | T | G | C | A | |
| T | G | T | A | C | |
| A | G | C | A | T | G |
| C | T | A | C | G | |
| G | A | T | G | C | |
| T | C | G | T | A | |
| A | T | G | C | A | T |
| C | G | T | A | C | |
| G | G | A | T | G | |
| T | A | C | G | T | |

FIG. 29B

| A | A | C | G | T |
|---|---|---|---|---|
| C | C | A | T | G |
| G | G | T | A | C |
| T | T | G | C | A |

|   | 1 | 2 | 3 | 4 |   |
|---|---|---|---|---|---|
| A | A | T | G | C |   |
| C | C | G | T | 4 | A |
| G | G | C | A | T |   |
| T | T | A | C | G |   |
| A | C | A | T | G |   |
| C | A | C | G | T |   |
| G | T | G | C | A | C |
| T | G | T | A | C |   |
| A | G | C | A | T |   |
| C | T | A | C | G | G |
| G | A | T | G | C |   |
| T | C | G | T | A |   |
| A | T | G | C | A |   |
| C | G | T | A | C | T |
| G | G | A | T | G |   |
| T | A | C | G | T |   |

FIG. 30

| OBSERVED LABEL | SEQUENCE POSSIBILITIES | | | | |
|---|---|---|---|---|---|
| | 5 | 4 | 3 | 2 | 1 |
| YELLOW | | | | C | C |
| | | | | T | A |
| | | | | G | G |
| | | | | A | T |
| GREEN | | | A | C | |
| | | | C | A | |
| | | | T | G | |
| | | | G | T | |
| RED | | T | C | | |
| | | G | A | | |
| | | A | G | | |
| | | C | T | | |
| BLUE | G | C | | | |
| | A | A | | | |
| | C | G | | | |
| | T | T | | | |
| | | | | | |
| FOUR POSSIBLE SEQUENCES | C | G | A | C | C |
| | A | A | G | T | A |
| | G | C | T | G | G |
| | T | T | C | A | T |

FIG. 31A

| LABEL | 5' | | | | | 3' |
|---|---|---|---|---|---|---|
| | | | | | | |
| RED | N | N | N | N | A | A |
| RED | N | N | N | N | C | C |
| RED | N | N | N | N | G | G |
| RED | N | N | N | N | T | T |
| | | | | | | |
| YELLOW | N | N | N | N | A | C |
| YELLOW | N | N | N | N | C | A |
| YELLOW | N | N | N | N | G | T |
| YELLOW | N | N | N | N | T | G |
| | | | | | | |
| GREEN | N | N | N | N | A | G |
| GREEN | N | N | N | N | C | T |
| GREEN | N | N | N | N | G | A |
| GREEN | N | N | N | N | T | C |
| | | | | | | |
| BLUE | N | N | N | N | A | T |
| BLUE | N | N | N | N | C | G |
| BLUE | N | N | N | N | G | C |
| BLUE | N | N | N | N | T | A |

FIG. 31B

| OBSERVED LABEL | SEQUENCE POSSIBILITIES | | | | |
|---|---|---|---|---|---|
| | 5 | 4 | 3 | 2 | 1 |
| YELLOW | | | | A | C |
| | | | | C | A |
| | | | | G | T |
| | | | | T | G |
| GREEN | | | A | G | |
| | | | C | T | |
| | | | G | A | |
| | | | T | C | |
| RED | | A | A | | |
| | | C | C | | |
| | | G | G | | |
| | | T | T | | |
| BLUE | A | T | | | |
| | C | G | | | |
| | G | C | | | |
| | T | A | | | |
| | | | | | |
| FOUR POSSIBLE SEQUENCES | C | G | G | A | C |
| | A | T | T | C | A |
| | G | C | C | T | G |
| | T | A | A | G | T |

FIG. 31C

| LABEL | 5' | | | | | 3' |
|---|---|---|---|---|---|---|
| RED | N | N | N | N | A | A |
| RED | N | N | N | N | C | G |
| RED | N | N | N | N | G | T |
| RED | N | N | N | N | T | C |
| YELLOW | N | N | N | N | A | C |
| YELLOW | N | N | N | N | C | T |
| YELLOW | N | N | N | N | G | G |
| YELLOW | N | N | N | N | T | A |
| GREEN | N | N | N | N | A | G |
| GREEN | N | N | N | N | C | A |
| GREEN | N | N | N | N | G | C |
| GREEN | N | N | N | N | T | T |
| BLUE | N | N | N | N | A | T |
| BLUE | N | N | N | N | C | C |
| BLUE | N | N | N | N | G | A |
| BLUE | N | N | N | N | T | G |

FIG. 32

| BASE | | | | | | LABEL |
|---|---|---|---|---|---|---|
| 1 | 2 | 3 | 4 | 5 | 6 | |
| A | A | | | | | 1 |
| A | C | | | | | |
| G | A | | | | | |
| G | C | | | | | |
| | C | A | | | | 2 |
| | C | C | | | | |
| | T | A | | | | |
| | T | C | | | | |
| | | A | G | | | 3 |
| | | A | T | | | |
| | | G | G | | | |
| | | G | T | | | |
| | | | C | G | | 4 |
| | | | C | T | | |
| | | | T | G | | |
| | | | T | T | | |
| | | | | A | A | 1 |
| | | | | A | C | |
| | | | | G | A | |
| | | | | G | C | |
| | | | | | | |
| A | C | A | T | G | A | 4 POSSIBLE SEQUENCES |
| G | C | A | T | G | A | |
| A | C | A | T | G | C | |
| G | C | A | T | G | C | |

Ditag Amplification Scheme:
Primer Design

FIG. 35C
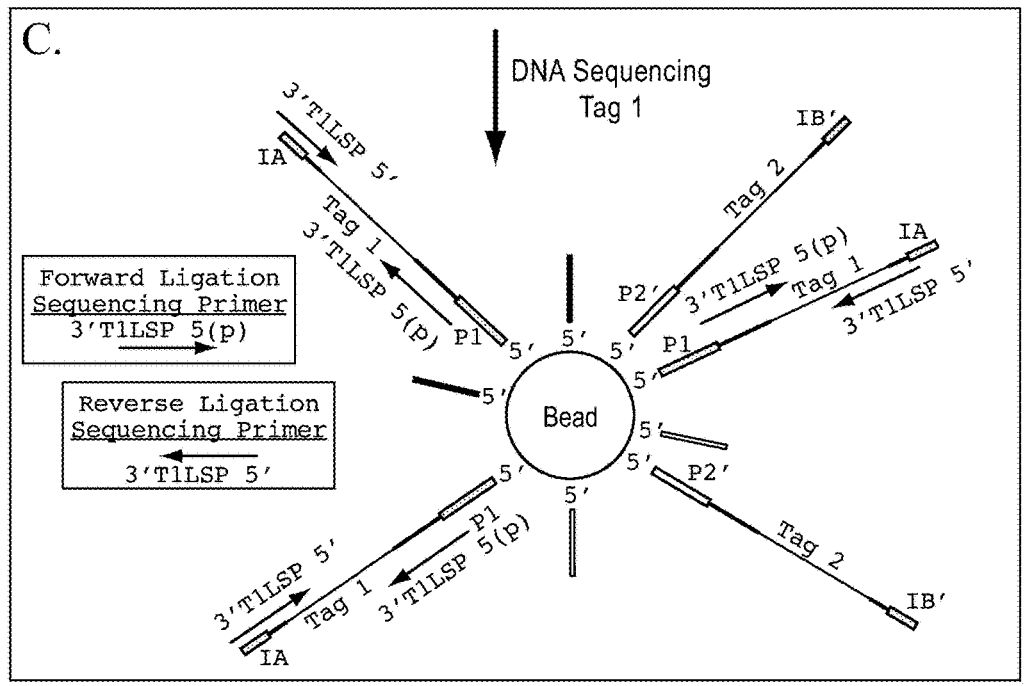
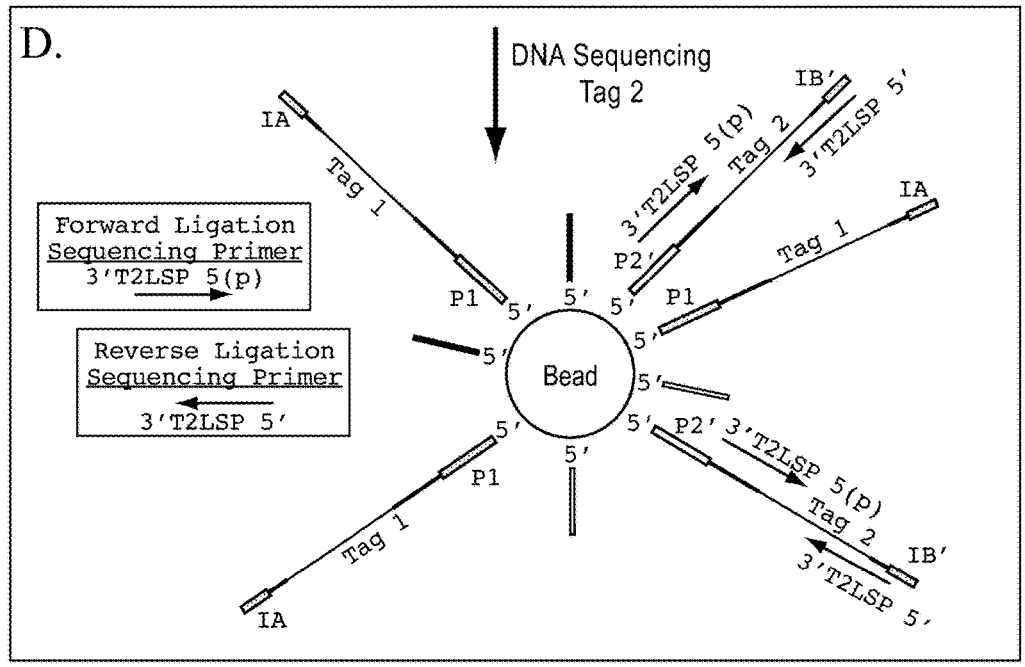
FIG. 35D

REAGENTS, METHODS, AND LIBRARIES FOR BEAD-BASED SEQUENCING

CROSS-REFERENCE TO RELATED APPLICATIONS

This application is a continuation of U.S. application Ser. No. 14/057,055 filed Oct. 18, 2013, now U.S. Pat. No. 9,493,830, which is a continuation of U.S. application Ser. No. 13/737,534 filed Jan. 9, 2013 (U.S. Pat. No. 9,217,177), which is a continuation of U.S. application Ser. No. 12/628,209 filed Nov. 30, 2009 (now abandoned), which is a continuation of U.S. application Ser. No. 12/220,201 filed Jul. 21, 2008 (now abandoned), which is a continuation of U.S. application Ser. No. 11/345,979 filed Feb. 1, 2006 (now abandoned), and claims priority to U.S. application No. 60/722,526 filed Sep. 30, 2005, U.S. application No. 60/699,541 filed Jul. 15, 2005, U.S. application No. 60/673,749 filed Apr. 21, 2005, U.S. application No. 60/656,599 filed Feb. 25, 2005, and U.S. application No. 60/649,294 filed Feb. 1, 2005, each of which disclosures are herein incorporated by reference in their entirety.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

BACKGROUND OF THE INVENTION

Nucleic acid sequencing techniques are of major importance in a wide variety of fields ranging from basic research to clinical diagnosis. The results available from such technologies can include information of varying degrees of specificity. For example, useful information can consist of determining whether a particular polynucleotide differs in sequence from a reference polynucleotide, confirming the presence of a particular polynucleotide sequence in a sample, determining partial sequence information such as the identity of one or more nucleotides within a polynucleotide, determining the identity and order of nucleotides within a polynucleotide, etc.

DNA strands are typically polymers composed of four types of subunits, namely deoxyribonucleotides containing the bases adenine (A), cytosine (C), guanine (G), and thymidine (T). These subunits are attached to one another by covalent phosphodiester bonds that link the 5' carbon of one deoxyribose group to the 3' carbon of the following group. Most naturally occurring DNA consists of two such strands, which are aligned in an antiparallel orientation and are held together by hydrogen bonds formed between complementary bases, i.e., between A and T and between G and C.

DNA sequencing first became possible on a large scale with the development of the chain termination or dideoxynucleotide method (Sanger, et al., *Proc. Natl. Acad. Sci.* 74:5463-5467, 1977) and the chemical degradation method (Maxam & Gilbert, *Proc. Natl. Acad. Sci.* 74:560-564, 1977), of which the former has been most extensively employed, improved upon, and automated. In particular, the use of fluorescently labeled chain terminators was of key importance in the development of automatic DNA sequencers. Common to both of the above approaches is the production of one or more collections of labeled DNA fragments of differing sizes, which must then be separated on the basis of length to determine the identity of the nucleotide at the 3' end of the fragment (in the chain termination method) or the identity of the nucleotide that was most recently removed from the fragment (in the case of the chemical degradation method).

Although currently available sequencing technologies have allowed the achievement of major landmarks such as the sequencing of a number of complete genomes, these techniques have a number of disadvantages, and considerable need for improvement remains in a number of areas. Separation of labeled DNA fragments has typically been achieved using polyacrylamide gel electrophoresis. However, this step has proven to be a major bottleneck limiting both the speed and accuracy of sequencing in many contexts. While capillary electrophoresis (CAE) proved to be the breakthrough that allowed the completion of the Human Genome Project (Venter, et al., *Science*, 291:1304-1351, 2001; Lander, et al., *Nature*, 409:860-921, 2001), significant shortcomings remain. For example, CAE still requires a time-consuming separation step and still involves discrimination based on size, which can be inaccurate.

A variety of alternatives to the chain termination method have been proposed. In one approach, often referred to as "sequencing by synthesis", an oligonucleotide primer is first hybridized to a target template. The primer is then extended by successive cycles of polymerase-catalyzed addition of differently labeled nucleotides, whose incorporation into the growing strand is detected. The identity of the label serves to identify the complementary nucleotide in the template. Alternately, multiple reactions can be performed in parallel using each of the nucleotides, and incorporation of a labeled nucleotide in the reaction that uses a particular nucleotide identifies the complementary nucleotide in the template. (See, e.g., Melamede, U.S. Pat. No. 4,863,849; Cheeseman, U.S. Pat. No. 5,302,509, Tsien et al, International application WO 91/06678; Rosenthal et al, International application WO 93/21340; Canard et al, Gene, 148: 1-6 (1994); Metzker et al, Nucleic Acids Research, 22: 4259-4267 (1994)).

To efficiently sequence polynucleotides of any significant length, it is desirable that the polymerase incorporates exactly one nucleotide in each cycle. Therefore it is generally necessary to use nucleotides that act as chain terminators, i.e., their incorporation prevents further extension by the polymerase. The incorporated nucleotide must then be modified, either enzymatically or chemically, to allow the polymerase to incorporate the next nucleotide. A variety of nucleotide analogs that can serve as chain terminators but can be modified after their incorporation such that they can be extended in a subsequent step have been proposed. Such "reversible terminators" have been described, for example, in U.S. Pat. Nos. 5,302,509; 6,255,475; 6,309,836; 6,613,513. However, it has proven difficult to identify reversible terminators that can be incorporated by polymerase with high efficiency, probably due to the fact that given the small size of a nucleotide, modifications that affect the ability of the nucleotide to act as a terminator also affect its incorporation into a growing polynucleotide strand.

Other sequencing approaches include pyrosequencing, which is based on the detection of the pyrophosphate (PPi) that is released during DNA polymerization (see, e.g., U.S. Pat. Nos. 6,210,891 and 6,258,568. While avoiding the need for electrophoretic separation, pyrosequencing suffers from a large number of drawbacks that have as yet limited its widespread applicability (França, et al., *Quarterly Reviews of Biophysics*, 35(2):169-200, 2002). Sequencing by hybridization has also been proposed as an alternative (U.S. Pat.

No. 5,202,231; WO 99/60170; WO 00/56937; Drmanac, et al., *Advances in Biochemical Engineering/Biotechnology*, 77:76-101, 2002) but has a number of disadvantages including the potential for error in discriminating between highly similar sequences. Single-molecule sequencing by exonuclease, which involves labeling every base in one strand and then detecting sequentially cleaved 3' terminal nucleotides in a sample stream is theoretically a very powerful method for rapidly determining the sequence of a long DNA molecule (Stephan, et al., *J. Biotechnol.*, 86:255-267, 2001). However, various technical hurdles remain to be overcome before realization of this potential (Stephan, et al., 2001).

Diagnostic tests based upon particular sequence variations are already in use for a variety of different diseases. The sequencing of the human genome is widely thought to herald an era of personalized medicine in which therapies, including preventive therapies, will be tailored to the particular genetic make-up of the patient or will be selected based upon the identification of particular alleles or mutations. There is an increasing need for rapid and accurate determination of sequence variants of pathogenic agents such as HIV. Thus it is evident that the demand for accurate and rapid sequence determination will expand greatly in the immediate future. Improved methods for sequence determination of all types are therefore needed.

SUMMARY OF THE INVENTION

The present invention provides new and improved sequencing methods that avoid the necessity for performing fragment separation and also in certain embodiments avoid the need to use polymerase enzymes. An alternative to the methods discussed in the Background is described in U.S. Pat. Nos. 5,750,341 and 6,306,597, to Macevicz. The methods are based on repeated cycles of duplex extension along a single-stranded template. In preferred embodiments of these methods a nucleotide is identified in each cycle. The present invention provides improvements to these methods. The improvements allow efficient implementation of the methods and are particularly suited for high throughput sequencing. In addition, the invention provides methods for sequence determination that involve repeated cycles of duplex extension along a single-stranded template but do not involve identification of any individual nucleotide during each cycle.

In one aspect, the invention provides improved methods for sequencing based on successive cycles of duplex extension along a single-stranded template, ligation of labeled extension probes, and detection of the label. In general, extension starts from a duplex formed by an initializing oligonucleotide and a template. The initializing oligonucleotide is extended by ligating an oligonucleotide probe to its end to form an extended duplex, which is then repeatedly extended by successive cycles of ligation. During each cycle, the identity of one or more nucleotides in the template is determined by identifying a label on or associated with a successfully ligated oligonucleotide probe. The label of the newly added probe can also be detected prior to ligation, instead of, or in addition to, after ligation. Generally it is preferred to detect the label after ligation.

In preferred embodiments the probe has a non-extendable moiety in a terminal position (at the opposite end of the probe from the nucleotide that is ligated to the growing nucleic acid strand of the duplex) so that only a single extension of the extended duplex takes place in a single cycle. By "non-extendable" is meant that the moiety does not serve as a substrate for ligase without modification. For example, the moiety may be a nucleotide residue that lacks a 5' phosphate or 3' hydroxyl group. The moiety may be a nucleotide with a blocking group attached thereto that prevents ligation. In preferred embodiments of the invention the non-extendable moiety is removed after ligation to regenerate an extendable terminus so that the duplex can be further extended in subsequent cycles.

To allow removal of the non-extendable moiety, in certain embodiments of the invention the probe contains at least one internucleoside linkage that can be cleaved under conditions that will not substantially cleave phosphodiester bonds. Such linkages are referred to herein as "scissile internucleosidic linkages" or "scissile linkages". Cleavage of the scissile internucleosidic linkage removes the non-extendable moiety and either regenerates an extendable probe terminus or leaves a terminal residue that can be modified to form an extendable probe terminus. The scissile internucleosidic linkage may be located between any two nucleosides in the probe. Preferably the scissile linkage is located at least several nucleotides away from (i.e., distal to) the newly formed bond. The nucleotides in the extension probe between the terminal nucleotide that is ligated to the extendable terminus and the scissile linkage need not hybridize perfectly to the template. These nucleotides may serve as a "spacer" and allow identification of nucleotides located at intervals along the template without performing a cycle for each nucleotide within the interval.

The scissile internucleosidic linkage and the label are preferably located such that cleavage of the scissile internucleosidic linkage separates the extension probe into a labeled portion and a portion that remains part of the growing nucleic acid strand, allowing the labeled portion to diffuse away (e.g., upon raising the temperature). For example, the label may be attached to the terminal nucleotide of the extension probe, at the opposite end from the nucleotide that is ligated. Alternately, the label may be removed using any of a number of approaches.

The present inventors have discovered that phosphorothiolate linkages, in which one of the bridging oxygen atoms in the phosphodiester bond is replaced by a sulfur atom, are particularly advantageous scissile internucleosidic linkages. The sulfur atom in the phosphorothiolate linkage may be attached to either the 3' carbon of one nucleoside or the 5' carbon of the adjacent nucleoside.

In certain embodiments of the methods described above a plurality of sequencing reactions is performed. The reactions use initializing oligonucleotides that hybridize to different sequences of the template such that the terminus at which the first ligation occurs is located at different positions with respect to the template. For example, the locations at which the first ligation occurs may be shifted, or "out of phase", relative to one another by 1 nucleotide increments. Thus after each cycle of extension with oligonucleotide probes of the same length, the same relative phase exists between the ends of the initializing oligonucleotides on the different templates. The reactions can be performed in parallel, in separate compartments each containing copies of the same template, or in series, i.e., by removing the extended duplex from the template after obtaining sequence information using a first initializing oligonucleotide and then performing additional reaction(s) using initializing oligonucleotides that hybridize to different sequences of the template.

In another aspect, the invention provides solutions that are of use for a variety of nucleic acid manipulations. In one embodiment, the invention provides a solution containing or consisting essentially of 1.0-3.0% SDS, 100-300 mM NaCl, and 5-15 mM sodium bisulfate (NaHSO$_4$) in water. The solution may contain or consist essentially of about 2% SDS, about 200 mM NaCl, and about 10 mM sodium bisulfate (NaHSO$_4$) in water. For example, in one embodiment the solution contains 2% SDS, 200 mM NaCl, and 10 mM sodium bisulfate (NaHSO$_4$) in water. In another embodiment the solution consists essentially of 2% SDS, 200 mM NaCl, and 10 mM sodium bisulfate (NaHSO$_4$) in water. In certain embodiments the solution has a pH between 2.0 and 3.0, e.g., 2.5. The solutions are useful to separate double-stranded nucleic acids, e.g., double-stranded DNA, into individual strands, i.e., to denature (melt) double-stranded nucleic acids. In certain embodiments both strands are DNA. In other embodiments both strands are RNA. In other embodiments one strand is DNA and the other strand is RNA. In other embodiments one or both strands contains both RNA and DNA. In other embodiments one or both of the strands contains at least one nucleotide other than A, G, C, or T. In some embodiments one or both of the strands contains a non-naturally occurring nucleotide. In yet other embodiments one or more of the residues is a trigger residue, e.g., an abasic residue or damaged base. In some embodiments one or more residues contains a universal base. In some embodiments one or both of the strands contains a scissile linkage.

The double-stranded nucleic acids may be fully or partially double-stranded. They may be free in solution or one or both strands may be physically associated with (e.g., covalently or noncovalently attached to) a solid or semi-solid support or substrate. Of particular note, double-stranded nucleic acids incubated in these solutions are effectively separated into single strands in the absence of heat or harsh denaturants that could cause gel delamination (e.g., when the nucleic acids are located in or attached to a semi-solid support such as a polyacrylamide gel) or could disrupt noncovalent associations such as streptavidin (SA)-biotin association (e.g., when the nucleic acids are attached to a support or substrate via a SA-biotin association). In one embodiment the solutions are used to separate double-stranded nucleic acids wherein one of the nucleic acids is attached to a bead via a SA-biotin association.

The invention also provides a method of separating strands of a double-stranded nucleic acid comprising the step of: contacting the double stranded nucleic acid with any of the afore-mentioned solutions, e.g., an aqueous solution containing about 1.0-3.0% SDS, about 100-300 mM NaCl, and about 5-15 mM sodium bisulfate (NaHSO$_4$), e.g., containing 1.0-3.0% SDS, 100-300 mM NaCl, and 5-15 mM sodium bisulfate (NaHSO$_4$). In one embodiment the solution contains about 2% SDS, 200 mM NaCl, and 10 mM sodium bisulfate (NaHSO$_4$), e.g., 2% SDS, 200 mM NaCl, and 10 mM sodium bisulfate (NaHSO$_4$). In another embodiment the solution consists essentially of 2% SDS, 200 mM NaCl, and 10 mM sodium bisulfate (NaHSO$_4$) in water. In certain embodiments the solution has a pH between 2.0 and 3.0, e.g., 2.5. In some embodiments the double-stranded nucleic acid is incubated in the solution. In other embodiments the double-stranded nucleic acid (preferably attached to a support or substrate) is washed with the solution. In some embodiments the double-stranded nucleic acid is contacted with the solution for a time sufficient to separate at least 10% of the double-stranded nucleic acid molecules into single strands. In some embodiments the double-stranded nucleic acid is contacted with the solution for a time sufficient to separate at least 20%, 30%, 40%, 50%, 60%, 70%, 80%, 90%, 95%, 98%, 99% or more of the double-stranded nucleic acids into single strands. In an exemplary embodiment the double-stranded nucleic acid is contacted with the solution for between 15 seconds and 3 hours. In another embodiment the double-stranded nucleic acid is contacted with the solution for between 1 minute and 1 hour. In certain embodiments the double-stranded nucleic acid is contacted with the solution for about 1, 2, 3, 4, 5, 10, 15, 20, 25, 30, 35, 40, 45, 50, 55, or 60 minutes. The methods may comprise a further step of removing the solution or removing some or all of the nucleic acids from the solution following a period of incubation.

The solutions find use in one or more steps of a number of the sequencing methods described herein and may be employed in any of these methods. For example, the solutions may be used to separate an extended duplex from a template. The solutions may be used following cleavage of a scissile linkage to remove the portion of an extension probe that is no longer attached to the extended duplex. The solutions are also of use in separating strands of a triple-stranded nucleic acid or in separating double-stranded regions of a single nucleic acid strand that contains self-complementary portions that have hybridized to one another.

In another aspect, the invention provides methods for obtaining information about a sequence using a collection of at least two distinguishably labeled oligonucleotide probe families. The probes in the probe families contain an unconstrained portion and a constrained portion. As in the methods described above, extension starts from a duplex formed by an initializing oligonucleotide and a template. The initializing oligonucleotide is extended by ligating an oligonucleotide probe to its end to form an extended duplex, which is then repeatedly extended by successive cycles of ligation. The probe has a non-extendable moiety in a terminal position (at the opposite end of the probe from the nucleotide that is ligated to the growing nucleic acid strand of the duplex) so that only a single extension of the extended duplex takes place in a single cycle. During each cycle, a label on or associated with a successfully ligated probe is detected, and the non-extendable moiety is removed or modified to generate an extendable terminus. The label corresponds to the probe family to which the probe belongs. Successive cycles of extension, ligation, and detection produce an ordered list of probe families to which successive successfully ligated probes belong. The ordered list of probe families is used to obtain information about the sequence. However, knowing to which probe family a newly ligated probe belongs is not by itself sufficient to determine the identity of a nucleotide in the template. Instead, knowing to which probe family the newly ligated probe belongs eliminates certain sequences as possibilities for the sequence of the constrained portion of the probe but leaves at least two possibilities for the identity of the nucleotide at each position. Thus there are at least two possibilities for the identity of the nucleotides in the template that are located at opposite positions to the nucleotides in the constrained portion of the newly ligated probe (i.e., the nucleotides that are complementary to the nucleotides in the constrained portion of the probe).

In certain embodiments, after performing a desired number of cycles, a set of candidate sequences is generated using the ordered series of probe family identities. The set of candidate sequences may provide sufficient information to achieve an objective. In preferred embodiments of the invention one or more additional steps are performed to select the correct sequence from among the candidate sequences. For example, the sequences can be compared with a database of known sequences, and the candidate sequence closest to one of the sequences in the database is selected as the correct sequence. In other embodiments the template is subjected to another round of sequencing by successive cycles of extension, ligation, detection, and cleavage, using a differently encoded set of probe families, and the information obtained in the second round is used to select the correct sequence. In other embodiments at least one item of information is combined with the information obtained from ordered list of probe family identities to determine the sequence.

The invention also provides methods of performing error checking when templates are sequenced using probe families. Certain of the methods distinguish between single nucleotide polymorphisms (SNPs) and sequencing errors.

The invention also provides nucleic acid fragments (e.g., DNA fragments) containing at least two segments of interest (e.g., at least two tags) and at least three primer binding regions (PBRs), such that at least two distinct templates, each corresponding to a segment of interest, can be amplified from each fragment. A "primer binding region" is a portion of a nucleic acid to which an oligonucleotide can hybridize such that the oligonucleotide can serve as an amplification primer, sequencing primer, initializing oligonucleotide, etc. Thus the primer binding region should have a known sequence in order to allow selection of a suitable complementary olignucleotide. As used herein and in the figures, a portion of a nucleic acid strand used in a method of the invention may be referred to as a primer binding region regardless of whether, in the practice of the method, the primer actually binds to the region or binds to the corresponding portion of a complementary strand of the nucleic acid strand. Thus a portion of a nucleic acid may be referred to as a primer binding region regardless of whether, when used in a method of the invention, a primer actually binds to that region (in which case the sequence of the primer is complementary or substantially complementary to that of the region) or binds to the complement of the region (in which case the sequence of the primer is identical to or substantially identical to the sequence of the primer binding region) A segment of interest is any segment of nucleic acid for which sequence information is desired. For example, a sequence of interest may be a tag, and for purposes of the present disclosure it will be assumed that the segment of interest is a tag (also referred to herein and elsewhere as an "end tag"). However, it is to be understood that the invention is not limited to segments of interest that are tags. In certain embodiments the at least two tags are a paired tag. The nucleic acid fragments can contain one or more pairs of tags, e.g., one or more paired tags, e.g., 2, 3, 4, 5, or more pairs of paired tags. The invention further provides libraries containing such nucleic acid fragments, and methods for making the templates and libraries.

The invention further provides a microparticle, e.g., a bead, having at least two distinct populations of nucleic acids attached thereto, wherein each of the at least two populations consists of a plurality of substantially identical nucleic acids, and wherein the populations were produced by amplification (e.g., PCR amplification) from a single nucleic acid fragment. In some embodiments the single nucleic acid fragment contains a 5' tag and 3' tag, wherein the 5' and 3' tags are a paired tag. In some embodiments in which the single nucleic acid fragment contains a 5' tag and a 3' tag of a pair, one of the populations of nucleic acids attached to the microparticle comprises at least a portion of the 5' tag and one of the populations of nucleic acids attached to the microparticle comprises at least a portion of the 3' tag. In preferred embodiments one of the populations comprises a complete 5' tag and one of the populations comprises a complete 3' tag.

The nucleic acid fragment contains multiple PBRs, at least one of which is located between the tags and at least two of which flank a portion of the nucleic acid fragment that contains the tags, so that a region comprising at least a portion of the 5' tag can be amplified, and a region comprising at least a portion of the 3' tag can be amplified, to produce two distinct populations of nucleic acids. In preferred embodiments the entire 5' tag and the entire 3' tag can be amplified. For example, the nucleic acid fragment can contain first and second primer binding sites flanking the 5' tag and also third and fourth primer binding sites flanking the 3' tag. A PCR amplification using primers that bind to the first and second primer binding sites amplifies the 5' tag. A PCR amplification using primers that bind to the third and fourth primer binding sites amplifies the 3' tag. It will be appreciated that the primers should be selected so that extension from each primer proceeds towards the region of the DNA fragment containing the tag to be amplified. Alternately, a first primer binding site can be located upstream of one of the tags, and a second primer binding site can be located downstream of the other tag, and a third primer binding site can be located between the two tags. The third primer binding site serves as a binding site for a forward primer for a PCR amplification that amplifies one of the tags and serves as a binding site for a reverse primer for a PCR amplification that amplifies the other tag. Thus in one embodiment the invention provides a microparticle, e.g., a bead, having at least two distinct populations of nucleic acids attached thereto, wherein each of the at least two populations consists of a plurality of substantially identical nucleic acids, and wherein a first distinct population comprises a 5' tag and a second distinct population comprises a 3' tag.

The invention further provides a population of microparticles, e.g., beads, wherein individual microparticles having at least two distinct populations of nucleic acids attached thereto, wherein each of the at least two populations consists of a plurality of substantially identical nucleic acids, and wherein the populations were produced by amplification (e.g., PCR amplification) from a single DNA fragment. The substantially identical populations can be, e.g., a 5' tag and a 3' tag. The invention further provides arrays of such microparticles and methods of sequencing that involve sequencing the populations of substantially identical nucleic acids. For example, in one embodiment, each of the two populations of substantially identical nucleic acids attached to an individual microparticle comprises a different primer binding region (PBR), so that by using different sequencing primers, one of the populations can be sequenced without interference from the other population. If more than two substantially identical populations of substantially identical nucleic acids are attached to a single microparticle, each of the populations can have a unique PBR, such that a primer that binds to a given PBR does not bind to a PBR present in the other substantially identical populations of nucleic acids attached to the microparticle. Thus the methods of the invention allow for producing microparticles having at least two different substantially identical populations of nucleic acids attached thereto (e.g., a multiple copies of template containing a 5' tag and multiple copies of template containing a 3' tag), wherein the tags are paired tags. In accordance with the inventive methods, the templates contain different PBRs, which provide binding sites for sequencing primers. Therefore, by selecting a sequencing primer complementary to the PBR in the template that contains the 5' tag, sequence information can be obtained from the 5' tag without interference from the template containing the 3' tag, even though the template containing the 3' tag is also present on the same microparticle. By selecting a sequencing primer complementary to the PBR in the template that contains the 3' tag, sequence information can be obtained from the 3' tag without interference from the template containing the 5' tag, even though the template containing the 5' tag is also present on the same microparticle. The fact that both of the paired tags are present on the same microparticle means that the sequence of the 5' and 3' paired tags can be associated with one another, just as would be the case if they were present within a single template as in the prior art.

The invention also provides automated sequencing systems that may be used, e.g., to sequence templates arrayed in or on a substantially planar support. The invention further provides image processing methods, which may be stored on a computer-readable medium such as a hard disc, CD, zip disk, flash memory, or the like. In certain preferred embodiments the system achieves 40,000 nucleotide identifications per second, or more. In certain preferred embodiments the system generates 8.6 gigabytes (Gb) of sequence data per day (24 hours), or more. In certain preferred embodiments the system produces 48 Gb of sequence information (nucleotide identifications) per day, or more.

In addition, the invention provides a computer-readable medium that stores sequence information generated by applying the inventive sequencing methods. The information may be stored in a database.

This application refers to various patents, patent applications, journal articles, and other publications, all of which are incorporated herein by reference. In addition, the following standard reference works are incorporated herein by reference: *Current Protocols in Molecular Biology*, John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001. In the event of a conflict between the instant specification and any document incorporated by reference, the specification shall control, it being understood that the determination of whether a conflict or inconsistency exists is within the discretion of the inventors and can be made at any time.

BRIEF DESCRIPTION OF THE DRAWING

FIG. 1A diagramatically illustrates initialization followed by two cycles of extension, ligation, and identification.

FIG. 1B diagramatically illustrates initialization followed by two cycles of extension, ligation, and identification in an embodiment in which extension proceeds inwards from the free end of the template towards a support.

FIG. 2 shows a scheme for assigning colors to oligonucleotide probes in which the identity of the 3' base of the probe is determined by identifying the color of a fluorophore.

FIG. 3B diagrammatically shows assembly of a continuous sequence (listed in the Sequence Listing as SEQ ID NO. 7) by using the extension, ligation, and cleavage method with extension probes designed to read every 6$^{th}$ base of the template molecule.

FIG. 6A-6F is a more detailed diagrammatic illustration of several sequencing reactions performed on a single template. The reactions utilize initializing oligonucleotides that bind to different portions of the template. The sequence of the extended strand depicted in FIG. 6D is listed as SEQ ID NO. 8 The sequence of the extended strand depicted in FIG. 6E is listed as SEQ ID NO. 9. The sequence of the extended strand depicted in FIG. 6F is listed as SEQ ID NO. 10. The sequence depicted in FIG. 6F corresponding to the template is listed as SEQ ID NO. 11.

FIG. 11A-11C shows results of an analysis conducted to assess the fidelity of each of two DNA ligases. FIG. 11A depicts sequences of the primer and LST1 template are listed as SEQ ID NOs. 17 and 18 respectively; FIG. 11B and FIG. 11C shows results of an analysis conducted to assess the fidelity of each of two DNA ligases (T4 DNA ligase and Taq DNA ligase) for 3'→5' extensions.

FIG. 13A-13C shows results of an experiment that demonstrates in-gel ligation when bead-based templates are embedded in polyacrylamide gels on slides. FIG. 13(A) shows a schematic of the ligation reaction. In gel ligation reactions were performed in the absence FIG. 13(B) and in the presence FIG. 13(C) of T4 DNA ligase. The sequences of the primer and LST1 template are listed as SEQ ID NOs. 15 and 26 respectively.

FIG. 17A-17D shows results from an experiment confirming ligation specificity of oligonucleotide extension probes. FIG. 17(A) shows a schematic outline of ligation. FIG. 17(B) is a bright light image, and FIG. 17(C) is a corresponding fluorescence image of a population of beads embedded in a polyacrylamide gel after ligation. FIG. 17(D) shows fluorescence detected from each label before (pre) or after (post) ligation. The sequences of the extended initializing oligonucleotided with probe and LST1 template are listed as SEQ ID NOs. 27 and 26 respectively.

FIG. 18A-18D shows results from another experiment confirming ligation specificity and selectivity of oligonucleotide extension probes. FIG. 18(A) shows a schematic outline of ligation. FIG. 18(B) is a bright light image, and FIG. 18(C) is a corresponding fluorescence image of a population of beads embedded in a polyacrylamide gel after ligation. FIG. 18(D) shows expected versus observed ligation frequencies, showing a high correlation between frequencies expected based on the proportion of particular extension probes in a population and frequencies observed. The sequences of the initializing oligonucleotide and LST1 template are listed as SEQ ID NOs. 15 and 26 respectively. The sequences of the extended initializing oligonucleotides with CAL560-, CAL610-, Cy5-, and FAM-labeled probes are listed as SEQ ID NOs. 34, 36, 38, and 27 respectively. The sequences of the LST1.A, LST1.G, LST1.C, and LST1.T templates are listed as SEQ ID NOs. 35, 37, 39 and 26 respectively.

FIG. 19(A) shows a schematic outline of the ligation experiment, illustrating four differentially labeled degenerate inosine-containing probe pools following ligation. FIG. 19(B) is a bright light image, and FIG. 19(C) is a corresponding fluorescence image of a population of beads embedded in a polyacrylamide gel after ligation. FIG. 19(D) shows expected versus observed ligation frequencies, showing a high correlation between frequencies expected based on the proportion of particular extension probes in a population and frequencies observed. FIG. 19(E) shows a scatter plot of the raw unprocessed data and filtered data representing the top 90% of bead signal values. The sequences of the initializing oligonucleotide and LST1 template are listed as SEQ ID NOs. 15 and 26 respectively. The sequences of the extended initializing oligonucleotides with FA-, Cy-, Cal61-, and Cal56-labeled probes are listed as SEQ ID NOs. 40, 41, 43, and 45 respectively. The sequences of the LST2, LST3, and LST4 templates are listed as SEQ ID NOs. 42, 44, and 46 respectively.

FIG. 25A shows an exemplary encoding for a preferred collection of probe families comprising partially constrained probes comprising constrained portions that are 2 nucleotides in length.

FIG. 25B shows a preferred collection of probe families (upper panel) and a cycle of ligation, detection, and cleavage (lower panel).

FIG. 26 shows an exemplary encoding for another preferred collection of probe families comprising partially constrained probes comprising constrained portions that are 2 nucleotides in length.

FIGS. 27A-27C represent an alternate method to schematically define the 24 preferred collections of probe families that are defined in Table 1.

FIG. 28 shows a less preferred collection of probe families in which the probes comprise constrained portions that are 2 nucleotides in length.

FIG. 29A shows a diagram that can be used to generate constrained portions for a collection of probe families that comprises probes with a constrained portion 3 nucleotides long.

FIG. 29B shows a diagram a mapping scheme that can be used to generate constrained portions for a collection of probe families that comprises probes with a constrained portion 3 nucleotides long from the 24 preferred collections of probe families.

FIG. 30 shows a method in which sequence determination is performed using a collection of probe families. An embodiment using a preferred set of probe families is depicted.

FIGS. 31A-31C show a method in which sequence determination is performed using a first collection of probe families to generate candidate sequences and a second collection of probe families to decode.

FIG. 32 shows a method in which sequence determination is performed using a less preferred collection of probe families.

FIGS. 35C and 35D show sequencing of the first and second tags, respectively, attached to a microparticle produced by the method of FIGS. 35A and 35B.

DEFINITIONS

Figure 3A:
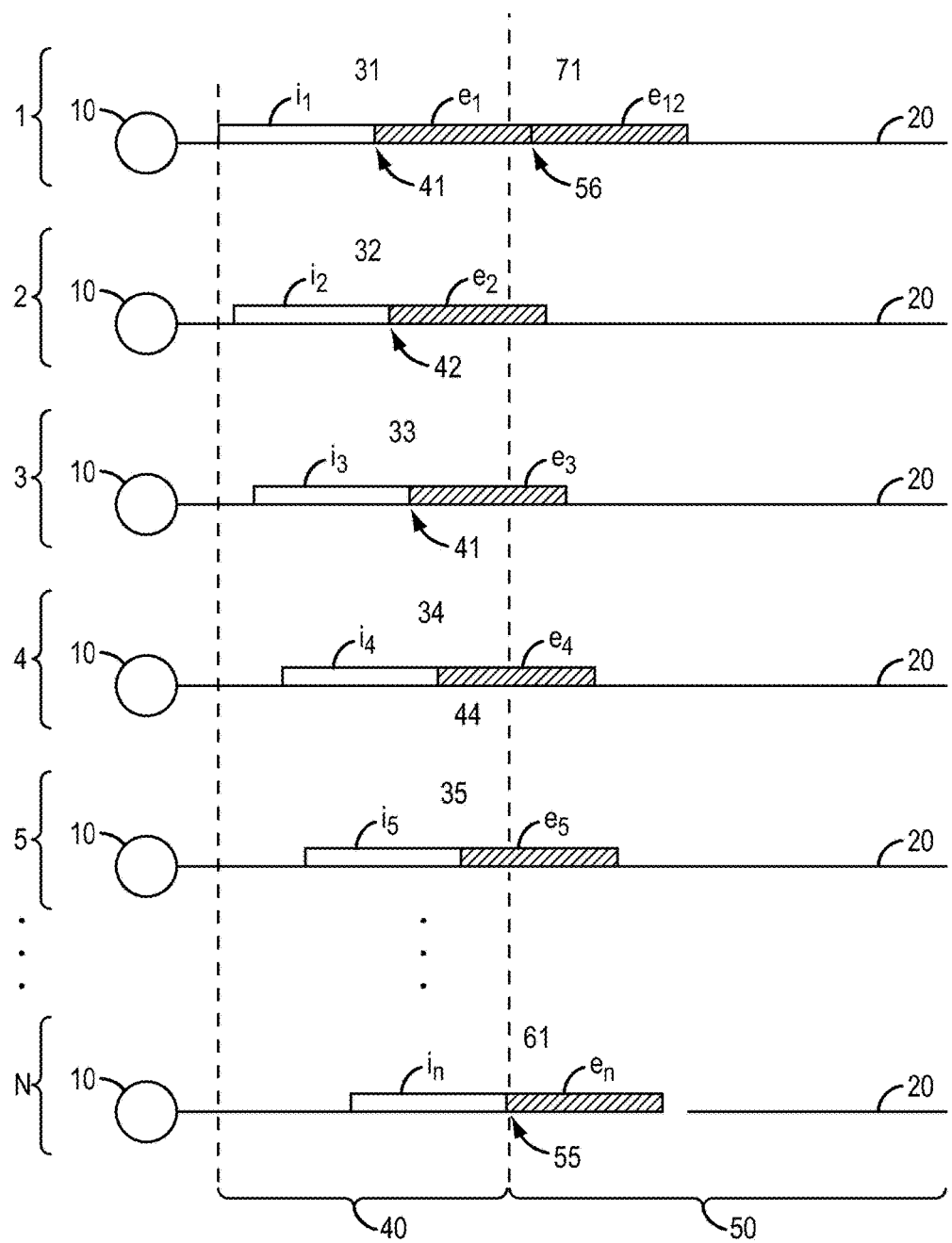
FIG. 3A diagramatically shows extended duplexes resulting from hybridization of initializing oligonucleotides at different positions in the binding region of a template followed by ligation of extension probes.

To facilitate understanding of the description of the invention, the following definitions are provided. It is to be understood that, in general, terms not otherwise defined are to be given their meaning or meanings as generally accepted in the art.

As used herein, an "abasic residue" is a residue that has the structure of the portion of a nucleoside or nucleotide that remains after removal of the nitrogenous base or removal of a sufficient portion of the nitrogenous base such that the resulting molecule no longer participates in hydrogen bonds characteristic of a nucleoside or nucleotide. An abasic residue may be generated by removing a nitrogenous base from a nucleoside or nucleotide. However, the term "abasic" is used to refer to the structural features of the residue and is independent of the manner in which the residue is produced. The terms "abasic residue" and "abasic site" are used herein to refer to a residue within a nucleic acid that lacks a purine or pyrimidine base.

An "apurinic/apyrimidinic (AP) endonuclease", as used herein, refers to an enzyme that cleaves a bond on either the 5' side, the 3' side, or both the 5' and 3' sides of an abasic residue in a polynucleotide. In certain embodiments of the invention the AP endonuclease is an AP lyase. Examples of AP endonucleases include, but are not limited to, *E. coli* endonuclease VIII and homologs thereof and *E. coli* endonuclease III and homologs thereof. It is to be understood that references to specific enzymes, e.g., endonucleases such as *E. coli* Endo VIII, Endo V, etc., are intended to encompass homologs from other species that are recognized in the art as being homologs and as possessing similar biochemical activity with respect to removal of damaged bases and/or cleavage of DNA containing abasic residues or other trigger residues.

As used herein, the term "array" refers to a collection of entities that is distributed over or in a support matrix; preferably, individual entities are spaced at a distance from one another sufficient to permit the identification of discrete features of the array by any of a variety of techniques. The entities may be, for example, nucleic acid molecules, clonal populations of nucleic acid molecules, microparticles (optionally having clonal populations of nucleic acid molecules attached thereto), etc. When used as a verb, the term "array" and variations thereof refers to any process for forming an array, e.g., distributing entities over or in a support matrix.

A "damaged base" is a purine or pyrimidine base that differs from an A, G, C, or T in such a manner as to render it a substrate for removal from DNA by a DNA glycosylase. Uracil is considered a damaged base for purposes of the present invention. In some embodiments of the invention the damaged base is hypoxanthine.

"Degenerate", with respect to a position in a polynucleotide that is one of a population of polynucleotides, means that the identity of the base that forms part of the nucleoside occupying that position varies among different members of the population. Thus the population contains individual members whose sequence differs at the degenerate position. The term "position" refers to a numerical value that is assigned to each nucleoside in a polynucleotide, generally with respect to the 5' or 3' end. For example, the nucleoside at the 3' end of an extension probe may be assigned position 1. Thus in a pool of extension probes of structure 3'-XXX-NXXXX-5', the N is at position 4. Position 4 is considered degenerate if, in different members of the pool, the identity of N can vary. The pool of extension probes is also said to be degenerate at position N. A position is said to be k-fold degenerate if it can be occupied by nucleosides having any of k different identities. For example, a position that can be occupied by nucleosides comprising either of 2 different bases is 2-fold degenerate.

"Determining information about a sequence" encompasses "sequence determination" and also encompasses other levels of information such as eliminating one or more possibilities for the sequence. It is noted that performing sequence determination on a polynucleotide typically yields equivalent information regarding the sequence of a perfectly complementary (100% complementary) polynucleotide and thus is equivalent to sequence determination performed directly on a perfectly complementary polynucleotide.

"Independent", with respect to a plurality of elements, e.g., nucleosides in an oligonucleotide probe molecule or portion thereof, means that the identity of each element does not limit and is not limited by the identity of any of the other elements, e.g., the identity of each element is selected without regard for the identity of any of the other element(s). Thus knowing the identity of one or more of the elements does not provide any information regarding the identity of any of the other elements. For example, the nucleosides in the sequence NNNN are independent if the identity of each N can be A, G, C, or T, regardless of the identity of any other N.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically.

The term "microparticle" is used herein to refer to particles having a smallest cross-sectional dimension of 50 microns or less, preferably 10 microns or less. In certain embodiments the smallest cross-sectional dimension is approximately 3 microns or less, approximately 1 micron or less, approximately 0.5 microns or less, e.g., approximately 0.1, 0.2, 0.3, or 0.4 microns. Microparticles may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. See, e.g., U.S. Pat. No. 6,406,848, for various suitable materials and other considerations. Dyna beads, available from Dynal, Oslo, Norway, are an example of commercially available microparticles of use in the present invention. Magnetically responsive microparticles can be used. The magnetic responsiveness of certain preferred microparticles permits facile collection and concentration of the microparticle-attached templates after amplification, and facilitates additional steps (e.g., washes, reagent removal, etc.). In certain embodiments of the invention a population of microparticles having different shapes (e.g., some spherical and others nonspherical) is employed.

The term "microsphere" or "bead" is used herein to refer to substantially spherical microparticles having a diameter of 50 microns or less, preferably 10 microns or less. In certain embodiments the diameter is approximately 3 microns or less, approximately 1 micron or less, approximately 0.5 microns or less, e.g., approximately 0.1, 0.2, 0.3, or 0.4 microns. In certain embodiments of the invention a population of monodisperse microspheres is used, i.e., the microspheres are of substantially uniform size. For example, the diameters of the microparticles may have a coefficient of variation of less than 5%, e.g., 2% of less, 1% or less, etc. However, in other embodiments the coefficient of variation of a population of microparticles is 5% or greater, e.g., 5%, between 5% and 10% (inclusive), between 10% and 25%, inclusive, etc. In certain embodiments a mixed population of microparticles is used. For example, a mixture of two populations, each of which has a coefficient of variation of less than 5%, may be used, resulting in a mixed population that is not monodisperse. As an example, a mixture of microspheres having diameters of 1 micron and 3 microns can be employed. In certain embodiments of the invention additional information is provided by the size of the microsphere when sequencing is performed using templates attached to microspheres of a population that is not monodisperse. For example, different libraries of templates may be attached to differently sized microspheres. Also, since fewer template molecules may be attached to smaller particles, the intensity of the signals may vary, which may facilitate multiplex sequencing.

The term "nucleic acid sequence" as used herein can refer to the nucleic acid material itself and is not restricted to the sequence information (i.e. the succession of letters chosen among the five base letters A, G, C, T, or U) that biochemically characterizes a specific nucleic acid, e.g., a DNA or RNA molecule. Nucleic acids shown herein are presented in a 5'→3' orientation unless otherwise indicated.

A "nucleoside" comprises a nitrogenous base linked to a sugar molecule. As used herein, the term includes natural nucleosides in their 2'-deoxy and 2'-hydroxyl forms as described in Kornberg and Baker, DNA Replication, 2nd Ed. (Freeman, San Francisco, 1992) and nucleoside analogs. For example, natural nucleosides include adenosine, thymidine, guanosine, cytidine, uridine, deoxyadenosine, deoxythymidine, deoxyguanosine, and deoxycytidine. Nucleoside "analogs" refers to synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, reduce degeneracy, increase specificity, and the like. Nucleoside analogs include 2-aminoadenosine, 2-thiothymidine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 2-thiocytidine, etc. Nucleoside analogs may comprise any of the universal bases mentioned herein.

The term "organism" is used herein to indicate any living or nonliving entity that comprises nucleic acid that is capable of being replicated and is of interest for sequence determination. It includes plasmids; viruses; prokaryotic, archaebacterial and eukaryotic cells, cell lines, fungi, protozoa, plants, animals, etc.

"Perfectly matched duplex" in reference to the protruding strands of probes and template polynucleotides means that the protruding strand from one forms a double stranded structure with the other such that each nucleoside in the double stranded structure undergoes Watson-Crick basepairing with a nucleoside on the opposite strand. The term also comprehends the pairing of nucleoside analogs, such as deoxyinosine, nucleosides with 2-aminopurine bases, and the like, that may be employed to reduce the degeneracy of the probes, whether or not such pairing involves formation of hydrogen bonds.

The term "plurality" means more than one.

The term "polymorphism" is given its ordinary meaning in the art and refers to a difference in genome sequence among individuals of the same species. A "single nucleotide polymorphism" (SNP) refers to a polymorphism at a single position.

"Polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. In certain embodiments of the invention one or more nucleosides in an extension probe comprises a universal base. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

In naturally occurring polynucleotides, the internucleoside linkage is typically a phosphodiester bond, and the subunits are referred to as "nucleotides". However, oligonucleotide probes comprising other internucleoside linkages, such as phosphorothiolate linkages, are used in certain embodiments of the invention. It will be appreciated that one or more of the subunits that make up such an oligonucleotide probe with a non-phosphodiester linkage may not comprise a phosphate group. Such analogs of nucleotides are considered to fall within the scope of the term "nucleotide" as used herein, and nucleic acids comprising one or more internucleoside linkages that are not phosphodiester linkages are still referred to as "polynucleotides", "oligonucleotides", etc. In other embodiments, a polynucleotide such as an oligonucleotide probe comprises a linkage that contains an AP endonuclease sensitive site. For example, the oligonucleotide probe may contain an abasic residue, a residue containing a damaged base that is a substrate for removal by a DNA glycosylase, or another residue or linkage that is a substrate for cleavage by an AP endonuclease. In another embodiment an oligonucleotide probe contains a disaccharide nucleoside.

The term "primer" refers to a short polynucleotide, typically between about 10-100 nucleotides in length, that binds to a target polynucleotide or "template" by hybridizing with the target. The primer preferably provides a point of initiation for template-directed synthesis of a polynucleotide complementary to the target, which can take place in the presence of appropriate enzyme(s), cofactors, substrates such as nucleotides, oligonucleotides, etc. The primer typically provides a terminus from which extension can occur. In the case of primers for synthesis catalyzed by a polymerase enzyme such as a DNA polymerase (e.g., in "sequencing by synthesis", polymerase chain reaction (PCR) amplification, etc.), the primer typically has, or can be modified to have, a free 3' OH group. Typically a PCR reaction employs a pair of primers (first and second amplification primers) including an "upstream" (or "forward") primer and a "downstream" (or "reverse") primer, which delimit a region to be amplified. In the case of primers for synthesis by successive cycles of extension, ligation (and optionally cleavage), the primer typically has, or can be modified to have, a free 5' phosphate group or 3' OH group that serves as a substrate for DNA ligase.

As used herein, a "probe family" refers to a group of probes, each of which comprises the same label.

As used herein "sequence determination", "determining a nucleotide sequence", "sequencing", and like terms, in reference to polynucleotides includes determination of partial as well as full sequence information of the polynucleotide. That is, the term includes sequence comparisons, fingerprinting, and like levels of information about a target polynucleotide, as well as the express identification and ordering of each nucleoside of the target polynucleotide within a region of interest. In certain embodiments of the invention "sequence determination" comprises identifying a single nucleotide, while in other embodiments more than one nucleotide is identified. In certain embodiments of the invention, sequence information that is insufficient by itself to identify any nucleotide in a single cycle is gathered. Identification of nucleosides, nucleotides, and/or bases are considered equivalent herein. It is noted that performing sequence determination on a polynucleotide typically yields equivalent information regarding the sequence of a perfectly complementary (100% complementary) polynucleotide and thus is equivalent to sequence determination performed directly on a perfectly complementary polynucleotide.

"Sequencing reaction" as used herein refers to a set of cycles of extension, ligation, and detection. When an extended duplex is removed from a template and a second set of cycles is performed on the template, each set of cycles is considered a separate sequencing reaction though the resulting sequence information may be combined to generate a single sequence.

"Semi-solid", as used herein, refers to a compressible matrix with both a solid and a liquid component, wherein the liquid occupies pores, spaces or other interstices between the solid matrix elements. Exemplary semi-solid matrices include matrices made of polyacrylamide, cellulose, polyamide (nylon), and cross-linked agarose, dextran and polyethylene glycol. A semi-solid support may be provided on a second support, e.g., a substantially planar, rigid support, also referred to as a substrate, which supports the semi-solid support.

"Support", as used herein, refers to a matrix on or in which nucleic acid molecules, microparticles, and the like may be immobilized, i.e., to which they may be covalently or noncovalently attached or, in or on which they may be partially or completely embedded so that they are largely or entirely prevented from diffusing freely or moving with respect to one another.

A "trigger residue" is a residue that, when present in a nucleic acid, renders the nucleic acid more susceptible to cleavage (e.g., cleavage of the nucleic acid backbone) by a cleavage agent (e.g., an enzyme, silver nitrate, etc.) or combination of agents than would be an otherwise identical nucleic acid not including the trigger residue, and/or is susceptible to modification to generate a residue that renders the nucleic acid more susceptible to such cleavage. Thus presence of a trigger residue in a nucleic acid can result in presence of a scissile linkage in the nucleic acid. For example, an abasic residue is a trigger residue since the presence of an abasic residue in a nucleic acid renders the nucleic acid susceptible to cleavage by an enzyme such as an AP endonuclease. A nucleoside containing a damaged base is a trigger residue since the presence of a nucleoside comprising a damaged base in a nucleic acid also renders the nucleic acid more susceptible to cleavage by an enzyme such as an AP endonuclease, e.g., after removal of the damaged base by a DNA glycosylase. The cleavage site may be at a bond between the trigger residue and an adjacent residue or may be at a bond that is one or more residues removed from the trigger residue. For example, deoxyinosine is a trigger residue since the presence of a deoxyinosine in a nucleic acid renders the nucleic acid more susceptible to cleavage by $E.\ coli$ Endonuclease V and homologs thereof. Such enzymes cleave the second phosphodiester bond 3' to deoxyinosine. Any of the probes disclosed herein may contain one or more trigger residues. The trigger residue may, but need not, comprise a ribose or deoxyribose moiety. Preferably the cleavage agent is one that does not substantially cleave a nucleic acid in the absence of a trigger residue but exhibits significant cleavage activity against a nucleic acid that contains the trigger residue under the same conditions, which conditions may include the presence of agents that modify the nucleic acid to render it sensitive to the cleavage agent. For example, preferably if the cleavage agent is present in a composition containing nucleic acids that are identical in length and composition except that one of them contains the trigger residue and the other of them does not contain the trigger residue, the likelihood that the nucleic acid containing the trigger residue will be cleaved is at least: 10; 25; 50; 100; 250; 500; 1000; 2500; 5000; 10,000; 25,000; 50,000; 100,000; 250,000; 500,000; 1,000,000 or more, as great as the likelihood that the nucleic acid not containing the trigger residue will be cleaved, e.g., the ratio of the likelihood of cleavage of a nucleic acid containing a trigger residue to the likelihood of cleavage of a nucleic acid not containing the trigger residue but otherwise identical is between 10 and $10^6$, or any integral subrange thereof. It will be appreciated that the ratio may differ depending upon the particular nucleic acid and location and nucleotide context of the trigger residue.

Preferably if the nucleic acid containing the trigger residue needs to be modified in order to render the nucleic acid susceptible to cleavage by a cleavage agent, such modification occurs readily in the presence of suitable modifying agent(s), e.g., the modification occurs in reasonable yield and in a reasonable period of time. For example, in certain embodiments of the invention at least 50%, at least 60%, at least 70%, preferably at least 80%, at least 90% or more preferably at least 95% of the nucleic acids containing the trigger residue are modified within, e.g., 24 hours, preferably within 12 hours, more preferably within less than 1 minute to 4 hours.

A variety of suitable trigger residues and corresponding cleavage reagents are exemplified herein. Any trigger residue and cleavage reagent having similar activity to those described herein may be used. One of ordinary skill in the art will be able to determine whether a particular trigger residue and cleavage reagent combination is suitable for use in the present invention, e.g., whether the cleavage efficiency and speed, the selectivity of the cleavage agent for nucleic acids containing a trigger residue, etc, are suitable for use in the methods of the invention. Note that a "trigger residue" is distinguished from a nucleotide that simply forms part of a restriction enzyme site in that the ability of the trigger residue to confer increased susceptibility to cleavage does not, in general, depend significantly on the particular sequence context in which the trigger residue is found although, as noted above, the context can have some influence on the susceptibility to modification and/or cleavage. Of course depending on the surrounding nucleotides, a trigger residue may form part of a restriction site. Thus, in most cases, the cleavage agent is not a restriction enzyme, though use of an enzyme that is both a restriction enzyme and has non-sequence specific cleavage ability is not excluded.

A "universal base", as used herein, is a base that can "pair" with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. Certain preferred universal bases (fully universal bases) can pair with any of the bases typically found in naturally occurring nucleic acids and can thus substitute for any of these bases in duplex. The base need not be equally capable of pairing with each of the naturally occurring bases. If a probe mix contains probes that comprise (at one or more positions) a universal base that does not pair with all of the naturally occurring nucleotides, it may be desirable to utilize two or more universal bases at that position in the particular probe so that at least one of the universal bases pairs with A, at least one of the universal bases pairs with G, at least one of the universal bases pairs with C, and at least one of the universal bases pairs with T.

A number of universal bases are known in the art including, but not limited to, hypoxanthine, 3-nitropyrrole, 4-nitroindole, 5-nitroindole, 4-nitrobenzimidazole, 5-nitroindazole, 8-aza-7-deazaadenine, 6H,8H-3,4-dihydropyrimido[4,5-c][1,2]oxazin-7-one (P. Kong Thoo Lin. and D. M. Brown, Nucleic Acids Res., 1989, 17, 10373-10383), 2-amino-6-methoxyaminopurine (D. M. Brown and P. Kong Thoo Lin, Carbohydrate Research, 1991, 216, 129-139), etc. Hypoxanthine is one preferred fully universal base. Nucleosides comprising hypoxanthine include, but are not limited to, inosine, isoinosine, 2'-deoxyinosine, and 7-deaza-2'-deoxyinosine, 2-aza-2' deoxyinosine.

Additional universal bases are known in the art as described, for example, in relevant portions of Loakes, D. and Brown, D. M., Nucl. Acids Res. 22:4039-4043, 1994; Ohtsuka, E. et al., J. Biol. Chem. 260(5):2605-2608, 1985; Lin, P. K. T. and Brown, D. M., Nucleic Acids Res. 20(19): 5149-5152, 1992; Nichols, R. et al., Nature 369(6480): 492-493, 1994; Rahmon, M. S. and Humayun, N. Z., Mutation Research 377 (2): 263-8, 1997; Berger, M., et al., Nucleic Acids Research, 28(15):2911-2914, 2000; Amosova, O., et al., Nucleic Acids Res. 25 (10): 1930-1934, 1997; and Loakes, D., Nucleic Acids Res. 29(12):2437-47, 2001. The universal base may, but need not, form hydrogen bonds with an oppositely located base. The universal base may form hydrogen bonds via Watson-Crick or non-Watson-Crick interactions (e.g., Hoogsteen interactions).

In certain embodiments of the invention rather than using an oligonucleotide probe comprising a universal base, an oligonucleotide probe comprising an abasic residue is used. The abasic residue can occupy a position opposite any of the four naturally occurring nucleotides and can thus serve the same function as a nucleotide comprising a universal base. In some embodiments of the invention the linkage adjacent to an abasic residue is cleaved by an AP endonuclease, but abasic residues are also of use as described here (i.e., to serve the function of a universal base) in embodiments in which other scissile linkages (e.g., phosphorothiolates) are present and other cleavage reagents are used.

DETAILED DESCRIPTION OF CERTAIN PREFERRED EMBODIMENTS OF THE INVENTION

A. Sequencing by Successive Cycles of Extension, Ligation, and Cleavage

The overall scheme of one aspect of the invention is shown diagrammatically in FIG. 1A, and generally resembles a method taught in U.S. Pat. Nos. 5,750,341 and 6,306,597, both issued to Macevicz. For purposes of convenience, these patents will be referred to collectively as "Macevicz" herein. In particular, Macevicz teaches a method for identifying a sequence of nucleotides in a polynucleotide, the method comprising the steps of: (a) extending an initializing oligonucleotide along the polynucleotide by ligating an oligonucleotide probe thereto to form an extended duplex; (b) identifying one or more nucleotides of the polynucleotide; and (c) repeating steps (a) and (b) until the sequence of nucleotides is determined.

Macevicz further teaches a method for determining a sequence of nucleotides in a template polynucleotide, the method comprising the steps of: (a) providing a probe-template duplex comprising an initializing oligonucleotide probe hybridized to a template polynucleotide, said probe having an extendable probe terminus; (b) ligating an extension oligonucleotide probe to said extendable probe terminus, to form an extended duplex containing an extended oligonucleotide probe; (c) identifying, in the extended duplex, at least one nucleotide in the template polynucleotide that is either (1) complementary to the just-ligated extension probe or (2) a nucleotide residue in the template polynucleotide which is immediately downstream of the extended oligonucleotide probe; (d) generating an extendable probe terminus on the extended probe, if an extendable probe terminus is not already present, such that the terminus generated is different from the terminus to which the last extension probe was ligated; and (e) repeating steps (b), (c) and (d) until a sequence of nucleotides in the target polynucleotide is determined. In certain embodiments of these methods each extension probe has a chain-terminating moiety at a terminus distal to the initializing oligonucleotide probe. In certain embodiments the step of regenerating includes cleaving a chemically scissile internucleosidic linkage in the extended oligonucleotide probe.

Referring to FIG. 1A, polynucleotide template 20 comprising a polynucleotide region 50 of unknown sequence and binding region 40 is attached to support 10. Nucleotide 41, at the distal end of binding region 40, and nucleotide 51, at the proximal end of polynucleotide region 50, are adjacent to one another. An initializing oligonucleotide 30 is provided that hybridizes with binding region 40 to form a duplex at a location in binding region 40. Initializing oligonucleotide 30 is also referred to as a "primer" herein, and binding region 40 may be referred to as a "primer binding region". The duplex may, but need not be, a perfectly matched duplex. The initializing oligonucleotide has an extendable terminus 31. In FIG. 1A, the initializing oligonucleotide binds to the binding region such that extendable terminus 31 is located opposite nucleotide 41. However, the initializing oligonucleotide could bind elsewhere in the binding region, as discussed further below. An extension oligonucleotide probe 60 of length N is hybridized to the template adjacent to the initializing oligonucleotide. Terminal nucleotide 61 of the extension oligonucleotide probe is ligated to extendable terminus 31.

Terminal nucleotide 61 is complementary to the first unknown nucleotide in polynucleotide region 50. Therefore, the identity of terminal nucleotide 61 specifies the identity of nucleotide 51. Preferably nucleotide 51 is identified by detecting a label (not shown) associated with an extension probe known to have A, G, C, or T, as terminal nucleotide 61. The label is removed following detection. FIG. 2 shows a scheme for assigning different labels, e.g., fluorophores of different colors, to extension probes having different 3' terminal nucleotides.

Following ligation and detection, an extendable probe terminus is generated on extension probe 60 if probe 60 does not already have such a terminus. A second extension probe 70, preferably also of length N, is annealed to the template adjacent to extension probe 60 and is ligated to the extendable terminus of probe 60. The identity of terminal nucleotide 71 of extension probe 70 specifies the identity of oppositely located nucleotide 52 in polynucleotide 50. Terminal nucleotide 71 therefore constitutes the "sequence determining portion" of the extension probe, by which is meant the portion of the probe whose hybridization specificity is used as a basis from which to determine the identity of one or more nucleotides in the template. It will be appreciated that typically additional nucleotides in the extension probe will hybridize with the template, but only those nucleotides in the probe whose identity is associated with a particular label are used to identify nucleotides in the template.

In preferred embodiments of the invention, generation of the extendable terminus involves cleavage of an internucleoside linkage as described further below. Preferably cleavage also removes the label. Cleavage removes a number of nucleotides M from the extension probe (not shown). Therefore, the duplex is extended by N-M nucleotides in each cycle, and nucleotides located at intervals of N-M in the template are identified. It is to be understood that multiple copies of a given template will typically be attached to a single support, and the sequencing reaction will be performed simultaneously on these templates.

Macevicz teaches that the oligonucleotide probes should generally be capable of being ligated to an initializing oligonucleotide or extended duplex to generate the extended duplex of the next extension cycle; the ligation should be template-driven in that the probe should form a duplex with the template prior to ligation; the probe should possess a blocking moiety to prevent multiple probe ligations on the same template in a single extension cycle; the probe should be capable of being treated or modified to regenerate an extendable end after ligation; and the probe should possess a signaling moiety (i.e., a detectable moiety) that permits the acquisition of sequence information relating to the template after a successful ligation.

Macevicz teaches characteristics of certain suitable initializing oligonucleotides, extension oligonucleotide probes, templates, binding sites, and various methods for synthesizing, designing, producing, or obtaining such components. Macevicz further teaches certain suitable ligases, ligation conditions, and a variety of suitable labels. Macevicz also teaches an alternative method for identification using polymerase extension to add a labeled chain-terminating nucleotide to a newly ligated extension probe. The identity of the added nucleotide identifies the nucleotide located oppositely in the template.

As will be appreciated by one of ordinary skill in the art, references to templates, initializing oligonucleotides, extension probes, primers, etc., generally mean populations or pools of nucleic acid molecules that are substantially identical within a relevant region rather than single molecules. Thus, for example, a "template" generally means a plurality of substantially identical template molecules; a "probe" generally means a plurality of substantially identical probe molecules, etc. In the case of probes that are degenerate at one or more positions, it will be appreciated that the sequence of the probe molecules that comprise a particular probe will differ at the degenerate positions, i.e., the sequences of the probe molecules that constitute a particular probe may be substantially identical only at the nondegenerate position(s). For purposes of description the singular form is to be understood to include single molecules and populations of substantially identical molecules. Where it is intended to refer to a single nucleic acid molecule (i.e., one molecule), the terms "template molecule", "probe molecule", "primer molecule", etc., will be used. In certain instances the plural nature of a population of substantially identical nucleic acid molecules will be explicitly indicated.

A population of substantially identical nucleic acid molecules may be obtained or produced using any of a variety of known methods including chemical synthesis, biological synthesis in cells, enzymatic amplification in vitro from one or more starting nucleic acid molecules, etc. For example, using methods well known in the art, a nucleic acid of interest can be cloned by inserting it into a suitable expression vector, e.g., a DNA or RNA plasmid, which is then introduced into cells, e.g., bacterial cells, in which it replicates. Plasmid DNA or RNA containing copies of the nucleic acid of interest is then isolated from the cells. Genomic DNA isolated from viruses, cells, etc., or cDNA produced by reverse transcription of mRNA) can also be a source of a population of substantially identical nucleic acid molecules (e.g., template polynucleotides whose sequence is to be determined) without an intermediate step of cloning or in vitro amplification, though generally it is preferred to perform such an intermediate step.

It will be understood that members of a population need not be 100% identical, e.g., a certain number of "errors" may occur during the course of synthesis. Preferably at least 50% of the members of a population are at least 90%, or more preferably at least 95% identical to a reference nucleic acid molecule (i.e., a molecule of defined sequence used as a basis for a sequence comparison). More preferably at least 60%, at least 70%, at least 80%, at least 90%, at least 95%, at least 99%, or more of the members of a population are at least 90%, or more preferably at least 95% identical, or yet more preferably at least 99% identical to the reference nucleic acid molecule. Preferably the percent identity of at least 95% or more preferably at least 99% of the members of the population to a reference nucleic acid molecule is at least 98%, 99%, 99.9% or greater. Percent identity may be computed by comparing two optimally aligned sequences, determining the number of positions at which the identical nucleic acid base (e.g., A, T, C, G, U, or I) occurs in both sequences to yield the number of matched positions, dividing the number of matched positions by the total number of positions, and multiplying the result by 100 to yield the percentage of sequence identity. It will be appreciated that in certain instances a nucleic acid molecule such as a template, probe, primer, etc., may be a portion of a larger nucleic acid molecule that also contains a portion that does not serve a template, probe, or primer function. In that case individual members of a population need not be substantially identical with respect to that portion.

Macevicz teaches methods in which a template is attached to a support such as a bead and extension proceeds towards the end of the template that is located distal to the support, as shown in FIG. 1A. Thus the binding region is located closer to the support than the unknown sequence, and the extended duplex grows in the direction away from the support. However, the inventors have unexpectedly discovered that the method can advantageously be practiced using an alternative approach in which the binding region is located at the end of the template that is distal to the support, and extension proceeds inwards toward the support. This embodiment is depicted in FIG. 1B, in which the various elements are numbered as in FIG. 1A. The inventors have determined that sequencing "inwards" from the distal end of the template towards the support provides superior results. In particular, sequencing from the distal end of the template towards a support such as a bead results in higher ligation efficiencies than sequencing outwards from the support.

As further taught by Macevicz, preferably the oligonucleotide probes are applied to templates as mixtures comprising oligonucleotides of all possible sequences of a predetermined length. For example, a mixture of probes containing all possible sequences of 6 nucleotides in length (hexamers) of structure NNNNNN (which may also be represented as $(N)_k$, where k=6) would contain $4^6$ (4096) probe species. Generally the probes are of structure $X(N)_kN^*$, where N represents any nucleotide, and k is between 1 and 100, * represents a label, and X represents a nucleotide whose identity corresponds to the label. In certain embodiments k is between 1 and 100, between 1 and 50, between 1 and 30, between 1 and 20, e.g., between 4 and 10. One or more of the nucleotides may comprise a universal base. Generally the probe is 4-fold degenerate at positions represented by N or comprises a degeneracy-reducing nucleotide at one or more positions represented by N. If desired, the mixture can be divided into subsets of probes ("stringency classes) whose perfectly matched duplexes with complementary sequences have similar stability or free energy of binding. The subsets may be used in separate hybridization reactions as taught by Macevicz.

The complexity (i.e., the number of different sequences) of probe mixtures can be reduced by a number of methods, including using so-called degeneracy-reducing nucleotides or nucleotide analogs. For example, a library of probes containing all possible sequences of 8 nucleotides would contain $4^8$ probes. The number of probes can be reduced to $4^6$ while retaining various desirable features of an octamer library, such as the length, by using universal bases at two of the positions. The present invention comprehends the use of any of the universal bases mentioned above or described in the references cited above.

Depending on the embodiment, the extended duplex or initializing oligonucleotide may be extended in either the 5'→3' direction or the 3'→5' direction by oligonucleotide probes, as described further below. Generally, the oligo-nucleotide probe need not form a perfectly matched duplex with the template, although such binding may be preferred. In embodiments in which a single nucleotide in the template is identified in each extension cycle, perfect base pairing is only required for identifying that particular nucleotide. For example, in embodiments where the oligonucleotide probe is enzymatically ligated to an extended duplex, perfect base pairing, i.e. proper Watson-Crick base pairing, is required between the terminal nucleotide of the probe which is ligated and its complement in the template. Generally, in such embodiments, the rest of the nucleotides of the probe serve as "spacers" that ensure the next ligation will take place at a predetermined site, or number of bases, along the template. That is, their pairing, or lack thereof, does not provide further sequence information. Likewise, in embodiments that rely on polymerase extension for base identification, the probe primarily serves as a spacer, so specific hybridization to the template is not critical.

The methods described above allow partial determination of a sequence, i.e., the identification of individual nucleotides spaced apart from one another in a template. In preferred embodiments of the invention, in order to gather more complete information, a plurality of reactions is performed in which each reaction utilizes a different initializing oligonucleotide i. The initializing oligonucleotides i bind to different portions of the binding region. Preferably the initializing oligonucleotides bind at positions such the extendable termini of the different initializing oligonucleotides are offset by 1 nucleotide from each other when hybridized to the binding region. For example, as shown in FIG. 3, sequencing reactions 1 . . . N are performed. Initializing oligonucleotides $i_1$ . . . $i_n$ have the same length and bind such that their terminal nucleotides 31, 32, 33, etc., hybridize to successive adjacent positions 41, 42, 43, etc., in binding region 40. Extension probes $e_1$ . . . $e_n$ thus bind at successive adjacent regions of the template and are ligated to the extendable termini of the initializing oligonucleotides. Terminal nucleotide 61 of probe $e_n$ ligated to $i_n$ is complementary to nucleotide 55 of polynucleotide region 50, i.e., the first unknown polynucleotide in the template. In the second cycle of extension, ligation, and detection, terminal nucleotide 71 of probe $e_{12}$ is complementary to nucleotide 56 of polynucleotide region 50, i.e., the second nucleotide of unknown sequence. Likewise, terminal nucleotides of extension probes ligated to duplexes initialized with initializing oligonucleotides $i_2$, $i_3$, $i_4$, and so on, will be complementary to the third, fourth, and fifth nucleotides of unknown sequence 50. It will be appreciated that the initializing oligonucleotides may bind to regions progressively further away from polynucleotide region 50 rather than progressively closer to it.

The spacer function of the non-terminal nucleotides of the extension probes allows the acquisition of sequence information at positions in the template that are considerably removed from the position at which the initializing oligonucleotide binds without requiring a correspondingly large number of cycles to be performed on any given template. For example, by successive cycles of ligation of probes of length N, followed by cleavage to remove a single terminal nucleotide from the extension probe, nucleotides at intervals of N−1 nucleotides can be identified in successive rounds. For example, nucleotides at positions 1, N, 2N−1, 3N−2, 4N−3, and 5N−4 in the template can be identified in 6 cycles where the nucleotide at position 1 in the template is the nucleotide opposite the nucleotide that is ligated to the extendable probe terminus in the duplex formed by the binding of the initializing oligonucleotide to the template.

Similarly, if cleavage removes two nucleotides from the extension probes of length N, then nucleotides at positions separated from each other by N−2 nucleotides can be identified in successive rounds. For example, nucleotides at positions 1, N−1, 2N−3, 3N−5, 4N−7 in the template can be identified in 6 cycles. Thus if the probes are 8 nucleotides in length and 2 nucleotides are removed in each cycle, nucleotides at positions 1, 7, 13, 19, and 25 are identified. Thus the number of cycles needed to identify a nucleotide at a distance X from the first nucleotide in the template is on the order of X/M, where M is the length of the extension probe that remains following cleavage, rather than on the order of X.

For example, the schematic depicted in FIG. 3B shows the net result of using the extension, ligation, and cleavage method with extension probes designed to read every 6th base of the template. By serially stripping and sequencing the template using 6 initializing nucleotides that bind to positions that are offset within the binding region and combining the results, all template bases are elucidated over a defined length. For instance, if 10 serial ligations are performed for each of the 6 reactions, the resulting read length will be 60 sequential base pairs, whereas if 15 serial ligations are performed for each reaction the resultant read length will be 90 sequential base pairs.

While not wishing to be bound by any theory, the inventors suggest that in contrast to this approach, most serial sequencing by synthesis methods struggle with error accumulation that ultimately limits the potential for long read lengths. An advantageous feature of certain of the methods described herein is that they allow the identification of every $n^{th}$ base (depending on the position of the cleavable moiety in the probe), such that after a given number of cycles (y), one reaches the $n*y-(n-1)^{th}$ base (e.g., the $71^{st}$ base in the foregoing example after 15 cycles, or the $115^{th}$ base after 20 cycles using a probe with 6 bases on the 3' side of the cleavage site). The ability to "reset" the initializing oligonucleotide at the n−1, n−2, etc., positions greatly minimizes serial error accumulation (via dephasing or attrition) for a given read length since the process of stripping the extended strands from the template and hybridizing a new initializing oligonucleotide effectively resets background signals to zero. For example, comparing the polymerase based sequencing by synthesis and the ligation based approaches described herein, if the signal to noise ratio at each extension cycle is 99:1, the ratio after 100 cycles for the polymerase based approach will be 37:63 and for the ligase based method, 85:15. The net result for the ligase based method is a large increase in read length over polymerase based methods.

The ability to identify nucleotides using fewer cycles than would be required if it was necessary to perform a cycle for each preceding nucleotide in the template is important for a number of reasons. In particular, it is unlikely that each step in the method will occur with 100% efficiency. For example, some templates may not be successfully ligated to an extension probe; some extension probes may not be cleaved, etc. Thus in each cycle the reactions occurring on different copies of the template become progressively dephased, and the number of templates from which useful and accurate information can be acquired is reduced. It is thus particularly desirable to minimize the number of cycles required to read nucleotides located more than a few positions away from the extendable terminus of the initializing oligonucleotide. However, increasing the length of the extension probe potentially results in greater complexity of the probe mixture, which decreases the effective concentration of each individual probe sequence. As described herein, degeneracy-reducing nucleotides can be used to reduce the complexity but may result in decreased hybridization strength and/or decreased ligation efficiency. The inventors have recognized the need to balance these competing factors in order to optimize results. Thus in a preferred embodiment of the invention extension probes 8 nucleotides in length are used, with degeneracy-reducing nucleotides at selected positions. In addition, the inventors have recognized the importance of selecting appropriate scissile linkages and cleavage conditions and times to optimize the efficiency of the cleavage step (i.e., the percentage of linkages that is successfully cleaved in each cleavage step) and its specificity for the appropriate linkage.

B. Oligonucleotide Extension Probe Design

While Macevicz mentions that degeneracy-reducing nucleoside analogs may be used in the oligonucleotide extension probes, he does not teach specific positions at which it is particularly desirable to include a residue comprising such residues in the extension probes and does not teach particular probe structures (i.e., sequences) that incorporate degeneracy-reducing nucleosides. The present inventors have recognized that it may be particularly advantageous to utilize degeneracy-reducing nucleosides (e.g., nucleosides that comprise a universal base) at particular positions and in particular numbers in the oligonucleotide extension probes. For example, in certain embodiments of the invention most or all of the nucleotides at position 6 or greater (counting from X), comprise a universal base. For example, at least 50%, at least 60%, at least 70%, at least 80%, at least 90%, or at least 100% of the nucleotides at position 6 or greater may comprise a universal base. The nucleotides need not all comprise the same universal base. In certain embodiments of the invention hypoxanthine and/or a nitro-indole is used as a universal base. For example, nucleosides such as inosine can be used.

The inventors have recognized that superior results may be achieved using extension probes that are greater than 6 nucleotides in length, and in which one or more of the nucleotides at position 6 or greater from the proximal terminus of the probe, counting from the nucleotide to be ligated to the extendable probe terminus, is a degeneracy-reducing nucleotide, e.g., comprises a universal base (i.e., if the most proximal nucleotide is considered position 1, one or more of the nucleotides at position 6 or greater comprises a universal base), e.g., 1, 2, or 3 of the nucleotides at position 6 or greater in the case of octamer probes comprises a universal base. For example, for sequencing in the 3'→5' direction, probes having the structure 3'-XNNNNsINI-5' can be used, where X and N represent any nucleotide, "s" represents a scissile linkage, such that cleavage occurs between the fifth and sixth residues counting from the 3' end, and at least one of the residues between the scissile linkage and the 5' end preferably has a label that corresponds to the identity of X. Another design is 3'-XNNNNsNII-5'. Yet another probe design is 3'-XNNNNsIII-5'. This design yields a probe mixture with a modest complexity of 1024 different species, is long enough to prevent formation of significant adenylation products (see Example 1), and has the advantage that the resulting extension product remaining after cleavage would consist of unmodified DNA. One drawback is that this probe extends the primer by only 5 bases at a time. Since the read length is a function of the extension length times the number of cycles, each additional base on the extension length has the potential to increase the read length by the 1× the cycle number (e.g. 20 bases if 20 cycles are used). Another probe design leaves one or more inosines (or other universal base) at the end of the extension probe following cleavage to create a 6 base, or longer, extended duplex. For example, with the probe 3'-XNNNNIsII-5', the duplex would be extended by 6 bases at a time, leaving a 5' inosine at the junction. In each of these designs, at least one of the residues between the scissile linkage and the 5' end preferably has a label that corresponds to the identity of X. In certain embodiments of the invention the third nucleotide from the distal terminus of the probe, counting from the end opposite the nucleotide to be ligated to the extendable probe terminus, comprises a universal base, (i.e., if the distal terminus is considered position K, the nucleotide at position K-2 comprises a universal base).

In certain embodiments of the invention locked nucleic acid (LNA) bases are used at one or more positions in an initializing oligonucleotide probe, extension probe, or both. Locked nucleic acids are described, for example, in U.S. Pat. No. 6,268,490; Koshkin, A A, et al., Tetrahedron, 54:3607-3630, 1998; Singh, S K, et al., Chem. Comm., 4:455-456, 1998. LNA can be synthesized by automatic DNA synthesizers using standard phosphoramidite chemistry and can be incorporated into oligonucleotides that also contain naturally occurring nucleotides and/or nucleotide analogues. They can also be synthesized with labels such as those described below.

C. Template and Support Preparation Methods

Macevicz teaches a process in which a template comprising a plurality of substantially identical template molecules is first synthesized, e.g., by amplification in a tube or other vessel as in conventional polymerase chain reaction (PCR) methods. Macevicz teaches that the amplified template molecules are preferably attached to supports such as magnetic microparticles (e.g., beads) after synthesis.

The inventors have recognized that templates to be sequenced may desirably be synthesized on or in a support itself, e.g., by using supports such as microparticles or various semi-solid support materials such as gel matrices to which one of a pair of amplification primers is attached prior to performing the PCR reaction. This approach avoids the need for a separate step of attaching the template molecules to the support after synthesis. Thus a plurality of template species of differing sequence can be conveniently amplified in parallel. For example, according to the methods described below, synthesis on microparticles results in a population of individual microparticles, each with multiple copies of a particular template molecule (or its complement) attached thereto, wherein the template molecules attached to each microparticle differ in sequence from the template molecules attached to other microparticles. Each of the supports thus has a clonal population of templates attached thereto, e.g., support A will have multiple copies of template X attached thereto; support B will have multiple copies of template Y attached thereto; support C will have multiple copies of template Z attached thereto, etc. By "clonal population of templates", "clonal population of nucleic acids", etc., is meant a population of substantially identical template molecules, preferably generated by successive rounds of amplification that start from a single template molecule of interest (starting template). The substantially identical template molecules may be substantially identical to the starting template or to its complement.

Amplification is typically performed using PCR, but other amplification methods may also be used (see below). It will be understood that members of a clonal population need not be 100% identical, e.g., a certain number of "errors" may occur during the course of synthesis, e.g., during amplification. Preferably at least 50% of the members of a clonal population are at least 90%, or more preferably at least 95% identical to a starting template molecule (or to its complement). More preferably at least 60%, at least 70%, at least 80%, at least 90%, at least 95%, at least 99%, or more of the members of a population are at least 90%, or more preferably at least 95% identical, or yet more preferably at least 99% identical to the starting template molecule (or to its complement). Preferably the percent identity of at least 95% or more preferably at least 99% of the members of the population to a starting template molecule (or to its complement) is at least 98%, 99%, 99.9% or greater.

Amplification primers may be attached to supports using any of a variety of techniques. For example, one end of the primer (the 5' end) of the primer may be functionalized with one member of a binding pair (e.g., biotin), and the support functionalized with the other member of the binding pair (e.g., streptavidin). Any similar binding pair may be used. For example, nucleic acid tags of defined sequence may be attached to the support and primers having complementary nucleic acid tags can be hybridized to the nucleic acid tags attached to the support. Various linkers and crosslinkers can also be used.

Methods for performing PCR are well known in the art and are described, for example, in U.S. Pat. Nos. 4,683,195, 4,683,202, and 4,965,188, and in Dieffenbach, C. and Dveksler, G S, *PCR Primer: A Laboratory Manual*, $2^{nd}$ ed., Cold Spring Harbor Laboratory Press, Cold Spring Harbor, 2003. Methods for amplifying nucleic acids on microparticles are well known in the art and are described, for example, standard PCR can be performed in wells of a microtiter dish or in tubes on beads with primers attached thereto (e.g., beads prepared as in Example 12. While PCR is a convenient amplification method, any of numerous other methods known in the art can also be used. For example, multiple strand displacement amplification, helicase displacement amplification (HDA), nick translation, Q beta replicase amplification, rolling circle amplification, and other isothermal amplification methods etc., can be used.

Template molecules can be obtained from any of a variety of sources. For example, DNA may be isolated from a sample, which may be obtained or derived from a subject. The word "sample" is used in a broad sense to denote any source of a template on which sequence determination is to be performed. The phrase "derived from" is used to indicate that a sample and/or nucleic acids in a sample obtained directly from a subject may be further processed to obtain template molecules. The source of a sample may be of any viral, prokaryotic, archaebacterial, or eukaryotic species. In certain embodiments of the invention the source is a human. The sample may be, e.g., blood or another body fluid containing cells; sperm; a biopsy sample, etc. Genomic or mitochondrial DNA from any organism of interest may be sequenced. cDNA may be sequenced. RNA may also be sequenced, e.g., by first reverse transcribing to yield cDNA, using methods known in the art such as RT-PCR. Mixtures of DNA from different samples and/or subjects may be combined. Samples may be processed in any of a variety of ways. Nucleic acids may be isolated, purified, and/or amplified from a sample using known methods. Of course entirely artificial, synthetic nucleic acids, recombinant nucleic acids not derived from an organism can also be sequenced.

Templates can be provided in double or single-stranded form. Typically when a template is initially provided in double-stranded form the two strands will subsequently be separated (e.g., the DNA will be denatured), and only one of the two strands will be amplified to produce a localized clonal population of template molecules, e.g., attached to a microparticle, immobilized in or on a semi-solid support, etc.

Templates may be selected or processed in a variety of additional ways. For example, templates obtained from DNA that has been subjected to treatment to with a methyl-sensitive restriction enzyme (e.g., MspI) can be used. Such treatment, which results in DNA fragments, can be performed prior to amplification. Fragments containing methylated bases do not amplify. Sequence information obtained from the hypomethylated templates may be compared with sequence information obtained from templates derived from the same source, which were not subjected to selection for hypomethylation.

Templates may be inserted into, provided in, or derived from a library. For example, hypomethylated libraries are known in the art. Inserting templates into libraries can allow for the convenient concatenation of additional nucleotide sequences to the ends of templates, e.g., tags, binding sites for primers or initializing oligonucleotides, etc. For example, certain strategies allow the addition of tags having a plurality of binding sites, e.g., a binding site for an amplification primer, a binding site for an initializing oligonucleotide, a binding site for a capture agent, etc.

A variety of suitable libraries are known in the art. For example, libraries of particular interest, and methods for their construction, are described in U.S. Ser. No. 10/978,224, PCT publications WO2005042781 and WO2005082098, and Shendure, J., et al., *Science,* 309 (5741):1728-32, 2005, *Sciencexpress,* 4 Aug. 2005 (www.sciencexpress.org). Of course it will be understood that other methods of generating such libraries could also be used. Certain libraries of particular interest contain a plurality of nucleic acid fragments (typically DNA), each of which contain two nucleic acid segments of interest, separated by sequences that are complementary to amplification and/or sequencing primers that are used in sequencing steps, i.e., these sequences serve as primer binding regions (PBRs). In embodiments of particular interest, the nucleic acid segments are portions of a contiguous piece of naturally occurring DNA. For example, the segments may be from the 5' and 3' end of a contiguous piece of genomic DNA as described in the afore-mentioned references. Such nucleic acid segments are referred to herein in a manner consistent with the afore-mentioned references, as "tags" or "end tags". Two tags derived from a single contiguous nucleic acid, e.g., from the 5' and 3' ends thereof, are referred to as "a paired tag", "paired tags", or "a ditag". It will be appreciated that a "paired tag" comprises two tags, even if used in the singular. By selecting the contiguous pieces of DNA from which the tags of a paired tag are derived to be within a predefined size limit, the distance separating the two tags is constrained.

In addition to being separated by sequences that are complementary to sequencing and/or amplification primers, the nucleic acid fragments of the libraries typically also contain sequences complementary to sequencing and/or amplification primers flanking the tags, i.e., a first such sequence may be located 5' to the tag that is closer to the 5' end of the fragment, and a second such sequence may be located 3' to the tag that is located closer to the 3' end of the fragment. It is noted that the position of the two tags as present in the contiguous nucleic acid from which the tags are derived may, but need not, correspond with the position of the tag in the DNA fragment of the library in various embodiments.

The nucleic acid fragments and the tags can have a range of different sizes. Typically the nucleic acid fragments may be, for example, between 80 and 300 nucleotides in length, e.g., between 100-200, 100-150, approximately 150 nucleotides in length, approximately 200 nucleotides in length, etc. The tags can be, e.g., between 15-25 nucleotides in length, e.g., approximately 17-18 nucleotides in length, etc. It is noted that these lengths are exemplary and are not intended to be limiting. Shorter or longer fragments and/or tags could be used.

It should also be noted that while obtaining the paired tags from a single contiguous nucleic acid affords a convenient method for library construction, the important aspect of the paired tags is the fact that they are separated from one another by a distance ("separation distance") in the nucleic acid from which they were originally derived, wherein the separation distance falls within a predetermined range of distances. The fact that the tags are separated by a separation distance that falls within a predetermined range allows the sequence of the tags to be aligned against a reference sequence (e.g., a reference genome sequence). Without wishing to be bound by any theory, this can be advantageous in certain applications such as genome resequencing, wherein it allows the use of shorter read lengths while still allowing accurate placement of the sequences with respect to the reference genome. The 5' and 3' tags of a paired tag represent (i.e., they have the sequence of) segments of a larger piece of nucleic acid, e.g., genomic DNA, which segments are located within a predefined distance from one another in a naturally occurring piece of DNA, e.g., within a piece of genomic DNA. For example, in certain embodiments of the invention the 5' and 3' tags of a paired tag represent segments of DNA located within up to 500 nucleotides of each other, within up to 1 kB of each other, within up to 2 kB of each other, within up to 5 kB of each other, within up to 10 kB of each other, within up to 20 kB of each other, in a naturally occurring piece of DNA. In certain embodiments the 5' and 3' tags of a paired tag are located between 500 nucleotides and 2 kB apart, e.g, between 700 nucleotides and 1.2 kB apart, approximately 1 kB apart, etc., in a naturally occurring piece of DNA. It is noted that the exact distance separating the two tags of a paired tag is not of major importance and is typically not known. In addition, while the tags are originally obtained from a larger piece of nucleic acid, the word "tag" applies to any nucleic acid segment that has the sequence of the tag, whether present in its original sequence context or in a library fragment, amplification product from a library fragment, template to be sequenced, etc.

A nucleic acid fragment (e.g., a library molecule) may have the following structure:

Linker 1-Tag 1-Linker 3-Tag 1-Linker 2

Tag 1 and Tag 2 can be 5' and 3' tags of a paired tag. Either of the tags can be the 5' tag or the 3' tag. Linker 1 and Linker 2 contain primer binding regions for one or more primers. In certain embodiments Linkers 1 and 2 each contain a PBR for an amplification primer and a PBR for a sequencing primer. The primers in each linker can be nested, such that the sequencing primer PBR is located internal to the amplification primer PBR. Linker 3 may contain PBRs for one or more sequencing primers to allow for sequencing of Tag 1 and Tag 2. The term "linker" refers to a nucleic acid sequence that is present in multiple nucleic acid fragments of a library, e.g., in substantially all fragments of the library.

A linker may or may not actually have served a linking function during construction of the library and can simply be considered to be a defined sequence that is common to most or all members of a given library. Such a sequence is also referred to as a "universal sequence". Thus a nucleic acid complementary to the linker or a portion thereof would hybridize to multiple members of the library and could be used as an amplification primer or sequencing primer for most or all molecules in the library.

In certain embodiments of the present invention, a nucleic acid fragment has the following structure:

Linker 1-Tag 1-Internal Adaptor-Tag 2-Linker 2

Tag 1 and Tag 2 and Linker 1 and Linker 2 contain PBRs as described above. Internal Adaptor contains two primer binding regions, which may be referred to as IA and IB, as discussed further below. These PBRs are of use to produce microparticles having two distinct substantially identical populations of nucleic acids attached thereto, wherein nucleic acids of one of the populations comprise Tag 1 and nucleic acids of the other population comprise Tag 2. The two distinct populations of nucleic acids have at least partially different sequences, e.g., they differ in the sequence of the tag regions. The Internal adaptor can contain a spacer region between the two primer binding regions. The spacer region may contain abasic residues, which will prevent a polymerase from extending through the spacer. Of course spacer regions containing any other blocking group that would prevent polymerase extension through the spacer could be used.

In other embodiments, a nucleic acid fragment includes one or more additional tags (e.g, 2, 4, 6, etc.) and one or more additional internal adaptors. For example, a nucleic acid fragment can have the following structure:

Linker 1-Tag 1-Internal Adaptor 1-Tag 2-Linker 2-Tag 3-Internal Adaptor 2-Tag 4-Linker 3

It is noted that the inventive nucleic acid fragments and libraries of such fragments, microparticles containing two or more substantially identical populations of nucleic acids, and arrays of such microparticles can be used in a wide variety of sequencing methods other than the ligation-based sequencing methods described herein. For example, sequencing methods such as FISSEQ, pyrosequencing, etc., can be used. See, e.g., WO2005082098. Of course the ligation-based methods can also advantageously be employed. It will be appreciated that in the context of the ligation-based methods described herein, the term "sequencing primer" may be understood to mean "initializing oligonucleotide".

In certain embodiments of the invention the templates to be sequenced are synthesized by PCR in individual aqueous compartments (also called "reactors") of an emulsion. Preferably the compartments each contain a particulate support such as a bead having a suitable first amplification primer attached thereto, a first copy of the template, a second amplification primer, and components needed for the PCR reaction (e.g., nucleotides, polymerase, cofactors, etc.). Methods for preparing emulsions are described for example, in U.S. Pat. No. 6,489,103 (Griffiths); U.S. Pat. No. 5,830, 663 (Embleton); and in U.S. Pub. No. 20040253731 (Ghadessy). Methods for performing PCR within individual compartments of an emulsion to produce clonal populations of templates attached to microparticles are described, e.g., in Dressman, D., et al., *Proc. Natl. Acad. Sci.*, 100(15):8817-8822, 2003, and in PCT publication WO2005010145.

Methods described in the afore-mentioned references, or modifications thereof, may be used to produce clonal populations of templates attached to microparticles for sequencing. In a preferred and non-limiting embodiment, short (<500 nucleotide) templates suitable for PCR are created by attaching (e.g., by ligation) a universal adaptor sequence to each end of a population of different target sequences (templates). (Universal in this context means that the same adaptor sequence is attached to each template, to create "adapted" templates that can be amplified using a single pair of PCR amplification primers.) A bulk PCR reaction is prepared with the adapted templates, one free amplification primer, microparticles with a second amplification primer attached thereto, and other PCR reagents (e.g., polymerase, cofactors, nucleotides, etc.). The aqueous PCR reaction is mixed with an oil phase (containing light mineral oil and surfactants) in a 1:2 ratio. This mixture is vortexed to create a water-in-oil emulsion. One milliliter of mixture is sufficient to create more than $4 \times 10^9$ aqueous compartments within the emulsion, each a potential PCR reactor. Aliquots of the emulsion sample are dispensed into the wells of a microtiter plate (e.g., 96 well plate, 384 well plate, etc.) and thermally cycled to achieve solid-phase PCR amplification on the microparticles. To ensure clonality, the microparticle and template concentrations are carefully controlled so that the reactors rarely contain more than one bead or template molecule. For example, in certain embodiments of the invention at least 10%, 20%, 30%, 40%, 50%, 60%, 70%, 80%, 90%, 95%, or more of the reactors contain a single bead and a single template. Members of each clonal populations of templates are thus spatially localized in proximity to one another as a result of their attachment to the microparticle. In general, the points of attachment of the templates may be substantially uniformly distributed on the surface of the particle.

It is of particular interest to use PCR emulsion methods to produce populations of microparticles in which individual microparticles have distinct populations of amplified nucleic acid fragments that contain a 5' tag and a 3' tag of a paired tag attached thereto. In other words, it is of particular interest to produce populations of microparticles in which individual particles have different nucleic acid fragments from a library such as those described above amplified and attached thereto.

Methods known in the art for amplifying DNA in emulsions (e.g., described in the references mentioned above), are limited in terms of their ability to achieve amplification of large nucleic acid molecules and attachment of these molecules to microparticles. For example, it has been demonstrated that the PCR efficiency decays exponentially with longer amplicons. This decrease in PCR efficiency reduces the efficiency with which nucleic acid fragments containing paired tags and primer binding sites, such as those described above, can be amplified in PCR emulsions and attached to microparticles via such amplification. Thus methods in which a single population of substantially identical nucleic acid fragments containing first and second tags of a paired tag are amplified in a PCR emulsion and attached to beads via such amplification suffer from a number of limitations.

The present invention provides an approach that allows the use of smaller amplicons while still preserving the paired tag information that arises when a single nucleic acid fragment containing 5' and 3' tags of a paired tags is attached via amplification to a microparticle. The invention provides a microparticle, e.g., a bead, having at least two distinct populations of nucleic acids attached thereto, wherein each of the at least two populations consists of a plurality of substantially identical nucleic acids, and wherein a first population of substantially identical nucleic acids comprises a first nucleic acid segment of interest, e.g., 5' tag, and a second population of nucleic acids comprises a second nucleic acid segment of interest, e.g., 3' tag. The first and second populations of nucleic acids are amplified from a single larger nucleic acid fragment that contains the two tags and also contains appropriately positioned primer binding sites flanking and separating the tags, so that two amplification reactions can be performed either sequentially or, preferably, simultaneously, in a single reactor of a PCR emulsion in the presence of a microparticle and amplification reagents. The microparticle has attached thereto two different populations of primers, one of which corresponds in sequence with a primer binding region external to one of the tags in the nucleic acid fragment, and the other of which corresponds in sequence with a primer binding region external to the other tag in the nucleic acid fragment, i.e., the primer binding regions flank the two tags.

Also provided are primers that bind to primer binding regions located between the two tags, so that two separate PCR reactions can be performed, each amplifying a portion of the nucleic acid fragment containing one of the tags. The amplified nucleic acid segments contain additional primer binding regions, which are different from one another. These additional primer binding regions are present in the nucleic acid fragment and are located internal to the PBRs for the amplification primers, i.e., they are nested. These additional PBRs serve as binding regions for two different sequencing primers. Thus by applying one or the other of the two different sequencing primers to a microparticle having the two populations of substantially identical nucleic acid segments attached thereto, either one or the other of the two nucleic acid segments can be sequenced without interference due to the presence of the other nucleic acid segment. Each of the nucleic acid segments is significantly shorter than the nucleic acid fragment from which it was amplified, thus improving the efficiency with which emulsion-based PCR can be performed using libraries of fragments containing paired tags, while still preserving the association between the tags of a paired tag.

Figure 34A:
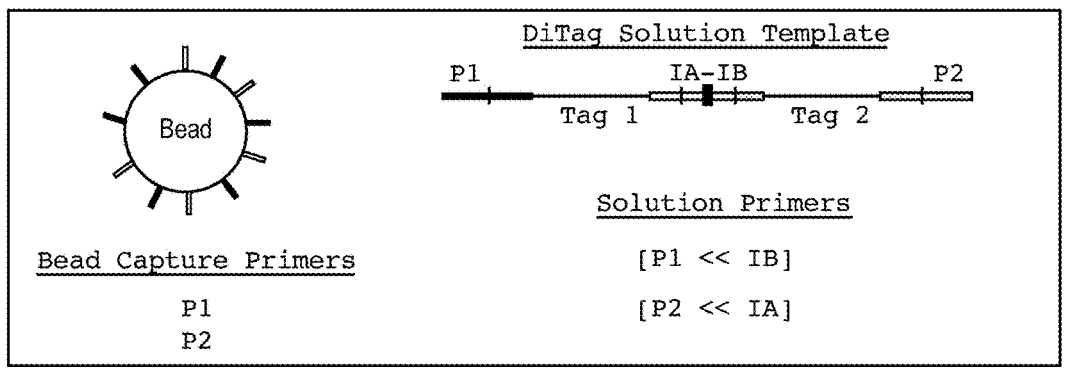
FIGS. 34A-34C show a scheme for amplifying both tags of a paired tag present in a nucleic acid fragment (template) as individual populations of nucleic acids and capturing them to a microparticle via the amplification process.
Figure 34B:
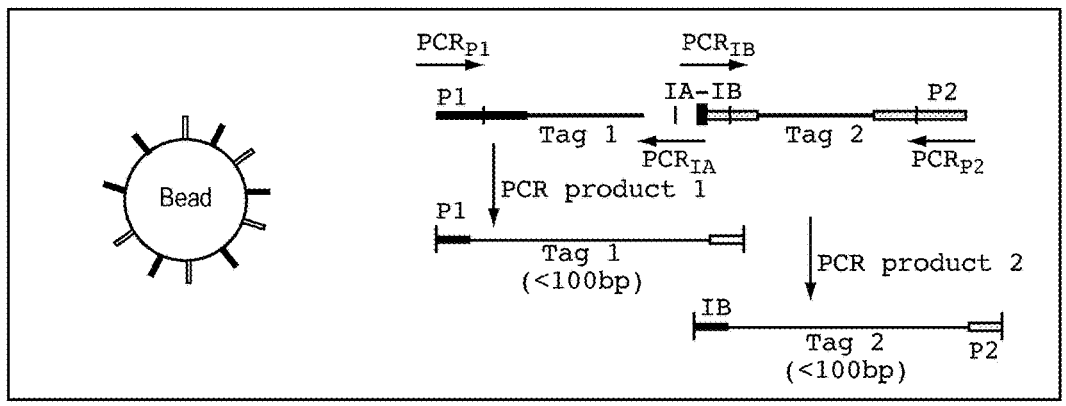
Figure 34C:
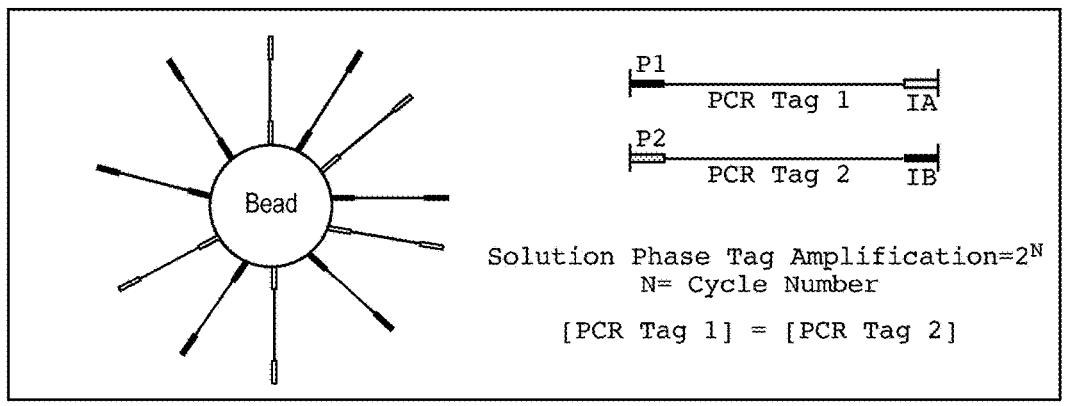
Figure 35A:
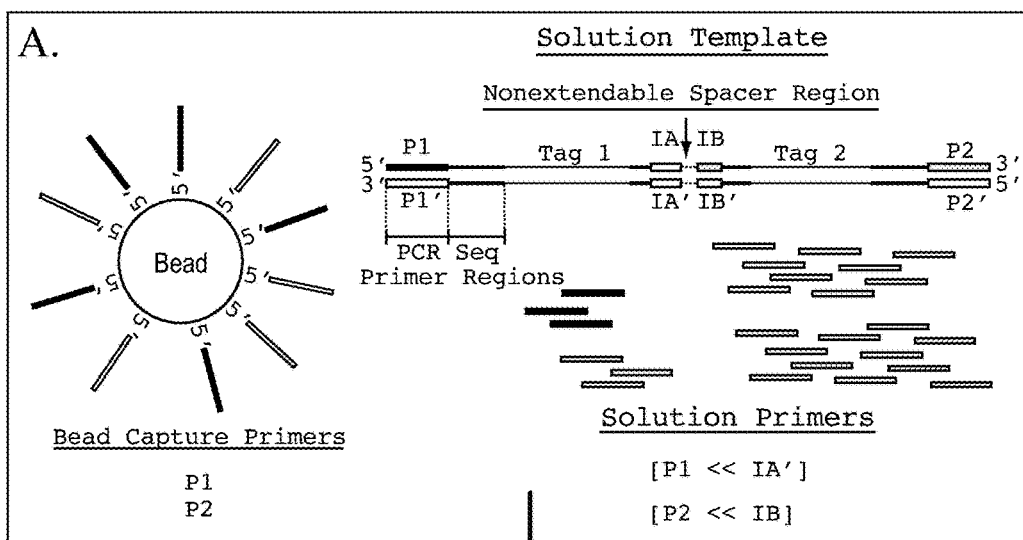
FIGS. 35A and 35B show details of primer design and amplification for the scheme of FIG. 35. Both strands of a nucleic acid fragment (template) are shown for clarity. Primers and primer binding regions having the same sequence are presented in the same color. For example, P1 is represented in dark blue, indicating that primer P1, which is present on the microparticle and in solution, has the same sequence as the correspondingly colored portion of the indicated strand of the template. The dark blue region of the template, labeled P1, may be referred to as a primer binding region even though the corresponding primer (P1) in fact binds to the complementary portion of the other strand and has the same sequence as primer P1.
Figure 35B:
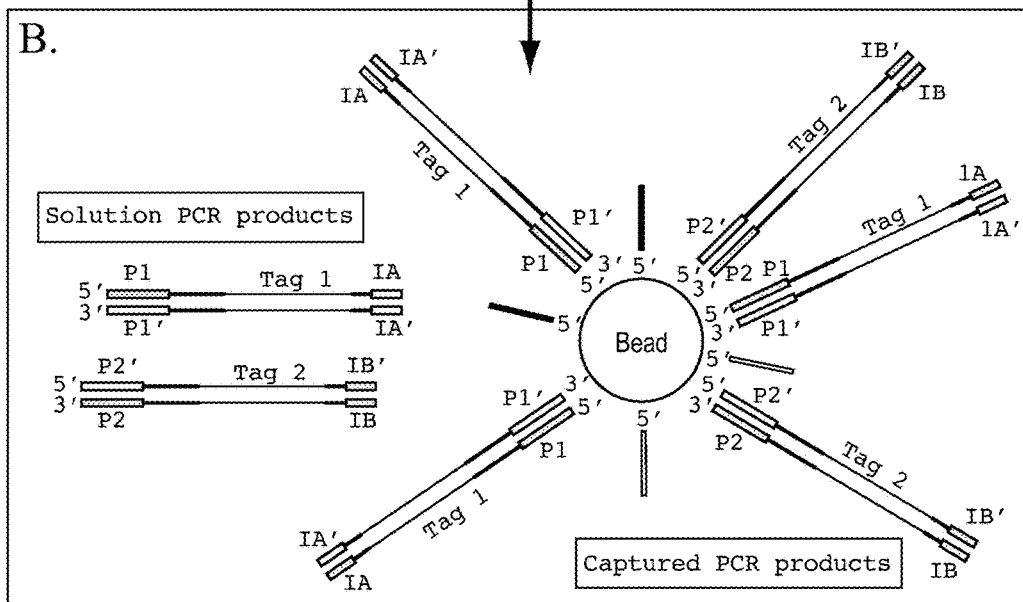

The methods described above may be better understood by reference to the various panels of FIGS. 34 and 35 in which portions of nucleic acids having the same sequence are assigned the same color. The description above is to be interpreted consistently with FIGS. 34 and 35. FIGS. 34A and 35A show the same steps, with FIG. 35A providing additional details. As shown in FIGS. 34A and 35A, paired-end library fragments containing two tags (Tag 1 and Tag 2) are constructed with an internal adapter cassette (IA-IB) and unique flanking linker sequences (P1 and P2). Both the internal adapter cassette and the flanking linker sequences contain nucleotide sequences that afford both PCR amplification and DNA sequencing. PCR primer regions are designed as to allow the use of nested DNA sequencing primers. DNA capture microparticles (beads) are generated by attaching two oligonucleotide sequences that are identical to the unique flanking linker sequences. For PCR amplification, DNA capture microparticles bound with oligonucleotides having P1 and P2 sequences, are seeded into reactions containing a single di-tag library fragment (i.e., a library fragment containing a 5' tag and 3' tag of a paired tag) and solution-based PCR primers.

Solution-based flanking linker primers (P1 and P2) are added in limiting amounts in comparison to the internal adapter primers (IA and IB) and will serve to promote efficient drive-to-bead amplification of PCR-generated tag products (i.e., [P1<<IB], [P2<<IA]). If desired, controlling the amount of primers appropriately can also ensure that the populations of nucleic acids contain substantially the same number of nucleic acids, e.g., approximately half the nucleic acids on an individual microparticle belong to the first population and approximately half the nucleic acids on an individual microparticle belong to the second population. Thus a form of asymmetric PCR can be employed, if desired, in order to control the ratio of the different populations.

During amplification, as shown in FIGS. 34B and 35B (where FIG. 35B again provides additional details relative to FIG. 34B), the single paired-end library fragment, in the presence of the four oligonucleotide primers (P1, P2, IA and IB), will generate two unique PCR products. One population contains Tag 1 flanked by P1 and IA, and a second population contains Tag 2 flanked by P2 and IB.

Following amplification microparticles will be loaded with two unique PCR populations corresponding to Tag 1 and Tag 2 generated from the initial library fragment. Each tag thus contains a unique set of priming regions to allow serial sequencing of each tag as shown in FIGS. 34C, 35C, and 35D. FIGS. 35C and 35D show sequential sequencing of tags 1 and 2, using different sequencing primers. Any of a variety of sequencing methods can be used.

The above methods can be used to generate microparticles having more than two distinct populations of nucleic acid sequences attached thereto, e.g., 4, 6, 8, 12, 16, 20, populations, e.g., wherein the populations comprise 2, 3, 4, 6, 8, 10 paired tags. Each population can be individually sequenced by providing a unique primer binding regionn in each sequence, as described above in the case of two tags.

The invention encompasses nucleic acid fragments having the structures shown in FIGS. 34 and 35 and described above, libraries of such fragments, microparticles having nucleic acid segments from such fragments attached thereto, populations of such microparticles wherein the individual microparticles have populations of nucleic acids attached thereto that differ in sequence from those of other microparticles, arrays of microparticles, amplification primers for amplifying nucleic acid segments (tags) from the nucleic acid fragments, sequencing primers for sequencing nucleic acid segments attached to microparticles, methods for making the fragments, libraries and microparticles, and methods of sequencing the nucleic acids attached to the microparticles. The invention encompasses kits containing any combination of the afore-mentioned components, optionally also containing one or more enzymes, buffers, or other reagents useful in amplification, sequencing, etc.

If desired, a variety of methods may be used to enrich for microparticles that have templates attached thereto. For example, a hybridization-based method can be used in which an oligonucleotide (capture agent) complementary to a portion of an amplification product (template) attached to the microparticles is attached to a capture entity such as another (preferably larger) microparticle, microtiter well, or other surface. The portion of the amplification product may be referred to as a target region. The target region may be incorporated into templates during amplification, e.g., at one end of the portion of the template having unknown sequence. For example, the target region may be present in the amplification primers that is not attached to the microparticle, so that a complementary portion is present in the amplified template. Thus multiple different templates can include the same target region, so that a single capture agent will hybridize to multiple different templates, allowing the capture of multiple microparticles using only a single oligonucleotide sequence as the capture agent. Microparticles that have been subjected to amplification are exposed to the capture agent under conditions in which hybridization can occur. As a result, microparticles having amplified templates attached thereto are attached to the capture entity via the capture agent. Unattached microparticles are then removed, and the retained microparticles released (e.g., by raising the temperature). In certain embodiments in which a particulate capture entity is used, aggregates consisting of the capture entity with microparticles attached thereto after hybridization are separated from particulate capture entities lacking attached microparticles and from microparticles that are not attached to a capture entity, e.g., by centrifugation in a viscous solution such as glycerol. Other methods of separation based on size, density, etc., can also be used. Hybridization is but one of a number of methods that can be used for enrichment. For example, capture agents having an affinity for any of a number of different ligands that can be incorporated into a template (e.g., during synthesis) may be used. Multiple rounds of enrichment can be used.

Figure 14A:
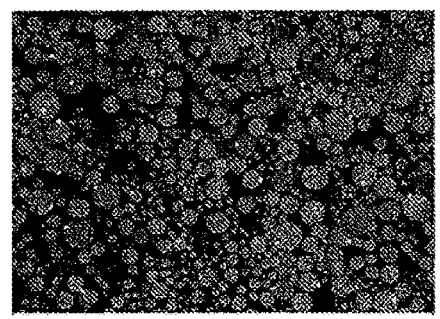
FIG. 14A shows an image of an emulsion PCR reaction performed on beads having attached first amplification primers, using a fluorescently labeled second amplification primer and an excess of template.

FIG. 14A shows an image of compartments of a water-in-oil emulsion, in which PCR reactions were performed on beads having first amplification primers attached thereto, using a fluorescently labeled second amplification primer and an excess of template. Aqueous reactors fluoresce weakly from diffuse free primer whereas beads strongly fluoresce from primers accumulating on the bead as a result of solid-phase amplification (i.e., fluorescent primers are incorporated into the amplified templates that are attached to the beads via the first amplification primer). Bead signal is uniform in the different sized reactors.

Following amplification, microparticles are collected (e.g., by use of a magnet in the case of magnetic particles) and used for sequencing by repeated cycles of extension, ligation, and cleavage as described herein. In certain embodiments of the invention the microparticles are arrayed in or on a semi-solid support prior to sequencing, as described below. Examples 12, 13, 14, and 15 provide additional details of representative and nonlimiting methods that may be used to (i) prepare microparticles having an amplification primer attached thereto, for synthesis of templates on the microparticles (Example 12); (ii) preparation of an emulsion comprising a plurality of reactors for performing PCR (Example 13); (iii) PCR amplification in compartments of an emulsion (Example 13); (iv) breaking the emulsion and recovering microparticles (Example 13); (v) enriching for microparticles having clonal template populations attached thereto (Example 14); (vi) preparation of glass slides to serve as substrates for a semi-solid polyacrylamide support (Example 15); and (vii) mixing microparticles with unpolymerized acrylamide, forming an array of microparticles having templates attached thereto, embedded in acrylamide on a substrate (Example 15). Example 15 also describes a protocol for polymerase trapping, which is used in certain of the methods when performing PCR in a semi-solid support. One of ordinary skill in the art will recognize that numerous variations on these methods may be used.

In other embodiments of the invention, the templates are amplified by PCR in a semi-solid support such as a gel having suitable amplification primers immobilized therein. Templates, additional amplification primers, and reagents needed for the PCR reaction are present within the semi-solid support. One or both of a pair of amplification primers is attached to the semi-solid support via a suitable linking moiety, e.g., an acrydite group. Attachment may occur during polymerization. Additional reagents (e.g., templates, second amplification primer, polymerase, nucleotides, cofactors, etc.) may be present in prior to formation of the semi-solid support (e.g., in a liquid prior to gel formation), or one or more of the reagents may be diffused into the semi-solid support after its formation. The pore size of the semi-solid support is selected to allow such diffusion. As is well known in the art, in the case of a polyacrylamide gel, pore size is determined mainly by the concentration of acrylamide monomer and to a lesser extent by the cross-linking agent. Similar considerations apply in the case of other semi-solid support materials. Appropriate cross-linkers and concentrations to achieve a desired pore size can be selected. In certain embodiments of the invention an additive such as a cationic lipid, polyamine, polycation, etc., is included in the solution prior to polymerization, which forms in-gel micelles or aggregates surrounding the microparticles. Methods disclosed in U.S. Pat. Nos. 5,705,628, 5,898,071, and 6,534,262 may also be used. For example, various "crowding reagents" can be used to crowd DNA near beads for clonal PCR. SPRI® magnetic bead technology and/or conditions can also be employed. See, e.g., U.S. Pat. No. 5,665,572, demonstrating effective PCR amplification in the presence of 10% polyethylene glycol (PEG). In certain embodiments of the inventive methods amplification (e.g., PCR), ligation, or both, are performed in the presence of a reagent such as betaine, polyethylene glycol, PVP-40, or the like. These reagents may be added to a solution, present in an emulsion, and/or diffused into a semi-solid support.

The semi-solid support may be located or assembled on a substantially planar rigid substrate. In certain preferred embodiments the substrate is transparent to radiation of the excitation and emission wavelengths used for excitation and detection of typical labels (e.g., fluorescent labels, quantum dots, plasmon resonant particles, nanoclusters), e.g., between approximately 400-900 nm. Materials such as glass, plastic, quartz, etc., are suitable. The semi-solid support may adhere to the substrate and may optionally be affixed to the substrate using any of a variety of methods. The substrate may or may not be coated with a substance that enhances adherence or bonding, e.g., silane, polylysine, etc. U.S. Pat. No. 6,511,803 describes methods for synthesizing clonal populations of templates using PCR in semi-solid supports, methods for preparing semi-solid supports on substantially planar substrates, etc. Similar methods may be used in the present invention. The substrate may have a well or depression to contain the liquid prior to formation of the semi-solid substrate. Alternately, a raised barrier or mask may be used for this purpose.

The above approach provides an alternative to the use of reactors in emulsions to generate spatially localized populations of clonal templates. The clonal populations are present at discrete locations in the semi-solid support, such that a signal can be acquired from each population during sequencing for purposes of detecting a newly ligated extension probe, e.g., by imaging. In some embodiments of the invention, two or more distinct clonal populations are amplified from a single nucleic acid fragment and are present as a mixture at a discrete location in the semi-solid support. Each of the clonal populations in the mixture may comprise a tag, e.g., so that the discrete location contains fragments containing a 5' tag and fragments containing a 3' tag. The clonal templates comprising the 5' tag and the 3' tag contain different sequencing primers, so that they can be sequenced independently of one another. This approach is identical to the approach described above for producing multiple populations of substantially identical nucleic acids on a microparticle and obtaining sequencing information for both members of a paired tag from a single microparticle.

In general, a semi-solid support for use in any of the inventive methods forms a layer of about 100 microns or less in thickness, e.g., about 50 microns thick or less, e.g., between about 20 and 40 microns thick, inclusive. A cover slip or other similar object having a substantially planar surface can be placed atop the semi-solid support material, preferably prior to polymerization, to help produce a uniform gel layer, e.g. to form a gel layer that is substantially planar and/or substantially uniform in thickness.

In yet other embodiments of the invention, modifications to the above methods are used, in which templates are synthesized by PCR on microparticles having a suitable amplification primer attached thereto, wherein the microparticles are immobilized in or on a semi-solid support prior to template synthesis, i.e., they are fully or partially embedded in the semi-solid support. Generally the microparticles are completely surrounded by the semi-solid support material, though they may rest on an underlying substrate. The microparticles thus remain at substantially fixed positions with respect to one another unless the semi-solid support is disrupted. This approach provides another alternative to the use of emulsions to generate spatially localized populations of clonal templates. Microparticles may be mixed with liquid prior to formation of the semi-solid support. Alternatively, microparticles may be arrayed on a substantially planar substrate, and liquid added to the microparticle array prior to polymerization, crosslinking, etc. The microparticles have a first amplification primer attached thereto. The second amplification primer may, but need not be, be attached to the semi-solid support. Additional reagents (e.g., template, second amplification primer, polymerase, nucleotides, cofactors, etc.) may be present prior to formation of the semi-solid support (e.g., in a liquid prior to gel formation), or one or more of these reagents may be diffused into the semi-solid support after gel formation. The semi-solid substrate is generally formed as described above, e.g., on a glass slide.

In certain embodiments of the invention the gel can be solubilized (e.g., digested or depolymerized or dissolved) so that microparticles with attached clonal template populations can be conveniently recovered (e.g., by use of a magnet in the case of magnetic particles) following template synthesis. Gels that can be solubilized, digested, depolymerized, dissolved, etc., are referred to herein as "reversible". Conventional polyacrylamide polymerization involves the use of N—N' methylenebisacrylamide (BIS) as a crosslinking agent together with a suitable catalyst to initiate polymerization (e.g., N,N,N',N'-tetramethylethylenediamine (TEMED)). To produce a reversible gel an alternative crosslinking agent such as N—N' diallyltartardiamide (DATD) may be used. This compound is structurally similar to BIS but possesses cis-diol groups that can be cleaved by periodic acid, e.g., in a solution containing sodium periodate (Anker, H. S.: F.E.B.S. Lett., 7: 293, 1970). Thus DATD gels can be readily solubilized. Gels made using DATD as the crosslinker are highly transparent and bind well to glass Another crosslinking agent with DATD-like properties of forming reversible gels is ethylene diacrylate (Choules, G. L. and Zimm, B. S.: Anal. Biochem., 13: 336-339, 1965). N,N'-bisacrylylcystamine (BAC) is another crosslinker that can be used to form a reversible polyacrylamide gel. Another crosslinking agent that can be used to form gels that dissolve in periodate is N,N'-(1,2-Dihydroxyethylene)bis-acrylamide (DHEBA). Any of a variety of other materials that form reversible semi-solid supports can also be used. For example, thermo-reversible polymers such as Pluronics (available from BASF) can be used. Pluronics are a family of poly(ethylene oxide)-poly(propylene oxide)-poly(ethylene oxide) (PEO-PPO-PEO) triblock copolymers (Nace, V. M., et al., Nonionic Surfactants, Marcel-Dekker, N Y, 1996). These materials become semi-solid (gel) at elevated temperatures (e.g., temperatures greater than room temperature) and liquify upon cooling. Various methods can be used to chemically derivatize Pluronics, e.g., to facilitate attachment of primers thereto (see, e.g., Neff, J. A. et al., J. Biomed. Mater. Res., 40:511, 1998; Prud'homme, R K, et al., Langmuir, 12:4651, 1996).

After solubilization, the microparticles can be collected and subjected to sequencing using repeated cycles of extension, ligation, and cleavage. Prior to sequencing, the microparticles may be arrayed in or on a second semi-solid support, e.g., at a higher density than that at which they were present in or on the first semi-solid support. The semi-solid support is typically itself supported by a substantially planar and rigid substrate, e.g., a glass slide.

Thus two general approaches may be used to produce semi-solid supports having an array of microparticles bearing clonal template populations embedded in or on the semi-solid support. The first approach involves performing amplification on microparticles that are not present in the semi-solid support (e.g., by emulsion-based PCR) and then immobilizing the microparticles in or on a semi-solid support. The second general approach involves immobilizing microparticles in or on a semi-solid support and then performing amplification. In either case, it may be desirable to employ procedures to reduce clumping of the microparticles and/or to align the microparticles substantially in a single focal plane. For example, when immobilizing particles in a polyacrylamide gel, the concentrations of monomer and crosslinker are selected so that the particles will sink to the bottom of the solution prior to complete polymerization, so that they settle on an underlying planar substrate and are thus arranged in a single plane. In certain embodiments of the invention an object having a substantially planar surface, such as a cover slip, is placed on top of the liquid acrylamide (or other material capable of forming a semi-solid support) containing microparticles so that the acrylamide is trapped between two layers of a "sandwich" structure. The sandwich is then turned over, so that by the action of gravity the microparticles sink down and rest on the cover slip (or other object having a substantially planar surface). After polymerization, the cover slip is removed. The microparticles are thus embedded in substantially a single plane, close to the surface of the semi-solid support. (e.g., tangent to the surface).

Rather than immobilizing supports such as microparticles in a semi-solid matrix as described above, in certain embodiments of the invention microparticles are either covalently or noncovalently attached to a substantially planar, rigid substrate without use of a semi-solid support to immobilize them. A variety of methods for attaching microparticles to substrates such as glass, plastic, quartz, silicon, etc., are known in the art. The substrate may or may not be coated (e.g., spin-coated) or functionalized with a material (e.g., any of a variety of polymers) or agent that facilitates attachment. The coating may be a thin film, self-assembled monolayer, etc. Either the microparticles, a moiety attached to the microparticles, or oligonucleotides attached to the microparticles (e.g., the templates) can be attached.

In general, any pair of molecules that exhibit affinity for one another such that they form a binding pair may be used to attach microparticles or templates to a substrate. The first member of the binding pair is attached covalently or noncovalently to the substrate, and the second member of the binding pair is attached covalently or noncovalently to the microparticles or templates. The first binding partner may be attached to the substrate via a linker. The second binding partner may be attached to the microparticles or templates via a linker. For example, according to one approach, a slide or other suitable substrate is modified with an amine-reactive group (e.g., using a PEG linker containing an amine-reactive group). The amine-reactive group reacts under aqueous conditions (e.g. at pH 8.0) with an amine, e.g., a lysine in any protein, for example, streptavidin. Microparticles functionalized with a moiety bearing an amine will therefore become immobilized on the substrate. The moiety bearing an amine can be a protein or a suitably functionalized nucleic acid, e.g., a DNA template. Multiple moieties can be attached to a bead. For example, a bead may have proteins attached thereto that react with the NHS ester to attach the bead to the substrate and may also have DNA templates attached thereto, which can be sequenced after the bead is attached to the substrate. Suitably coated slides bearing a polymer tether having an amine-reactive NHS moiety on one end are commercially available, e.g., from Schott Nexterion, Schott North America, Inc., Elmsford, N.Y. 10523). Alternately, coated slides (e.g., biotin-coated slides) are available from Accelr8 Technology Corporation, Denver, Colo. Their OptiChem™ technology represents but one method for attaching microparticles to a substrate. See, e.g., U.S. Pat. No. 6,844,028. Alternately, microparticles may be attached to a substrate by functionalising polynucleotides on the bead with biotin by, e.g., the use of terminal transferase with biotin-dideoxyATP and/or biotin-deoxyATP, and then contacting them with a streptavidin-coated slide (available from, e.g., Accelr8 Technology Corporation, Denver, Colo.) under conditions which promote a biotin-streptavidin bond.

In general, any of a wide variety of methods known in the art can be used to modify nucleic acids such as oligonucleotide primers, probes, templates, etc., to facilitate the attachment of such nucleic acids to microparticles or to other supports or substrates. In addition, any of a wide variety of methods known in the art can be used to modify microparticles or others supports to facilitate the attachment of nucleic acids thereto, to facilitate the attachment of microparticles to supports or substrates, etc. Microspheres are available that have surface chemistries that facilitate the attachment of a desired functionality. Some examples of these surface chemistries include, but are not limited to, amino groups including aliphatic and aromatic amines, carboxylic acids, aldehydes, amides, chloromethyl groups, hydrazide, hydroxyl groups, sulfonates and sulfates. These groups may react with groups present in nucleic acids, or nucleic acids may be modified by attachment of a reactive group. In addition, a large number of stable bifunctional groups are well known in the art, including homobifunctional and heterobifunctional linkers. See, e.g., Pierce Chemical Technical Library, available at the Web site having URL www.piercenet.com (originally published in the 1994-95 Pierce Catalog) and G. T. Hermanson, *Bioconjugate Techniques*, Academic Press, Inc., 1996. See also U.S. Pat. No. 6,632,655.

Arrays of microparticles formed according to the methods described herein are generally random. As used herein, the terms "randomly-patterned" or "random" refer to a non-ordered, non-Cartesian distribution (in other words, not arranged at pre-determined points or locations along the x- and y axes of a grid or at defined 'clock positions', degrees or radii from the center of a radial pattern) of entities (features) over a support, that is not achieved through an intentional design (or program by which such a design may be achieved) or by placement of individual entities. Such a "randomly-patterned" or "random" array of entities may be achieved by dropping, spraying, plating, spreading, distributing, etc., a solution, emulsion, aerosol, vapor or dry preparation comprising a pool of entities onto or into a support and allowing them to settle onto or into the support without intervention in any manner to direct them to specific sites in or on the support. For example, entities may be suspended in a solution that contains precursors to a semi-solid support (e.g., acrylamide monomers). The solution is then distributed on a second support and the semi-solid support forms on the second support. Entities are embedded in or on the semi-solid support. Of course non-random arrays can also be used. Generally the methods for forming arrays used herein are distinct from methods in which, for example, synthesis of a polynucleotide occurs by sequential application of individual nucleotide subunits at predefined locations on a substrate.

Figure 14B:
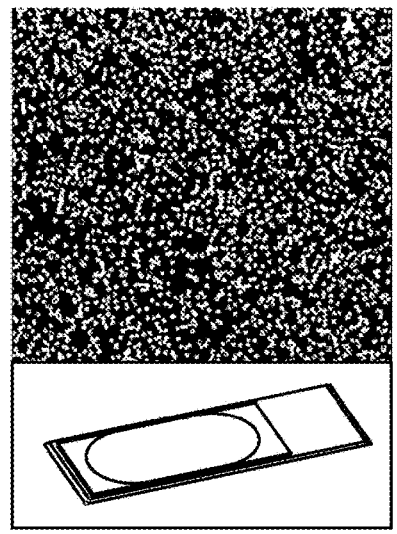
FIG. 14B (top) shows a fluorescence image of a portion of a slide on which beads with an attached template, to which a Cy3-labeled oligonucleotide was hybridized, were immobilized within a polyacrylamide gel. (This slide was used in a different experiment, but is representative of the slides used here.) FIG. 14B (bottom) shows a schematic diagram of a slide equipped with a Teflon mask to enclose the polyacrylamide solution.

FIG. 14B (top) shows a fluorescence image of a slide (1 inch by 3 inch) having a polyacrylamide gel thereon. Beads (1 micron diameter) with a fluorescently labeled oligonucleotide hybridized to templates attached to the beads are immobilized in the gel. The image shows a bead surface density (i.e., number of beads per unit area of the substrate, within the region where the beads are located) sufficient to image approximately 280 million beads per slide. The surface density and imageable area are sufficient to image at least 500 million beads on a single slide. For example, FIG. 14B (bottom) shows a schematic diagram of a slide with a Teflon® mask surrounding a clear area in which beads are to be embedded in a semi-solid support layer such as a polyacrylamide gel. The area of this mask is 864 mm$^2$. With 500 million beads, the surface density is 578,000 beads per mm$^2$. A close-packed hexagonal array of 1 micron beads gives 1,155,000 beads per mm$^2$, so this embodiment results in an array having 52% of the theoretical maximum density. It will be appreciated that smaller and larger numbers of beads, and greater or lesser bead surface densities, can be used than in this particular embodiment.

Microparticles may be arrayed in or on a substantially planar semi-solid support, or on another support or substrate, at a variety of densities, which can be defined in a number of ways. For example, the density may be expressed in terms of the number of microparticles (e.g., spherical microparticles) per unit area of a substantially planar array. In certain embodiments of the invention the number of microparticles per unit area of a substantially planar array is at least 80% of the number of microparticles in a hexagonal array (by "hexagonal array" is meant a substantially planar array of microparticles in which every microparticle in the array contacts at least six other adjacent microparticles of equal area as described in U.S. Pat. No. 6,406,848). However, in other embodiments of the invention the microparticle density is lower, e.g., the number of microparticles per unit area of a substantially planar array is less than 80%, less than 70%, less than 60%, or less than 50% of the number of microparticles in a hexagonal array. Without wishing to be bound by any theory, it may be preferable to utilize lower densities such as these in order, for example, to allow adequate diffusion of reagents such as enzymes, primers, cofactors, etc., and to avoid a reagent partitioning effect that may occur if certain reagents have differential affinity for microparticles or become entrapped therein. Such an effect may result in different reaction conditions at different positions on the array and may even prevent access to certain locations on the array by these reagents. These problems may be exacerbated when reactions are performed in a flow cell since the reagents move through the flow cell in a directional manner. In certain embodiments of the invention a mixing device, e.g., devices that achieve fluid mixing by mechanical or acoustical means, is included within the chamber of a flow cell. A number of suitable mixing devices are known in the art.

The inventive sequencing methods can be practiced using templates arranged in array formats of all types, including both random and nonrandom arrays, which can be arrays of microparticles or arrays of templates themselves. For example, supports with templates arrayed thereon are described in U.S. Pat. No. 5,641,658 and PCT Pub. No. WO0018957. Arrays may be located on a wide variety of substrates such as filters, membranes (e.g., nylon), metal surfaces, etc. Additional examples of array formats on which sequencing by repeated cycles of extension, ligation, and cleavage can be performed are arrays of beads located in wells at the terminal or distal end of individual optical fibers in a fiber optic bundle. See, e.g., bead arrays and "arrays of arrays" described in US publications and patents, e.g., U.S. Pat. Nos. 6,023,540; 6,429,027, 20040185483, 2002187515, PCT applications US98/05025, and PCT US98/09163, and PCT publication WO0039587. Beads with templates attached thereto can be arrayed as described therein. Amplification is preferably performed prior to formation of the array. Arrays formed on such substrates need not necessarily be substantially planar.

In other embodiments, PCR is performed on arrays that comprise oligonucleotides attached to a substrate or support, (see, e.g., U.S. Pat. Nos. 5,744,305; 5,800,992; 6,646,243 and related patents (Affymetrix); PCT publications WO2004029586; WO03065038; WO03040410 (Nimblegen)). In general, such oligonucleotides have a free 3' or 5' end. If desired, the end can be modified, e.g., by adding a phosphate group or an OH group to a 3' end if one is not already present. Template molecules comprising a region complementary to the oligonucleotide attached to the support or substrate are hybridized to the oligonucleotide, and PCR is performed in situ on the array, resulting in a clonal template population at each location on the array. The oligonucleotide attached to the array may serve as one of the amplification primers. The templates are then sequenced using the ligation-based methods described herein. Sequencing can also be performed on templates in arrays such as those described in U.S. Pub. No. 20030068629.

Yet other methods for preparation of DNA arrays on surfaces can be used. For example, alkanethiols modified with terminal aldehyde groups can used to prepare a self-assembled monolayer (SAM) on a gold surface. The aldehyde groups of the monolayer may be reacted with amine-modified oligonucleotides or other amine-bearing biomolecules to form a Schiff base, which may then be reduced to a stable secondary amine by treatment with sodium cyanoborohydride (Peelen & Smith, Langmuir, 21(1):266-71, 2005). PCR amplification of templates can then be performed. Alternately, microparticles having clonal populations of templates attached thereto may be attached to surfaces by reacting an amine group on the microparticle or on templates or oligonucleotides attached to the particle, with such surfaces.

Still another method of obtaining microparticles with clonal template populations attached thereto is the "solid phase cloning" approach described in U.S. Pat. No. 5,604,097, which makes use of oligonucleotide tags for sorting polynucleotides onto microparticles such that only polynucleotides of the same sequence will be attached to any particular microparticle.

In certain embodiments of the invention sequencing by repeated cycles of extension, ligation, and cleavage is performed by diffusing sequencing reagents (e.g., extension probes, ligase, phosphatase, etc.) into a semi-solid support such as a gel having clonal populations of templates immobilized in or on the support such that each clonal population is localized to a spatially distinct region of the support. In certain embodiments the templates are attached directly to the semi-solid support as described above. However, in preferred embodiments the templates are immobilized on a second support such as a microparticle that is in turn immobilized in or on the semi-solid support, as also described above.

As described in Example 1, the inventors have shown that robust ligation and cleavage can be performed on templates attached to beads that are immobilized in polyacrylamide gels. The invention thus provides a method of ligating a first polynucleotide to a second polynucleotide comprising steps of: (a) providing a first polynucleotide immobilized in or on a semi-solid support; (b) contacting the first polynucleotide with a second polynucleotide and a ligase; and (c) maintaining the first and second polynucleotides in the presence of ligase under suitable conditions for ligation. Suitable conditions include the provision of appropriate buffers, cofactors, temperature, times, etc., for the particular ligase being used. In a preferred embodiment the semi-solid support is a gel such as an acrylamide gel. In a further preferred embodiment the first polynucleotide is immobilized in or on the semi-solid support as a result of attachment to a support such as a bead, which is itself immobilized in or on the semi-solid support, e.g., by being partly or completely embedded in the support matrix. Alternately, the first polynucleotide may be attached directly to the semi-solid support via a linkage such as an acrydite moiety. The linkage may be covalent or noncovalent (e.g., via a biotin-avidin interaction). U.S. Pat. No. 6,511,803 describes a variety of methods that may be used to a attach a nucleic acid molecule to a preferred support of the invention, i.e., a polyacrylamide gel.

The invention further provides a method of cleaving a polynucleotide comprising steps of: (a) providing a polynucleotide immobilized in or on a semi-solid support, wherein the polynucleotide comprises a scissile linkage; (b) contacting the polynucleotide with a cleavage agent; and (c) maintaining the polynucleotide in the presence of the cleavage agent under conditions suitable for cleavage. Suitable conditions include the provision of appropriate buffers, temperatures, times, etc., for the particular cleavage agent. In a preferred embodiment the semi-solid support is a gel such as an acrylamide gel. In a further preferred embodiment the polynucleotide is immobilized in the semi-solid support as a result of attachment to a support such as a bead, which is itself immobilized in the semi-solid support. Alternately, the polynucleotide may be attached directly to the semi-solid support via a linkage such as an acrydite moiety. The linkage may be covalent or noncovalent (e.g., via a biotin-avidin interaction).

Macevicz discloses sequencing a single template species having a particular sequence. He does not discuss the possibility of performing his method in parallel to simultaneously sequence a plurality of templates having different sequences. The inventors have recognized that in order to efficiently perform sequencing in a high throughput manner, it is desirable to prepare a plurality of supports (e.g., beads), as described above, such that each support has templates of a particular sequence attached thereto, and to perform the methods described herein simultaneously on templates attached to each support. In certain embodiments of this approach, a plurality of such supports are arrayed in or on a planar substrate such as a slide. In certain embodiments the supports are arrayed in or on a gel. The supports may be arrayed in a random fashion, i.e., the location of each support on the substrate is not predetermined. The supports need not be located at regularly spaced intervals or positioned in an ordered arrangement of rows and columns, etc. Preferably the supports are arrayed at a density such that it is possible to detect an individual signal from many or most of the supports. In certain preferred embodiments the supports are primarily distributed in a single focal plane. Multiple supports having templates of the same sequence attached thereto may be included, e.g., for purposes of quality control. Sequencing reactions are performed in parallel on templates attached to each of the supports.

Signals may be collected using any of a variety of means, including various imaging modalities. Preferably, for embodiments in which sequencing is performed on microparticles that are arrayed on a substrate (e.g., beads embedded in a semi-solid support positioned on a substrate) prior to detection, the imaging device has a resolution of 1 µm or less. For example, a scanning microscope fitted with a CCD camera, or a microarray scanner with sufficient resolution could be used. Alternately, beads can be passed through a flow cell or fluidics workstation attached to a microscope equipped for fluorescence detection. Other methods for collecting signal include fiber optic bundles. Appropriate image acquisition and processing software may be used.

In certain embodiments of the invention sequencing is performed in a microfluidic device. For example, beads with attached templates may be loaded into the device and reagents flowed therethrough. Template synthesis, e.g., using PCR, can also be performed in the device. U.S. Pat. No. 6,632,655 describes an example of a suitable microfluidic device.

D. Sequencing with Re-Initialization Using Different Initializing Oligonucleotides In a preferred embodiment of the instant invention, the extended strand generated by extending a first initializing oligonucletide is removed from the template following a sufficient number of cycles and a second initializing oligonucleotide is annealed to the binding region, followed by cycles of extension, ligation, and detection. The process is repeated with any number of different initializing oligonucleotides. In embodiments in which the extension probes are cleaved, preferably the number of different initializing oligonucleotides used (and thus the number of reactions) equals the length of the portion of the extension probe that remains hybridized to the template following release of the distal portion of the probe. Thus according to this embodiment sequence information (e.g., the order and identity of each nucleotide) can be obtained from the templates that are attached to a single support while still reading deep into the sequence using substantially fewer cycles than would be required if successive nucleotides were identified in each cycle.

Embodiments in which the initializing oligonucleotides are bound sequentially to the same template have certain advantages over an approach that requires dividing the template into multiple aliquots, such as the methods taught by Macevicz. For example, applying the initializing oligonucleotides to the same template avoids the need to keep track of, and later, combine data acquired from multiple aliquots. In embodiments in which the supports are arrayed in a random fashion such that the position of individual supports is not predetermined, it would be difficult or impossible to reliably combine partial sequence information from multiple supports each of which had templates of the same sequence attached thereto.

E. Identification of Multiple Nucleotides in Each Cycle on a Single Template Macevicz teaches identification of single nucleotides in the template in each cycle of extension, ligation, and detection. However, the inventors have recognized that the methods may be modified to allow identification of multiple nucleotides in the template in each cycle. In this case the extension probes are labeled so that the identity of two or more, preferably contiguous, nucleotides abutting the extended duplex can be determined from the label. In other words, the sequence determining portion of the extension probes is more than a single nucleotide and typically comprises the proximal nucleotide, the immediately adjacent nucleotide, and possibly one or more additional, preferably contiguous nucleotides, all of which hybridize specifically to the template. For example, rather than using 4 labels to identify the bases A, G, C, and T, 16 distinguishably labeled probes or probe combinations are used to identify the 16 possible dinucleotides AA, AG, AC, AT, GA, GG, GC, GT, CA, CG, CC, CT, TA, TG, TC, and TT. The sequence determining portion of each distinguishably labeled extension probe is complementary to one of these dinucleotides. Similar methods utilizing more labels allow identification of longer nucleotide sequences in each cycle.

F. Labels

The term "label" is used herein in a broad sense to denote any detectable moiety or plurality of detectable moieties attached to or associated with a probe, by which probes of different species (e.g., probes with different terminal nucleotides) may be distinguished from one another. Thus there need not be a one to one correspondence between a label and a specific detectable moiety. For example, multiple detectable moieties can be attached to a single probe, resulting in a combined signal that allows the probe to be distinguished from probes having a different detectable moiety or set of detectable moieties attached thereto. For example, combinations of detectable moieties can be used in accordance with a labeling scheme referred to as "Combinatorial Multicolor Coding", which is described in U.S. Pat. No. 6,632,609 and in Speicher, et al., *Nature Genetics*, 12:368-375, 1996.

The probes of the invention can be labeled in a variety of ways, including the direct or indirect attachment of fluorescent or chemiluminescent moieties, colorimetric moieties, enzymatic moieties that generate a detectable signal when contacted with a substrate, and the like. Macevicz teaches that the probes may be labeled with fluorescent dyes, e.g. as disclosed by Menchen et al, U.S. Pat. No. 5,188,934; Begot et al PCT application PCT/US90105565. The terms "fluorescent dye", and "fluorophore" as used herein refer to moieties that absorb light energy at a defined excitation wavelength and emit light energy at a different wavelength. Preferably the labels selected for use with a given mixture of probes are spectrally resolvable. As used herein, "spectrally resolvable" means that the labels may be distinguished on the basis of their spectral characteristics, particularly fluorescence emission wavelength, under conditions of operation. For example, the identity of the one or more terminal nucleotides may be correlated to a distinct wavelength of maximum light emission intensity, or perhaps a ratio of intensities at different wavelengths. The spectral characteristic(s) of a label that is/are used to detect and identify a label is referred to as a "color" herein. It will be appreciated that a label is frequently identified on the basis of a specific spectral characteristic, e.g., the frequency of maximum emission intensity in the case of labels that consist of a single detectable moiety, or the frequencies of emission peaks in the case of labels that consist of multiple detectable moieties.

Preferably, four probes are provided that allow a one-to-one correspondence between each of four spectrally resolvable fluorescent dyes and the four possible terminal nucleotides of the probes. Sets of spectrally resolvable dyes are disclosed in U.S. Pat. Nos. 4,855,225 and 5,188,934; International application PCT/US90/05565; and Lee et al, Nucleic Acids Researchs, 20: 2471-2483 (1992). In certain embodiments a set consisting of FITC, HEX™, Texas Red, and Cy5 is preferred. Numerous suitable fluorescent dyes are commercially available, e.g., from Molecular Probes, Inc., Eugene Oreg. Specific examples of fluorescent dyes include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), CAL dyes, Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Oyster dyes, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X. See The Handbook of Fluorescent Probes and Research Products, 9$^{th}$ ed., Molecular Probes, Inc., for further description.

Rather than being directly detectable themselves, some fluorescent groups transfer energy to another group in the process of nonradiative fluorescent resonance energy transfer (FRET), and the second group produces the detected signal. The use of quenchers, i.e., is also within the scope of the invention. The term "quencher" refers to a moiety that is capable of absorbing the energy of an excited fluorescent label when located in close proximity and of dissipating that energy without the emission of visible light. Examples of quenchers include, but are not limited to DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinimidyl ester (QSY-33) (all available from Molecular Probes), quencher1 (Q1; available from Epoch), or "Black hole quenchers" BHQ-1, BHQ-2, and BHQ-3 (available form BioSearch, Inc.).

In addition to the various detectable moieties mentioned above, the present invention also comprehends use of spectrally resolvable quantum dots, metal nanoparticles or nanoclusters, etc., which may either be directly attached to an oligonucleotide probe or may be embedded in or associated with a polymeric matrix which is then attached to the probe. As mentioned above, detectable moieties need not themselves be directly detectable. For example, they may act on a substrate which is detected, or they may require modification to become detectable.

As described above, in certain embodiments of the invention a label consists of a plurality of detectable moieties. The combined signal from these detectable moieties produces a color that is used to identify the probe. For example, a "purple" probe of a particular sequence could be constructed by attaching "blue" and "red" detectable moieties thereto. Alternatively, a distinct color can be generated by combining two species of probe having the same sequence but labeled with different detectable moieties to produce a mixed probe. Thus a "purple" probe of a particular sequence can be produced by constructing two species of probe having that sequence. "Red" detectable moieties are attached to the first species, and "blue" detectable moieties are attached to the second species. Aliquots of these two species are mixed. Various shades of purple can be produced by mixing aliqots in different ratios. This approach offers a number of advantages. Firstly, it allows the production of multiple distinguishable probes using a smaller number of detectable moieties. Secondly, using a mixed probe can provide a degree of redundancy that may help reduce bias that may result from interactions between particular detectable moieties and particular nucleotides.

In certain embodiments of the invention a detectable moiety is attached to a nucleotide in an oligonucleotide extension probe by a cleavable linkage, which allows removal of the detectable moiety following ligation and detection. Any of a variety of different cleavable linkages may be used. As used herein, the term "cleavable linkage" refers to a chemical moiety that joins a detectable moiety to a nucleotide, and that can be cleaved to remove the detectable moiety from the nucleotide when desired, essentially without altering the nucleotide or the nucleic acid molecule it is attached to. Cleavage may be accomplished, for example, by acid or base treatment, or by oxidation or reduction of the linkage, or by light treatment (photocleavage), depending upon the nature of the linkage. Examples of cleavable linkages and cleavage agents are described in Shirnkus et al., 1985, Proc. Natl. Acad. Sci. USA 82: 2593-2597; Soukup et al., 1995, Bioconjug. Chem. 6: 135-138; Shimikus et al., 1986, DNA 5: 247-255; and Herman and Fenn, 1990, Meth. Enzymol. 184: 584-588.

For example, as described in U.S. Pat. No. 6,511,803, a disulfide linkage can be reduced and thereby cleaved using thiol compound reducing agents such as dithiothreitol (DTT). Fluorophores are available with a sulfhydryl (SH) group available for conjugation (e.g., Cyanine 5 or Cyanine 3 fluorophores with SH groups; New England Nuclear—DuPont), as are nucleotides with a reactive aryl amino group (e.g., dCTP). A reactive pyridyldithiol will react with a sulflhydryl group to give a sulfhydryl bond that is cleavable with reducing agents such as dithiothreitol. An NHS-ester heterobifunctional crosslinker (Pierce) can be used to link a deoxynucleotide comprising a reactive aryl amino group to a pyridyldithiol group, which is in turn reactive with the SH on a fluorophore, to yield a disulfide bonded, cleavable nucleotide-fluorophore complex useful in the methods of the invention. Alternatively, a cis-glycol linkage between a nucleotide and a fluorophore can be cleaved by periodate. A variety of cleavable linkages are described in U.S. Pat. Nos.

6,664,079, and 6,632,655, US Published Application 20030104437, WO 04/18497 and WO 03/48387.

In other embodiments of the invention a detectable moiety that can be rendered nondetectable by exposure to electromagnetic energy such as light (photobleaching) is used.

In those embodiments of the invention that employ extension probes having a label that is attached to the probe by a cleavable linkage, or having a label that can be photobleached, a the sequencing methods will typically include a step of cleavage or photobleaching in one or more cycles after ligation and label detection have been performed. As mentioned above, cleavage of the scissile linkage present in the oligonucleotide extension probes may not proceed to completion (i.e., less than 100% of the newly ligated probes may be cleaved in the cycle in which they were ligated). Since such probes generally comprise a non-extendable terminus, or are capped, they will not contribute to successive cycles. However, failure to cleave the probe means that the label remains associated with the template molecule to which the probe ligated, which contributes background signal (i.e., background fluorescence) that can increase the noise in subsequent cycles. Incorporating a step of cleavage or photobleaching to remove the label or render it undetectable reduces this background and improves the signal to noise ratio. Cleavage or photobleaching can be performed as often as every cycle, or less frequently, such as every other, every third, or every fifth or more cycles. In certain embodiments of the invention it is not necessary to actually add any additional steps to achieve cleavage of the cleavable linker. For example, a cleavage agent such as DTT may already be present in a wash buffer that may be used to remove unligated extension probes.

G. Preferred Scissile Linkages

Figure 4A:
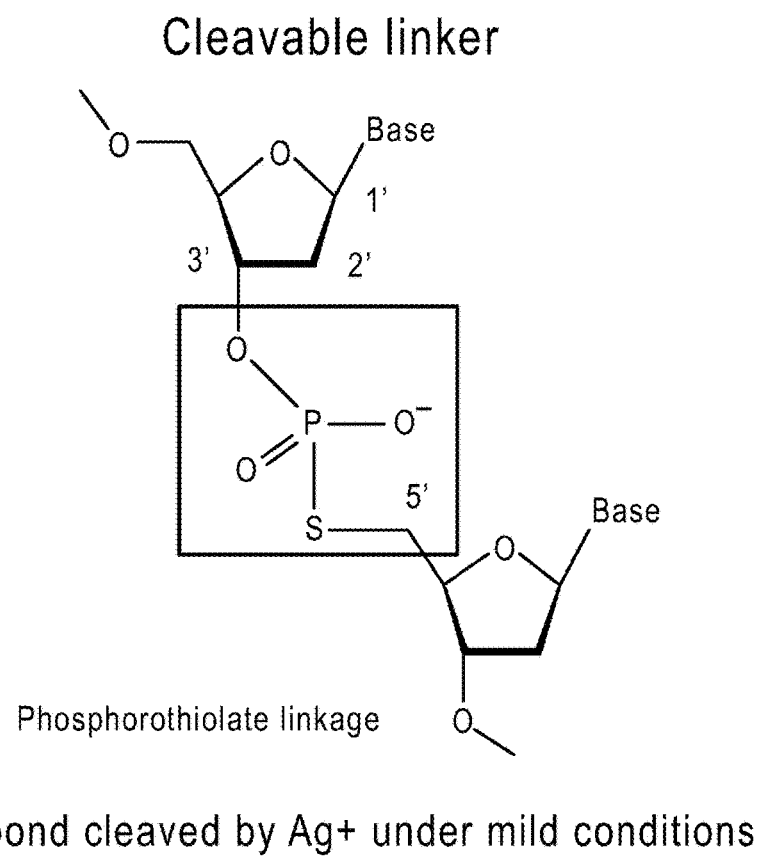
FIG. 4A illustrates a 5'-S-phosphorothiolate linkage (3'-O—P—S-5').
Figure 4B:
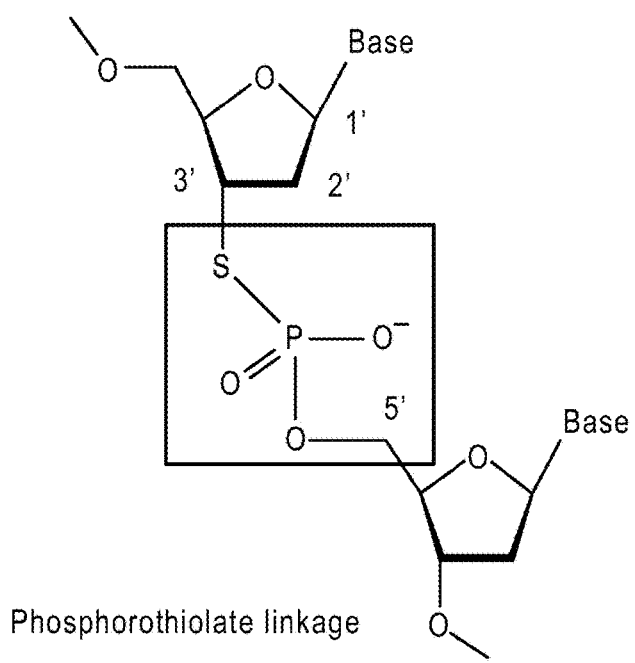
FIG. 4B illustrates a 3'-S-phosphorothiolate linkage (3'-S—P—O-5').

The inventors have discovered that extension probes having at least one phosphorothiolate linkage are particularly useful in the practice of methods for sequencing by successive cycles of extension, ligation, detection, and cleavage. In such linkages one of the bridging oxygen atoms of a phosphodiester bond is replaced by a sulfur atom. The phosphorothiolate linkage can be either a 5'-S-phosphorothiolate linkage (3'-O—P—S—S') as shown in FIG. 4A or a 3'-S-phosphorothiolate linkage (3'-S—P—O-5') as shown in FIG. 4B. It is to be understood that the phosphorus atom in linkages represented as 3'-O—P—S-5' or 3'-S—P—O-5' may be attached to two non-bridging oxygen atoms as shown in FIGS. 4A and 4B (as in typical phosphodiester bonds). Alternately, the phosphorus atom could be attached to any of a variety of other atoms or groups, e.g., S, $CH_3$, $BH_3$, etc. Thus one aspect of the invention is labeled olignucleotide probes comprising phosphorothiolate linkages. While the probes find particular use in the sequencing methods described herein, they may also be used for a variety of other purposes. In particular, the invention provides (i) an oligonucleotide of the form 5'-O—P—O—X—O—P—S—$(N)_k N_B$*-3'; and (ii) an oligonucleotide of the form 5'-$N_B$*$(N)_k$—S—P—O—X-3'. In each of these probes N represents any nucleotide, $N_B$ represents a moiety that is not extendable by ligase, * represents a detectable moiety, X represents a nucleotide, and k is between 1 and 100. In certain embodiments k is between 1 and 50, between 1 and 30, between 1 and 20, e.g., between 4 and 10, with the proviso that a detectable moiety may be present on any nucleotide of $(N)_k$ instead of, or in addition to, $N_B$. The terminal nucleotides in any of these probes may or may not include a phosphate group or a hydroxyl group. Furthermore, it will be appreciated that the phosphorus atoms will generally be attached to two additional (non-bridging) oxygen atoms in preferred embodiments.

Figure 7:
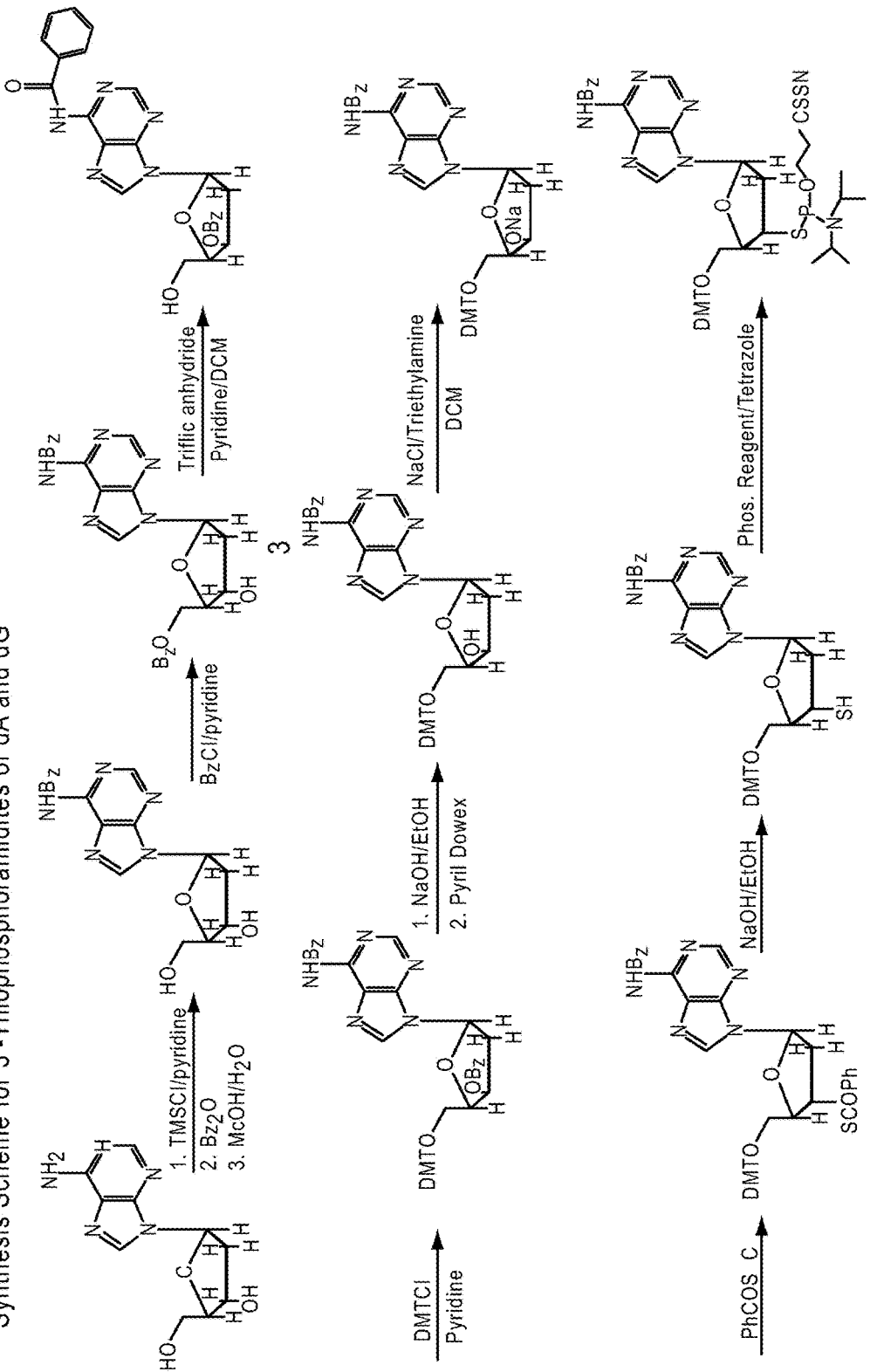
FIG. 7 is a schematic showing a synthesis scheme for 3'-phosphoroamidites of dA and dG.

Methods for synthesizing oligonucleotides containing 5'-S-phosphorothiolate or 3'-S-phosphorothiolate linkages are known in the art, and certain of these methods are amenable to automated solid phase oligonucleotide synthesis. Synthesis procedures are described, for example, in Cook, A F, J. Am. Chem. Soc., 92:190-195, 1970; Chladek, S. et al., J. Am. Chem. Soc., 94:2079-2084, 1972; Rybakov, V N, et al., Nucleic Acids Res., 9:189-201, 1981; Cosstick, R. and Vyle, J S, J. Chem. Soc. CHem. Commun., 992-992, 1988; Mag, M., et al., Nucleic Acids Res., 19(7); 1437-1441, 1991; Xu, Y, and Kool, E T, Nucleic Acids Res., 26(13): 3159-3164, 1998; Cosstick, R. and Vyle, J S, Tetrahedron Lett., 30:4693-4696, 1989; Cosstick, R. and Vyle, J S, Nucleic Acids Res., 18:829-835, 1990; Sun, S G and Piccirilli, J A, Nucl. Nucl., 16:1543-1545, 1997; Sun S G, et al., RNA, 3:1352-1363, 1997; Vyle, J S, et al., Tetrahedron Lett., 33:3017-3020, 1992; Li, X., et al., J. Chem. Soc. Perkin Trans., 1:2123-22129, 1994; Liu, X H and Reese, C B, Tetrahedron Lett., 37: 925-928, 1996; Weinstein, L B, et al., J. Am. Chem. Soc., 118:10341-10350, 1996; and Sabbagh, G., et al., Nucleic Acids Res., 32(2):495-501, 2004. In addition, the present inventors have developed new synthesis methods. For example, FIG. 7 shows a synthesis scheme for a 3'-phosphoroamidite of dA. A similar scheme may be used for synthesis of a 3'-phosphoroamidite of dG. These phosphoroamidites may be used to synthesize oligonucleotides containing 3'-S-phosphorothiolate linkages associated with purine nucleosides, e.g., using an automated DNA synthesizer.

Phosphorothiolate linkages can be cleaved using a variety of metal-containing agents. The metal can be, for example, Ag, Hg, Cu, Mn, Zn or Cd. Preferably the agent is a water-soluble salt that provides $Ag^+$, $Hg^{++}$, $Cu^{++}$, $Mn^{++}$, $Zn^+$ or $Cd^+$ anions (salts that provide ions of other oxidation states can also be used). $I_2$ can also be used. Silver-containing salts such as silver nitrate ($AgNO_3$), or other salts that provide $Ag^+$ ions, are particularly preferred. Suitable conditions include, for example, 50 mM $AgNO_3$ at about 22-37° C. for 10 minutes or more, e.g., 30 minutes. Preferably the pH is between 4.0 and 10.0, more preferably between 5.0 and 9.0, e.g., between about 6.0 and 8.0, e.g., about 7.0. See, e.g., Mag, M., et al., Nucleic Acids Res., 19(7):1437-1441, 1991. An exemplary protocol is provided in Example 1.

Figure 5A:
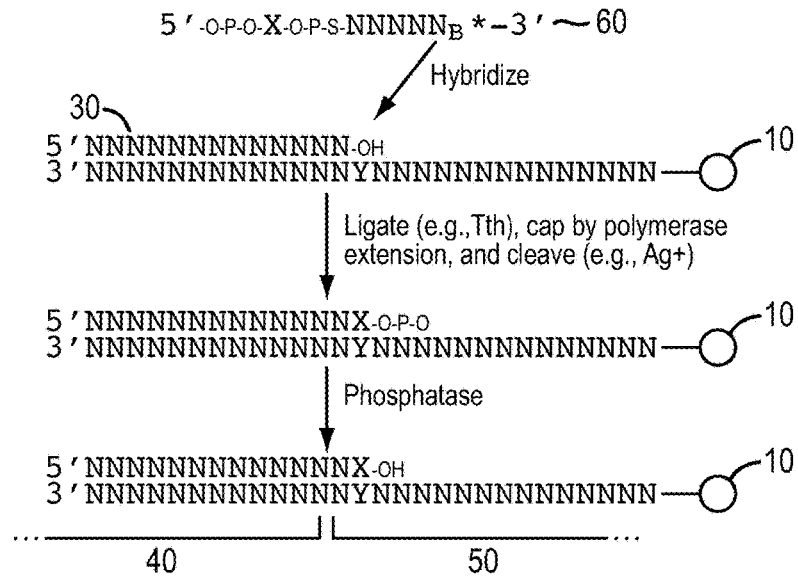
FIG. 5A diagramatically illustrates a single cycle of extension, ligation, and cleavage for sequencing in the 5'→3' direction using extension probes having 3'-O—P—S-5' phosphorothiolate linkages.

Sequencing in the 5'→3' direction may be performed using extension probes containing a 3'-O—P—S-5' linkage. FIG. 5A shows a single cycle of hybridization, ligation, and cleavage using an extension probe of the form 5'-O—P—O—X—O—P—S—NNNNN$_B$*-3' where N represents any nucleotide, $N_B$ represents a moiety that is not extendable by ligase (e.g., $N_B$ is a nucleotide that lacks a 3' hydroxyl group or has an attached blocking moiety), * represents a detectable moiety, and X represents a nucleotide whose identity corresponds to the detectable moiety. Alternately, any of a large number of blocking moieties can be attached to the 3' terminal nucleotide to prevent multiple ligations. For example, attaching a bulky group to the sugar portion of the nucleotide, e.g., at the 2' or 3' position, will prevent ligation. A fluorescent label may serve as an appropriate bulky group.

A template containing binding region 40 and polynucleotide region 50 of unknown sequence is attached to a support, e.g., a bead. In a preferred embodiment, as shown in FIG. 5A, the binding region is located at the opposite end of the template from the point of attachment to the support. An initializing oligonucleotide 30 with an extendable terminus (in this case a free 3' OH group) is annealed to binding region 40. Extension probe 60 is hybridized to the template in polynucleotide region 50. Nucleotide X forms a complementary base pair with unknown nucleotide Y in the template. Extension probe 60 is ligated to the initializing oligonucleotide (e.g., using T4 ligase). Following ligation, the label attached to extension probe 60 is detected (not shown). The label corresponds to the identity of nucleotide X. Thus nucleotide Y is identified as the nucleotide complementary to nucleotide X. Extension probe 60 is then cleaved at the phosphorothiolate linkage (e.g., using $AgNO_3$ or another salt that provides $Ag^+$ ions), resulting in an extended duplex. Cleavage leaves a phosphate group at the 3' end of the extended duplex. Phosphatase treatment is used to generate an extendable probe terminus on the extended duplex. The process is repeated for a desired number of cycles.

Figure 5B:
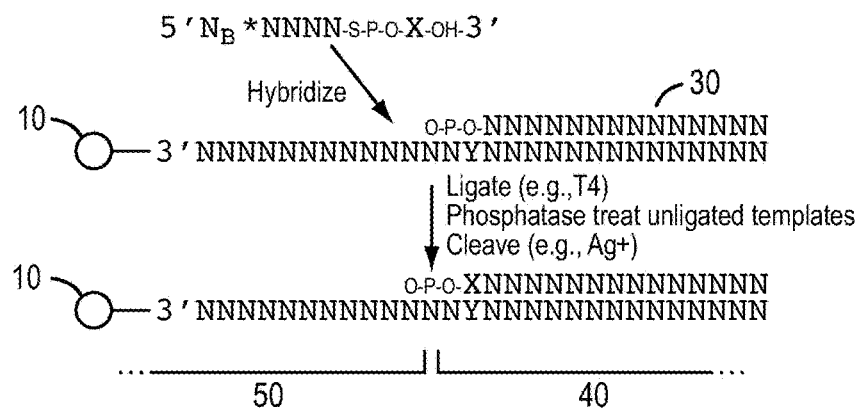
FIG. 5B diagramatically illustrates a single cycle of extension, ligation, and cleavage for sequencing in the 3'→5' direction using extension probes having 3'-S—P—O-5' phosphorothiolate linkages.

In a preferred embodiment sequencing is performed in the 3'→5' direction using extension probes containing a 3'-S—P—O-5' linkage. FIG. 5B shows a single cycle of hybridization, ligation, and cleavage using an extension probe of the form 5'-$N_B$*—NNNN—S—P—O—X-3' where N represents any nucleotide, $N_B$ represents a moiety that is not extendable by ligase (e.g., $N_B$ is a nucleotide that lacks a 5' phosphate group or has an attached blocking moiety), * represents a detectable moiety, and X represents a nucleotide whose identity corresponds to the detectable moiety.

A template containing binding region 40 and polynucleotide region 50 of unknown sequence is attached to a support, e.g., a bead. In a preferred embodiment, as shown in FIG. 5B, the binding region is located at the opposite end of the template from the point of attachment to the support. An initializing oligonucleotide 30 with an extendable terminus (in this case a free 5' phosphate group) is annealed to binding region 40. Extension probe 60 is hybridized to the template in polynucleotide region 50. Nucleotide X forms a complementary base pair with unknown nucleotide Y in the template. Extension probe 60 is ligated to the initializing oligonucleotide (e.g., using T4 ligase). Following ligation, the label attached to extension probe 60 is detected (not shown). The label corresponds to the identity of nucleotide X. Thus nucleotide Y is identified as the nucleotide complementary to nucleotide X. Extension probe 60 is then cleaved at the phosphorothiolate linkage (e.g., using $AgNO_3$ or another salt that provides $Ag^+$ ions), resulting in an extended duplex. Cleavage leaves an extendable monophosphate group at the 5' terminus of the extended duplex and it is therefore unnecessary to perform an additional step to generate an extendable terminus. The process is repeated for a desired number of cycles.

It will be appreciated that a number of variations of this scheme can be used. For example, the probe may be shorter or longer than 6 nucleotides; the label need not be on the 3' terminal nucleotide; the P—S linkage can be located between any two adjacent nucleotides, etc. In the embodiments described above, successive cycles of extension, ligation, detection, and cleavage, result in identification of adjacently located nucleotides. However, by placing the P—S linkage closer to the distal end of the extension probe (i.e., the end opposite to that at which ligation occurs), the nucleotides that are sequentially identified will be spaced at intervals along the template, as described above and shown in FIGS. 1 and 6.

FIG. 6A-6F is a more detailed diagrammatic illustration of several sequencing reactions performed sequentially on a single template. Sequencing is performed in the 3'→5' direction using extension probes containing 3'-S—P—O-5' linkages. Each sequencing reaction comprises multiple cycles of extension, ligation, detection, and cleavage. The reactions utilize initializing oligonucleotides that bind to different portions of the template. The extension probes are 8 nucleotides in length and contain phosphorothiolate linkages located between the $6^{th}$ and $7^{th}$ nucleotides counting from the 3' end of the probe. Nucleotides 2-6 serve as a spacer such that each reaction allows the identification of a plurality of nucleotides spaced at intervals along the template. By performing multiple reactions in series and appropriately combining the partial sequence information obtained from each reaction, the complete sequence of a portion of the template is determined.

Figure 6D:
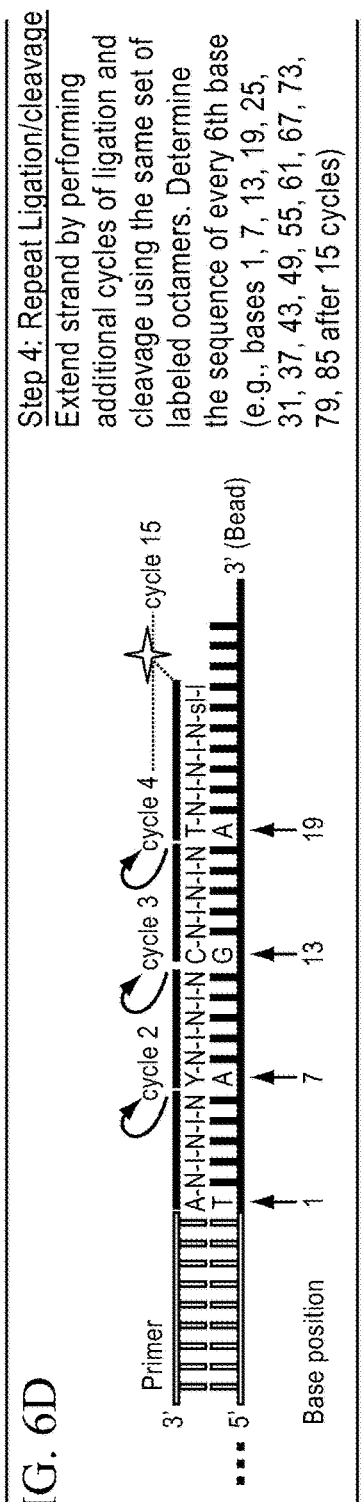

FIG. 6A shows initialization using a first initializing oligonucleotide (referred to as a primer in FIGS. 6A-6F) that is hybridized to an adapter sequence (referred to above as a binding region) in the template to provide an extendable duplex. FIGS. 6B-6D show several cycles of nucleotide identification in which every $6^{th}$ base of the template is read. In FIG. 6B, a first extension probe having a 3' terminal nucleotide complementary to the first unknown nucleotide in the template sequence binds to the template and is ligated to the extendable terminus of the primer. The label attached to the extension probe identifies the probe as having an A as the 3' terminal nucleotide and thus identifies the first unknown nucleotide in the template sequence as A. FIG. 6C shows cleavage of the extension oligonucleotide at the phosphorothiolate linkage with $AgNO_3$ and release of a portion of the extension probe to which a label is attached. FIG. 6D shows additional cycles of extension, ligation, and cleavage. Since the probes contain a spacer 5 nucleotides in length, the sequencing reaction identifies every $6^{th}$ nucleotide in the template.

Figure 6E:
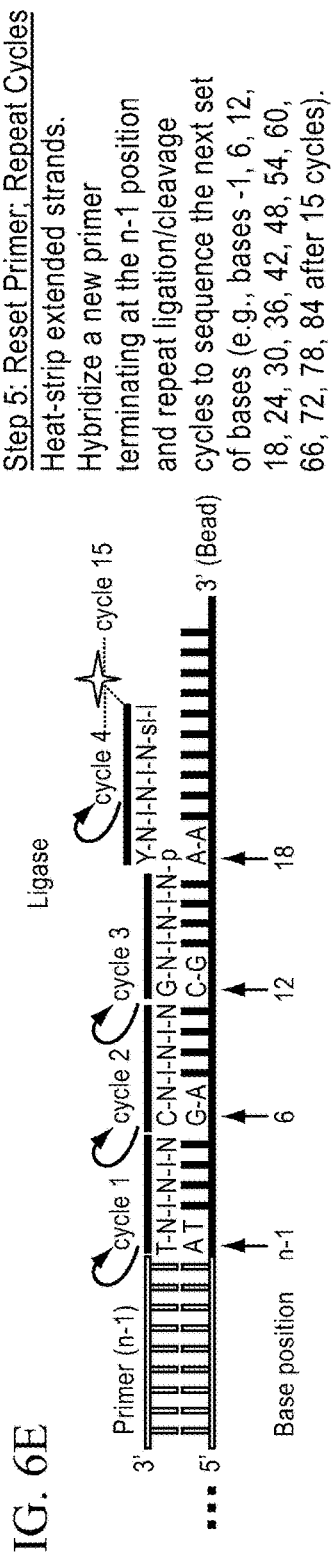
Figure 6F:
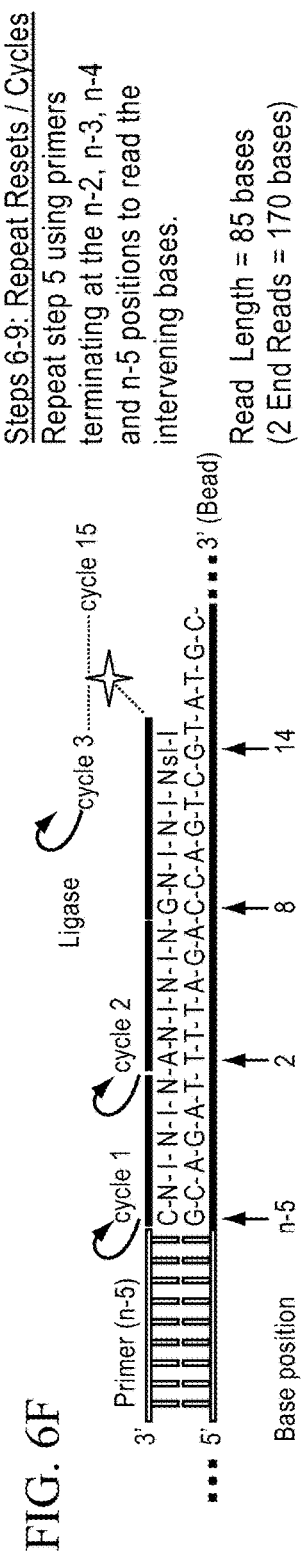

Following a desired number of cycles the extended strand, including the first initializing oligonucleotide, is removed and a second initializing oligonucleotide that binds to a different portion of the binding region from that at which the first initializing oligonucleotide bound, is hybridized to the template. FIG. 6E shows a second sequencing reaction in which initialization is performed with a second initializing oligonucleotide, followed by several cycles of nucleotide identification. FIG. 6F shows initialization using a third initializing oligonucleotide followed by several cycles of nucleotide identification. Extension from the second initializing oligonucleotide allows identification of every $6^{th}$ base in a different "frame" from the nucleotides identified in the first sequencing reaction.

Although extension probes comprising phosphorothiolate linkages are preferred in certain embodiments of the invention, a variety of other scissile linkages may be advantageously employed. For example, a large number of variations on the O—P—O linkage found in naturally occurring nucleic acids are known (see, e.g., Micklefield, J. Curr. Med. Chem., 8:1157-1179, 2001). Any structures described therein that contain a P—O bond can be modified to contain a scissile P—S bond. For example, an NH—P—O bond can be changed to an NH—P—S bond.

In some embodiments of the invention the extension probes comprise a trigger residue that renders the nucleic acid susceptible to cleavage by a cleavage agent or combination thereof, optionally following modification of the trigger residue by a modifying agent. In particular, the inventors have discovered that enzymes involved in DNA repair are advantageous cleavage reagents for use in the practice of methods for sequencing by successive cycles of extension, ligation, detection, and cleavage. In general, the presence of a trigger residue such as a damaged base or abasic residue in an extension probe may render the probe susceptible to cleavage by one or more DNA repair enzymes, optionally following modification by a DNA glycosylase. Thus extension probes comprising linkages that are substrates for cleavage by enzymes involved in DNA repair such as AP endonucleases are of use in the invention. Extension probes containing residues that are substrates for modification by enzymes involved in DNA repair, such as DNA glycosylases, wherein the modification renders the probe susceptible to cleavage by an AP endonuclease, are also of particular use in the invention. In some embodiments the extension probe comprises an abasic residue, i.e., it lacks a purine or pyrimidine base. The linkage between the abasic residue and an adjacent nucleoside is susceptible to cleavage by an AP endonuclease and is therefore a scissile linkage. In certain embodiments of the invention the abasic residue comprises 2' deoxyribose. In some embodiments the extension probe comprises a damaged base. The damaged base is a substrate for an enzyme that removes damaged bases, such as a DNA glycosylase. Following removal of the damaged base, the linkage between the resulting abasic residue and an adjacent nucleoside is susceptible to cleavage by an AP endonuclease and is therefore considered a scissile linkage in accordance with the invention.

Many different AP endonucleases are of use as cleavage reagents in the present invention. Two major classes of AP endonuclease have been distinguished on the basis of the mechanism by which they cleave linkages adjacent to abasic residues. Class I AP endonucleases, such as endonuclease III (Endo III) and endonuclease VIII (Endo VIII) of E. coli and the human homologs hNTH1, NEIL1, NEIL2, and NEIL3, are AP lyases that cleave DNA on the 3' side of the AP residue, resulting in a 5' portion that has a 3' terminal phosphate and a 3' portion that bears a 5' terminal phosphate. Class II AP endonucleases such as endonuclease IV (Endo IV) and exonuclease III (Exo III) of E. coli cleave the DNA 5' of the AP site, which produces a 3' OH and 5' deoxyribose phosphate moiety at the termini of the resulting fragments. See, e.g., Doublie, S., et al., *Proc. Natl. Acad. Sci.* 101(28), 10284-10289, 2004; Haltiwanger, B. M., et al, *Biochem J.*, 345, 85-89, 2000; Levin, J. and Demple, B., *Nucl. Acids. Res,* 18(17), 1990, and references in all of the foregoing for further discussion of various Class I and Class II AP endonucleases and conditions under which they remove damaged bases from DNA and/or cleave DNA containing an abasic residue. One of ordinary skill in the art will appreciate that a variety of homologs of these enzymes exist in other organisms (e.g., yeast) and are of use in the present invention.

Certain enzymes are bifunctional in that they possess both glycosylase activity that removes a damaged base to generate an AP residue and also display a lyase activity that cleaves the phosphodiester backbone 3' to the AP site generated by the glycosylase activity. Thus these dual activity enzymes are both AP endonucleases and DNA glycosylases. For example, Endo VIII acts as both an N-glycosylase and an AP-lyase. The N-glycosylase activity releases damaged pyrimidines from double-stranded DNA, generating an apurinic (AP site). The AP-lyase activity cleaves 3' and 5' to the AP site leaving a 5' phosphate and a 3' phosphate. Damaged bases recognized and removed by Endonuclease VIII include urea, 5,6-dihydroxythymine, thymine glycol, 5-hydroxy-5-methylhydanton, uracil glycol, 6-hydroxy-5,6-dihydrothymine and methyltartronylurea. See, e.g., Dizdaroglu, M., et al., *Biochemistry,* 32, 12105-12111, 1993 and Hatahet, Z. et al., *J. Biol. Chem.,* 269, 18814-18820, 1994; Jiang, D., et al., *J. Biol. Chem.,* 272(51), 32220-32229, 1997; Jiang, D., et al., *J. Bact.,* 179(11), 3773-3782, 1997.

Fpg (formamidopyrimidine [fapy]-DNA glycosylase) (also known as 8-oxoguanine DNA glycosylase) also acts both as a N-glycosylase and an AP-lyase. The N-glycosylase activity releases damaged purines from double stranded DNA, generating an apurinic (AP site). The AP-lyase activity cleaves both 3' and 5' to the AP site thereby removing the AP site and leaving a 1 base gap. Some of the damaged bases recognized and removed by Fpg include 7,8-dihydro-8-oxoguanine (8-oxoguanine), 8-oxoadenine, fapy-guanine, methy-fapy-guanine, fapy-adenine, aflatoxin B1-fapy-guanine, 5-hydroxy-cytosine and 5-hydroxy-uracil. See, e.g., Tchou, J. et al. *J. Biol. Chem.,* 269, 15318-15324, 1994; Hatahet, Z. et al. *J. Biol. Chem.,* 269, 18814-18820, 1994; Boiteux, S., et al, *EMBO J.,* 5, 3177-3183, 1987; Jiang, D., et al., *J. Biol. Chem.,* 272(51), 32220-32229, 1997; Jiang, D., et al., *J. Bact.,* 179(11), 3773-3782, 1997.

A number of DNA glyscosylases and AP endonucleases are commercially available, e.g., from New England Biolabs, Ipswich, Mass.

In some embodiments of the invention extension probes comprising a site that is a substrate for cleavage by an AP endonuclease are used in the sequencing method as described above for extension probes containing a phosphorothiolate linkage or in sequencing methods AB (see below). In any of these methods, following ligation of an extension probe to a growing nucleic acid strand, the extension probe is cleaved using an AP endonuclease to remove the portion of the probe that comprises a label.

Depending on the particular AP endonuclease, and depending on whether sequencing is performed in the 3'→5' or the 5'→3' direction, it may be necessary or desirable to treat the extended duplex with a polynucleotide kinase or a phosphatase following cleavage in order to generate an extendable probe terminus on the extended duplex (see FIGS. 5A and 5B for depiction of extendable probe termini). Thus in certain methods of the invention an extendable terminus is generated by treatment with a polynucleotide kinase or phosphatase. One of ordinary skill in the art will appreciate that appropriate buffers will be employed for the various enzymes, and additional steps of washing may be included to remove enzymes and provide appropriate conditions for subsequent steps in the methods.

In other embodiments the extension probe comprises a damaged base that is a substrate for removal by a DNA glycosylase. A wide range of cytotoxic and mutagenic DNA bases are removed by different DNA glycosylases, which initiate the base excision repair pathway following damage to DNA (Krokan, H. E., et al., *Biochem J.,* 325 (Pt 1):1-16, 1997). DNA glycosylases cleave the N-glycosydic bond between the damaged base and deoxyribose, thus releasing a free base and leaving an apurinic/apyrimidinic (AP) site. In some embodiments the extension probe comprises a uracil residue, which is removed by a uracil-DNA glycosylase (UDG). UDGs are found in all living organisms studied to date, and a large number of these enzymes are known in the art and are of use in this invention (Frederica, et al, *Biochemistry,* 29, 2353-2537, 1990; Krokan, supra). For example, mammalian cells contain at least 4 types of UDG: mitochondrial UNG1 and nuclear UNG2, SMUG1, TDG, and MBD4 (Krokan, et al., *Oncogene,* 21, 8935-8948, 2002). UNG1 and UNG2 belong to a highly conserved family typified by E. coli Ung.

In embodiments in which the extension probe comprises a damaged base, following ligation of the extension probe to an extendable probe terminus, the extended duplex is contacted with a glycosylase that removes the damaged base, thereby producing an abasic residue. An extension probe that comprises a damaged base that is subject to removal by a glycosylase is considered to be "readily modifiable to comprise a scissile linkage". The extended duplex is then contacted with an AP endonuclease, which cleaves a linkage between the abasic residue and an adjacent nucleoside, as described above. In certain embodiments of the invention a dual activity enzyme that is both a DNA glycosylase and an AP endonuclease is used to perform both of these reactions. In some embodiments the extended duplex containing a damaged base is contacted with a DNA glycosylase and an AP endonuclease. The enzymes can be used in combination or sequentially (i.e., glycosylase followed by endonuclease) in various embodiments of the invention.

In some embodiments of the invention an extension probe comprises a trigger residue which is deoxyinosine. As noted above, E. coli Endonuclease V (Endo V), also called deoxyinosine 3' endonuclease, and homologs thereof cleave a nucleic acid containing deoxyinosine at the second phosphodiester bond 3' to the deoxyinosine residue, leaving a 3' OH and 5' phosphate termini. Thus this bond serves as a scissile linkage in the extension probe. Endo V and its cleavage properties are known in the art (Yao, M. and Kow Y. W., *J. Biol. Chem.*, 271, 30672-30673 (1996); Yao, M. and Kow Y. W., *J. Biol. Chem.*, 270, 28609-28616 (1995); He, B, et al., *Mutat. Res.*, 459, 109-114 (2000). In addition to deoxyinosine, Endo V also recognizes deoxyuridine, deoxyxanthosine, and deoxyoxanosine (Hitchcock, T. et al., *Nuc. Acids Res.*, 32(13), 32(13) (2004). Mammalian homologs such as mEndo V also exhibit cleavage activity (Moe, A., et al., *Nuc. Acids Res.*, 31(14), 3893-3900 (2004). While Endo V is a preferred cleavage agent for probes comprising deoxyinosine, other cleavage reagents may also be used to cleave probes comprising deoxyinosine. For example, as a damaged base, hypoxanthine may be subject to removal by an appropriate DNA glycosylase, and the resulting extension probe containing an abasic residue is then subject to cleavage by an endonuclease.

It will be appreciated that if deoxyinosine is used as a trigger residue, it may be desirable to avoid using deoxyinosine elsewhere in the probe, particularly at positions between the terminus that will be ligated to the extendable probe terminus and the trigger residue. Thus if the probe comprises one or more universal bases, a nucleoside other than deoxyinosine may be used. It will also be appreciated that where a trigger residue that renders a nucleic acid containing the trigger residue susceptible to cleavage by a particular cleavage agent is used in an extension probe, it may be desirable to avoid including other residues in the probe (or in other probes that would be used in a sequencing reaction together with that extension probe) that would trigger cleavage by the same cleavage agent.

The present invention encompasses the use of any enzyme that cleaves a nucleic acid that comprises a trigger residue. Additional enzymes may be identified by perusing the catalog of enzyme suppliers such as New England Biolabs®, Inc. The New England Biolabs Catalog, 2005 edition (New England Biolabs, Ipswich, Mass. 01938-2723) is incorporated herein by reference, and the present invention contemplates use of any enzyme disclosed therein that cleaves a nucleic acid containing a trigger residue, or a homolog of such an enzyme. Other enzymes of use include, e.g., hOGG1 and homologs thereof (Radicella, J P, et al., *Proc Natl Acad Sci USA.*, 94(15):8010-5, 1997).

Methods for synthesizing oligonucleotides containing a trigger residue such as a damaged base, abasic residue, etc. are known in the art. Methods for synthesizing oligonucleotides containing site that is a substrate for an AP endonuclease, e.g., oligonucleotides containing an abasic residue are known in the art and are generally amenable to automated solid phase oligonucleotide synthesis. In some embodiments an oligonucleotide containing uridine at the desired location of the abasic residue is synthesized. The oligonucleotide is then treated with an enzyme such as a UDG, which removes uracil, thereby producing an abasic residue wherever uridine was present in the oligonucleotide.

In some embodiments of the invention the oligonucleotide probe comprises a disaccharide nucleoside as described in Nauwelaerts, K., et al, *Nuc. Acids. Res.*, 31(23), 2003. Following ligation, the extended duplex is cleaved using periodate (NaIO$_4$), followed by treatment with base (e.g., NaOH) to remove the label, resulting in a free 3' OH and P5-OPO$_3$H$_2$ group. Depending on whether sequencing is performed in the 3'→5' or 5'→3', it may be necessary or desirable to treat the extended duplex with a polynucleotide kinase or phosphatase to generate an extendable terminus. Thus in certain methods of the invention an extendable terminus is generated by treatment with a polynucleotide kinase or phosphatase.

A polynucleotide comprising a disaccharide nucleoside is considered to comprise an abasic residue. For example, a polynucleotide containing a ribose residue inserted between the 3'OH of one nucleotide and the 5' phosphate group of the next nucleotide is considered to comprise an abasic residue.

Capping

In some cases, fewer than all probes with extendable termini participate in a successful ligation reaction in each cycle of extension, ligation, and cleavage. It will be appreciated that if such probes participated in succeeding cycles, the accuracy of each nucleotide identification step would progressively decline. Although the inventors have shown that use of extension probes containing phophorothiolate linkages allows ligation with high efficiency, in certain embodiments of the invention a capping step is included to prevent those extendable termini that do not undergo ligation from participating in future cycles. When sequencing in the 5'→3' direction using extension probes containing a 3'-O—P—S-5' phosphorothiolate linkage, capping may be performed by extending the unligated extendable termini with a DNA polymerase and a non-extendable moiety, e.g., a chain-terminating nucleotide such as a dideoxynucleotide or a nucleotide with a blocking moiety attached, e.g., following the ligation or detection step. When sequencing in the 3'→5' direction using extension probes containing a 3'-S—P—O-5' phosphorothiolate linkage, capping may be performed, e.g., by treating the template with a phosphatase, e.g., following ligation or detection. Other capping methods may also be used.

H. Sequencing Using Oligonucleotide Probe Families

In the sequencing methods described above, referred to collectively as "Methods A", there is a direct and known correspondence between the label attached to any particular extension probe and the identity of one or more nucleotides at the proximal terminus of the probe (i.e., the terminus that is ligated to the extendable probe terminus of the extended duplex. Therefore, identifying the label of a newly ligated extension probe is sufficient to identify one or more nucleotides in the template. The invention provides additional sequencing methods, referred to collectively as "Methods AB", and also involving successive cycles of extension, ligation, and, preferably, cleavage, that adopt a different approach to nucleotide identification.

The invention provide sequencing methods AB that use a collection of at least two distinguishably labeled oligonucleotide probe families. Each probe family is assigned a name based on the label, e.g., "red", "blue", "yellow", "green". As in the methods described above, extension starts from a duplex formed by an initializing oligonucleotide and a template. The initializing oligonucleotide is extended by ligating an oligonucleotide probe to its end to form an extended duplex, which is then repeatedly extended by successive cycles of ligation. The probe has a non-extendable moiety in a terminal position (at the opposite end of the probe from the nucleotide that is ligated to the growing nucleic acid strand of the duplex) so that only a single extension of the extended duplex takes place in a single cycle. During each cycle, a label on or associated with a successfully ligated probe is detected, and the non-extendable moiety is removed or modified to generate an extendable terminus. Detection of the label identifies the name of the probe family to which the probe belongs.

Successive cycles of extension, ligation, and detection produce an ordered series of label names. The labels correspond to the probe families to which successfully ligated probes that hybridize to the template at successive positions belong. The probes have proximal termini that are located opposite different nucleotides in the template following ligation. Thus there is a correspondence between the order of probe family names and the order of nucleotides in the template.

In embodiments of the invention in which the scissile linkage is located between the proximal nucleoside in the extension probe and the adjacent nucleoside, the ordered list of probe family names may be obtained by successive cycles of extension, ligation, detection, and cleavage that begin from a single initializing oligonucleotide since the extended oligonucleotide probe is extended by one nucleotide in each cycle. If the scissile linkage is located between two of the other nucleosides, the ordered list of probe family names is assembled from results obtained from a plurality of sequencing reactions in which initializing oligonucleotides that hybridize to different positions within the binding reaction are used, as described for sequencing methods A.

Knowing which probe family a newly ligated probe belongs to is not by itself sufficient to determine the identity of a nucleotide in the template. Instead, determining the probe family name eliminates certain combinations of nucleotides as possibilities for the sequence of at least a portion of the probe but leaves at least two possibilities for the identity of each nucleotide. Thus knowledge of the probe family name, in the absence of additional information, leaves open least two possibilities for the identity of the nucleotides in the template that are located at opposite positions to the nucleotides in the newly ligated probe. Therefore any single cycle of extension, ligation, detection (and, optionally, cleavage) does not itself identify any nucleotide in the template. However, it does allow elimination of one or more possible sequences for the template and thereby provides information about the sequence. In certain embodiments of the invention, with appropriate design of the probes and probe families as described below, the sequence of the template can still be determined. In certain embodiments of the invention sequencing methods AB thus comprise two phases: a first phase in which an ordered list of probe family names is obtained, and a second phase in which the ordered list is decoded to determine the sequence of the template.

Unless otherwise indicated, sequencing methods A and AB generally employ similar methods for synthesizing probes, preparing templates, and performing the steps of extension, ligation, cleavage, and detection.

Features of Oligonucleotide Extension Probes and Probe Families for Sequencing Methods AB Probe families for use in sequencing methods AB are characterized in that each probe family comprises a plurality of labeled oligonucleotide probes of different sequence and, at each position in the sequence, a probe family comprises at least 2 probes having different bases at that position. Probes in each probe family comprise the same label. Preferably the probes comprise a scissile internucleoside linkage. The scissile linkage can be located anywhere in the probe. Preferably the probes have a moiety that is not extendable by ligase at one terminus. Preferably the probes are labeled at a position between the scissile linkage and the moiety that is not extendable by ligase, such that cleavage of the scissile linkage following ligation of a probe to an extendable probe terminus results in an unlabeled portion that is ligated to the extendable probe terminus and a labeled portion that is no longer attached to the unlabeled portion.

The probes in each probe family preferably comprise at least j nucleosides X, wherein j is at least 2, and wherein each X is at least 2-fold degenerate among the probes in the probe family. Probes in each probe family further comprise at least k nucleosides N, wherein k is at least 2, and wherein N represents any nucleoside. In general, j+k is equal to or less than 100, typically less than or equal to 30. Nucleosides X can be located anywhere in the probe. Nucleosides X need not be located at contiguous positions. Similarly nucleosides N need not be located at contiguous positions. In other words, nucleosides X and N can be interspersed. Nevertheless, nucleosides X can be considered to have a 5'→3' sequence, with the understanding that the nucleosides need not be contiguous. For example, nucleosides X in a probe of structure $X_A NX_G NNX_C N$ would be considered to have the sequence AGC. Similarly, nucleosides N can be considered to have a sequence.

Nucleosides X can be identical or different but are not independently selected, i.e., the identity of each X is constrained by the identity of one or more other nucleosides X in the probe. Thus in general only certain combinations of nucleosides X are present in any particular probe and within the probes in any particular probe family. In other words, in each probe, the sequences of nucleosides X can only represent a subset of all possible sequences of length j. Thus the identity of one or more nucleotides in X limits the possible identities for one or more of the other nucleosides.

Nucleosides N are preferably independently selected and can be A, G, C, or T (or, optionally, a degeneracy-reducing nucleoside). Preferably the sequence of nucleosides N represents all possible sequences of length k, except that one or more N may be a degeneracy-reducing nucleoside. The probes thus contain two portions, of which the portion consisting of nucleosides N is referred to as the unconstrained portion and the portion consisting of nucleosides X is referred to as the constrained portion. As described above, the portions need not be contiguous nucleosides. Probes that contain a constrained portion and an unconstrained portion are referred to herein as partially constrained probes. Preferably one or more nucleosides in the constrained portion is at the proximal end of the probes, i.e., at the end that contains the nucleoside that will be ligated to the extendable probe terminus, which can be either the 5' or 3' end of the oligonucleotide probe in different embodiments of the invention.

Since the constrained portion of any oligonucleotide probe can only have certain sequences, knowing the identity of one or more of the nucleosides in the constrained portion of a probe provides information about one or more of the other nucleosides. The information may or may not be sufficient to precisely identify one or more of the other nucleosides, but it will be sufficient to eliminate one or more possibilities for the identity of one or more of the other nucleosides in the constrained portion. In certain preferred embodiments of sequencing methods AB, knowing the identity of one nucleoside in the constrained portion of a probe is sufficient to precisely identify each of the other nucleosides in the constrained portion, i.e., to determine the identity and order of the nucleosides that comprise the constrained portion.

As in the sequencing methods described above, the most proximal nucleoside in an extension probe that is complementary to the template is ligated to an extendable terminus of an initializing oligonucleotide (in the first cycle of extension, ligation, and detection) and to an extendable terminus of an extended oligonucleotide probe in subsequent cycles of extension, ligation, and detection. Detection determines the name of the probe family to which the newly ligated probe belongs. Since each position in the constrained portion of the probe is at least 2-fold degenerate, the name of the probe family does not in itself identify any nucleotide in the constrained portion. However, since the sequence of the constrained portion is one of a subset of all possible sequences of length j, identifying the probe family does eliminate certain possibilities for the sequence of the constrained portion. The constrained portion of the probe constitutes its sequence determining portion. Therefore, eliminating one or more possibilities for the identity of one or more nucleosides in the constrained portion of the probe by identifying the probe family to which it belongs eliminates one or more possibilities for the identity of a nucleotide in the template to which the extension probe hybridizes. In preferred embodiments of the invention the partially constrained probes comprise a scissile linkage between any two nucleosides.

In certain embodiments the partially constrained probes have the general structure $(X)_j(N)_k$, in which X represents a nucleoside, $(X)_j$ is at least 2-fold degenerate at each position such that X can be any of at least 2 nucleosides having different base-pairing specificities, N represents any nucleoside, j is at least 2, k is between 1 and 100, and at least one N or X other than the X at the probe terminus comprises a detectable moiety. Preferably $(N)_k$ is independently 4-fold degenerate at each position so that, in each probe, $(N)_k$ represents all possible sequences of length k, except that one or more positions in $(N)_k$ may be occupied by a degeneracy-reducing nucleotide. Nucleosides in $(X)_j$ can be identical or different but are not independently selected. In other words, in each probe, $(X)_j$ can only represent a subset of all possible sequences of length j. Thus the identity of one or more nucleotides in $(X)_j$ limits the possible identities for one or more of the other nucleosides. The probes thus contain two portions, of which $(N)_k$ is the unconstrained portion and $(X)_j$ is the constrained portion.

In certain preferred embodiments of the invention the partially constrained probes have the structure 5'-$(X)_j(N)_kN_B$*-3' or 3'-$(X)_j(N)_kN_B$*-5', wherein N represents any nucleoside, $N_B$ represents a moiety that is not extendable by ligase, * represents a detectable moiety, $(X)_j$ is a constrained portion of the probe that is at least 2-fold degenerate at each position, nucleosides in $(X)_j$ can be identical or different but are not independently selected, at least one internucleoside linkage is a scissile linkage, j is at least 2, and k is between 1 and 100, with the proviso that a detectable moiety may be present on any nucleoside N or X other than the X at the probe terminus instead of, or in addition to, $N_B$. The scissile linkage can be between two nucleosides in $(X)_j$, between the most distal nucleotide in $(X)_j$ and the most proximal nucleoside in $(N)_k$, between nucleosides within $(N)_k$, or between the terminal nucleoside in $(N)_k$ and $N_B$. Preferably the scissile linkage is a phosphorothiolate linkage.

In yet more preferred embodiments of the invention the probes have the structure 5'-(XY)$(N)_kN_B$*-3' or 3'-(XY)$(N)_kN_B$*-5', wherein N represents any nucleoside, $N_B$ represents a moiety that is not extendable by ligase, * represents a detectable moiety, XY is a constrained portion of the probe in which X and Y represent nucleosides that are identical or different but are not independently selected, X and Y are at least 2-fold degenerate, at least one internucleoside linkage is a scissile linkage, and k is between 1 and 100, inclusive, with the proviso that a detectable moiety may be present on any nucleotide N or X other than the X at the probe terminus instead of, or in addition to, $N_B$. Preferably the scissile linkage is a phosphorothiolate linkage. Probes having the structure 5'-(XY)$(N)_kN_B$*-3' are of use for sequencing in the 5'→3' direction. Probes having the structure 3'-(XY)$(N)_kN_B$*-5' are of use for sequencing in the 3'→5' direction.

The structure of certain preferred probes is represented in more detail as follows. For sequencing in the 5'→3' direction, partially constrained probes having the structure 5'-O—P—O—$(X)_j(N)_k$—O—P—S—$(N)_iN_B$*-3' where N represents any nucleoside, $N_B$ represents a moiety that is not extendable by ligase, * represents a detectable moiety, $(X)_j$ is a constrained portion of the probe that is at least 2-fold degenerate at each position, nucleosides in $(X)_j$ can be identical or different but are not independently selected, j is at least 2, (k+i) is between 1 and 100, k is between 1 and 100, and i is between 0 and 99, with the proviso that a detectable moiety may be present on any nucleoside of $(N)_i$ instead of, or in addition to, $N_B$. In certain embodiments of the invention $(X)_j$ is (XY) in which X and Y are at least 2-fold degenerate and represent nucleotides that are identical or different but are not independently selected. In certain embodiments of the invention i is 0.

Other preferred probes for sequencing in the 5'→3' direction have the structure 5'-O—P—O—$(X)_j$—O—P—S—$(N)_iN_B$*-3' in which N represents any nucleoside, $N_B$ represents a moiety that is not extendable by ligase, * represents a detectable moiety, $(X)_j$ is a constrained portion of the probe that is at least 2-fold degenerate at each position, nucleotides in $(X)_j$ can be identical or different but are not independently selected, j is at least 2, and i is between 1 and 100, with the proviso that a detectable moiety may be present on any nucleoside of $(N)_i$ instead of, or in addition to, $N_B$. In certain embodiments of the invention $(X)_j$ is (XY), in which positions X and Y are at least 2-fold degenerate and X and Y represent nucleosides that are identical or different but are not independently selected. Yet other preferred probes for sequencing in the 5'→3' direction have the structure 5'-O—P—O—$(X)_j$—O—P—S—$(X)_k(N)_iN_B$*-3' in which N represents any nucleoside, $N_B$ represents a moiety that is not extendable by ligase, * represents a detectable moiety, $(X)_j$—O—P—S—$(X)_k$ is a constrained portion of the probe that is at least 2-fold degenerate at each position, positions in $(X)_j$—O—P—S—$(X)_k$ are at least 2-fold degenerate and can be identical or different but are not independently selected, j and k are both at least 1 and (j+k) is at least 2 (e.g., 2, 3, 4, or 5), and i is between 1 and 100, with the proviso that a detectable moiety may be present on any nucleoside of $(N)_i$ instead of, or in addition to, $N_B$. In certain embodiments of the invention j and k are both 1.

For sequencing in the 3'→5' direction, partially constrained probes having the structure 5'-$N_B$*(N)$_i$—S—P—O—(N)$_k$—O—P—O—(X)$_j$-3' where N represents any nucleoside, $N_B$ represents a moiety that is not extendable by ligase, * represents a detectable moiety, (X)$_j$ is a constrained portion of the probe that is at least 2-fold degenerate at each position, nucleosides in (X)$_j$ can be identical or different but are not independently selected, j is at least 2, (k+i) is between 1 and 100, k is between 1 and 100, and i is between 0 and 99, with the proviso that a detectable moiety may be present on any nucleoside of (N)$_i$ instead of, or in addition to, $N_B$. In certain embodiments of the invention (X)$_j$ is (XY) in which X and Y are at least 2-fold degenerate and represent nucleosides that are identical or different but are not independently selected. In certain embodiments of the invention i is 0.

Other preferred probes for sequencing in the 3'→5' direction have the structure 5'-$N_B$*(N)$_i$—S—P—O—(X)$_j$-3' in which N represents any nucleoside, $N_B$ represents a moiety that is not extendable by ligase, * represents a detectable moiety, (X)$_j$ is a constrained portion of the probe that is at least 2-fold degenerate at each position, nucleosides in (X)$_j$ can be identical or different but are not independently selected, j is at least 2, and i is between 1 and 100, with the proviso that a detectable moiety may be present on any nucleoside of (N)$_i$ instead of, or in addition to, $N_B$. In certain embodiments of the invention (X)$_j$ is (XY) in which X and Y are at least 2-fold degenerate and represent nucleosides that are identical or different but are not independently selected. In certain embodiments of the invention j is between 2 and 5, e.g., 2, 3, 4, or 5, in any of the partially constrained probes.

Yet other preferred probes for sequencing in the 3'→5' direction have the structure 5'-$N_B$*(N)$_i$—S—P—O—(X)$_k$—O—P—O—(X)$_j$-3' where N represents any nucleoside, $N_B$ represents a moiety that is not extendable by ligase, * represents a detectable moiety, —(X)$_k$—O—P—O—(X)$_j$ is a constrained portion of the probe that is at least 2-fold degenerate at each position, nucleosides in —(X)$_k$—O—P—O—(X)$_j$ can be identical or different but are not independently selected, j and k are both at least 1 and (j+k) is at least 2 (e.g., 2, 3, 4, or 5), i is between 1 and 100, with the proviso that a detectable moiety may be present on any nucleoside of (N)$_i$ instead of, or in addition to, $N_B$. In certain embodiments j=1 and k=1.

In embodiments of the invention in which the scissile linkage is located between the most proximal nucleoside in (X)$_j$ and the next most proximal nucleoside in (X)$_j$, the ordered list of probe family names may be obtained by successive cycles of extension, ligation, detection, and cleavage that begin from a single initializing oligonucleotide since the extended oligonucleotide probe is extended by one nucleotide in each cycle. In embodiments of the invention in which the scissile linkage is located between two of the other nucleosides, the ordered list of probe family names is assembled from results obtained from a plurality of sequencing reactions in which initializing oligonucleotides that hybridize to different positions within the binding reaction are used, as described for sequencing methods A.

It will be understood that probes having any of a large number of structures other than those described above can be employed in sequencing methods AB. For example, probes can have structures such as XNY(N)$_k$ in which the constrained nucleosides X and Y are not adjacent, or XIY(N)$_k$ where I is a universal base. (N)$_k$X(N)$_l$, (N)$_i$X(N)$_j$Y (N)$_k$Z(N)$_l$, (N)$_i$X(N)$_j$YIZ(N)$_l$, and (N)$_i$X(N)$_j$Y(N)$_k$Z(I)$_l$ represent additional possibilities. As in the probes described above, these probes comprise a scissile linkage, a detectable moiety, and a moiety at one terminus that is not extendable by ligase. Preferably the probes do not comprise a detectable moiety attached to the nucleotide at the opposite end of the probe from the moiety that is not extendable by ligase. Probe families comprising probes having any of these structures, or others, satisfy the criterion that each probe family comprises a plurality of labeled probes of different sequence and, at each position in the sequence, a probe family comprises at least 2 probes having different bases at that position. Preferably the total number of nucleosides in each probe is 100 or less, e.g., 30 or less.

Encoding Oligonucleotide Extension Probe Families.

The inventive sequencing method makes use of encoded probe families. An "encoding" refers to a scheme that associates a particular label with a probe comprising a portion that has one of a defined set of sequences, such that probes comprising a portion that has a sequence that is a member of the defined set of sequences are labeled with the label. In general, an encoding associates each of a plurality of distinguishable labels with one or more probes, such that each distinguishable label is associated with a different group of probes, and each probe is labeled by only a single label (which can comprise a combination of detectable moieties). Preferably the probes in each group of probes each comprise a portion that has a sequence that is a member of the same defined set of sequences. The portion may be a single nucleoside or may be multiple nucleosides in length, e.g., 2, 3, 4, 5, or more nucleosides in length. The length of the portion may constitute only a small fraction of the entire length of the probe or may constitute up to the entire probe. The defined set of sequences may contain only a single sequence or may contain any number of different sequences, depending on the length of the portion. For example, if the portion is a single nucleoside, the defined set of sequences could have at most 4 elements (A, G, C, T). If the portion is two nucleosides in length, the defined set of sequences could have up to 16 elements (AA, AG, AC, AT, GA, GG, GC, GT, CA, CG, CC, CT, TA, TG, TC, TT). In general, the defined set of sequences will contain fewer elements than the total number of possible sequences, and an encoding will employ more than one defined set of sequences.

Sequencing methods A described herein generally make use of a set of probes having a simple encoding in which there is a direct correspondence between the proximal nucleoside in the probe (i.e., the nucleoside that is ligated to the extendable probe terminus) and the identity of the label. The proximal nucleoside is complementary to the nucleotide with which it hybridizes in the template, so the identity of the proximal nucleoside in a newly ligated probe determines the identity of the nucleotide in the template that is located at the opposite position in the extended duplex. In a general sense, probes of use in the other sequencing methods described herein have the structure X(N)$_k$, in which X is the proximal nucleoside, and each nucleoside N is 4-fold degenerate, such that all possible sequences of length k are represented in the pool of oligonucleotide probe molecules that constitutes the probe. Thus, for example, some oligonucleotide probe molecules will contain A at position k=1, others will contain G at position k=1, others will contain C at position k=1, others will contain T at position k=1, and similarly for other positions k, where the nucleoside adjacent to X in (N)$_k$ is considered to occupy position k=1; the next nucleoside in (N)$_k$ is considered to occupy position k=2, etc. However, in any given oligonucleotide probe, X represents only a single base pairing specificity, which typically corresponds to a particular nucleoside identity, e.g., A, G, C, or T. Thus X is typically uniformly A, G, C, or T in the pool of probe molecules that constitute a particular probe. FIG. 2 shows a suitable encoding for probes having the structure $X(N)_k$. According to this encoding, probes having X=C are assigned the label "red"; probes having X=A are assigned the label "yellow"; probes having X=G are assigned the label "green"; and probes having X=T are assigned the label "blue". Thus there is a one-to-one correspondence between the sequence determining portion of the probe and its label.

It will be appreciated that the above approach in which the identity of the label of a newly ligated extension probe corresponds to the identity of the most proximal nucleoside in the extension probe may be broadened to encompass encodings in which the identity of the label corresponds not to the identity of only the most proximal nucleoside in the extension probe but rather to the sequence of the most proximal 2 or more nucleosides in the extension probe, so that the identity of multiple nucleotides in the template can be determined in a single cycle of extension, ligation, and detection (typically followed by cleavage). However, such encodings would still associate a label with a single sequence in the oligonucleotide extension probe so that the identity of the oppositely located complementary nucleotides in the template could be identified. For example, as described above, in order to identify two nucleotides in a single cycle, 16 different oligonucleotide probes, each with a corresponding label (i.e., 16 distinguishable labels) would be needed.

Sequencing method AB employs an alternative approach to associating labels with probes. Rather than a one-to-one correspondence between the identity of the label and the sequence of the sequence determining portion of the probe, the same label is assigned to multiple probes having different sequence determining portions. The probes are partially constrained, and the constrained portion of the probe is its sequence determining portion. Thus the same label is assigned to a plurality of different probes, each having a constrained portion with a different sequence, wherein the sequence is one of a defined set of sequences. As mentioned above, probes comprising the same label constitute a "probe family". The method employs a plurality of such probe families, each comprising a plurality of probes having a constrained portion with a different sequence, wherein the sequence is one of a defined set of sequences.

A plurality of probe families is referred to as a "collection" of probe families. Probes in each probe family in a collection of probe families are labeled with a label that is distinguishable from labels used to label other probe families in the collection. Each probe family preferably has its own defined set of sequences. Preferably the constrained portions of the probes in each probe family are the same length, and preferably the constrained portions of probe families in a collection of probe families are of the same length. Preferably the combination of sets of defined sequences for probe families in a collection of probe families includes all possible sequences of the length of the constrained portion. Preferably a collection of probe families comprises or consists of 4 distinguishably labeled probe families. Preferably the constrained portion of the probes is 2 nucleosides in length.

A wide variety of differently encoded collections of distinguishably labeled probe families will satisfy the above criteria and may be used to practice the inventive method. However, certain collections of probe families are preferred. An exemplary encoding for a preferred collection of 4 distinguishably labeled probe families comprising partially constrained probes is shown in FIG. 25A. As depicted in FIG. 25A, the constrained portion consists of the 2 most 3' nucleosides in the probe. The probe families are labeled "red", "yellow", "green", and "blue". Probes in each probe family comprise a constrained portion whose sequence is one of a defined set of sequences, the defined set being different for each probe family. For example, beginning at the 3' end of each sequence, which is considered to be the proximal end of the probe, the defined set of sequences for the "red" probe family is {CT, AG, GA, TC}; the defined set of sequences for the "yellow" probe family is {CC, AT, GG, TA}; the defined set of sequences for the "green" probe family is {CA, AC, GT, TG}; the defined set of sequences for the "blue" probe family is {CG, AA, GC, TT}. Each defined set does not contain any member that is present in one of the other sets, a characteristic that is preferred. In addition, the combination of sets of defined sequences for probe families in a collection of probe families includes all possible sequences of length 2, i.e., all possible dinucleosides. Another characteristic of this collection of probe families, which is preferred but not required, is that each position in the constrained portion of the probes is 4-fold degenerate, i.e., it can be occupied by either A, G, C, or T. Another characteristic of this collection of probe families, which is preferred but not required, is that within each set of defined sequences only a single sequence has any specific nucleoside at any position, e.g., at the most proximal position or at any of other positions. It is particularly preferred, but not required, that within each set of defined sequences only a single sequence has any specific nucleoside at position 2 or higher within the constrained portion, considering the most proximal nucleoside to be at position 1. For example, in the defined set of sequences for the Red probe family, only one sequence has T at position 2; only one sequence has G at position 2; only one sequence has A at position 2; only one sequence has C at position 2.

Given any particular encoding such as that depicted in FIG. 25A, knowing the identity of one or more nucleosides in the constrained portion of a probe in one of the probe families provides information about the other nucleotides in the constrained portion of that probe. In the most general sense, knowing the identity of one or more nucleosides in the constrained portion of a probe in a probe family provides sufficient information to eliminate one or more possible identities for a nucleoside at one of the other positions, because the defined set of sequences for that probe family will not contain a sequence having a nucleoside with that identity at that position. Typically knowing the identity of one or more nucleosides in the constrained portion of a probe in a probe family provides sufficient information to eliminate one or more possible identities for a plurality of nucleosides, e.g., each of the other nucleosides. For preferred encodings, knowing the identity of one or more nucleosides in the constrained portion of a probe in the probe family eliminates all but one possibility for each of the other nucleosides in the probe. For example, in the case of the encoded probe families shown in FIG. 25A, if it is known that a probe is a member of the red family, and if it is also known that the most proximal nucleoside is C, then the adjacent nucleoside must be T. Similarly, if it is known that a probe is a member of the green family, and if it is also known that the most proximal nucleoside is G, then the adjacent nucleoside must be T. Thus knowing the identity of one nucleoside in the constrained portion is sufficient to eliminate all possibilities for the other nucleoside except one, so the identity of the other nucleoside is completely specified. Yet without knowing the identity of at least one nucleoside in the constrained portion of a probe it is not possible to gain any information at all about the identity of any specific nucleoside in the probe based only on knowing the name of the probe family to which it belongs since the nucleoside at each position of the constrained portion could be A, G, C, or T. FIG. 25B shows a preferred collection of probe families (upper panel) and a cycle of ligation, detection, and cleavage (lower panel) using sequencing methods AB.

The inventors have designed 24 collections of probe families containing constrained portions that are 2 nucleosides in length and that have the advantageous features of the collection of probe families depicted in FIG. 25A. These probe families are maximally informative in that knowing the name of the probe family to which a probe belongs, and knowing the identity of one nucleoside in the probe, is sufficient to precisely identify the other nucleoside in the constrained portion. This is the case for all probes, and for all nucleosides in each constrained portion. The encoding schemes for each of the 24 preferred collections of probe families are shown in Table 1. Table 1 assigns an encoding ID ranging from 1 to 24 to each collection of probe families. Each encoding defines the constrained portions of a collection of preferred probe families of general structure $(XY)N_k$ for use in sequencing methods AB, and thereby defines the collection itself. In Table 1 a value of 1 in the column under an encoding ID indicates that, according to that encoding, a probe comprising nucleosides X and Y as indicated in the first and second columns, respectively, is assigned to the first probe family; (ii) a value of 2 in the column under an encoding ID indicates that, according to that encoding, a probe comprising nucleosides X and Y as indicated in the first and second columns, respectively, is assigned to the second probe family; (iii) a value of 3 in the column under an encoding ID indicates that, according to that encoding, a probe comprising nucleosides X and Y as indicated in the first and second columns, respectively, is assigned to the third probe family; and (iv) a value of 4 in the column under an encoding ID indicates that, according to that encoding, a probe comprising nucleosides X and Y as indicated in the first and second columns, respectively, is assigned to the fourth probe family. The values 1, 2, 3, and 4, each represent a label. For example, encoding 9 defines the collection of probe families depicted in FIG. 25A, in which 1 represents blue, 2 represents green, 3 represents red, and 4 represents yellow. It will be appreciated that the assignment of values to labels is arbitrary, e.g., 1 could equally well represent green, red, or yellow. Changing the association between values 1, 2, 3, and 4, and the labels would not change the set of probes in each probe families but would merely associate a different label with each probe family.

17. According to this encoding, probes having constrained portions AA, GC, TG, and CT are assigned to label 1 (e.g., red); probes having constrained portions CA, AC, GG, and TT are assigned to label 2 (e.g., yellow); probes having constrained portions TA, CC, AG, and GT are assigned to label 3 (e.g., green); and probes having constrained portions GA, TC, CG, and AT are assigned to label 4 (e.g., blue). The resulting collection of probe families is depicted in FIG. 26.

FIGS. 27A-27C represent an alternate method to schematically define the 24 preferred collections of probe families. The method makes use of diagrams such as that in FIG. 27A. The first column in such a diagram represents the first base. Each label is attached to four different base sequences, each of which is given by juxtaposing the base from the first column with the base from the chosen label's column. For example, if there is an A in the column with the heading "First base", then a probe with constrained portion having sequence AA is assigned to probe family 1 (label 1); a probe with constrained portion having sequence AC is assigned to probe family 2 (label 2); a probe with constrained portion having sequence AG is assigned to probe family 3 (label 3); and a probe with constrained portion having sequence AT is assigned to probe family 4 (label 4). Assignments to probe families are made in a similar manner for probes with constrained portions beginning with C, G, or T. Thus a diagram filled in with bases as shown in FIG. 27A translates to the encoding shown in FIG. 27B, in which probes having constrained portions in the set {AA, CC, GG, TT} are assigned to probe family 1; probes having constrained portions in the set {AC, CA, GT, TG} are assigned to probe family 2; probes having constrained portions in the set {AG, CT, GC, TA} are assigned to probe family 3; and probes having constrained portions in the set {AT, CG, GA, TC} are assigned to probe family 4. FIG. 27C shows diagrams that may be inserted in place of the shaded portion of the diagram in FIG. 27A in order to generate each of the 24 preferred collections of probe families. Methods of using the preferred collections of probe families in sequencing methods AB are described further below.

The 24 collections of encoded probe families defined by Table 1 represent only the preferred embodiments of collections of probe families for use in sequencing methods AB. A wide variety of other encoding schemes, probe families, and probe structures can be used that employ the same basic

TABLE 1

Oligonucleotide Probe Family Encodings
Encoding ID

| 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
|---|---|---|---|---|---|---|---|---|---|---|---|---|---|---|---|---|---|---|---|---|---|---|---|
| 2 | 4 | 3 | 2 | 2 | 4 | 3 | 2 | 2 | 3 | 4 | 3 | 2 | 3 | 3 | 4 | 2 | 3 | 4 | 4 | 2 | 4 | 3 | 4 |
| 4 | 3 | 2 | 3 | 3 | 2 | 4 | 4 | 3 | 2 | 2 | 4 | 4 | 2 | 4 | 3 | 4 | 2 | 3 | 2 | 3 | 2 | 4 | 3 |
| 3 | 2 | 4 | 4 | 4 | 3 | 2 | 3 | 4 | 4 | 3 | 2 | 3 | 4 | 2 | 2 | 3 | 4 | 2 | 3 | 4 | 3 | 2 | 2 |
| 2 | 2 | 2 | 2 | 2 | 2 | 2 | 2 | 2 | 2 | 2 | 2 | 2 | 2 | 2 | 2 | 2 | 2 | 2 | 2 | 2 | 2 | 2 | 2 |
| 1 | 1 | 1 | 1 | 1 | 1 | 1 | 1 | 4 | 4 | 3 | 4 | 4 | 4 | 4 | 3 | 3 | 4 | 3 | 3 | 3 | 3 | 4 | 3 |
| 3 | 4 | 4 | 4 | 4 | 3 | 3 | 3 | 1 | 1 | 1 | 1 | 3 | 3 | 3 | 4 | 1 | 1 | 1 | 1 | 4 | 4 | 3 | 4 |
| 4 | 3 | 3 | 3 | 3 | 4 | 4 | 4 | 3 | 3 | 4 | 3 | 1 | 1 | 1 | 1 | 4 | 3 | 4 | 4 | 1 | 1 | 1 | 1 |
| 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| 4 | 2 | 4 | 4 | 4 | 2 | 4 | 4 | 1 | 1 | 1 | 1 | 1 | 1 | 1 | 4 | 2 | 2 | 2 | 4 | 2 | 2 | 2 | 2 |
| 1 | 1 | 1 | 1 | 2 | 4 | 2 | 2 | 4 | 4 | 4 | 2 | 4 | 2 | 2 | 2 | 4 | 4 | 4 | 1 | 1 | 1 | 1 | 1 |
| 2 | 4 | 2 | 2 | 1 | 1 | 1 | 1 | 2 | 2 | 2 | 4 | 4 | 2 | 4 | 4 | 1 | 1 | 1 | 1 | 2 | 4 | 4 | 4 |
| 4 | 4 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| 3 | 3 | 2 | 3 | 3 | 3 | 2 | 3 | 3 | 2 | 2 | 2 | 3 | 2 | 2 | 2 | 1 | 1 | 1 | 1 | 1 | 1 | 1 | 1 |
| 2 | 2 | 3 | 2 | 1 | 1 | 1 | 1 | 2 | 3 | 3 | 3 | 1 | 1 | 3 | 1 | 3 | 2 | 3 | 2 | 3 | 2 | 2 | 2 |
| 1 | 1 | 1 | 1 | 2 | 2 | 3 | 2 | 1 | 1 | 1 | 1 | 2 | 3 | 1 | 3 | 2 | 3 | 2 | 3 | 2 | 3 | 3 | 3 |

To further illustrate the use of Table 1 to define the collections of preferred probe families, consider encoding principle, in which knowing a probe family name, together with knowledge of the identity of one or more nucleosides in a constrained portion, provides information about one or more other nucleosides. As compared with a preferred collection of probe families, the less preferred collections of probe families are generally less preferred because: (i) at least with respect to some probes, the amount of information afforded by knowing a probe family name and a nucleoside identity is less; or (ii) at least with respect to some probes, the amount of information afforded by knowing a probe family name is more.

In general, less preferred collections of probe families may be used to perform sequencing methods AB in a similar manner to the way in which preferred collections of probe families are used. However, the steps needed for decoding may differ. For example, in some situations comparing candidate sequences with each other may be sufficient to determine at least a portion of a sequence.

An example of a less preferred collection of probe families in which the probes comprise constrained portions that are 2 nucleosides in length is shown in FIG. 28. According to this encoding, probes having constrained portions in the set {AA, AC, GA, GC} are assigned to probe family 1; probes having constrained portions in the set {CA, CC, TA, TC} are assigned to probe family 2; probes having constrained portions in the set {AG, AT, GG, GT} are assigned to probe family 3; and probes having constrained portions in the set {CG, CT, TG, TT} are assigned to probe family 4. In this collection of probe families, knowing the name of a probe family eliminates certain possibilities for the identity of a nucleotide in the template that is located opposite the proximal nucleoside in a newly ligated extension probe whose label was detected to determine the name of the probe family. For example, if the probe family name is 1, then the proximal nucleoside in a newly ligated extension probe must be A or G, so the complementary nucleotide in the template must be T or C. Since there are at least two possibilities at each position in the constrained portion, the nucleotide cannot be precisely identified, but information sufficient to rule out some possibilities is obtained from the single cycle, in contrast to the situation when preferred collections of probe families are employed.

In certain embodiments of the invention partially constrained probes in which the constrained portion is 3 nucleosides in length are used. In order to contain probes whose constrained portions include all possible sequences of length 3, as is preferred, the collection of probe families should comprise $4^3=64$ different probes. FIG. 29A shows a diagram that can be used to generate constrained portions for a collection of probe families that comprises probes with a constrained portion 3 nucleosides long (trinucleosides). The figure shows 4 sets of rows indicated A, G, C, and T, and 4 columns with probe family names 1, 2, 3, and 4. Each set of 4 rows is opposite a box with a nucleoside identity inside. To determine a probe family for a trinucleoside, the box containing the last nucleoside in the trinucleoside is first selected. Within the four rows adjacent to that box, the row labeled with the letter identifying the first nucleoside in the trinucleoside is selected. Within that row, the column containing the second nucleoside of the trinucleoside is selected. The trinucleoside is assigned to the probe family indicated at the top of the column. For example, the following procedure is followed to assign the trinucleoside "TCG" to a probe family: Since the last nucleoside is a "G", attention is confined to the set of 4 rows located opposite the box containing "G", i.e., the third set of rows. Since the first nucleoside is "T", consideration is further limited to the last row in the set of 4. The probe family assignment is determined by the heading of the column that contains middle nucleoside. Since the middle nucleoside is "C", the trinucleoside is assigned to probe family 1. A similar process yields the following probe family assignments: AAA=1; ATA=2; AGA=3; GTA=4; GAG=1; TGG=2, etc. The process continues until all possible trinucleosides have been assigned to a probe family.

FIG. 29B shows a procedure for constructing additional constrained portions for a collection of probe families that comprises probes with a constrained portion 3 nucleosides long. The procedure is used to construct such a collection from each of the 24 preferred collections of probe families described above, in which constrained portions are 2 nucleosides in length and the collection contains 4 probe families. An exemplary diagram representing a preferred collection of probe families is shown in the upper portion of the figure. The columns of this diagram map directly into the columns of the lower portion of the figure in accordance with the color assigned to each column in the upper diagram. Thus the columns in the upper diagram are blue, green, yellow, and red, moving from left to right. The entries under column 1 in the lower diagram are blue, green, yellow, and red, moving from top to bottom, with each set of 4 nucleosides corresponding to a column in the upper diagram. Columns 2, 3, and 4 in the lower diagram are generated by progressively moving each set of 4 nucleosides in column 1 downwards.

It will be appreciated that a "probe family" can be considered to be a single "super-probe" comprising a plurality of different probes, each with the same label. In this case, the probe molecules that constitute the probe will generally not be a population of substantially identical molecules across any portion of the probe. Use of the term "probe family" is not intended to have any limiting effect but is used for convenience to describe the characteristics of probes that would constitute such a "super-probe".

Decoding

As described above, successive cycles of extension, ligation, detection, and cleavage using a collection of probe families comprising at least two distinguishably labeled probe families yields an ordered list of probe family names either from a single sequencing reaction or from assembling probe family names determined in multiple sequencing reactions that initiate from different sites in the template into an ordered list. The number of cycles performed should be approximately equivalent to the length of sequence desired. The ordered list contains a substantial amount of information but not in a form that will immediately yield the sequence of interest. Further step(s), at least one of which involves gathering at least one item of additional information about the sequence, must be performed in order to obtain a sequence that is most likely to represent the sequence of interest. The sequence that is most likely to represent the sequence of interest is referred to herein as the "correct" sequence, and the process of extracting the correct sequence from the ordered list of probe families is referred to as "decoding". It will be appreciated that elements in an "ordered list" as described above could be rearranged either during generation of the list or thereafter, provided that the information content, including the correspondence between elements in the list and nucleotides in the template, is retained, and provided that the rearrangement, fragmentation, and/or permutation is appropriately taken into consideration during the decoding process (discussed below). The term "ordered list" is thus intended to encompass rearranged, fragmented, and/or permuted versions of an ordered list generated as described above, provided that such rearranged, fragmented, and/or permuted versions include substantially the same information content.

The ordered list can be decoded using a variety of approaches. Some of these approaches involve generating a set of at least one candidate sequence from the ordered list of probe family names. The set of candidate sequences may provide sufficient information to achieve an objective. In preferred embodiments one or more additional steps are performed to select the sequence that is most likely to represent the sequence of interest from among the candidate sequences or from a set of sequences with which the candidate sequence is compared. For example, in one approach at least a portion of at least one candidate sequence is compared with at least one other sequence. The correct sequence is selected based on the comparison. In certain embodiments of the invention, decoding involves repeating the method and obtaining a second ordered list of probe family names using a collection of probe families that is encoded differently from the original collection of probe families. Information from the second ordered list of probe families is used to determine the correct sequence. In some embodiments information obtained from as little as one cycle of extension, ligation, and detection using the alternately encoded collection of probe families is sufficient to allow selection of the correct sequence. In other words, the first probe family identified using the alternately encoded probe family provides sufficient information to determine which candidate sequence is correct.

Other decoding approaches involve specifically identifying at least one nucleotide in the template by any available sequencing method, e.g., a single cycle of sequencing method A. Information about the one or more nucleotide(s) is used as a "key" to decode the ordered list of probe family names. Alternately, the portion of the template that is sequenced may comprise a region of known sequence in addition to a region whose sequence is unknown. If sequencing methods AB are applied to a portion of the template that includes both unknown sequence and at least one nucleotide of known sequence, the known sequence can be used as a "key" to decode the ordered list of probe family names. The following section describes the process of generating candidate sequences. Subsequent sections describe using the candidate sequences to select the correct sequence by comparing with known sequences, by comparing with a second set of candidate sequences, and by utilizing a known nucleotide identity.

Generating Candidate Sequences

It will be appreciated that the region of the template to be sequenced is complementary to the extended duplex that is produced by successive cycles of extension, ligation, and cleavage. Therefore, generating a candidate sequence for the extended duplex is equivalent to generating a candidate sequence for the region of the template to be sequenced. In practice, one could generate candidate sequences for the region of the template to be sequenced, or one could generate candidate sequences for the extended duplex and take their complement to determine candidate sequences for the region of the template to be sequenced. The latter approach is described here. To generate a candidate sequence from a list of probe family names, the first member of the list of probe families is considered. The set of constrained portions associated with that probe family limits the possibilities for the initial nucleotides in the sequence, out to a length equivalent to the length of the constrained portion. For example, if the constrained portion is a dinucleotide, then the possible sequences for the first dinucleotide in the extended duplex are limited to those constrained portions that occur in probes that fall within that probe family (and thus the possible sequences for the first dinucleotide in the region of the template to be sequenced are limited to those combinations that are complementary to the constrained portions that occur in probes that fall within that probe family). The possibilities for the first dinucleotide are recorded, typically by a computer. Similarly, the possible sequences for the second dinucleotide in the extended duplex (i.e., the dinucleotide that is one nucleotide offset from the first dinucleotide) are limited to those constrained portions that occur in probes that fall within the second probe family (and therefore, the possible sequences for the second dinucleotide in the template, i.e., the dinucleotide that is one nucleotide offset from the first dinucleotide are limited to those combinations that are complementary to the constrained portions that occur in probes that fall within the second probe family). The possible sequences for the second dinucleotide are also recorded. Possibilities for succeeding dinucleotides are likewise recorded until possibilities have been recorded for dinucleotides that correspond to the desired length of the sequence to be determined or there are no more probe families in the list.

A representative example of the process of recording possibilities is depicted in FIG. 30, in which it is assumed that a list of probe family names has been generated using the probe family collection shown in FIG. 25A. The leftmost column of FIG. 30 shows the list of probe families in order from top to bottom: Yellow, Green, Red, Blue. The sequence possibilities for the dinucleotide corresponding to each probe family in the list are shown on the right side of the figure. Nucleotide positions are indicated above the sequence possibilities. The sequence begins at position 1, so the first dinucleotide occupies positions 1 and 2; the second dinucleotide occupies positions 2 and 3, etc. For the Yellow probe family, the possibilities are CC, AT, GG, and TA, as shown in FIG. 30. For the Green probe family, the possibilities are CA, AC, GT, and TG, etc. The process of recording the possible sequences of each dinucleotide is continued until a desired sequence length has been reached.

After the sets of possibilities are generated, a first assumption is made about the identity of the first nucleotide in the candidate sequence, which is assumed to be at the 5' position of the sequence, indicated as position 1 in FIG. 30. The first assumption can be that the nucleotide is A, that the nucleotide is G, that the nucleotide is C, or that the nucleotide is T.

It will be observed that the possible sequences for each dinucleotide are limited by the possible sequences of the adjacent dinucleotides, since adjacent dinucleotides overlap, i.e., the second nucleotide of the first dinucleotide is also the first nucleotide of the second dinucleotide. For example, if the first nucleotide is assumed to be C, then the first dinucleotide must be CC. If the first dinucleotide is CC, then the second dinucleotide must have a C at its first position. Since the only possible sequence for the second dinucleotide that has a C at its first position is CA, it is evident that the second dinucleotide must be CA. Therefore the sequence of the first 3 nucleotides must be CCA. Similarly, the possible sequences for the third dinucleotide are limited by the possible sequences of the second dinucleotide. If the second dinucleotide is CA, then the third dinucleotide must be AG since that is the only possibility that has A at its first position. Thus the sequence of the first 4 nucleotides must be CCAG. Continuing this process results in a sequence of 5'-CCAGC-3' for the first 5 nucleotides. CCAGC is thus the first candidate sequence.

A second candidate sequence is generated by assuming that the first nucleotide is A. This assumption yields AT for the first dinucleotide. TG is the only possible sequence for the second dinucleotide that is consistent with a sequence of AT for the first dinucleotide. GA is the only possible sequence for the third dinucleotide that is consistent with a sequence of TG for the second dinucleotide. AA is the only possible sequence for the fourth dinucleotide that is consistent with a sequence of GA for the third dinucleotide. Assembling these dinucleotides into a full length candidate sequence yields ATGAA. Similarly, an assumption that the first nucleotide is a G yields the candidate sequence GGTCG, and an assumption that the first nucleotide is a T yields the candidate sequence TACTT. Thus 4 candidate sequences are generated, each beginning with a different nucleotide assumed to be the first nucleotide in the sequence.

There is no requirement that the assumption must be made about the first nucleotide rather than one of the other nucleotides. For example, an assumption could equally well have been made about the identity of the fourth nucleotide, in which case the candidate sequences would have been generated by moving "backwards" along the template (i.e., in a 3'→5' direction). For example, assuming that the fourth nucleotide is T means that the fourth dinucleotide must be TT; the third dinucleotide must be CT; the second dinucleotide must be AC; and the first dinucleotide must be CC. (Nucleotides are written in the 5'→3' orientation although their identities are generated by moving from 3'→5' in the sequence.) Alternately, an assumption can be made about any nucleotide in the middle of the sequence, and dinucleotide identities generated by moving both in the 5'→3' and the 3'→5 directions. It will be appreciated that in the absence of an assumption about one of the nucleotides, the identity of each nucleotide remains completely undetermined since each position could be occupied by A, G, C, or T.

When using preferred collections of probe families, assuming the identity of any single nucleotide (e.g., the first nucleotide) generates one and only one candidate sequence. However, when less preferred collections of probe families are used it may be necessary to assume an identity for more than one nucleotide, i.e., assuming an identity for a first nucleotide does not entirely specify the rest of the sequence. For example, a less preferred collection of probe families may include a family with members whose defined sequences are AA and AC. In such a case, assuming that the first nucleotide is A leaves two possibilities for the second nucleotide. Sequencing using less preferred collections of probe families is discussed further below. It will be appreciated that if the constrained portions consist of noncontiguous nucleotides, the approach described above can still be used with minor modifications.

Sequence Identification by Comparing Candidate Sequences with Known Sequences

Generally if the candidate sequences of the extended duplexes were determined, as described above, corresponding candidate sequences for the region of the template to be sequenced are obtained by taking their complements. In some instances, the candidate sequences themselves will provide enough information to achieve an objective. For example, if the purpose of sequencing is simply to rule out certain sequence possibilities, then comparing the candidate sequences with those possibilities would be sufficient. The candidate sequences shown in FIG. 30 would allow a determination that the region being sequenced was not part of a polyA tail, for example. A longer sequence could confirm that the region being sequenced was not part of a vector.

In many instances it will be desirable to explicitly determine the correct sequence. According to a preferred embodiment of the invention the correct sequence is identified by comparing the candidate sequences for the region of the template to be sequenced with a set of known sequences. The set of known sequences may, for example, be a set of sequences for a particular organism of interest. For example, if human DNA is being sequenced, then the candidate sequences can be compared with the Human Draft Genome Sequence. See the web site having URL www.ncbi.nih.gov/genome/guide/human/for a guide to publicly available human genome sequence resources As another example, if nucleic acid derived from an infectious agent (e.g., a bacterium or virus isolated from a subject) is being sequenced, a database containing sequences of variant strains of that bacterium or virus can be searched. Many such organism-specific databases, containing either complete or partial sequences, are known in the art, and more will become available as sequencing efforts accelerate. Some representative examples include databases for the mouse (see, e.g., the web site having URL www.ncbi.nlm.nih.gov/genome/seq/MmHome.html), human immunodeficiency virus (see, e.g., the web site having URL hiv-web.lanl.gov/content/hiv-db/mainpage.html), malaria species *Plasmodium falciparum* (see, e.g., the web site having URL www.tigr.org/tdb/edb2/pfa1/htmls/index.shtml), etc. Of course it is not necessary to use an organism-specific set of sequences. A database such as GenBank (web site having URL www.ncbi.nlm.nih.gov/Genbank/), which contains sequences from a wide variety of organisms and viruses, can be searched. The database need not even contain any sequences from the organism or virus from which the template was derived. In general, the sequences can be genomic sequences, cDNA sequences, ESTs, etc. Multiple sequences can be searched.

Simply performing the search may be sufficient to achieve an objective. For example, if viral nucleic acid is isolated from a patient, comparing the candidate sequences with a set of known sequences of that virus can determine that the viral nucleic acid either does or does not contain sequences from that virus, even if the matching sequence is never examined. The existence of a match would confirm that the patient is infected with the virus, while lack of a match would indicate that the patient is not infected with the virus.

In certain embodiments the set of known sequences contains a narrower range of sequences, which may be specifically tailored to the purpose for which the sequencing is performed. Thus information about the nucleic acid being sequenced may be used to select the set of known sequences. For example, if it is known that the template represents sequence of a particular gene, the known sequences may represent different alleles of a gene, mutant and wild type sequences at a given locus of interest, etc. It may only be necessary to compare the candidate sequences with a single known sequence to determine which of the candidate sequences is correct. For example, in certain embodiments of the invention the template is obtained by amplifying DNA that contains a region of interest (e.g., using primers that flank the region of interest). The region of interest may encompass a site at which mutations or polymorphisms may exist, e.g., mutations or polymorphisms that are associated with a particular disease. If it is known that the template represents a sequence from a particular region of interest, then the candidate sequences need only be compared with a single reference sequence for that region, e.g., a wild type or mutant form of the sequence. In other words, if part or all of the sequence of the template is known, it may not be necessary to perform a comparison with a plurality of known sequences. Instead, a candidate sequence that comprises all or part of the known sequence is selected as correct. For example, mutations in the BRCA1 and BRCA2 genes are known to be associated with an increased risk of breast cancer, and there is significant interest in determining whether subjects carry such mutations. If it is known that the template comprises sequence from the BRCA1 gene, e.g., if primers flanking a region of interest that encompasses a portion of the gene were used to produce a clonal population of templates, then the candidate sequences need only be compared against the wild type or mutant BRCA1 sequence to determine the correct sequence.

In the more general case, comparing the candidate sequences with the set of known sequences will identify any known sequences that are similar to any of the candidate sequences. Provided that the candidate sequences are of sufficient length, the likelihood that a database will contain sequences that is identical to or closely resemble more than one of the candidate sequences are very small. In other words, if the candidate sequences are long enough, it is unlikely that more than one of them will be represented in the set of known sequences. The candidate sequences are compared with any sequences that are considered to be a "match". It will typically be desirable to set a threshold for the degree of identity required to establish that a match exists. For example, a known sequence may be considered to be a match if a candidate sequence and the known sequence are at least 50%, at least 60%, at least 70%, at least 80%, at least 90%, at least 95%, at least 99%, or even 100% identical. Typically the percent identity will be evaluated over a window of at least 10 nucleotides in length, e.g, 10-15 nucleotides, 15-20 nucleotides, 20-25 nucleotides, 25-30 nucleotides, etc. The length of the window may be selected according to a variety of different criteria including, but not limited to, the number of sequences in the plurality of known sequences, the identity or source of the plurality of known sequences, etc. For example, if a candidate sequence is being compared against sequences in a large database such as GenBank, it may be desirable to use a longer length than if a database containing fewer sequences is used. In certain embodiments of the invention sequences are compared across a plurality of different windows, not necessarily adjacent to one another. Preferably the combined length of the windows is at least 10 nucleotides in length, e.g, 10-15 nucleotides, 15-20 nucleotides, 20-25 nucleotides, 25-30 nucleotides, etc. In some instances multiple sequences in the set of known sequences may match. The sequences may, for example, represent homologous genes found in the same organism as that from which the template was derived, homologous genes from different organisms, pseudogenes, cDNA and genomic sequences, etc.

In general, the candidate sequence that most closely resembles a sequence in the set of known sequences is selected as correct. Alternately, e.g., if there is reason to believe that the sequencing method may have been subject to a high error rate it may be preferable to select the corresponding sequence from the database as correct. For example, if the error rate is known to be above a predetermined threshold it may be preferable to select a sequence from the database as the correct sequence.

The length required in order to ensure that the likelihood of matches being found for multiple candidate sequences will depend on a variety of considerations including, but not limited to, the particular set of known sequences, the threshold for accepting matches, etc. In general, a sequence of length ~25-26 nucleotides would only be represented once in the genome of a typical organism. Therefore generating candidate sequences of approximately this length is sufficient to identify the correct sequence. In general, the candidate sequence should be at least 10 nucleotides in length, preferably at least 15, at least 20 nucleotides in length, e.g., between 20-25, 25-30, 30-35, 35-40, 45-50, or even longer.

Sequence Identification by Comparing a First Set of Candidate Sequences with a Second Set of Candidate Sequences In certain embodiments of the invention decoding is performed by generating a first ordered list of probe families using a first collection of probe families encoded according to a first encoding, generating a first set of candidate sequences therefrom and then generating a second ordered list of probe families from the same template using a second collection of probe families encoded according to a second encoding and generating a second set of candidate sequences therefrom. The newly synthesized DNA strand is removed from the template between the two sequencing reactions, or a template of identical sequence is sequenced using the second collection of probe families. The sets of candidate sequences are compared. It will be appreciated that regardless of which collection of probe families is used, one of the candidate sequences will be the correct sequence while the others are not correct (or are at best partially correct). Thus every set of candidate sequences will contain the correct sequence, but in most cases the other candidate sequences in any given set candidate sequences will differ from those found in another set of candidate sequences. Therefore, by simply comparing the two sets of candidate sequences, the correct sequence can be determined. It is not necessary to generate candidate sequences of equal length using the two differently encoded collections of probe families. In preferred embodiments of the invention the candidate sequences generated using the second collection of probe families can be as short as 2 nucleotides or, equivalently, the ordered list of probe families generated using the second collection of probe families can be as short as 1 element (i.e., a single cycle of ligation and detection).

FIGS. 31A-31C show an example of candidate sequence generation and decoding using two distinguishably labeled preferred probe families. FIG. 31A shows a preferred collection of probe families encoded according to a first encoding. FIG. 31B shows generation of 4 candidate sequences from the ordered list of probe families Yellow, Green, Red, Blue (which could be represented as "2314" in which Red=1, Yellow=2, Green=3, and Blue=4), of which the correct sequence is assumed to be CAGGC (shown in bold). FIG. 31C shows a preferred collection of probe families encoded according to a second encoding. Since the first dinucleotide in the template is CA, the uppermost probe in the Yellow probe family will ligate to the extendable terminus in the first cycle of extension. This results in the following set of candidate sequences for the first dinucleotide: CA, TC, GG, AT. Among the candidate sequences generated using the first collection of probe families, only the sequence CAGGC begins with any of these dinucleotides. Therefore it must be the correct sequence. In general, it is preferred that the first and second collections of probe families should fulfill the following criteria: When the first and second collections of probe families are compared, (i) 3 of the 4 probes in each of the probe families in the first collection should be assigned to a new probe family in the second collection; and (ii) each of the 3 reassigned probes should be assigned to a different probe family in the second collection.

Using a Known Nucleotide Identity to Decode an Ordered List of Probe Families

As described above, candidate sequences can be generated by assuming an identity for a single nucleotide in the extended duplex or template. Depending on the specific probe family collection used, it will generally be necessary to generate at least 4 candidate sequences. However, generation of multiple candidate sequences can be avoided if the identity of at least one nucleotide in the template (and therefore also in the extended duplex) is known. In that case, it will only be necessary to generate a single candidate sequence. The method for generating the candidate sequence is identical to that described above. The identity of the at least one nucleotide in the template may be determined using any sequencing method including, but not limited to sequencing methods A, primer extension from an initializing oligonucleotide using a set of distinguishably labeled nucleotides and a polymerase, etc. It will be appreciated that one or more nucleotides in the template can first be sequenced using a sequencing method other than sequencing method AB, and the initializing oligonucleotide and any extension products can then be removed, and the same template subjected to sequencing using sequencing methods AB (or vice versa).

Another approach is to simply sequence a template that contains one or more known nucleotides of known identity in addition to a portion whose sequence is to be determined. For example, the portion of the template between the region to which the initializing oligonucleotide binds and at which the unknown sequence begins can include one or more nucleotides of known identity. By subjecting this portion of the template to sequencing methods AB, the identity of one or more nucleotides in the sequence will be predetermined and can thus be used to generate a single candidate sequence, which will be the correct sequence.

The methods described above therefore comprise steps of (i) assigning an identity to a nucleotide in the template adjacent to a nucleotide of known identity by determining which identity is consistent with the identity of the known nucleotide and the possible sequences of the constrained portion of the probe whose proximal nucleotide ligated opposite the nucleotide adjacent to the nucleotide of known identity; (ii) assigning an identity to a succeeding nucleotide by determining which identity is consistent with possible sequences of the constrained portion of the probe whose proximal nucleotide ligated opposite the succeeding nucleotide; and (iii) repeating step (ii) until the sequence is determined. It is to be understood that these steps are equivalent to performing the same steps on the extended duplex since there is a precise correspondence between the extended duplex and the region of the template to be sequenced.

Sequencing with Less Preferred Probe Families

Less preferred collections of probe families may be used to perform sequencing methods AB in a similar manner to the way in which preferred collections of probe families are used. However, the results may differ in a number of respects. For example, certain portions of the sequence may be fully identified from the candidate sequences without the need for additional information. FIG. 32 shows an example of sequence determination using a less preferred collection of probe families encoded as shown in FIG. 28. Sequence determination generally proceeds as described for preferred collections of probe families. The template of interest has the sequence "GCATGA", which results in "12341" as the ordered list of probe families. Assuming that the nucleotide at position 1 is A yields "ACATGA" as a candidate sequence. However, unlike the case with the preferred collections of probe families, there are two possibilities for the second nucleotide since the label "1" is associated with two different dinucleotides that have A as the first nucleotide, i.e., "AA" and "AG". Thus assuming that the nucleotide at position 1 is A yields "ACATGC" as a second candidate sequence. Assuming that the nucleotide at position 1 is G yields "GCATGA" as a candidate sequence and also yields "GCATGC" as a candidate sequence. Since the label "1" is not associated with any dinucleotides that have C or T at position 1, no candidate sequences beginning with "C" or "T" are generated. FIG. 32 shows the 4 candidate sequences aligned with each other. It will be observed that the middle 4 nucleotides of all the candidate sequences are CATG. Therefore, the correct sequence must include CATG at positions 2-5. If only these nucleotides are of interest, there is no need to perform further decoding steps.

As mentioned above, collections of probe families need not consist of four different probe families but can consist of any number greater than 2, up to $4^N$, where N is the length of the constrained portion. However, if fewer than 4 families are used it may be necessary to generate more than 4 candidate sequences, while if more than 4 probe families are used additional labels will be required. For these and other reasons collections consisting of 4 probe families are preferred.

Sequence Identification by Comparing Candidate Sequences with Each Other

In certain embodiments of the invention part or all of a sequence of interest may be determined by comparing candidate sequences with each other. In general, such a comparison may not be sufficient to determine which of the candidate sequences is correct across its entire length. However, if two or more of the candidate sequences are identical or sufficiently similar over a portion of the sequences, this information may be sufficient to explicitly identify the sequence of nucleotides in the template within that portion as described above.

If desired, the template can be sequenced one or more additional times using alternatively encoded probe families to yield additional portions with an identified sequence. These portions can be combined to assemble a sequence of a desired length.

Error Correction Using Probe Families.

It is often desirable to sequence multiple templates that represent all or part of the same DNA sequence and to align the sequences. If the templates contain only part of a region of interest, a longer sequence is then obtained by assembling overlapping fragments. For example, when sequencing the genome of an organism, typically the DNA is fragmented, and enough fragments are sequenced so that each stretch of DNA is represented in several (e.g., 4-12) different fragments. Computer software for assembling overlapping sequences into a longer sequence is known to one of skill in the art.

When conventional sequencing methods are used, it is frequently the case that multiple fragments align perfectly over a region except that one of the fragments (referred to as an anomalous fragment) differs from the others at a single position within the region. Determining whether the isolated difference represents a sequencing error or whether a genuine difference (e.g., a single nucleotide polymorphism) exists at the position the can be problematic.

The invention provides novel methods of performing error checking using sequencing methods AB. According to the method, templates comprising fragments that represent the same stretch of DNA are sequenced using a collection of distinguishably labeled probe families as described above, resulting in an ordered list of probe families for each template. The ordered lists of probe families are aligned. If several lists align perfectly over a predetermined length, e.g., 10, 15, 20, or 25 or more elements in the lists, except for one list that differs at a single position from the other fragments, the difference is ascribed to a sequencing error. If an actual polymorphism exists, the ordered probe list generated from the anomalous fragment will differ at two or more adjacent positions from the ordered probe lists generated from the other fragments.

For example, applying sequencing methods AB using a preferred collecting of probe families that uses encoding 4 in Table 1 to a template comprising the sequence 5'-CAGAC-GACAAGTATAATG-3' (SEQ ID NO. 1) yields the following ordered list of probe families: "23324322132444142", as shown below:

```
23324322132444142
                          (SEQ ID NO. 1)
CAGACGACAAGTATAATG
```

If there is an actual SNP (e.g., CAGACGA GAAGTATAATG (SEQ ID NO. 2)), in which the underlined nucleotide represents the polymorphic site), it results in changes in two consecutive elements in the list: 233243 33132444142, in which underlining indicates the change that occurs as a result of the SNP. The correspondence between the ordered list of probe families and sequence containing a SNP is shown below:

```
23324333132444142
                          (SEQ ID NO. 2)
CAGACGAGAAGTATAATG
```

However, an error in identifying the label associated with a ligated extension probe results in a single error in the ordered list of probe families and a change in the resulting candidate sequence from that point forward. For example, an error in determining the label associated with the 7$^{th}$ ligated extension probe 23324332132444142 (in which the underlined number represents the misidentified label) changes the resulting candidate sequence to CAGACGA GTTCATATTAC (SEQ ID NO. 3), in which the underlined portion indicates the change that occurs as a result of the sequencing error. The correspondence between the ordered list of probe families and the sequence is shown below:

```
23324332132444142
                          (SEQ ID NO. 3)
CAGACGAGTTCATATTAC
```

When using a 3 base, 4 label scheme, a fragment that contains a SNP results in 3 consecutive differences in the ordered list of probe families for the anomalous fragment, while a sequencing error results in only 1 difference. For example, when the collection of probe families encoded as shown in FIG. 29 is used, an ordered list of probe family identities for the sequence CAGACGACAAGTATAATG (SEQ ID NO. 1) is shown below:

```
2322224132412244
                          (SEQ ID NO. 1)
CAGACGACAAGTATAATG
```

An anomalous fragment containing a SNP, e.g., CAGACGAGAAGTATAATG (SEQ ID NO. 2), would result in an ordered list of probe families that differs at 3 consecutive positions relative to ordered lists generated from fragments that do not contain the SNP, as shown below:

```
2322213332412244
                          (SEQ ID NO. 2)
CAGACGAGAAGTATAATG
```

A sequencing error would result in only a single difference in the ordered list of probe families and would result in a completely different generated candidate sequence from the point of the error forward.

Thus when an ordered list of probe families generated from a fragment (an anomalous fragment) aligns with ordered lists of probe families generated from other fragments that represent the same stretch of DNA but differs from the other ordered lists at a single isolated position, it is likely that the ordered list containing the difference represents a sequencing error (misidentification of a probe family). When an ordered list of probe families generated from a fragment (an anomalous fragment) aligns with ordered lists of probe families generated from other fragments that represent the same stretch of DNA but differs from the other ordered lists at 2 or more consecutive positions, it is likely that the anomalous fragment contains a SNP. Preferably the aligned portions of the ordered lists of probe families are at least 3 or 4 elements in length, preferably at least 6, 8, or more elements in length. Preferably the aligned portions are at least 66% identical, at least 70% identical, at least 80% identical, at least 90% identical, or more, e.g., 100% identical.

Similarly, when a candidate sequence for a fragment aligns with candidate sequences for other fragments that represent the same stretch of DNA over a first portion of the sequence but differs substantially from candidate sequences for other fragments over a second portion of the sequence, is it likely that a sequencing error occurred. When a candidate sequence for a fragment aligns with candidate sequences for other fragments that represent the same stretch of DNA over two portions of the sequence but differ at a single position, it is likely that the anomalous fragment contains a SNP. Preferably the aligned portions of the candidate sequences are at least 4 nucleotides in length. Preferably the aligned portions are at least 66% identical, at least 70% identical, at least 80% identical, at least 90% identical, or more, e.g., 100% identical.

The invention therefore provides a method of distinguishing a single nucleotide polymorphism from a sequencing error comprising steps of: (a) sequencing a plurality of templates using sequencing methods AB, wherein the templates represent overlapping fragments of a single nucleic acid sequence; (b) aligning the sequences obtained in step (a); and (c) determining that a difference between the sequences represents a sequencing error if the sequences are substantially identical across a first portion and substantially different across a second portion, each portion having a length of at least 3 nucleotides. The invention further provides a method of distinguishing a single nucleotide polymorphism from a sequencing error comprising steps of: (a) obtaining a plurality of ordered lists of probe families by performing sequencing methods AB using a plurality of templates that represent overlapping fragments of a single nucleic acid sequence; (b) aligning the ordered lists of probe families obtained in step (a) to obtain an aligned region within which the lists are at least 90% identical; and (c) determining that a difference between the ordered lists of probe families represents a sequencing error if the lists differ at only one position within the aligned region; or (d) determining that a difference between the ordered lists of probe families represents a single nucleotide polymorphism if the lists differ at two or more consecutive positions within the aligned region.

Delocalized Information Collection

As is well known in the art, a "bit" (binary digit) refers to a single digit number in base 2, in other words, either a 1 or a zero, and represent the smallest unit of digital data. Since a nucleotide can have any of 4 different identities, it will be appreciated that specifying the identity of a nucleotide requires 2 bits. For example, A, G, C, and T could be represented as 00, 01, 10, and 11, respectively. Specifying the name of a probe family in a preferred collection of distinguishably labeled probe families requires 2 bits since there are four distinguishably labeled probe families.

In most conventional forms of sequencing, and in sequencing methods A, each nucleotide is identified as a discrete unit, and information corresponding to one nucleotide at a time is gathered. Each detection step acquires two bits of information from a single nucleotide. In contrast, sequencing methods AB acquire less than two bits of information from each of a plurality of nucleotides in each detection step while still acquiring 2 bits of information per detection step when a preferred collection of probe families is used. Each probe family name in an ordered list of probe families represents the identity of at least 2 nucleotides in the template, with the exact number being determined by the length of the sequence determining portion of the probes. For example, consider the ordered list of probe families obtained from the sequence 5'-CAGACGACAAG-TATAATG-3' (SEQ ID NO. 1) using a collection of probe families encoded according to encoding 4 in Table 1:

```
23324322132444142
                              (SEQ ID NO. 1)
CAGACGACAAGTATAATG
```

Probe family 2 is the first probe family in the list since the dinucleotide CA is one of the specified portions present in probes of probe family 2. Probe family 3 is the second probe family in the list since the dinucleotide AG is one of the specified portions present in probes of probe family 3. As mentioned above, since there are 4 probe families, each probe family identity represents 2 bits of information. Thus each detection step gathers 2 bits of information about 2 nucleotides, resulting in an average of 1 bit of information from each nucleotide.

The invention therefore provides a method for determining a sequence, wherein the method comprises multiple cycles of extension, ligation, and detection, and wherein the detecting step comprises simultaneously acquiring an average of two bits of information from each of at least two nucleotides in the template without acquiring two bits of information from any individual nucleotide. The invention further provides a method for determining a sequence of nucleotides in a template polynucleotide using a first collection of oligonucleotide probe families, the method comprising the steps of: (a) performing sequential cycles of extension, ligation, detection, and cleavage, wherein an average of two bits of information are simultaneously acquired from each of at least two nucleotides in the template during each cycle without acquiring two bits of information from any individual nucleotide; and (b) combining the information obtained in step (a) with at least one bit of additional information to determine the sequence. In various embodiments of the invention the at least one bit of additional information comprises an item selected from the group consisting of: the identity of a nucleotide in the template, information obtained by comparing a candidate sequence with at least one known sequence; and information obtained by repeating the method using a second collection of oligonucleotide probe families.

Thus while the methods do not acquire 2 bits of information from individual nucleotides, an average of 2 bits of information is gathered from the template in each cycle, but in a delocalized manner when preferred collections of probe families are used. When using collections of 2 or 3 probe families, less than 2 bits of information are gathered during each cycle.

Delocalized information collection has a number of advantages including allowing the application of error checking methods such as those described above. In addition, since each nucleotide in the template is interrogated more than once in preferred embodiments, delocalized information collection can help avoid systematic biases in detecting fluorophores associated with particular nucleotides.

The probe families and collections of probe families described herein can be used in a variety of sequencing methods in addition to methods that involve successive cycles of extension, ligation, and cleavage of the probe. The invention also provides probe families and collections of probe families having the sequences and structures as described above, wherein the probes optionally do not contain a scissile linkage. For example, the probes can contain only phosphodiester backbone linkages and/or may not contain a trigger residue. In some embodiments of the invention the probe families are used to perform sequencing using successive cycles of extension and ligation, but not involving cleavage during each cycle. For example, the probe families can be used in a ligation-based method such as that described in WO2005021786 and elsewhere in the art. To use the probe families in such a method, the label on the probe should be attached by a cleavable linker, e.g., as disclosed in in WO2005021786, such that it can be removed without cleaving a scissile linkage of the nucleic acid. Such a method can be used to generate an ordered list of probe families, e.g., by performing multiple reactions in parallel or sequentially, using the probe families rather than the ligation cassettes described in WO2005021786, and then assembling the list of probe families. The list is decoded as described above.

I. Kits

A variety of kits may be provided for carrying out different embodiments of the invention. Certain of the kits include extension oligonucleotide probes comprising a phosphorothiolate linkage. The kits may further include one or more initializing oligonucleotides. The kits may contain a cleavage reagent suitable for cleaving phosphororothiolate linkages, e.g., $AgNO_3$ and appropriate buffers in which to perform the cleavage. Certain of the kits include extension oligonucleotide probes comprising a trigger residue such as a nucleoside containing a damaged base or an abasic residue. The kits may further include one or more initializing oligonucleotides. The kits may contain a cleavage reagent suitable for cleaving a linkage between a nucleoside and an adjacent abasic residue and/or a reagent suitable for removing a damaged base from a polynucleotide, e.g., a DNA glycosylase. Certain kits contain oligonucleotide probes that comprise a disaccharide nucleotide and contain periodate as a cleavage reagent. In certain embodiments the kits contain a collection of distinguishably labeled oligonucleotide probe families.

Kits may further include ligation reagents (e.g., ligase, buffers, etc.) and instructions for practicing the particular embodiment of the invention. Appropriate buffers for the other enzymes that may be used, e.g., phosphatase, polymerases, may be included. In some cases, these buffers may be identical. Kits may also include a support, e.g. magnetic beads, for anchoring templates. The beads may be functionalized with a primer for performing PCR amplification. Other optional components include washing solutions; vectors for inserting templates for PCR amplification; PCR reagents such as amplification primers, thermostable polymerase, nucleotides; reagents for preparing an emulsion; reagents for preparing a gel, etc.

In certain preferred kits, fluorescently labeled oligonucleotide probes comprising phosphorothiolate linkages are provided such that probes corresponding to different terminal nucleotides of the probe carry distinct spectrally resolvable fluorescent dyes. More preferably, four such probes are provided that allow a one-to-one correspondence between each of four spectrally resolvable fluorescent dyes and the four possible terminal nucleotides of a probe.

An identifier, e.g., a bar code, radio frequency ID tag, etc., may be present in or on the kit. The identifier can be used, e.g., to uniquely identify the kit for purposes of quality control, inventory control, tracking, movement between workstations, etc.

Kits will generally include one or more vessels or containers so that certain of the individual reagents may be separately housed. The kits may also include a means for enclosing the individual containers in relatively close confinement for commercial sale, e.g., a plastic box, in which instructions, packaging materials such as styrofoam, etc., may be enclosed.

J. Automated Sequencing Systems

Figure 21:
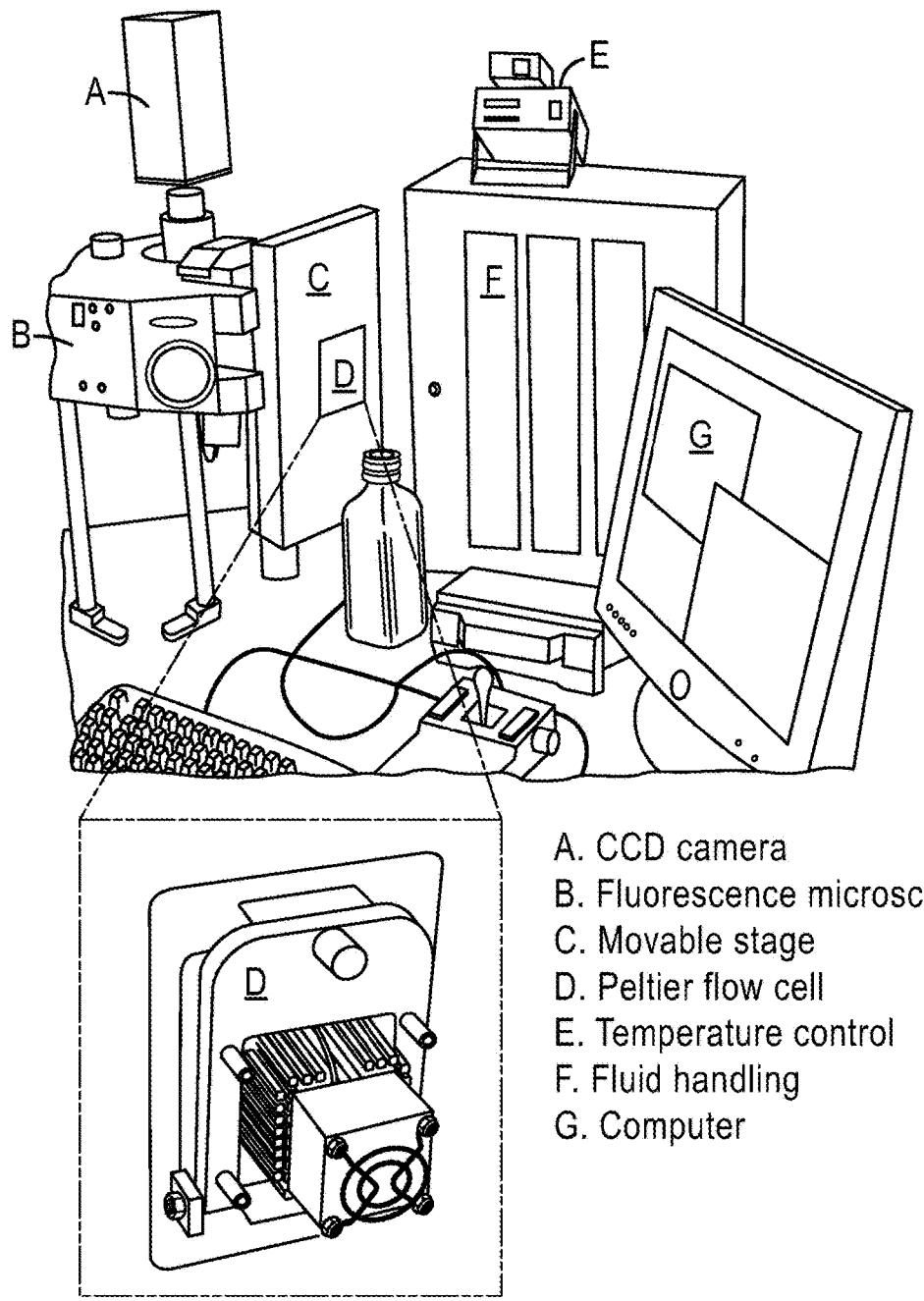
FIG. 21 is a photograph of an automated sequencing system that may be used to gather sequence information, e.g., from templates arrayed in or on a substantially planar support. Also shown is a dedicated computer for controlling operation of various components of the system, processing and storing collected image data, providing a user interface, etc. The lower portion of the figure shows an enlarged view of a flow cell oriented to achieve gravimetric bubble displacement.

The invention provides a variety of automated sequencing systems that can be used to gather sequence information from a plurality of templates in parallel, i.e., substantially simultaneously. Preferably the templates are arrayed on a substantially planar substrate. FIG. 21 shows a photograph of one of the inventive systems. As shown in the upper part of the photograph, the inventive system comprises a CCD camera, a fluorescence microscope, a movable stage, a Peltier flow cell, a temperature controller, a fluid handling device, and a dedicated computer. It will be appreciated that various substitutions of these components can be made. For example, alternative image capture devices can be used. Further details of this system are provided in Example 9.

It will be appreciated that the inventive automated sequencing system and associated image processing methods and software can be used to practice a variety of sequencing methods including both the ligation-based methods described herein and other methods including, but not limited to, sequencing by synthesis methods such as fluorescence in situ sequencing by synthesis (FISSEQ) (see, e.g., Mitra R D, et al., Anal Biochem., 320(1):55-65, 2003). As is the case for the ligation-based sequencing methods described herein, FISSEQ may be practiced on templates immobilized directly in or on a semi-solid support, templates immobilized on microparticles in or on a semi-solid support, templates attached directly to a substrate, etc.

One important aspect of the inventive system is a flow cell. In general, a flow cell comprises a chamber that has input and output ports through which fluid can flow. See, e.g., U.S. Pat. Nos. 6,406,848 and 6,654,505 and PCT Pub. No. WO98053300 for discussion of various flow cells and materials and methods for their manufacture. The flow of fluid allows various reagents to be added and removed from entities (e.g., templates, microparticles, analytes, etc.) located in the flow cell.

Preferably a suitable flow cell for use in the inventive sequencing system comprises a location at which a substrate, e.g. a substantially planar substrate such as a slide, can be mounted so that fluid flows over the surface of the substrate, and a window to allow illumination, excitation, signal acquisition, etc. In accordance with the inventive methods, entities such as microparticles are typically arrayed on the substrate before it is placed within the flow cell.

In certain embodiments of the invention the flow cell is vertically oriented, which allows air bubbles to escape from the top of the flow cell. The flow cell is arranged such that the fluid path runs from bottom to top of the flow cell, e.g., the input port is at the bottom of the cell and the output port is at the top of the cell. Since any bubbles that may be introduced are buoyant, they rapidly float to the output port without obscuring the illumination window. This approach, in which gas bubbles are allowed to rise to the surface of a liquid by virtue of their lower density relative to that of the liquid is referred to herein as "gravimetric bubble displacement". Thus the invention provides a sequencing system comprising a flow cell oriented so as to allow gravimetric bubble displacement. Preferably the substrate having microparticles directly or indirectly attached thereto (e.g., covalently or noncovalently linked to the substrate) or immobilized in or on a semi-solid support that is adherent to or affixed to the substrate is mounted vertically within the flow cell, i.e., the largest planar surface of the substrate is perpendicular to the ground plane. Since in preferred embodiments the microparticles are immobilized in or on a support or substrate, they remain at substantially fixed positions with respect to one another, which facilitates serial acquisition of images and image registration.

FIGS. 24A-J shows schematic diagrams of inventive flow cells or portions thereof, in various orientations. The inventive flow cells can be used for any of a variety of purposes including, but not limited to, analysis methods (e.g., nucleic acid analysis methods such as sequencing, hybridization assays, etc.; protein analysis methods, binding assays, screening assays, etc. The flow cells may also be used to perform synthesis, e.g., to generate combinatorial libraries, etc.

Figure 22:
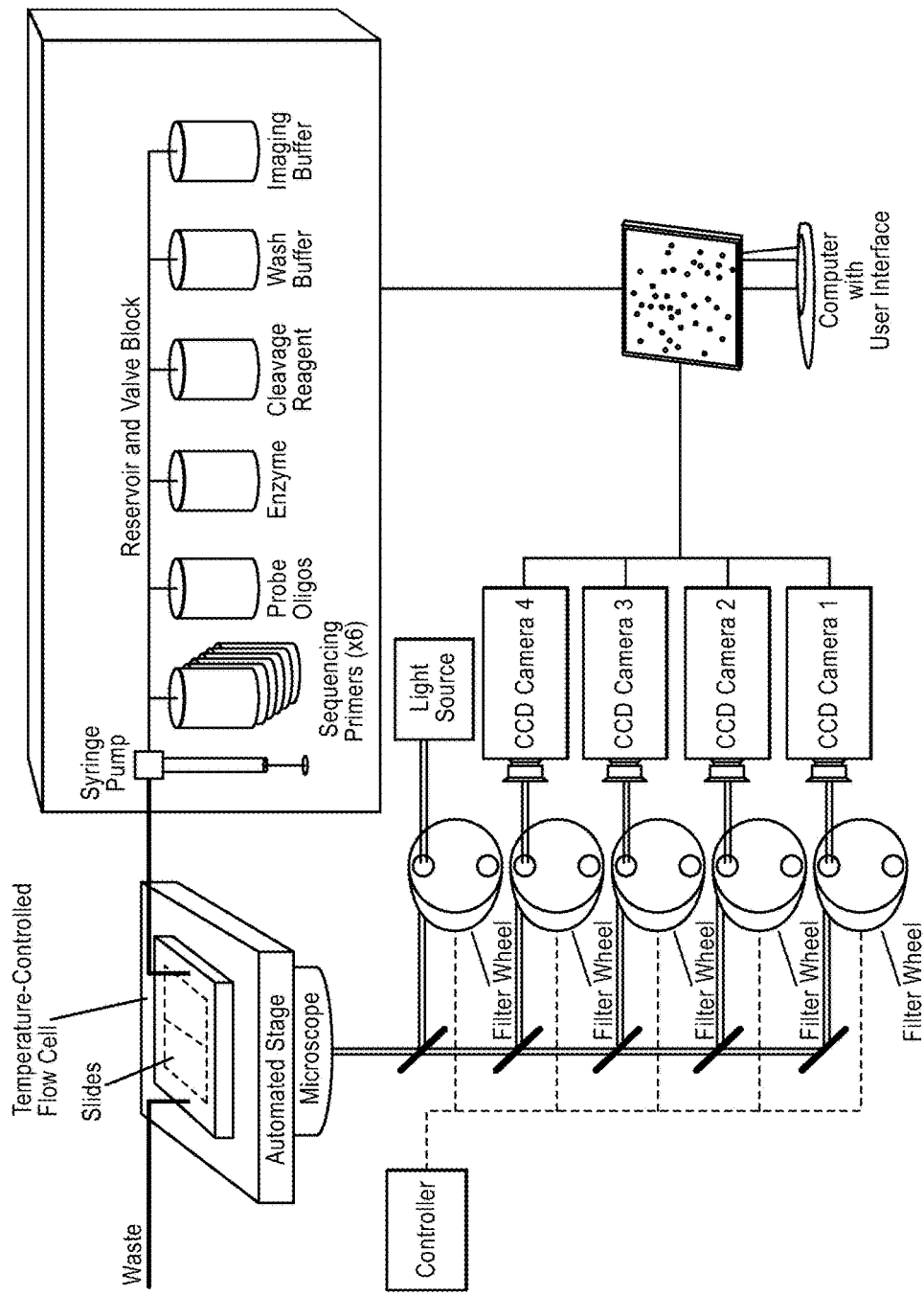
FIG. 22 shows a schematic diagram of a high throughput automated sequencing instrument that may be used to sequence templates arrayed in or on a substantially planar support.

FIG. 22 shows a schematic diagram of another inventive automated sequencing system. The flow cell is mounted on a temperature-controlled, automated stage (similar to the one described in Example 9) and is attached to a fluid handling system, such as a syringe pump with a multi-port valve. The stage accommodate multiple flow cells in order to allow one flow cell to be imaged while other steps such as extension, ligation, and cleavage are being performed on another flow cell. This approach maximizes utilization of the expensive optical system while increasing the throughput.

The fluid lines are equipped with optical and/or conductance sensors to detect bubbles and to monitor reagent usage. Temperature control and sensors in the fluidics system assure that reagents are maintained at an appropriate temperature for long term stability but are raised to the working temperature as they enter the flow cell to avoid temperature fluctuations during the annealing, ligation and cleavage steps. Reagents are preferably pre-packaged in kits to prevent errors in loading.

The optics includes four cameras—each taking one image through one of four filter sets. In order to reduce the effects of photobleaching, the illumination optics may be engineered to illuminate only the area being imaged, to avoid multiple illumination of the edges of the fields. The imaging optics may be built from standard infinity-corrected microscope objectives and standard beam-splitters and filters. Standard 2,000×2,000 pixel CCD cameras can be used to acquire the images. The system incorporates appropriate mechanical supports for the optics. Illumination intensity is preferably monitored and recorded for later use by the analysis software.

In order to rapidly acquire a plurality of images (e.g., approximately 1800 or more non-overlapping image fields in a representative embodiment), the system preferably uses a fast autofocus system. Autofocus systems based on analysis of the images themselves are well known in the art. These generally require at least 5 frames per focusing event. This is both slow and costly in terms of the extra illumination required to acquire the focusing images (increases photobleaching). In certain embodiments of the invention an alternate autofocusing system is used, e.g., a system based on independent optics that can focus as quickly as the mechanical systems can respond. Such systems are known in the art and include, for examples the focusing systems used in consumer CD players, which maintain sub-micron focusing in real time as the CD spins.

In certain embodiments of the invention the system is operated remotely. Scripts for implementing specific protocols may be stored in a central database and downloaded for each sequencing run. Samples can be barcoded to maintain integrity of sample tracking and associating samples with the final data. Central, real-time monitoring will allow quick resolution of process errors. In certain embodiments images gathered by the instruments will immediately be uploaded to a central, multi-terabyte storage system and a bank of one or more processor(s). Using tracking data from the central database, the processor(s) analyze the images and generate sequence data and, optionally, process metrics, such as background fluorescence levels and bead density, in order, e.g., to track instrument performance.

Control software is used to properly sequence the pumps, stage, cameras, filters, temperature control and to annotate and store the image data. A user interface is provided, e.g., to assist the operator in setting up and maintaining the instrument, and preferably includes functions to position the stage for loading/unloading slides and priming the fluid lines. Display functions may be included, e.g., to show the operator various running parameters, such as temperatures, stage position, current optical filter configuration, the state of a running protocol, etc. Preferably an interface to the database to record tracking data such as reagent lots and sample IDs is included.

K. Image and Data Processing Methods

The invention provides a variety of image and data processing methods that may be implemented at least in part as computer code (i.e., software) stored on a computer readable medium. Further details are presented in Examples 9 and 10. In addition, in general, both sequencing methods A and B generally employ appropriate computer software to perform the processing steps involved, e.g., keeping track of data gathered in multiple sequencing reactions, assembling such data, generating candidate sequences, performing sequence comparisons, etc.

L. Computer-Readable Media Storing Sequence Information

In addition, the invention provides a computer-readable medium that stores information generated by applying the inventive sequencing methods. Information includes raw data (i.e., data that has not been further processed or analyzed), processed or analyzed data, etc. Data includes images, numbers, etc. The information may be stored in a database, i.e., a collection of information (e.g., data) typically arranged for ease of retrieval, for example, stored in a computer memory. Information includes, e.g., sequences and any information related to the sequences, e.g., portions of the sequence, comparisons of the sequence with a reference sequence, results of sequence analysis, genomic information, such as polymorphism information (e.g., whether a particular template contains a polymorphism) or mutation information, etc., linkage information (i.e., information pertaining to the physical location of a nucleic acid sequence with respect to another nucleic acid sequence, e.g., in a chromosome), disease association information (i.e., information correlating the presence of or susceptibility to a disease to a physical trait of a subject, e.g., an allele of a subject), etc. The information may be associated with a sample ID, subject ID, etc. Additional information related to the sample, subject, etc., may be included, including, but not limited to, the source of the sample, processing steps performed on the sample, interpretations of the information, characteristics of the sample or subject, etc. The invention also includes a method comprising receiving any of the aforesaid information in a computer-readable format, e.g., stored on a computer-readable medium. The method may further include a step of providing diagnostic, prognostic, or predictive information based on the information, or a step of simply providing the information to a third party, preferably stored on a computer-readable medium.

The following examples are provided for illustrative purposes and are not intended to limit the invention.

Example 1

Efficient Cleavage and Ligation of Phosphorothiolated Oligonucleotides

This example describes an experiment demonstrating efficient ligation and cleavage of extension oligonucleotides containing a 3'-S phosphorothiolate linkage.

Materials and Methods

Ligation Sequencing Protocol

Template Preparation:

To demonstrate evaluate the potential of sequencing by cycled oligonucleotide ligation and cleavage and to explore the effect of variations in certain aspects of the method, two sets of model bead-based template populations were prepared. In preferred implementations, as described in the Examples, cycled oligonucleotide ligation and cleavage extends strands in the 3'→5' direction. Therefore, to evaluate ligation efficiencies, model templates were bound to beads at the 5' end and designed with the same binding region at the 3' end. One set was comprised of short (70 bp) oligonucleotides bound to streptavidin-coated magnetic beads (1 micron) via a dual biotin moiety. Each of these short template populations were designed with an identical primer binding region (40 bp) and a unique sequence region (30 bp) at the 3' end. The short oligonucleotide template populations were termed ligation sequencing templates 1-7 (LST1-7).

The second set of bead-based template populations were designed from long, PCR-generated DNA fragments (232-bp) derived by inserting 183-bp of spacer sequence (from a human p53 exon) into each template population. Templates were amplified with dual biotin-containing forward primers and reverse primers containing the same 30 base unique 3' end sequence as the short template populations. The templates were made single-stranded by melting off one of the strands with sodium hydroxide-containing buffer. These long template populations were designed to mimic the species generated from short-fragment paired-end libraries described in a copending patent application and were termed long-LST1-7.

Primer Hybridization:

2.5 µL of 100 µM FAM-labeled primer was premixed with 100 µL 1× Klenow Buffer. This solution was added to a 30 µL aliquot of magnetic beads ($10^6$/µL) with attached template after removal of the buffer, and the resulting solution was well mixed. After allowing template/primer hybridization to occur (hybridization reaction was carried out for 2 minutes at 65° C., 2 minutes at 40° C. and 2 minutes on ice), the primer/buffer was removed, and the beads were washed using 3× Wash 1E buffer, and then resuspended in 300 µL ($10^6$/mL) in TENT buffer (containing 10 mM Tris, 2 mM EDTA, 30 mM NaOAc, and 0.01% Triton X-100).

Ligation 1:

$2.5 \times 10^6$ LST7 beads with hybridized LigSeq-FAM were then incubated for 30 minutes at 37° C. in a mixture containing 1 µL of 100 µM LST7-1 Nonamer, 4 µL 5×T4 Ligase Buffer (Invitrogen), 14 µL of $H_2O$ and 1 µL of T4 Ligase (1 u/µL, Invitrogen).

Cleavage 1:

The beads were then washed 3 times with 100 µL of LSWash1 (containing 1×TE, 30 mM sodium acetate, 0.01% Triton X100); a 10 µL-aliquot of this solution was removed and saved for analysis. The beads (1×) were then washed in 100 µL of 30 mM sodium acetate. 50 µL of 50 mM $AgNO_3$ was added to this solution and the resulting mixture was incubated at 37° C. for 20 minutes. $AgNO_3$ was removed, and the beads were washed once in 100 µL of 30 mM sodium acetate. The beads were then washed in 3 times with 100 µL of LSWash1, resuspended in 90 µL Wash (TENT buffer); and a 10 µL-aliquot of this solution was removed and saved for analysis.

Ligation 2:

After removal of the TENT buffer, the beads were resuspended in 14 µL of $H_2O$, and incubated at 37° C. for 30 minutes with a mixture containing 1 µL of 100 µM LST7-5 Nonamer, 4 µL of 5×T4 Ligase Buffer (Invitrogen) and 1 µL of T4 Ligase (1 u/µL, Invitrogen).

Cleavage 2:

The beads were washed 3 times in 100 µL of LSWash1 (1×TE, 30 mM sodium acetate, 0.01% Triton X100), and resuspended in 45 µL Wash1E. A 15 µL-aliquot of this mixture was removed and saved for analysis. The beads were then washed once with 100 µL of 30 mM sodium acetate and resuspended in 5 µL of 20 mM sodium acetate. 50 µL of 50 mM $AgNO_3$ was added to the beads and the mixture was incubated at 37° C. for 20 minutes. After removal of $AgNO_3$, the beads were washed once with 100 µL of 30 mM sodium acetate. The beads were then washed three times in 100 µL of LSWash1, and resuspended in 30 µL Wash1E. A 20 µL-aliquot of this mixture was removed and saved for analysis.

Results

Figure 8:
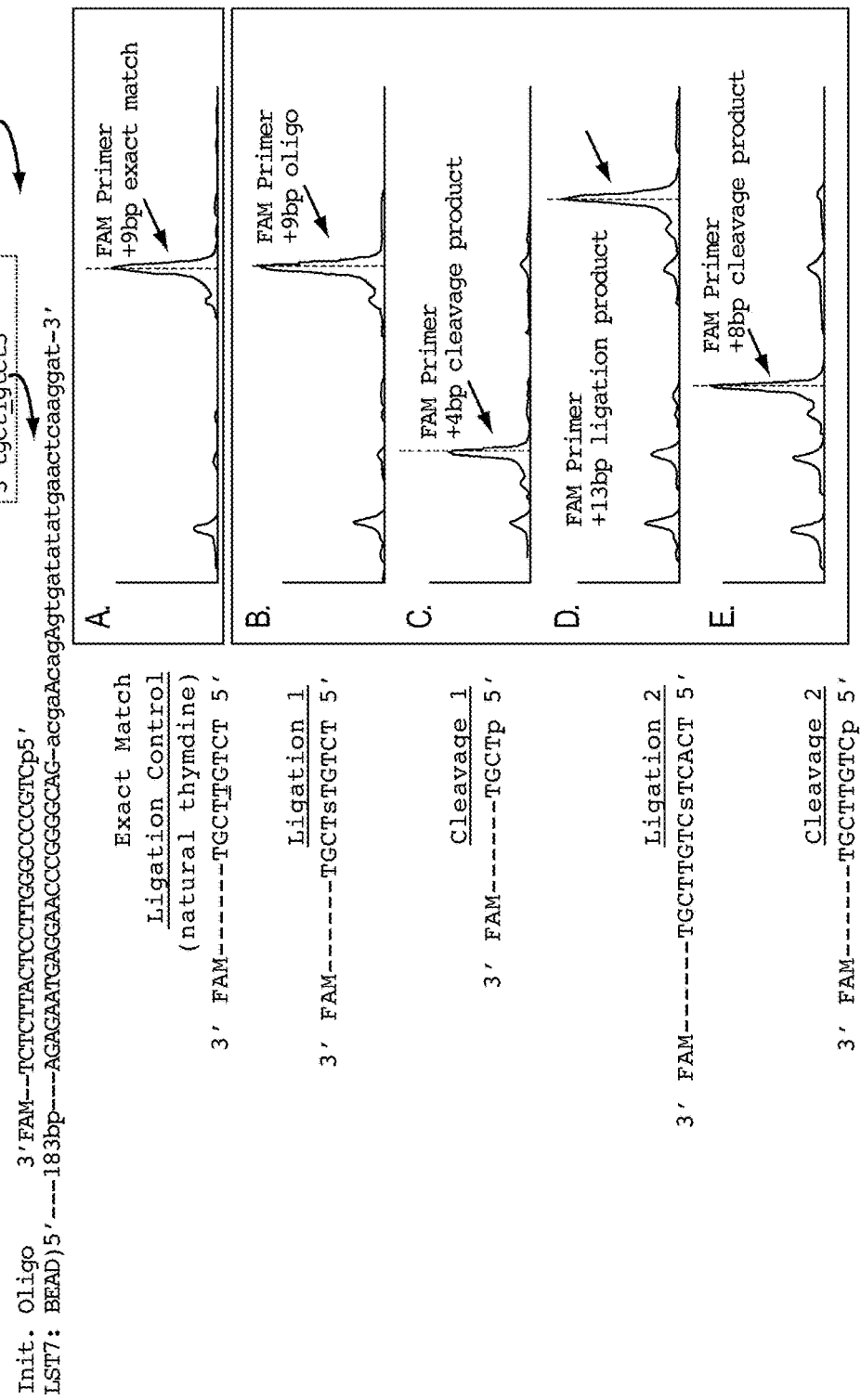
FIG. 8 shows results of a gel shift assay demonstrating two cycles of successful ligation and cleavage of extension probes containing phosphorothiolate linkages. The sequence of the initializing oligonucleotide is listed as SEQ ID NO. 12. The sequence of the LST7 template is listed as SEQ ID NO. 13. The sequence depicted under the label "Ligation 2" is listed as SEQ ID NO. 14.

The experiment will be better understood with reference to FIG. 8. The upper section of FIG. 8 shows an overall outline of the experimental procedure. An initializing oligonucleotide (primer) was hybridized to a template (designated LST7), which was attached to a bead via a biotin linkage. The initializing oligonucleotide contained a 5' phosphate and was fluorescently labeled with FAM at its 3' end. Two 9mer (nonamer) oligonucleotide probes ($1^{st}$ cleavable oligo and $2^{nd}$ cleavable oligo) were synthesized to contain an internal phosphorothiolated thymidine base (sT) (underlined). The first cleavable probe was ligated to the extendable terminus of the primer using T4 DNA ligase and was then cleaved using silver nitrate. Cleavage removed the terminal 5 nucleotides of the extension probe and generated an extendable terminus on the portion of the probe that remained ligated to the primer. The second cleavable probe was then ligated to the extendable terminus and was then similarly cleaved.

Figure 8F:
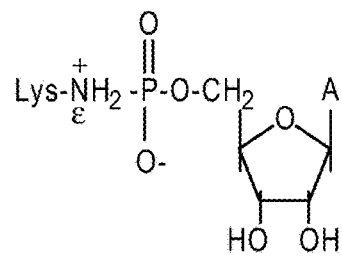
FIG. 8F shows a schematic diagram of the mechanism of ligation by DNA ligases.

A fluorescent capillary electrophoresis gel shift assay was used to monitor steps of ligation and cleavage. In this assay, the primer is hybridized to a template strand such that the 5' phosphate can serve as a ligation substrate for incoming oligonucleotide probes (the fluorophore serves as a reporter for mobility-based capillary gel electrophoresis). After each step an aliquot of beads was removed for analysis. Following ligation of oligonucleotide probes, the magnetic beads were collected using a magnet and the ligated species consisting of the primer and probe(s) ligated thereto was released from the template beads by heat denaturation and subjected to fluorescent capillary electrophoresis using an automated DNA sequencing instrument (ABI 3730) with labeled size standards (lissamine ladder; size range 15-120 nucleotides; appears as a set of orange peaks in chromatograms, see FIG. 8). In a typical gel shift, the potential peaks include, i) primer peaks (due to no extension or the lack of primer extension), ii) adenylation peaks (due to the attachment of an adenosine residue at the 5' end of a nonproductive ligation junction by the action of DNA ligase—see mechanism in FIG. 8F, see also Lehman, I. R., *Science,* 186:790-797, 1974), and iii) completion peaks (due to the attachment of an oligo probe). One benefit of using gel shift assays to evaluate ligation efficiency is that the areas under the peaks directly correlate with the concentration of each species.

FIG. 8A shows a control ligation performed using T4 DNA ligase and an exact match probe containing only phosphodiester linkages (shown to the left of FIG. 8A). Orange peaks represent size markers. The blue peak at the left indicates the position of the primer in the absence of ligation. Ligation of the exact match probe results in a shift to the left (arrow). FIG. 8B shows a ligation performed under the same conditions using a probe containing an internal thiolated T base (shown to the left of FIG. 8B). A shift identical to that observed with the control probe was seen (arrow). Bead-linked template populations containing the ligated phosphorothiolated probes were then incubated with silver nitrate to induce probe cleavage. Gel-shift analysis confirmed efficient cleavage by demonstration of a left-shifted, 4-bp cleavage product (FIG. 8C). The expected cleavage product is shown to the left of FIG. 8C. Cleaved bead-based template populations were then exposed to a second round of ligation and demonstrated productive ligation by the appearance of a right-shifted, 13-bp extension product (FIG. 8D). The expected cleavage product is shown to the left of FIG. 8D. A second round of cleavage confirmed efficient multiple cleavage steps could be accomplished as demonstrated by the expected left-shifted, 8-bp cleavage product (FIG. 8E). These results demonstrate successful ligation and cleavage of probes containing phosphorothiolate linkages.

It is evident that ligation did not proceed to 100% completion in these experiments, although a greater degree of completion was observed in other experiments using T4 DNA ligase (see below). While it is certainly desirable that the ligation proceed to completion it is not a requirement. For example, it is possible to effectively "cap" any unligated 5' ends by treating with a 5'-phosphatase after the ligation step as described above. In that case, however, there would be a limit to the number of sequential ligations that could be performed, due to attrition of ligatable molecules. With a given number of sequential ligations, the read length will depend on the length of the probe remaining after each ligation/cleavage cycle and on the number of sequencing reactions, each followed by removal of the primer and hybridization of a primer that binds to a different portion of the primer binding site, that can be performed on a given template, also referred to as the number of "resets"). This argues for the use of longer probes with the cleavable linkage located towards the 5' end of the probe. In our experiments, hexamer probes lead to greater amounts of un-ligatable adenylation products than octamers and longer probes. Thus octamers and longer probes will ligate substantially to completion (see below). In addition, adding a fluorescent moiety to the 5' end of a hexamer probe seems to reduce the efficiency of ligation, whereas adding a fluorescent moiety to an octamer probe has little or no effect. For these reasons, use of octamers or longer probes is considered preferable.

Additional experiments (described below) have demonstrated ligation and cleavage of probes containing phosphorothiolate linkages and degeneracy-reducing nucleotides; 3' end specificity and selectivity of ligated extension probes; in-gel ligation and cleavage; sequential cycles of primer hybridization and removal with minimal loss of signal; 100% fidelity for T4 or Taq ligase for 3'→5' extensions; and 4-color spectral resolvability of ligated extension probes. An automated system for performing the methods has been constructed.

Example 2

Efficient Cleavage and Ligation of Phosphorothiolated Oligonucleotides Containing Degeneracy-Reducing Nucleotides A competing consideration to probe length, however, is the fidelity of the extended oligonucleotide and its effect on subsequent ligation efficiency. The fidelity of T4 DNA ligase has been shown to decrease rapidly following the $5^{th}$ base after the junction (Luo et al., Nucleic Acid Res., 24: 3071-3078 and 3079-3085, 1996). If mismatches are introduced at the 5' side of a new ligation junction, the ligation efficiency may be reduced by attrition, however, no dephasing or increase in background signal will be generated (a major obstacle encountered in polymerase-based sequencing by synthesis methods).

Probe sets should preferably be capable of hybridizing to any DNA sequence in order to permit de novo sequencing of uncharacterized DNA. However, the complexity of a labeled probe set grows exponentially with the length and number of 4-fold degenerate bases. In addition, a complex probe set is more challenging to synthesize while maintaining approximately equal representation of all probe species, and is harder to purify. It also requires a higher concentration of probe mixture to maintain a constant concentration of each species. One way to manage this complexity is to use nucleotides incorporating universal bases, such as deoxyinosine, at certain positions instead of 4-fold degenerate bases.

Twelve octanucleotide probes were designed with 4-fold degenerate bases (N; equimolar amounts of A, C, G, T) and the universal base inosine (I) at various positions within the octamer (inosine is capable of bi-dentate hydrogen bonding with any of the four canonical bases in B-DNA; the order of stabilities of inosine base pairs is I:C>I:A>I:T≈I:G). One purpose for evaluating these probe designs was to determine how low an octamer complexity could be achieved while still supporting efficient ligation in the presence of inosine bases.

Figure 9:
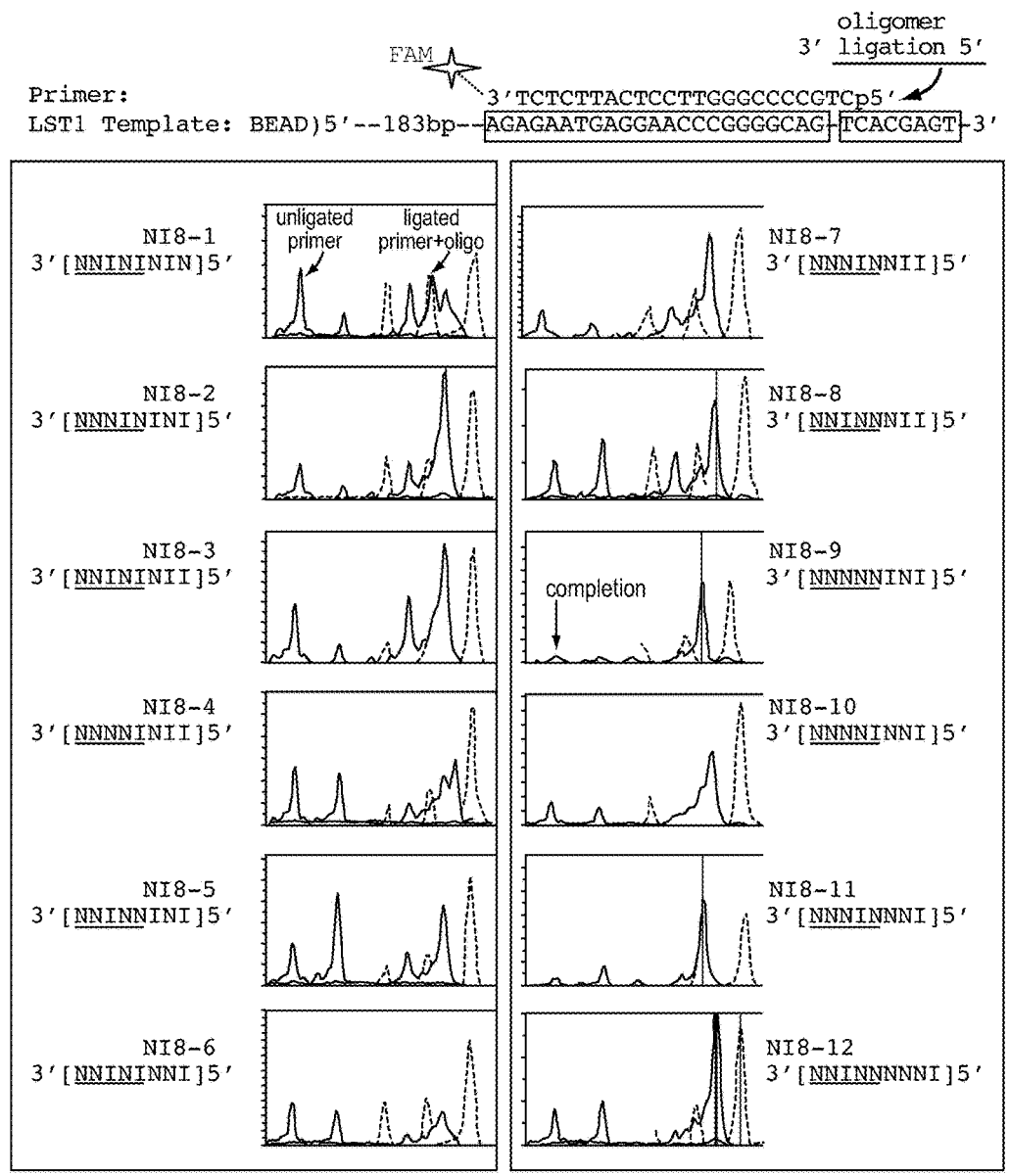
FIG. 9 shows results of a gel shift assay demonstrating the ligation efficiency of degenerate inosine-containing oligonucleotide probes. The sequences of the primer and LST1 template are listed as SEQ ID NOs. 15 and 16 respectively.

In initial studies, several oligonucleotide probes were ligated to bead-based templates (long-LST1) using T4 DNA ligase. Upon ligation, the fluorophore-labeled primer (3'FAM Primer) shifts right in proportion to the amount of oligonucleotide probe ligated. Probe design NI8-9 showed the highest level of completion, with >99% of the primer population shifting right due to efficient ligation of the probe (see FIG. 9). These reactions were conducted at 25° C.; when the reaction temperature was increased to 37° C., ligation was somewhat less efficient and the completion rates were more variable.

Figure 10A:
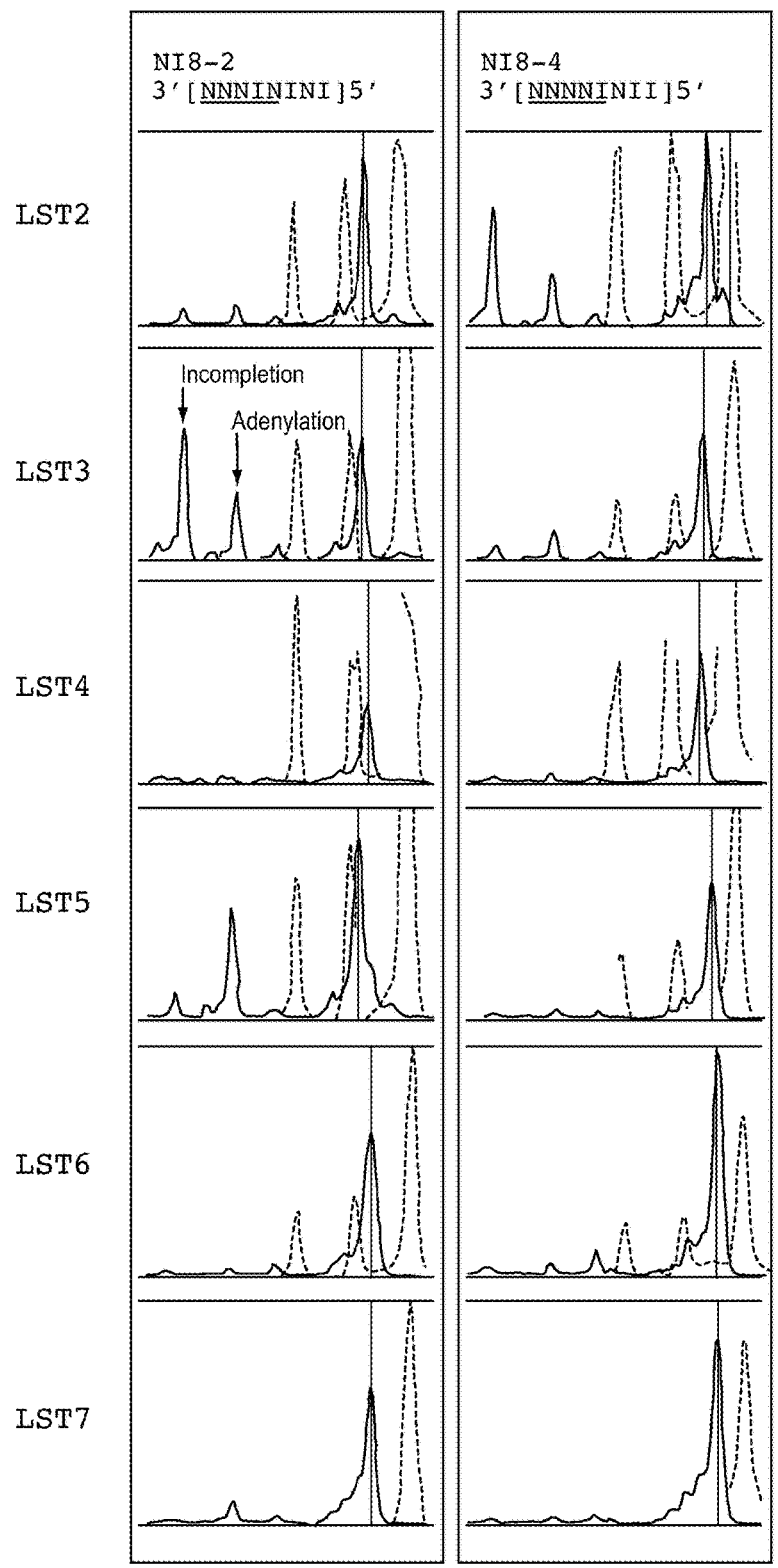
FIG. 10A and FIG. 10B shows results of a gel shift assay demonstrating the ligation efficiency of degenerate inosine-containing oligonucleotide probes on multiple templates.
Figure 10B:
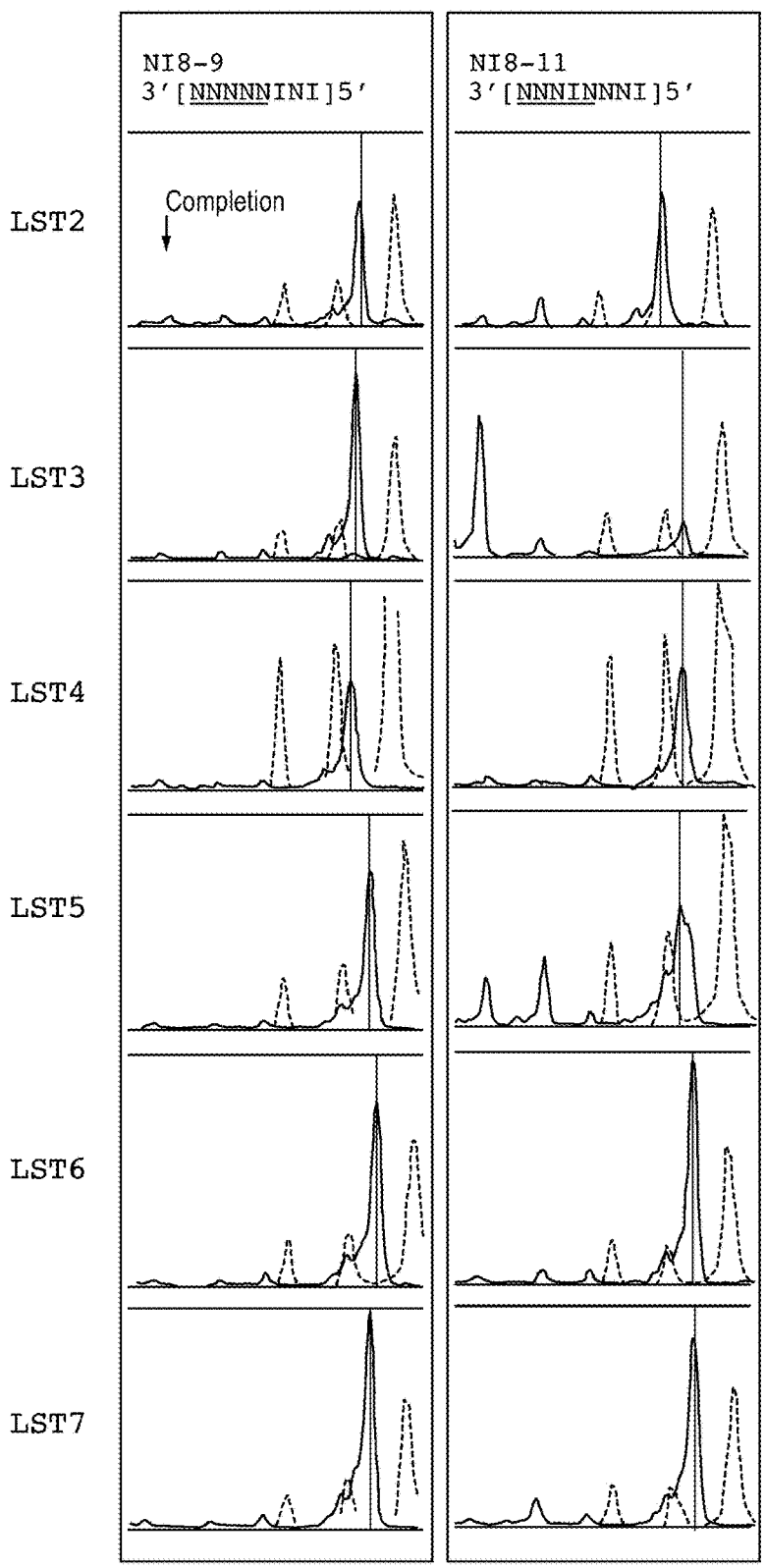

Closer examination of the data indicated that probes with fewer inosine bases within the first five nucleotides on the 3' side of the junction (underlined) showed higher ligation efficiencies. To investigate further and to evaluate potential sequence context effects on ligation efficiencies, four oligonucleotide probe designs with only a single inosine residue within the first five bases 3' of the ligation junction were screened across all templates. FIG. 10 demonstrates ligation completion as evaluated using the gel-shift assay with selected probe compositions on multiple templates using T4 DNA ligase. Data from these initial experiments demonstrated that ligation efficiency, and hence completion, is variable and sequence-dependent when inosine residues are placed within the first five 3' positions of the ligation junction (underlined). Efficient ligation of octamers was observed consistently, however, with oligonucleotide probe design NI8-9, as demonstrated here with >99% completion on all templates tested.

While not wishing to be bound by any theory, this data (including the presence of adenylated intermediates) support the conclusion that unfavorable inosine base pairs within the core DNA binding site for T4 DNA ligase destabilize the DNA protein complex sufficiently to reduce enzyme binding and subsequent ligation. An interesting question, however, was whether such destabilizing inosine base pairs would affect the fidelity of the ligated oligonucleotide probes.

Example 3

Fidelity of Probe Ligation

Bacterial NAD-dependent ligases, such as Taq DNA ligase, have been reported to have high sequence fidelity across ligation junctions, with mismatches on the 3' side having essentially no nick-closure activity, but mismatches on the 5' side being tolerated to some degree (Luo et al., Nucleic Acid Res., 24: 3071-3078 and 3079-3085, 1996). T4 DNA ligase, on the other hand, has been reported to be somewhat less stringent, allowing mismatches on both the 3'- and 5'-sides of the junction. It was therefore of interest to evaluate the fidelity of probe ligation with T4 DNA ligase in comparison to Taq DNA ligase in the context of our system.

We developed two methods to evaluate the sequence fidelity of ligated oligonucleotides using standard ABI sequencing technology. The first method was designed to clone and sequence ligation products. In this method, ligation extension products were attached to adapter sequences, cloned and transformed into bacteria. Individual colonies were picked and sequenced to provide a quantitative assessment of the mismatch frequency at each position across the ligation junction. The second method was designed to sequence of ligation products directly. In that approach, single-stranded ligation products were denatured from bead-based templates and sequenced directly using a complementary primer. Positions with low accuracy display multiple overlapping peaks in the resulting sequence traces, providing a qualitative assessment that is indicative of the sequence fidelity at that position.

The first method was used to assess the relative fidelity of probe ligation by T4 and Taq DNA ligases. A single bead-based template population (LST1) was hybridized to a universal sequencing primer, which was used as an initializing oligonucleotide. Solution-based ligation reactions were then performed in the presence of a degenerate oligonucleotide probe (N7A, 3'ANNNNNNN5', 2000 pmoles) at 37° C. for 30 minutes with either T4 DNA ligase (15 U per 1×10$^6$ beads) or Taq DNA ligase (60 U per 1×10$^6$ beads) (FIG. 11, panel A). The ligation products were cloned and sequenced to evaluate the positional fidelity of each DNA ligase on the 3' side of its ligation junction (Positions 1-8) (FIG. 11, panels B and C). The results indicated that T4 DNA ligase has essentially the same level of fidelity across the first 5 positions as Taq DNA ligase, but lower fidelity in positions 6-8. These results were further substantiated by subsequent cloning experiments that evaluated DNA sequences across ligation junctions of all seven templates (LST1-7) for three degenerate, inosine-containing probe designs (3'-NNNNNIII-5', 3'-NNNNNINI-5', and 3'-NNNINNNI-5'). The studies confirmed that T4 DNA ligase has low sequence fidelity across ligation junctions at positions 6-8, however, high fidelity was exhibited across the first 5 positions in all templates tested (data not shown).

Figure 12:
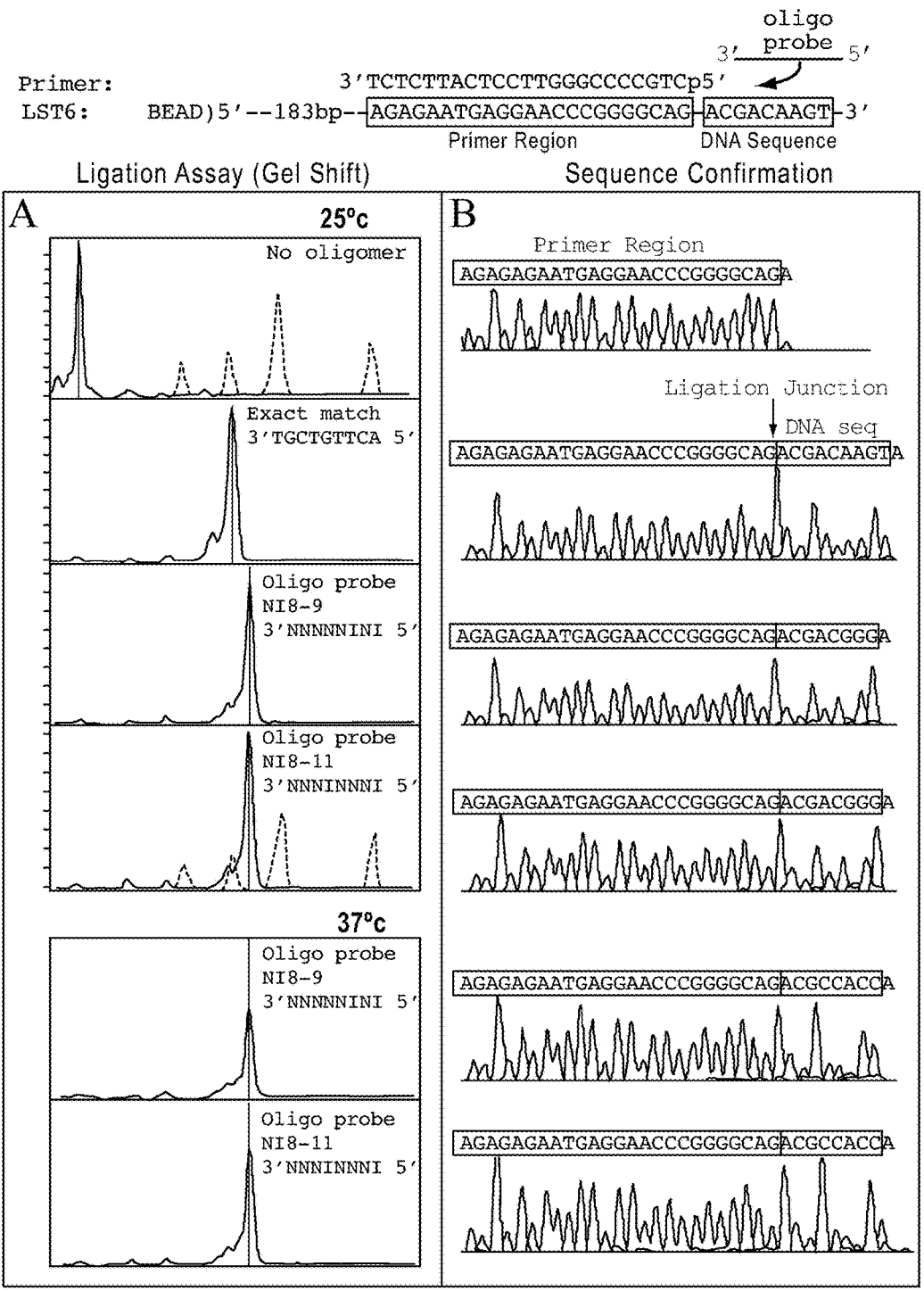
FIG. 12 shows results of a gel shift assay (A) demonstrating the ligation efficiency of degenerate inosine-containing oligonucleotide probes and of a direct sequencing analysis of the ligation reactions (B) conducted to assess the fidelity of T4 DNA ligase in oligonucleotide probe ligation. Results are tabulated in panels C-F.

The direct sequencing method was used to assess the fidelity of T4 DNA ligase with degenerate, inosine-containing probes. Oligonucleotide probes were evaluated at 25° C. and 37° C. in ligation reactions that contained T4 DNA ligase and bead-based templates. Oligonucleotide probe ligation efficiencies were evaluated using a gel-shift assay (FIG. 12, panel A). Direct sequencing of the ligation reactions using an ABI3730x1 DNA Analyzer was conducted to assess the fidelity of T4 DNA ligase in oligonucleotide probe ligation (FIG. 12, panel B). Ligation of an exact match oligo probe and two representative degenerate inosine-containing oligo probes (NI8-9 and NI8-11) gave >99% completion and a very low frequency of mismatches (absence of multiple peaks in the sequencing traces). The data suggest that probes which are efficiently ligated also give high sequence fidelity.

In additional experiments, a single bead-based template population (LST1) was hybridized to a universal sequencing primer that contained 5' phosphates, which was used as an initializing oligonucleotide. Solution-based ligation reactions were performed at 37 C for 30 minutes with T4 DNA ligase (1 U per 250,000 beads) in the presence of a degenerate, inosine-containing oligonucleotide probe (3'NNNNNiii5', 3'NNNNNiNi5', or 3'NNNiNNNi5', 600 pmoles). Ligation products were cloned and colonies were picked and sequenced. Sequence fidelity was determined by calculating the number of clones represented for each position across the ligation junction. Results are tabulated in FIG. 12, panels C-F. These studies demonstrate that 3'→5' ligation of degenerate, inosine-containing probes with T4 DNA ligase has high-level fidelity in the first 1-5 positions.

Example 4

In-Gel Ligation and Cleavage

The initial experiments to explore, develop and optimize methods for cycled oligonucleotide ligation were conducted using bead-based templates in solution, as described above. In a second set of experiments, ligation and cleavage were performed on bead-based templates that were embedded in polyacrylamide gels on slides.

Slides were prepared by mixing millions of beads, each having a clonal population of single-stranded DNA templates attached thereto, with 5% polyacrylamide and allowing polymerization to occur on a glass slide. A Teflon® mask was used to enclose the bead-containing polyacrylamide solution. FIG. 14 (top) shows a fluorescence image of a portion of a slide on which beads with an attached template, to which a Cy3-labeled primer was hybridized, were immobilized within a polyacrylamide gel. (This slide was used in a different experiment, but is representative of the slides used here.) FIG. 14 (bottom) shows a schematic diagram of a slide equipped with a Teflon mask to enclose the polyacrylamide solution.

Figure 15:
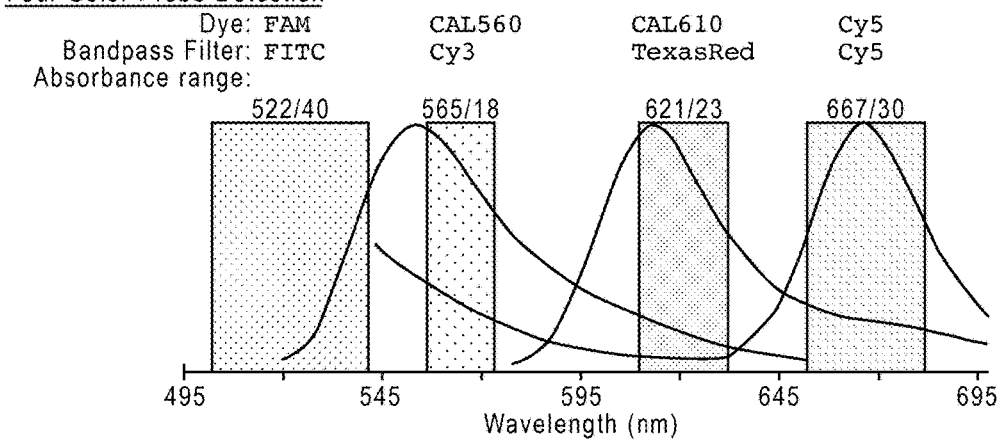
FIG. 15 illustrates three sets of labeled oligonucleotide probes designed to address issues of probe specificity and selectivity and also shows excitation and emission values for a set of four spectrally resolvable labels.
Figure 16A:
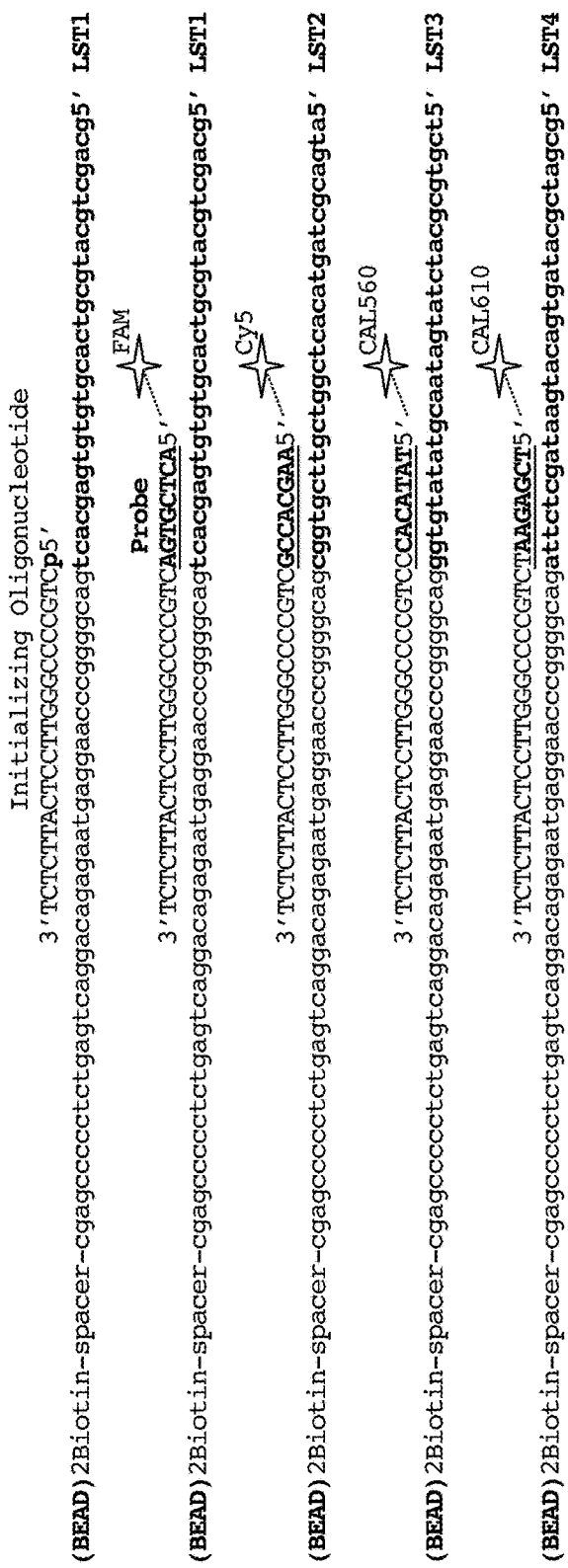
FIG. 16A-16D shows results of an experiment confirming 4-color spectral identity of oligonucleotide probes. Slides containing four unique single-stranded template populations FIG. 16(A) were subjected to hybridization and ligation reactions using an oligonucleotide probe mixture that contained four unique fluorophore probes, were imaged under bright light FIG. 16(B) and with fluorescence excitation using four bandpass filters before and after ligation. Individual populations were pseudocolored FIG. 16(C). The spectral identity, which showed minimal signal overlap, is plotted in FIG. 16(D). The sequences of the initializing oligonucleotide and LST1 template are listed as SEQ ID NOs. 15 and 26 respectively. The sequences of the extended initializing oligonucleotides with FAM-, Cy5-, CAL560-, and CAL610-labeled probes are listed as SEQ ID NOs. 27, 28, 30, and 32 respectively. The sequences of the LST2, LST3, and LST4 templates are listed as SEQ ID NOs. 29, 31, and 33 respectively.
Figure 16D:
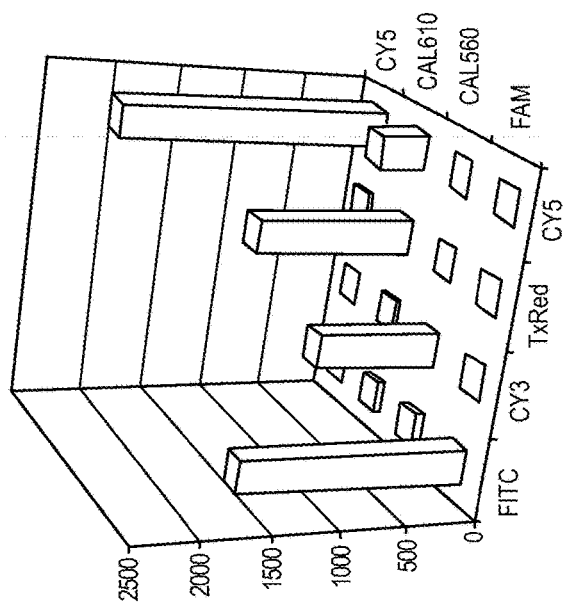
Figure 16B:
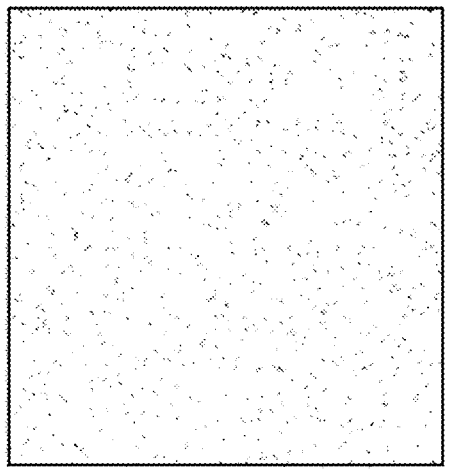
Figure 16C:
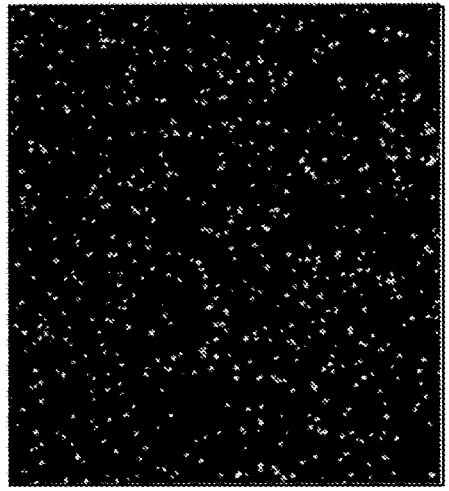

Reactants were introduced into slides either by manual dipping of slides into appropriate solutions or by placing the slides in an automated, laminar flow cell. Initial studies confirmed that efficient in-gel ligation could indeed be performed on templates attached to beads immobilized in a polyacryamide matrix on such slides. In the experiment shown in FIG. 15, single-stranded DNA template beads were immobilized on slides containing acrylamide and DATD. Following polymerization, a universal, 3' fluorophore-labeled, 5' phosphorylated primer (Seq Primer) was diffused into the gel and allowed to hybridize (panel A). Slides were washed to remove unbound seq primer, overlaid with a ligation cocktail that contained T4 DNA ligase (10 U) and an oligonucleotide probe, and incubated at 37° C. for 30 minutes. Slides were then incubated in a buffer containing sodium periodate (0.1M) to digest the acrylamide polymer and to release the bead-based template populations. Ligated products were denatured from the template strand by heat, collected and analyzed using the gel shift assay described above. In-gel ligation reactions performed in the absence of T4 DNA ligase demonstrated a single peak representative of unligated sequencing primer (panel B). Ligation reactions performed with octamer probes in the presence of T4 DNA ligase demonstrated efficient in gel oligonucleotide ligation with >99% of bead-based template populations efficiently ligated (panel C).

Example 5

Four-Color Detection

To maximize detection efficiency, it is desirable to employ a set of oligonucleotide probes with distinct labels corresponding to each possible base addition product. This was modeled in our automated sequencing instrument equipped with appropriate excitation and emission filters, as outlined in FIG. 15. Three sets of octamer probes were designed to address issues of probe specificity and selectivity. The first set included four octamers, complementary to four unique template populations, with different 3' bases and 5' dye labels. The second set included seven unique octamers with unique 3' bases and 5' dyes. The third set corresponded to a probe design with four degenerate, inosine-containing octamers, each having a unique 3' end base identified by a different 5' dye label.

To confirm four-color spectral identity, probe set #1 was employed to detect four unique template populations (see FIG. 16). Slides were prepared containing four, unique single-stranded template populations attached to beads, which were embedded in polyacrylamide (panel A). Each bead had a clonal population of templates attached thereto. A universal sequencing primer containing 5' phosphates was hybridized, in situ, and ligation reactions were performed using an oligonucleotide probe mixture that contained four unique fluorophore probes (Cy5, CAL 610, CAL 560, FAM; 100 pmoles each) and T4 DNA ligase (10 U/slide). Slides were incubated at 37° C. for 30 minutes and washed to remove unbound probes. The slides were imaged in bright light to create a white light base image (panel B) and with fluorescence excitation using the four bandpass filters (FITC, Cy3, TxRed, and Cy5). Fluorescence image capture was conducted pre- and post-ligation. Individual populations were pseudocolored (panel C) and the spectral identity of image values were plotted and confirm minimal signal overlap (panel D).

Example 6

Demonstration of Ligation Specificity and Selectivity in Gels

Figure 17D:
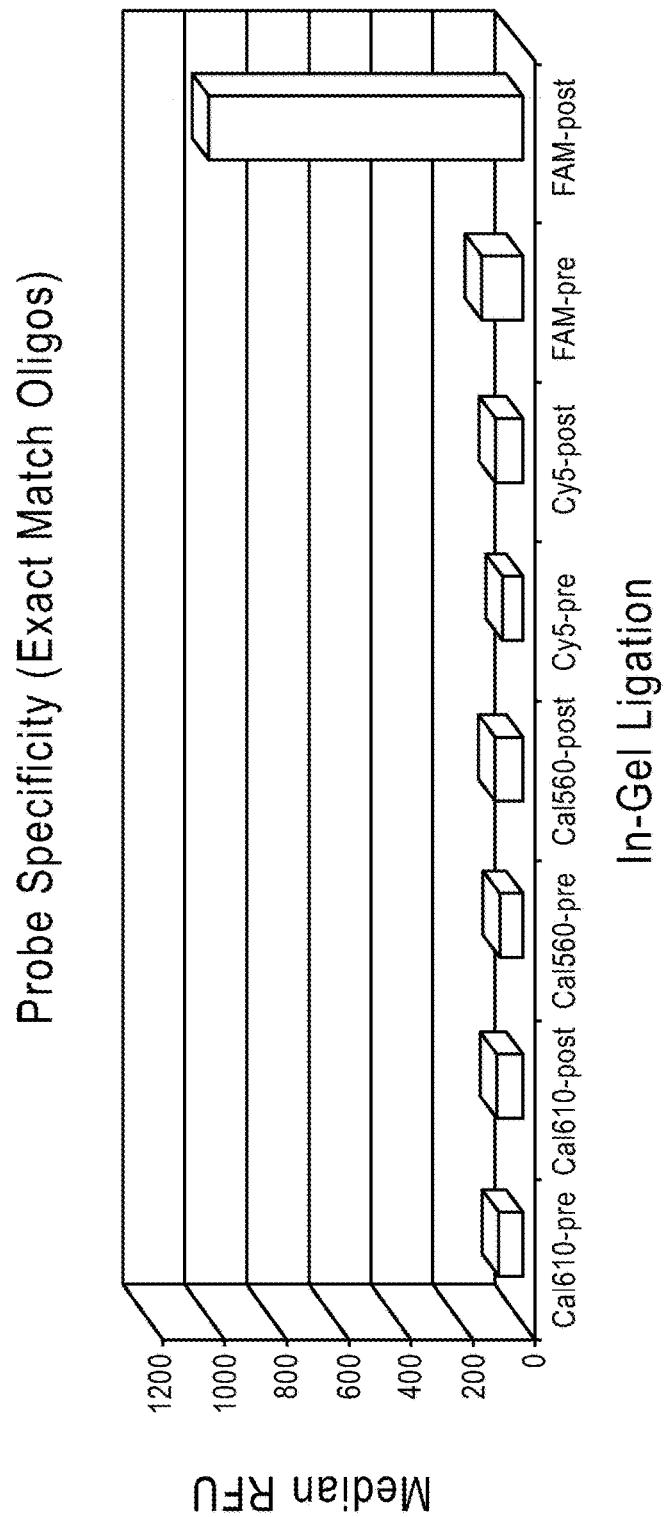
Figure 19A:
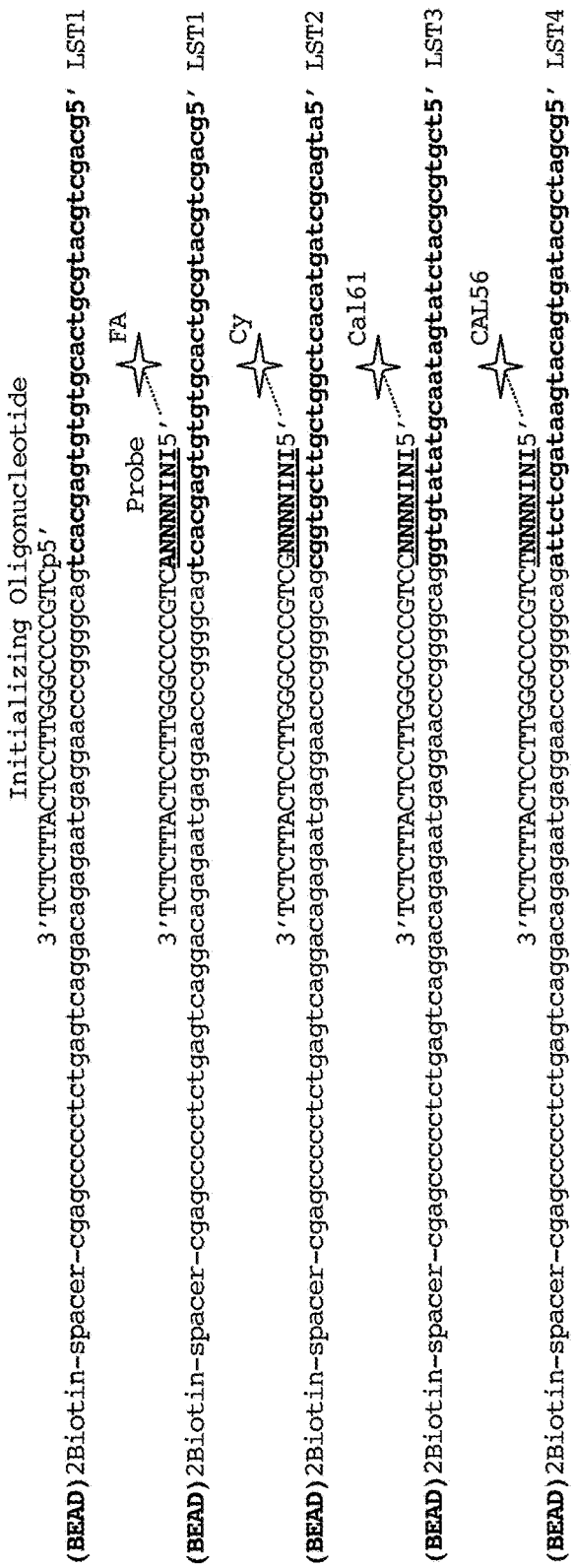
FIG. 19A-19E shows results from an experiment confirming that degenerate and universal base containing oligonucleotide extension probe pools can be used to afford specific and selective in-gel ligation.
Figure 19B:
Figure 19C:
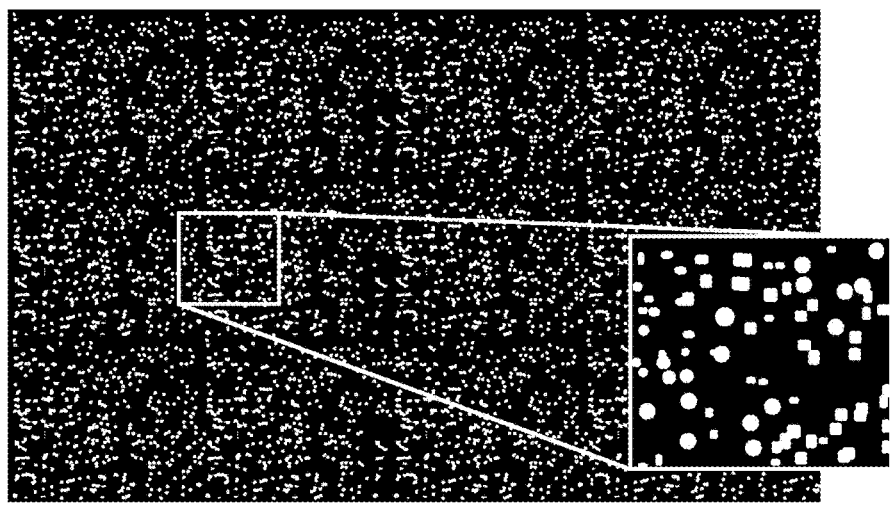
Figures 19D, 19E:
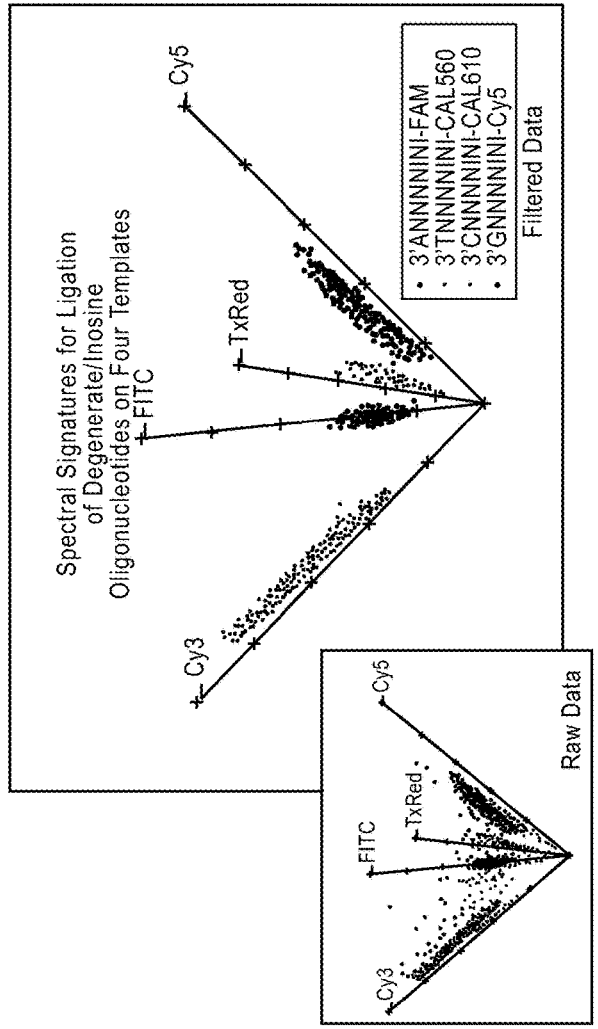

To confirm 3' end specificity, probe set #2, was used to interrogate a single template population (see FIG. 17). Slides were prepared with a beads having a single template population (LST1.T) attached thereto embedded in a polyacrylamide gel, and were hybridized, in situ, with a universal sequencing primer (panel A). In-gel ligation reactions were conducted with T4 DNA ligase (10 U/slide) using an oligonucleotide probe mixture comprised of four 5' end-labeled probes that differed only by a single 3' base. Slides were incubated at 37° C. for 30 minutes and washed to remove unbound probe populations. Slides were imaged in white light to create a base image (panel B) and with fluorescence excitation using four bandpass filters (FITC, Cy3, TxRed, and Cy5). Fluorescence image capture conducted pre- and post-ligation confirmed a single FAM-based probe population (blue spots) present following in-gel ligation with T4 DNA ligase, with no spectral overlap (panels C, D). This data demonstrates that probe specificity with T4 DNA ligase is stringent and is determined by the first 3' end base of the ligation junction.

To further substantiate 3' end specificity and selectivity, probe set #2 was used to identify a mixture of bead-based template populations containing single base differences and present in different amounts. Slides were prepared with mixtures of beads each having one of four template populations, each with a single nucleotide polymorphism (LST1; A, G, C or T), attached thereto, as indicated in panel A of FIG. 18. The beads were embedded in a polyacrylamide gel on the slide. Bead-based template populations were used at various different frequencies, as outlined in panel D. Slides were hybridized, in situ, with universal sequencing primers. In-gel ligation reactions were conducted using T4 DNA ligase (10 U/slide) and an oligonucleotide probe mixture containing equimolar amounts (100 pmoles, each) of four 5' end-labeled probes that differed only by a single 3' base. Slides were incubated at 37° C. for 30 minutes and washed to remove unbound probe populations. Slides were imaged in white light to create a base image (panel B) and with fluorescence using four distinct bandpass filters (FITC, Cy3, TxRed, and Cy5). Individual probe images were overlaid and pseudocolored (panel C). Fluorescent images were enumerated using bead-calling software. The results are presented in panel D and confirm that observed ligation frequencies (Obs) correlated with the expected frequencies (Exp). The data demonstrate high probe specificity and probe selectivity after ligation in the presence of multiple templates and demonstrate the capability of detecting single nucleotide polymorphisms (SNPs), i.e., alterations that occur in a single nucleotide base in a stretch of genomic DNA in different individuals of a population, by ligation.

Example 7

Demonstration of Ligation Specificity and Selectivity in Gels Using Four-Color Degenerate Inosine-Containing Extension Probes Another set of experiments were conducted, using probe set #3, to evaluate the specificity and selectivity of probe ligation using four-color degenerate, inosine-containing oligonucleotide probe pools. Results are presented in FIG. 19. Bead-based slides were prepared as described above, but with four, unique single-stranded template populations present on beads in different amounts and were then hybridized, in situ, with a universal sequencing primer (panel A). In-gel ligation reactions were performed in the presence of T4 DNA ligase (10 U/slide) using probe pools consisting of octamers designed with five degenerate bases (N; complexity $4^5=1024$), two universal bases (I, inosine), and single known nucleotide at the 3' end corresponding to a specific 5' fluorophore (G-Cy5, A-CAL 610, T-CAL560, A-FAM; 600 pmoles each). Slides were incubated at 37° C. for 30 minutes and washed to remove unbound probe populations. Slides were imaged in white light to create a base image (panel B) and with fluorescence using four bandpass filters (FITC, Cy3, TxRed, and Cy5). Individual probe images were overlaid and pseudocolored (panel C). Fluorescent images were enumerated and the frequencies of each ligation product tabulated using bead-calling software (panel D); spectral scatter plots of unprocessed raw data and filtered data representing the top 90% of bead signal values are shown in panel E. The data demonstrate that the observed ligation frequencies (Obs) correlated with the expected frequencies (Exp) based on the known concentrations of each template. This confirms that degenerate and universal base-containing probe pools can be used with T4 DNA ligase to afford specific and selective in-gel ligation.

Example 8

Figure 20:
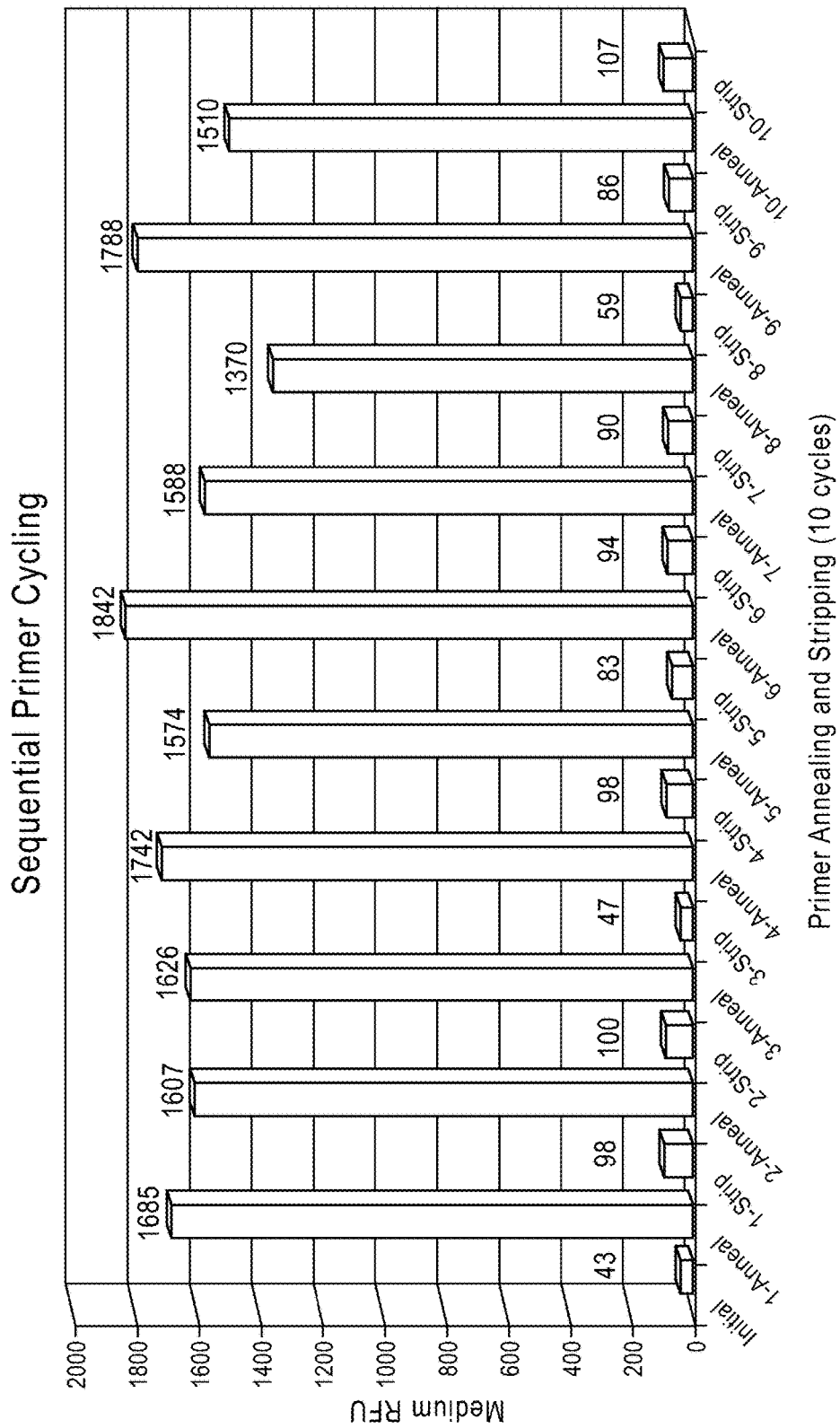
FIG. 20 is a chart showing the signal detected in sequential cycles of hybridization and stripping of an initializing oligonucleotide (primer) to a template. As shown in the figure, minimal signal loss occurred over 10 cycles.

Demonstration of Repeated Cycles of Hybridization and Removal of Initializing Oligonucleotide in Gel Experiments conducted on templates immobilized in a gel on a microscope slide mounted in an automated flow cell (see below) confirmed that multiple cycles of annealing and stripping an initializing oligonucleotide could be applied to templates attached to beads embedded in gels on slides with minimal signal loss. A 44 base fluorescently labeled initializing oligonucleotide was used. As shown in FIG. 20, minimal signal loss occurred over 10 cycles. The initializing oligonucleotide is referred to as a primer in FIG. 20. As indicated above, one of the major drawbacks of polymerase based sequencing-by-synthesis procedures is the propensity for both positive and negative dephasing to occur on individual template strands. Positive dephasing occurs when nucleotides are misincorporated in a growing strand, hence causing the base sequence of that particular strand to run ahead of the sequence obtained from the remaining templates and to be out of phase by n+1 base calls. Negative dephasing, which is more common, occurs when strands are not fully extended, resulting in background base calls that run behind the growing strand (n–1). The ability to efficiently strip extension products and to "reset" templates by hybridizing a differentially positioned initializing oligonucleotide allows very long read lengths with little to no signal attrition.

Example 9

Automated Sequencing System

This example describes a representative inventive automated sequencing system that can be used to gather sequence information from one or more templates. Preferably the templates are located on a substantially planar substrate such as a glass microscope slide. For example, the templates may be attached to beads that are arrayed on the substrate. A photograph of the system is presented in FIG. 21. The system is based on an Olympus epi-fluorescence microscope body (mounted sideways) with an automated, auto-focusing stage and CCD camera. Four filter cubes in a rotating holder permit four-color detection at a variety of excitation and emission wavelengths. A flow cell with peltier temperature control, which can be opened and closed to accept a substrate such as a slide (with a gasket to seal around the edge of an area containing a semi-solid support such as a gel), is mounted on the stage. The vertical orientation of the flow cell is an important aspect of the inventive system and allows air bubbles to escape from the top of the flow cell. The cell can be completely filled with air to eject all reagents prior to each wash step. The flow cell is connected to a fluid handler with two 9-port Cavro syringe pumps, which allow delivery of 4 differentially labeled probe mixtures, cleavage reagent, any other desired reagents, enzyme equilibration buffer, wash buffer and air to the flow cell through a single port. The operation of the system is completely automated and programmable through control software using a dedicated computer with multiple I/O ports. The Cooke Sensicam camera incorporates a 1.3 megapixel cooled CCD though cameras having lesser or greater sensitivity could also be used (e.g., 4 megapixel, 8 megapixel, etc., can be used). The flow cell utilizes a 0.25 micron stage, with a 1 micron feature size.

Example 10

Image Acquisition and Processing Methods

This example describes representative methods for acquiring and processing images from arrays of beads having labeled nucleic acids attached thereto. Accurate feature identification and alignment are important for reliable analysis of each acquired image. The features are identified by first discarding all but the most intense pixels for each bead. The pixel values for a given image are plotted in a histogram; pixels corresponding to background are discarded and the remaining pixel values are sorted. In uniform images, where all the beads are roughly the same intensity, the algorithm eliminates the bottom 80-90% of pixel values. Pixels having values in the top 10-20% are then scanned to identify those at a local maximum in a 4 pixel radius. The average intensity in that region as well as the average intensity of the perimeter are then recorded. These values form a normal distribution and pixels whose values fall outside that distribution are then removed. The percentage of pixels initially ignored, the size of the circular region, and the cutoff values that eliminate possible beads in the normal distribution are all parameterized and can be tuned if necessary. Alignment is accomplished by creating feature matrices for each image in the alignment set. The resulting matrices are then searched for the most frequent x,y coordinate offsets to identify the optimal alignment.

Bead images are collected in the Cy5 channel (corresponding to the sequencing primer) prior to extension probe addition. These images are used to create a feature map marking both positional coordinates and raw signal intensities as fluorescent units (RFU values) for each bead. For each subsequent duplex extension, an image set is acquired both before and after the Cy3-labeled nucleotides are added. These images are aligned to the original Cy5 images and RFU values are then assigned to each of the beads and recorded. A baseline correction is applied by subtracting the difference of intensities between the unlabeled (pre-extension) and labeled (fluorescent-addition) images of each base addition. These baseline-subtracted values are then normalized by the intensity found in the Cy5 image for each feature to form the basis by which a bead is considered to have been extended or not (i.e., a bead is considered to be extended if duplexes attached to the bead were extended). Using these methods thousands of features per image with ~1,300 images per slide can be analyzed to afford an analysis of 5-100 million template species per experimental run. The algorithms have been designed so that they can be easily ported from MATLAB to C+ at a later date for further efficiency enhancements.

Example 11

Bead Alignment and Tracking and Sequence Decoding

This example describes representative methods for processing images from arrays of beads having labeled nucleic acids attached thereto and for sequence determination from the acquired data.

Image analysis starts by convolving the image using a zero-integral circular top-hat kernel with a diameter matched to the bead size. This will automatically normalize the background to zero while identifying the centers of individual beads through local maxima. The maxima are located and those which are isolated from other local maxima are used as alignment points. These alignment points are computed for each image in a time-series. For each pair of images, the alignment points are compared and a displacement vector is computed based on the average displacement of all the common alignment points. This provides pair-wise image displacements with sub-pixel resolution.

Figure 23:
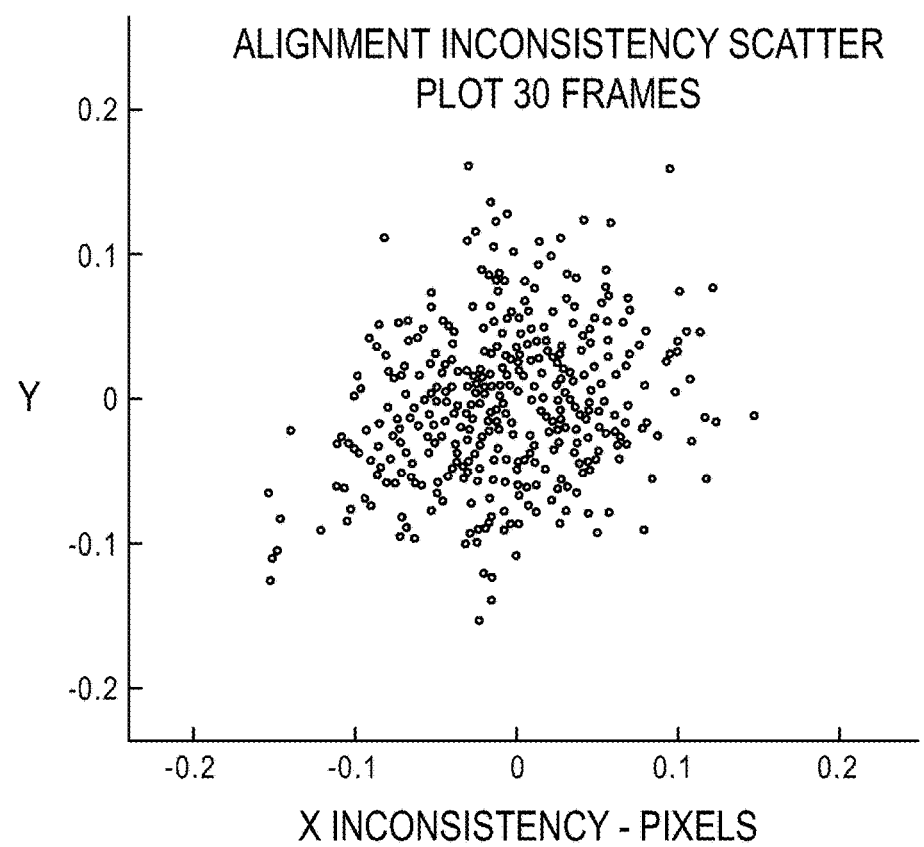
FIG. 23 shows a scatter plot of alignment inconsistency, illustrating minimal inconsistency over 30 frames.
Figure 24A:
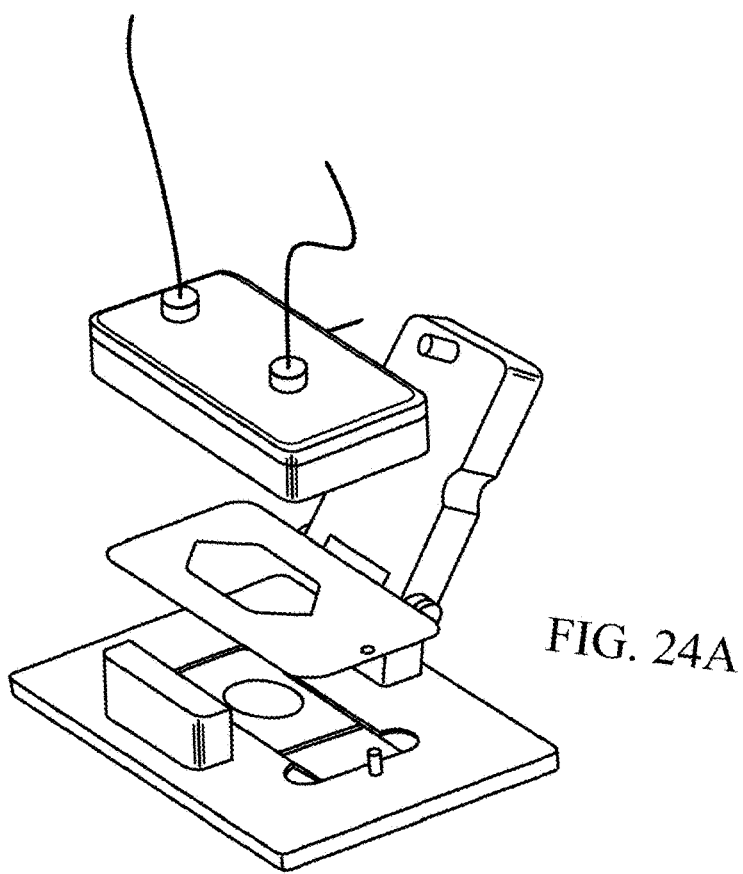
FIGS. 24A-24I shows schematic diagrams of inventive flow cells or portions thereof in a variety of different views.
Figure 24B:
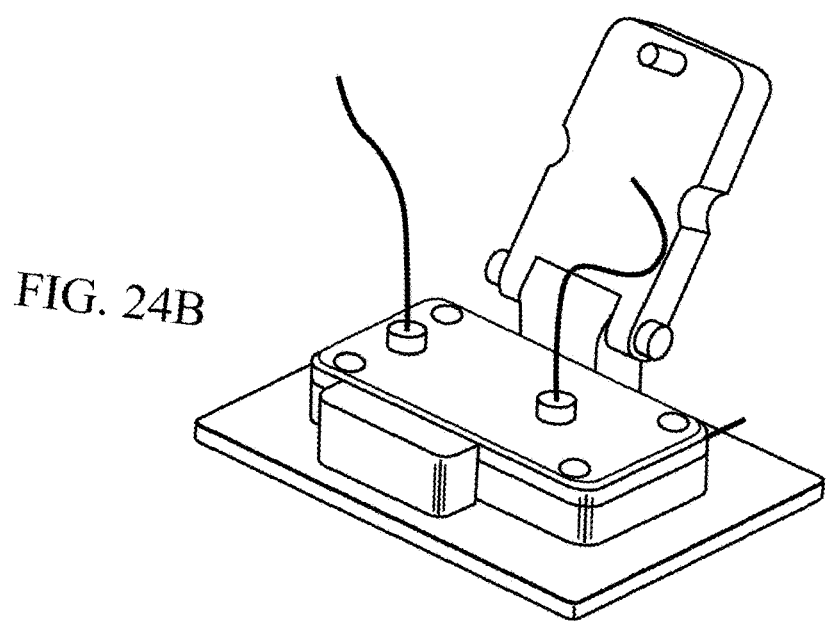
Figure 24C:
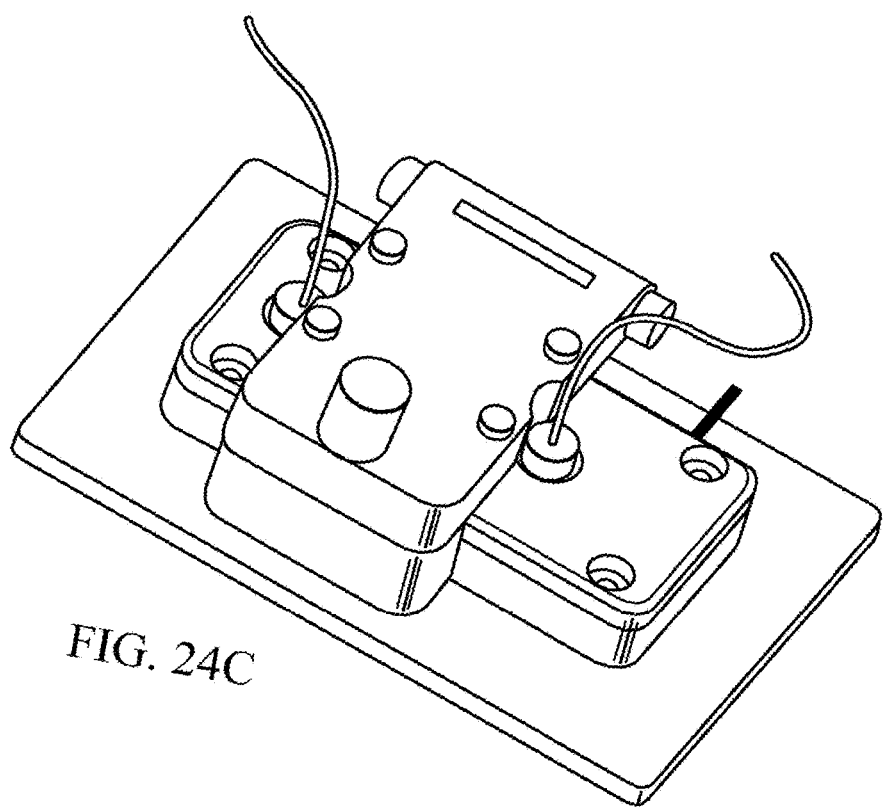
Figure 24D:
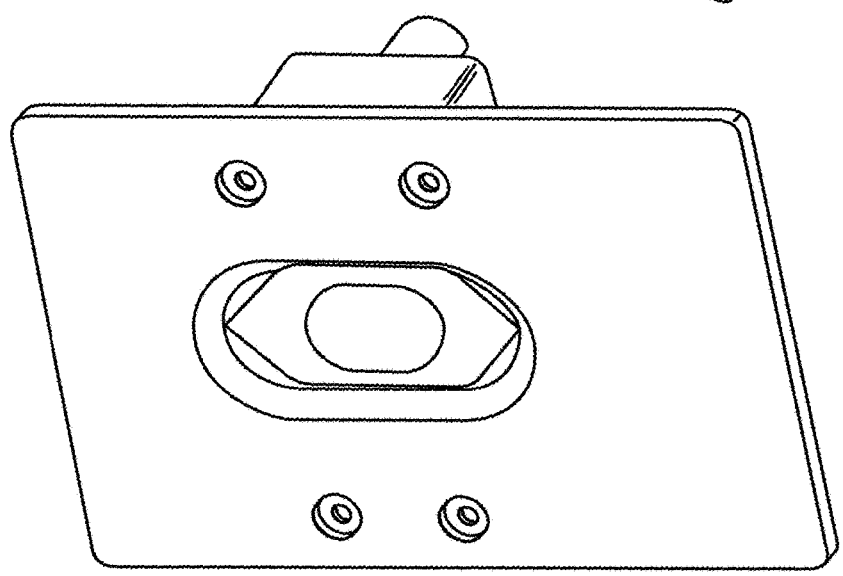
Figure 24E:
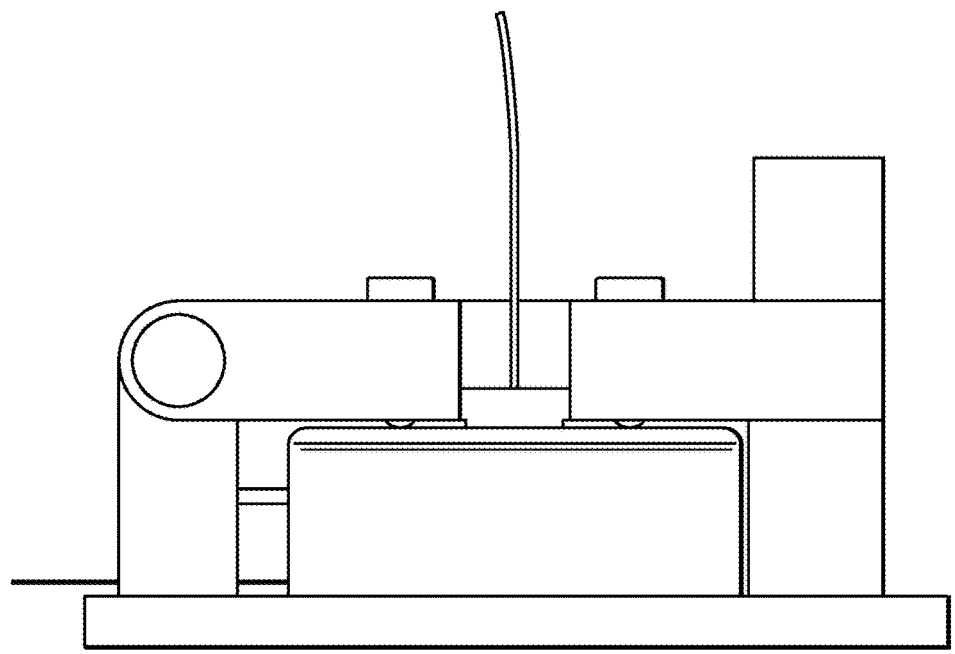
Figure 24F:
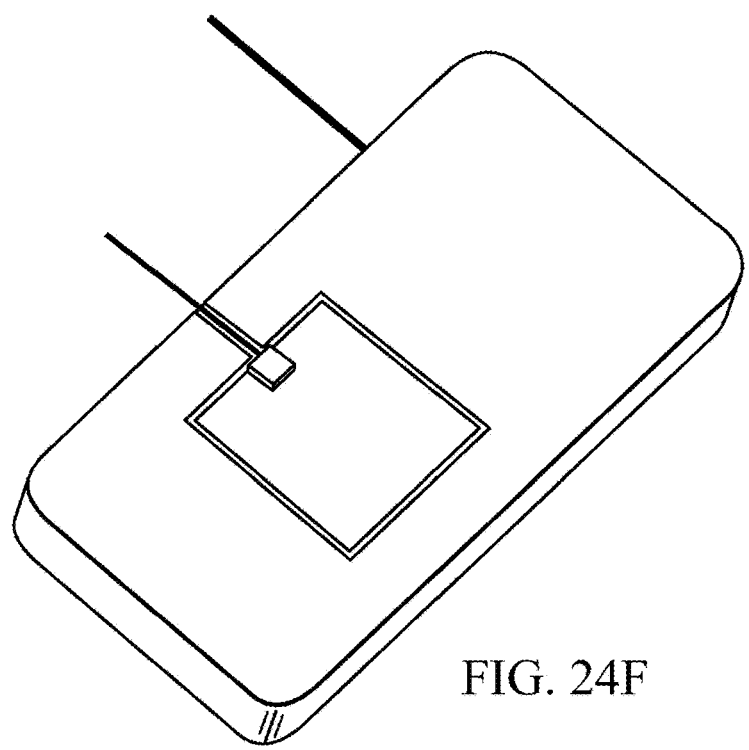
Figure 24G:
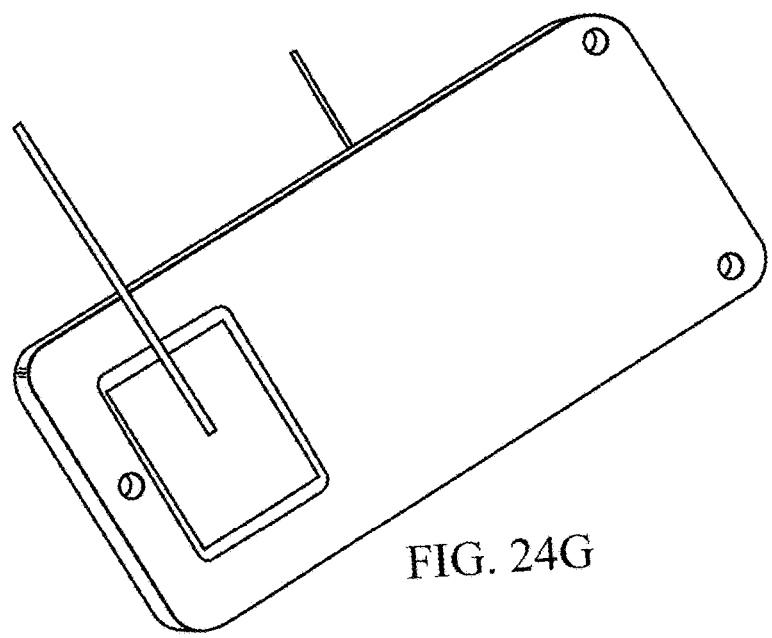
Figure 24H:
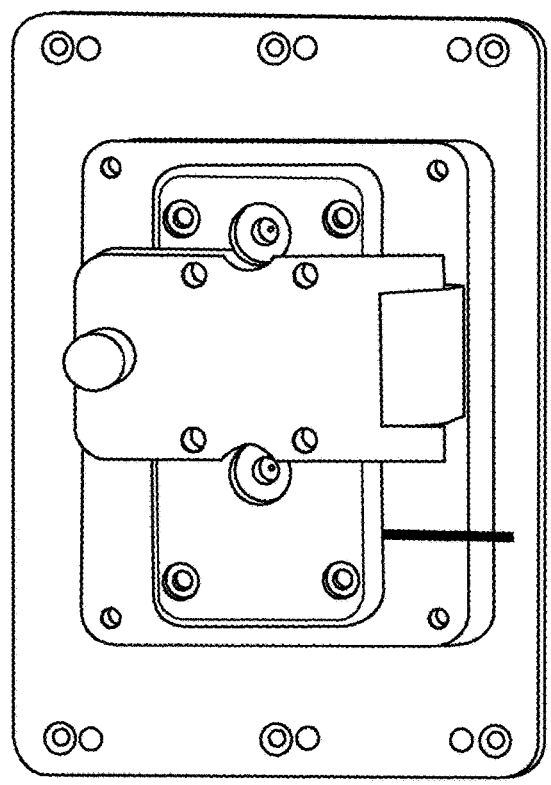
Figure 24I:
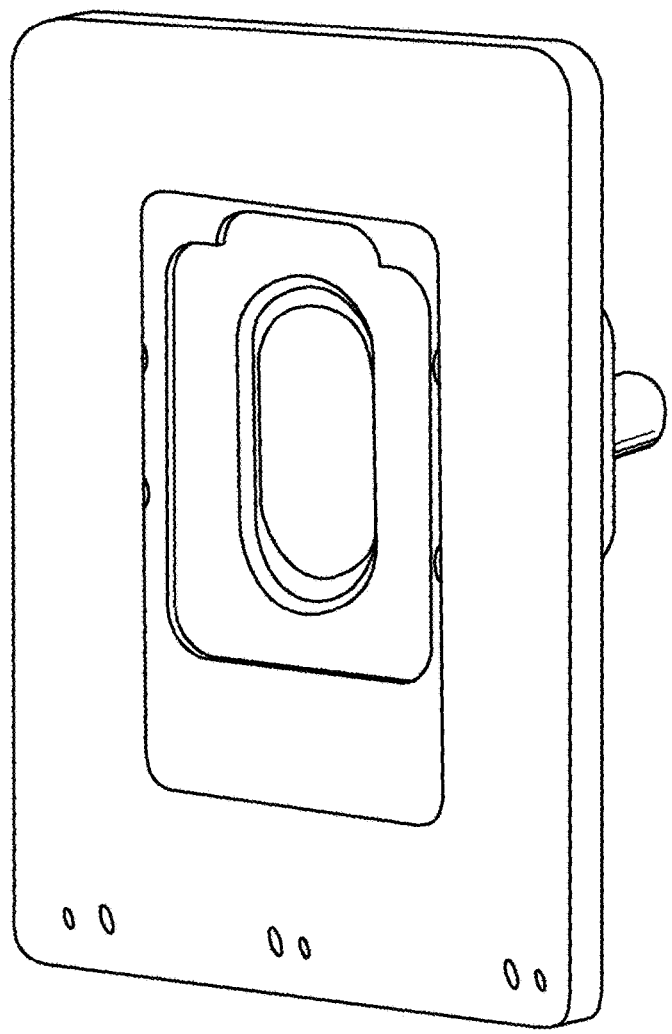

For N images, there are N*(N−1)/2 pairwise displacements, but only N−1 of these are independent since the rest can be calculated from the independent set. For example, measuring the displacements between images 1 and 2 and between images 1 and 3 implies a displacement between images 2 and 3. If the measured displacement between images 2 and 3 is not the same as the implied displacement, then the measurements are inconsistent. The magnitude of this inconsistency can be used as a metric to gauge how well the alignment algorithm is working. Our initial tests show inconsistencies that are generally less than 0.1 pixel in each dimension (see FIG. 23).

Once a time-series of images is aligned, there are two ways to track the individual beads. If the bead density is low with most of the beads not touching another bead, the optical center-of-mass of each individual bead can be identified and a region around the bead integrated to compute the bead intensity. If the bead density is so high that most of the beads touch, then it is not possible to identify individual beads by a dark background band around them. However, with all the images aligned to sub-pixel resolution, it is possible to identify pixels belonging to the same bead by computing the correlation, in time, of adjacent pixels. Highly correlated pixel pairs can be confidently assigned to the same bead. A similar technique has been applied to lane tracking in DNA sequencing gels with good results (Blanchard, A. P. Sequence-specific effects on the incorporation of dideoxynucleotides by a modified T7 polymerase, California Institute of Technology, 1993). Once the beads have been tracked through the entire 4-color time-series, the sequence is decoded by knowing which color corresponds to which 3'-most base of the probe oligonucleotides.

Example 11

Throughput Calculations

In general, the throughput of the sequencing system is defined primarily by the number of images that the machine can generate per day and the number of nucleotides (bases) of sequence data per image. Since the machine is preferably designed to keep the cameras constantly busy, calculations are based on 100% camera utilization. In implementations in which each bead is imaged in 4 colors to determine the identity of one base, either 4 images by one camera, 2 images by 2 cameras, or one image by 4 cameras can be used. Four-camera imaging permits dramatically higher throughputs than the other options, and preferred systems utilize that approach.

Our initial tests show that a pixel density of 50 pixels per bead, representing 5.4 square microns, provides a comfortable density for standard image analysis. By using a 4 megapixel CCD camera (now commonplace), a single CCD frame can image ~80,000 beads (based on our current image data). Capturing four images with separate cameras and moving to the next field on the flow cell will take no longer than 1.5 seconds. If 75% of the beads yield useful information, we will be able to collect data from approximately 80,000 beads*0.75/1.5=40,000 bases/sec of raw sequence data.

One significant issue in maintaining 100% camera utilization is matching the time it takes to perform one cycle of ligation/cleavage chemistry with the time required to image the entire flow cell. A reasonable estimate for the time taken by a cycle of extension, cleavage, and ligation is 1½ hours (5,400 seconds). That 5,400 seconds will accommodate 1,800 image fields, or an area of about 15 mm×45 mm, which is a comfortable size for a flow cell. A conservative estimate of the throughput of the system utilizing four cameras is 40,000 bases per second with a 15 mm×45 mm flow cell. This is equivalent to approximately 2,000 ABI3730x1 sequencing machines, based on a throughput of 28 runs per day with ~650 base read lengths (20 bases/sec), which we have achieved using these machines. A 2.5 fold increase in bead density, to 200,000 per image enables an overall increase in throughput to 100,000 bases per second, approximately equivalent to 5,000 ABI3730x1 machines. The total output per day at this throughput level is ~8.6 Gb per day, so the time required to complete a 12× human genome sequence would be ~4.2 days.

It is noted that the inventive sequencing methods described herein may be practiced using a variety of different sequencing systems, image capture and processing methods, etc. See, e.g., U.S. Pat. Nos. 6,406,848 and 6,654,505 and PCT Pub. No. WO98053300 for discussion.

Example 12

Methods for Preparing Microparticles for Template Synthesis Thereon

This example describes a protocol preparation of microparticles (in this example, magnetic beads) with amplification primers attached thereto so that a template can be amplified (e.g., by PCR) so as to result in a clonal population of template molecules attached to each microparticle. In general, amplification beads have one primer needed in the clonal PCR reaction attached thereto. This primer can be covalently coupled or, for example, biotin labeled and bound to streptavidin on the bead surface. Beads can be used in a standard PCR reaction (e.g., in wells of a microtiter plate, tubes, etc.), in an emulsion PCR reaction as described in Example 13, etc., to obtain beads having clonal populations of template molecules attached thereto.

Materials
1×TE: 10 mM Tris (pH 8) 1 mM EDTA
1×PCR buffer: (ThermoPol Buffer, NEB)
20 mM Tris-HCl (pH 8.8)
10 mM KCl
10 mM $(NH_4)_2SO_4$
2 mM $MgSO_4$
0.1% Triton X-100
1M Betaine (add only for 1×PCR-B buffer)
1× Bind & Wash Buffer
5 mM Tris HCl (pH 7.5)
0.5 mM EDTA
1 M NaCl
DNA Capture Primer (20-mer, 500 µM stock)
Dual Biotin-(HEG)5-P1: 5'-Dual Biotin-(HEG)5-CTA AGG TAG CGA CTG TCC TA-3' (SEQ ID NO. 4)
(HEG)5=Hexaethylene glycol linker, an 18 carbon containing spacer, one of a number of different spacer moieties that could be used. Including a spacer is useful, e.g., to raise the P1 primer portion of the oligo off the surface of the bead. Any of the primers described herein may incorporate such spacer moieites.

Dynal stock magnetic beads (1 µm diameter)=10 mg/ml (7-12×10$^6$ beads/µl).

Methods
1. Remove 50 µl beads (~450×10$^6$ beads).
2. Add 200 µl 1×TE buffer, mix well. Separate with magnet.
3. Wash 1× with 200 µl 1×TE buffer. Separate with magnet.
4. Resuspend in 100 µl B/W buffer.
5. Add 3 µl of P1 oligo (500 µM stock=1500 pmol).
6. Rotate at RT for >30 minutes.
7. Wash 3× with 200 µl 1×TE buffer.
8. Resuspend in 50 µl (initial volume) 1×TE buffer.
9. Store DNA capture beads at 4 C or place on ice prior to use. Beads should be used within 1 week (beads will tend to clump at storage times >1 week).

Example 13

Methods for Performing PCR on Microparticles in an Emulsion

This example describes methods that can be used to perform PCR on microparticles in an emulsion to produce microparticles with clonal templates attached thereto. The microparticles (DNA beads in the nomenclature used below) are first functionalized with a first primer (P1). A second primer (P2) is present in the aqueous phase, where the PCR reaction occurs. If desired, a low concentration of P1 may also be included, e.g., (20-fold less) in the aqueous phase. Doing so allows a rapid build-up of templates in the aqueous phase, which are substrates for additional amplification. As P1 is depleted in solution, the reaction is driven towards utilization of P1 attached to the microparticles. P1_P2 degen10 is an oligonucleotide template (100 bp) that has sequences that hybridize to P1 and P2 to afford amplification by PCR and a stretch of approx 10 degenerate bases (incorporated during oligonucleotide synthesis) that give the oligonucleotide population a complexity of $4^{10}$.

I. Emulsion Protocol (1 µm Beads)
1. Prepare Oil Phase:

Span 80 (7%)
Tween 80 (0.4%)
Prepared in Light Mineral Oil
Use only freshly made oil phase
Total Oil Phase = 450 µl 2. Prepare aqueous phase: (Estimated to produce $2 \times 10^9$ droplets, 115 fL per droplet)

| Reagent (stock) | (µl) per reaction | Final |
|---|---|---|
| dH₂O | 156.0 | — |
| MgCl₂ Buffer (10X) | 32.0 | 1X |
| dNTP (100 mM ea) | 11.3 | 3.5 mM each |
| MgCl₂ (1M) | 7.3 | 23 mM |
| Betaine (5M) | 32.0 | 0.5M |
| P1 (Primer 1)(10 µM) | 1.6 | 11.25 pmole |
| P2 (Primer 2)(200 µM) | 40.0 | 5625 pmole |
| P1_P2 degen10 (100 pM) | 6.6 | $5.9 \times 10^7$/ul |
| DNA Beads (8M/µl) | 25.0 | 150M/emulsion |
| Platinum Taq (5 U/µl) | 9.0 | 0.28 U/ul |
| Total aqueous volume = 320 µl | | |
| Final reaction = 255 µl aqueous phase: 450 µl oil phase | | |

3. Transfer aqueous phase tube to ice until addition to emulsion.
4. Add 450 µl oil phase to a 2 ml cryovial.
5. Place cryovial UPRIGHT into foam adapter attached to IKA vortex. Set vortex to 2500 rpm.
6. Aliquot aqueous phase (3 aliquots, 85 µl each=255 µl) to shaking oil phase. Add monodispersed aqueous phase to the agitating 2 ml cryovial by placing the tip into tube and slowly dispensing the aqueous phase from the tip into the shaking oil phase. Repeat addition 2× with the remaining aqueous phase.
7. Continue shaking emulsion for 24 minutes at 2500 rpm.
8. Transfer ~100 µl aliquots of the emulsion into a 96-well plate (total=4 wells). Also, aliquot remaining aqueous phase (65 µl) into a separate well for a solution-based PCR control reaction. Seal plate and cycle as outlined in next section.

II. Emulsion Amplification (1 µm Beads)
1. PCR cycling parameters for 1 µm bead emulsions (with primer Tms=62 C):
Program: DTB-PCR
94 C, 2 min n=1
94 C, 15 s
57 C, 30 s n=100
70 C, 60 s
55 C, 5 min n=1
10 C, for arbitrary time period
2. Cycling time is ~6 hours.

3. Observe emulsions following cycling. Successful emulsions will appear uniformly amber in color with no observable separated aqueous phase. Emulsions that "break" (fall out of solution) will have a distinct aqueous phase at the bottom of the tube. Avoid collecting this phase, as this population of beads will not be clonal.
4. Assess post-cycled emulsions using bright field microscopy. Remove a 2 µl aliquot of the cycled emulsion and drop onto a glass slide. Overlay emulsion sample with a 22×60 mm glass coverslip.
5. View emulsions using the 20× objective. Beads should preferably be monodispersed, with the majority of droplets containing single beads.

NOTE: If the emulsion sample contains a high number of multi-bead droplets, pool emulsion reactions into a single 1.5 ml eppendorf tube and spin at 6000 rpm for 15 seconds. Remove the bead suspension that accumulates at bottom of tube. This population will be comprised of both free beads and multi-bead droplets that are heavier than single-bead droplets and thus will settle to the bottom of the tube following a brief spin. This bead population is not clonal and should therefore be avoided prior to subsequent processing. Re-evaluate emulsion by repeating Steps 4 and 5 to confirm integrity of single bead-containing droplets in emulsion sample.
6. Disrupt (break) emulsions using the protocol outlined in the next section.

III. Emulsion Break and Melt (1 µm Beads)
Bead Break Wash (BBW) Buffer
2% Triton X-100 2% Tween 20; 10 mM EDTA
Melt Solution 100 mM NaOH
1×TE: 10 mM Tris (pH 8) 1 mM EDTA
1× Bind & Wash (B/W) Buffer
5 mM Tris-HCl (pH 7.5)
0.5 mM EDTA
1 M NaCl
1. Pool each emulsion set (4 aliquots) into a single 1.5 ml eppendorf tube.
2. Add 800 µl BBW buffer. Break emulsions by vortexing reaction tube for 10 seconds.
3. Spin at 8000 rpm for 2 min.
4. Remove top 800 µl (mainly oil phase). DNA beads will be pelleted at the bottom of tube.
5. Add 800 µl BBW, vortex and spin at 8000 rpm for 2 min. Remove top 600 µl.
6. Wash an additional 2× with 600 µl 1×TE using a magnet to exchange each wash.
8. Add 50 µl Melt solution to bead pellet and resuspend sample by vigorous pipetting. Incubate beads in Melt solution for 5 minutes at room temperature, flicking tube intermittently.
9. Place tube in magnet to remove Melt solution. Wash 1× with 100 µl Melt solution to ensure complete removal of second strand.
10. Wash bead pellet 2× with 1×TE and resuspend into 20 µl TE buffer for storage at 4 C or 20 µl 1× B/W buffer if next step is enrichment. If beads appear to be clumped, exchange into 1×PCR-B buffer.
11. Continue with enrichment protocol (optional).

Example 14

Methods for Enriching for Microparticles Having Clonal Template Populations Attached Thereto This example describes a method for enriching for microparticles on which template amplification has successfully occurred in, e.g., in a PCR emulsion. The method makes use of larger microparticles that have a capture oligonucleotide attached thereto. The capture oligonucleotide comprises a nucleotide region that is complementary to a nucleotide region present in the templates.

I. Emulsion Enrichment (1 µm)

A. Preparation of Enrichment Beads (Capture Entities)

Enrichment Beads:

Spherotech streptavidin-coated polystyrene beads (~6.5 um)

Bead stock (0.5% w/v): 33,125 beads/µl

Per Protocol: (33,125 beads/µl) (800 µl)=26.5×10$^6$ beads

Usage:

119 million beads per emulsion—estimate of emulsion clonality (2%): ~3M template-positive beads per emulsion. Add 2-3 enrichment beads per estimated template-positive emulsion bead=10 million enrichment beads per emulsion reaction.

Enrichment Oligonucleotide (Capture Agent):

P2-enrich (35-mer, Tm=73 C)

```
                                        (SEQ ID NO. 5)
5'-Dual biotin-18-carbon spacer-ttaggaccgttatagtta ggtgatgcattaccctg 3'
```

(or)

P2-enrich (e.g., up to 35-mer, Tm=52 C)

```
                                        (SEQ ID NO. 6)
5'-Dual Biotin-18-carbon spacer-ggtgatgcattaccc tg 3'
```

Glycerol Solution—60% (v/v)

6 ml glycerol 4 ml nuclease-free H$_2$O

1. Remove 800 µl of beads and exchange into B/W buffer by centrifugation at 13,000 rpm for 1 minute. Wash 1× with 500 µl B/W buffer and resuspend into 100 µl B/W buffer.
2. Add 20 µl enrichment oligo (500 µM stock=10,000 pmoles per rxn).
3. Rotate bead reaction at room temperature for 1 hour.
4. Wash beads 3× using 500 µl 1×TE buffer. Pellet beads between washes by centrifugation at 13,000 rpm for 1 minute.
5. Resuspend beads into 25 µl B/W buffer. Concentration=1M enrichment beads/µl.

NOTE: Pooling four enriched emulsion populations into 20-30 µl 1×B/W buffer yields ~40M template-positive beads. Multiple slides can then be run.

B. Enrichment Procedure

1. Add 20 µl of the enrichment beads to the tube containing emulsion-derived beads (20 µl). Resuspend bead mixture with gentle pipetting (or use ratios that give rise to 2-3 enrichment beads for every estimated template-positive emulsion bead).
2. If using enrichment beads coated with the biotinylated P2-enrich primer, incubate bead mixture at 65 C for 2 minutes. Remove tube to ice for 10 minutes.

NOTE: Initial experiments have suggested that using enrichment beads containing primer sequences used for the 100-cycle PCR (e.g., P2PCR) may be less efficient at enrichment due to the ability to enrich for beads containing primer: dimer species driven to bead in droplets that were devoid of template. If using enrichment beads loaded with the P2-enrich primer described above, incubate bead mixture at 50 C for 2 minutes due to the reduced Tm of this shorter primer.

3. Overlay bead mixture into 1.5 ml eppendorf tube containing 300 µl 60% Glycerol solution.
4. Centrifuge at 13,000 rpm for 1 minute.
5. Following spin, negative beads will pellet to bottom of tube. Enrichment beads containing attached template beads will float to the top of the glycerol phase. Collect top-phase bead population and transfer to a clean 1.5 ml eppendorf tube.

NOTE: Beads pelleted to the bottom of the tube (beads with no template) can be washed and analyzed using a magnet following the same wash regimen as outlined for template-positive beads.

6. To beads pulled from top phase, add 1 ml nuclease-free H$_2$O to dilute the glycerol concentration. Resuspend bead mixture using gentle pipetting. Spin at 13,000 rpm for 1 minute.
7. Following spin, remove supernatant and wash 2× using 100 µl TE.
8. Add 100 µl Melt solution to the washed bead pellet. Rotate tube for 5 minutes at room temperature.
9. Add an additional 100 µl Melt solution and isolate template beads using a magnet.
10. Remove non-magnetic enrichment beads by washing 2× using 100 µl TE and a magnet to pull DNA beads away from enrichment beads.
11. Resuspend template beads into 10-20 µl 1× TE. If beads appear to be clumped, dilute into 1×PCR-B buffer.
12. Template-containing beads can be pooled with other enriched populations and loaded onto slides as described in the next Example.

Example 15

Methods for Preparing a Microparticle Array Immobilized in or on a Semi-Solid Support This example describes preparation of slides on which microparticles having templates attached thereto are immobilized (e.g., embedded) in a semi-solid support located on the slide. Such slides may be referred to as polony slides. The semi-solid support used in this example is polyacrylamide. One of the protocols employs methods that trap polymerase molecules in the vicinity of templates to enhance amplification.

Preparation of Slides

A. Glass Slides: Bind-Silane Treatment

Bind-Silane facilitates the attachment of the acrylamide gel to the glass slide surface. Slides should be pre-treated with Bind-Silane prior to use.

Notes:
  Store Bind-Silane solution in chemical hood.
  Bind-Silane is an irritant. Work in a chemical when preparing solution.
  Ensure that the stock Bind-Silane solution has not expired.
  Try not to touch surfaces of slides while transferring to and from racks. Prepare Bind-Silane Solution:

1. In a 1-L plastic container add:
1 L dH2O, 1 Stir bar
  Add 220 ul concentrated Acetic Acid (to generate pH 3.5)
  Add 4 ml Bind-Silane reagent Mix solution for >15 minutes using stir plate.
  Treat Slides:
2. Load slides (facing the same direction) into upside-down plastic 384-well plates.
3. Wash slides by rinsing with dH$_2$O, drain well.

4. Rinse with 100% ethanol, drain well.
5. Rinse again with dH₂O, drain well and place in tissue culture hood with vent and UV light running. Allow washed slides to dry (~30 min).
6. Place plate into a plastic container and cover slides with Bind-Silane solution.
7. Allow solution and slides to react for 1 hour. Agitate container intermittently to ensure even coating of Bind-Silane to glass.
8. Following incubation, rinse slides 3× with dH2O.
9. Rinse 1× with 100% ethanol, drain well.
10. Allow slides to dry thoroughly prior to use.
11. Store Bind-Silane-treated slides in dessicator.
B. Acrylamide-Based Slides (Small Mask)
   Non-Trapping Protocol
1. Place all reagents on ice. Add the following chilled reagents to a 1.5 ml eppendorf tube:

|  | amt (µl) 2 slides | 1 slide |
|---|---|---|
| 1× TE | 13 | 6.5 |
| Beads (1-3M, diluted in 1× TE) | 10 | 5 |
| Rhinohide | 1 | 0.5 |
| 40% Acrylamide:Bis (19:1, F/S) | 5 | 2.5 |
| TEMED (5%, in 1× TE) | 2 | 1 |
| APS (0.5%, made fresh) | 3 | 1.5 |
|  | 34 µl | 17 µl |

Pipet mixture vigorously to distribute beads.
Load 17 µl per slide under a glass coverslip.
Polymerize upside down at room temperature for 60 minutes.
Remove coverslip with a clean razorblade.
Soak slide and wash 2× in 1E buffer for 15 minutes (to remove unbound beads).
Slides with embedded beads can be stored at 4 C in wash 1E.
2. Hybridize fluorophore-labeled sequencing primer to embedded bead population.
   Equilibrate slide from wash 1E to 1×PCR-B buffer by dipping briefly into Coplin jar containing 1×PCR-B buffer.
3. In a 1.5 ml eppendorf tube, add 1-6 µl (100 µM stock) primer to 99 µl 1×PCR buffer. Over the acrylamide matrix, drop 100 µl primer solution and overlay with a glass coverslip or sealing gasket.
4. Hybridize primer to embedded beads by heating slide using <DEVIN> program (65 C for 2 minutes, slow anneal to 30 C). Wash slide 2× for 2 minutes in wash 1E. Slide is ready to be subjected to ligation based sequencing.
   Trapping Protocol
1. ssDNA template beads are prepared at 1M/µl. [Prepare polony slides with 4-5M beads per slide].
2. Resuspend bead mixture into 30 µl 1×PCR buffer.
3. Add 1 ul sequencing primer (100 µM stock); mix well.
4. Heat to 65 C for 2 min.
5. Remove to ice for 5 min.
6. Wash 3× with 80 µl 1×TE
7. Remove all soln using a magnet.
8. Add reagents as outlined below:

|  | amt(µl) 2slides |
|---|---|
| 1× buffer | 1.5 |
| 10× buffer | 2.0 |
| High conc. (HC) enzyme | 16.0 |

|  | amt(µl) 2slides |
|---|---|
| 40% Acrylamide:Bis (19:1, F/S) | 14.4 |
| Rhinohide | 2.0 |
| TEMED (5%, in 1× TE) | 2.0 |
| APS (0.5%, made fresh) | 1.5 |
|  | 39.4 µl |

Pipet mixture to distribute beads.
Load 17 µl per slide under a glass coverslip.
9. Polymerize, preferably upside down, e.g., using <Pol-1> cycling profile on MJ Research Tetrad PCR machine.
10. Remove coverslip with a clean razorblade. Soak slide and wash 2× in 1E buffer for 10 min. (to remove unbound beads).
11. Polony slides are ready to be subjected to ligation-based sequencing.
12. Polony slides with embedded beads can be stored in gaskets at 4 C in wash 1E.

Example 16

Methods for Preparing a Microparticle Array Attached to a Solid Support

Figure 33A:
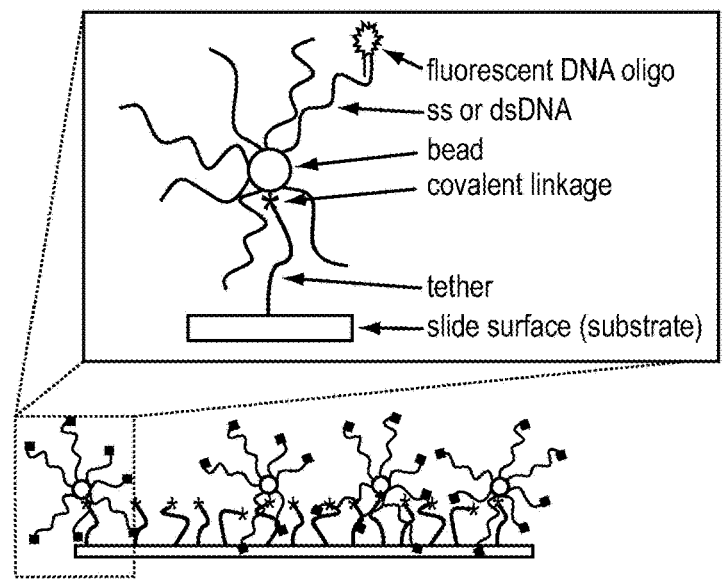
FIG. 33A shows a schematic diagram of a slide with beads attached thereto. DNA templates are attached to the beads.

This example describes preparation of slides on which microparticles having templates attached thereto are attached to a solid support.
   1. Glass slides prepared with polymer tethers with reactive NHS are stored at −20 C. (Slide H, Product No. 1070936; Schott Nexterion; Schott North America, Inc., Elmsford, N.Y.)
   2. In the presence of dessicant, equilibrate slides to room temperature before use.
   3. Wash slides in 50 mls 1×PBS (300 mM sodium phosphate, pH 8.7) for 5 minutes. Repeat washes 2×.
   4. Remove slide from solution and cover with an adhesive gasket (to allow sample loading).
   5. In a separate tube, aliquot 100-400 million protein-coated or DNA-coated beads into 1×PBS, pH 8.7. The DNA can be, e.g., DNA templates for sequencing. The DNA can include, e.g., an amine linker for reaction with NHS.
   6. Wash bead sample 3× with 1×PBS, pH 8.7 by buffer exchange.
   7. Resuspend beads into 125 ml 1×PBS, pH 8.7.
   8. Load bead solution into the slide gasket to evenly coat slide surface.
   9. Enclose slides in a dark chamber and allow reaction to incubate for 1-2 hrs at room temperature.
   10. Following incubation, remove unbound bead solution and transfer slide to 50 mls 1×TE (10 mM Tris, 1 mM EDTA, pH 8).
   11. Wash slide 5× using 50 mls 1×TE with constant agitation for 15 minutes per wash.
   12. Slides can be stored in 1×TE at 4 C for several weeks.
   13. If desired, bead populations can be assessed by bright field image analysis using white light (WL) or by fluorescence using complementary DNA oligonucleotides attached to fluorophore-based dyes. DNA templates can be sequenced, e.g., using ligation-based sequencing.
   FIG. 33A shows a schematic diagram of the slide with beads attached thereto. Note that only a small proportion of the DNA template molecules are attached to the slide. One micron beads (Dynabeads MyOne Streptavidin beads;

Dynal Biotech, Inc., Product No. 650.01) were used. However, a wide variety of beads could be used.

Figure 33B:
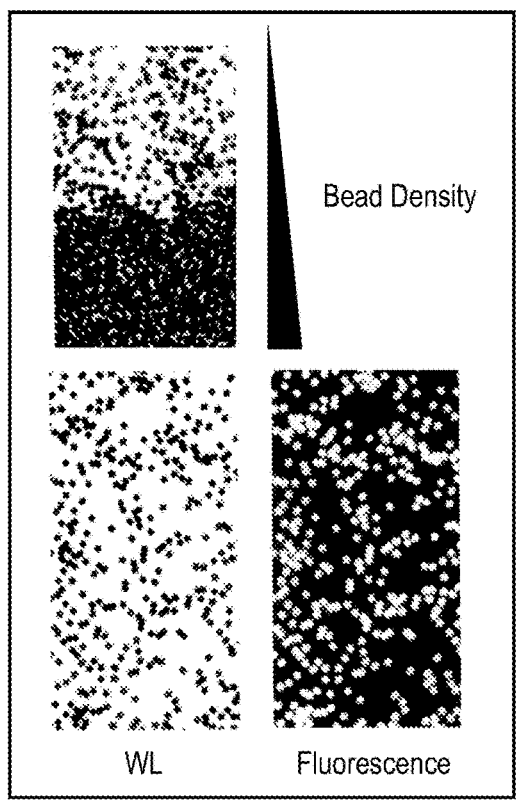
FIG. 33B shows a population of beads attached to a slide. The lower panels show the same region of the slide under white light (left) and fluorescence microscopy. The upper panel shows a range of bead densities.

FIG. 33B shows a population of beads attached to a slide. The lower panels show the same region of the slide under white light (left) and fluorescence microscopy. The upper panel shows a range of bead densities.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the following claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim.

In addition, it is to be understood that any one or more embodiments may be explicitly excluded from the claims even if the specific exclusion is not set forth explicitly herein. It should also be understood that where the specification and/or claims disclose a reagent (e.g., a template, microsphere, probe, probe family, etc.) of use in sequencing, such disclosure also encompasses methods for sequencing using the reagent according either to the specific methods disclosed herein, or other methods known in the art unless one of ordinary skill in the art would understand otherwise, or unless otherwise indicated in the specification. In addition, where the specification and/or claims disclose a method of sequencing, any one or more of the reagents disclosed herein may be used in the method, unless one of ordinary skill in the art would understand otherwise, or unless use of the reagent in such method is explicitly excluded in the specification. It should further be understood that where particular components of use in sequencing are disclosed in the specification or claims, the invention encompasses methods for making the reagents also. The term "component" is used broadly to refer to any item used in sequencing, including templates, microparticles having templates attached thereto, libraries, etc. Furthermore, the figures are an integral part of the specification, and the invention includes structures shown in the figures, e.g., microparticles having templates attached thereto, and methods disclosed in the figures.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

What is claimed:

1. A method for identifying a sequence of nucleotides in a template polynucleotide, the method comprising the steps of:
   (I) extending an initializing oligonucleotide along the template polynucleotide by ligating an oligonucleotide probe thereto to form an extended duplex, wherein the oligonucleotide probe comprises a phosphorothiolate linkage and is from one of at least two distinguishably labeled probe families to which the template polynucleotide is exposed prior to the ligating, and wherein each probe family comprises a plurality of oligonucleotide probes having identical labels but different sequences that comprise:
   (1) a constrained portion of least two constrained nucleosides, wherein the constrained nucleosides: (i) are at least 2-fold degenerate among the probes in the probe family, (ii) need not be located contiguously, and (iii) are not selected independently of each other, such that
   (2) knowing the label of a probe eliminates one or more combinations of nucleosides as possibilities for the sequence of the constrained portion, and
   (3) knowing the identity of a constrained nucleoside in that probe further eliminates at least one possible identity for another constrained nucleoside in the probe;
   (II) identifying one or more nucleotides of the polynucleotide; and
   (III) repeating steps I and II until the sequence of nucleotides is determined;
   wherein the template polynucleotide is attached to a solid support and/or immobilized in or on a semi-solid support during the extending step.

2. The method of claim 1, comprising the steps of:
   (a) providing a probe-template duplex comprising an oligonucleotide probe from one of the at least two distinguishably labeled probe families hybridized to a template polynucleotide, the probe covalently attached to the extended duplex and having an extendable terminus;
   (b) ligating an extension oligonucleotide probe from one of the at least two distinguishably labeled probe families to said extendable terminus, to form an extended duplex containing an extended oligonucleotide probe, wherein the extension probe comprises a phosphorothiolate linkage;
   (c) identifying, in the extended duplex, at least one nucleotide in the template polynucleotide that is either (1) complementary to the just-ligated extension probe or (2) a nucleotide residue in the template polynucleotide which is immediately downstream of the extended oligonucleotide probe;
   (d) generating an extendable terminus on the extended oligonucleotide probe, if an extendable terminus is not already present, such that the terminus generated is different from the terminus to which the last extension probe was ligated; and
   (e) repeating steps (b), (c) and (d) until a sequence of nucleotides in the template polynucleotide is determined.

3. The method of claim 2, wherein each extension probe has a non-extendable moiety at one terminus.

4. The method of claim 2, wherein the step of identifying includes detecting a label attached to the most recently ligated extension probe.

5. The method of claim 2, wherein the step of identifying includes removing said non-extendable moiety and extending said extended oligonucleotide probe with a nucleic acid polymerase in the presence of one or more labeled chain-terminating nucleoside triphosphates.

6. The method of claim 2, further including a step of capping an extended oligonucleotide probe whenever no extension probe has ligated to the extendable terminus in the ligation step.

7. The method of claim 2, wherein the generating step comprises cleaving the phosphorothiolate linkage with a cleavage agent comprising an atom selected from the group consisting of: Ag, Hg, Cu, Mn, Zn and Cd.

8. The method of claim 2, wherein the ligating and generating steps are performed while the template polynucleotide is attached to a solid support and/or immobilized in or on a semi-solid support.

9. The method of claim 2, wherein step (a) includes providing, in separate aliquots, a plurality of distinct probe-template duplexes, each distinct duplex comprising an initializing oligonucleotide probe hybridized to a template polynucleotide, wherein the template polynucleotide in each duplex is the same, but the initializing oligonucleotide probe in each duplex is bound to a different sequence of the template polynucleotide; and steps (b) to (e) are carried out independently on each aliquot.

10. The method of claim 9, wherein for each aliquot, said extension oligonucleotide probe has a non-extendable moiety at one terminus and, optionally, wherein for each aliquot, said step of identifying includes (a) detecting a label attached to the most recently ligated extension probe or (b) removing said non-extendable moiety and extending said extended oligonucleotide probe with a nucleic acid polymerase in the presence of one or more labeled chain-terminating nucleoside triphosphates.

11. The method of claim 10, further including a step of capping an extended oligonucleotide probe whenever no extension probe has ligated to the extendable terminus in the ligation step.

12. The method of claim 2, further comprising the steps of:
(f) removing the ligated probes and the initializing oligonucleotide from the template;
(g) repeating step (a) using a second oligonucleotide that is bound to a different sequence of the template polynucleotide; and
(h) repeating steps (b) to (e).

13. The method of claim 12, wherein the method is repeated a plurality of times using initializing oligonucleotides bound to different sequences of the template polynucleotide.

14. A method for identifying a sequence of nucleotides in a template polynucleotide attached to a support at a point of attachment, the method comprising the steps of:
(a) extending an initializing oligonucleotide along the template polynucleotide by ligating an oligonucleotide probe thereto to form an extended duplex, wherein extension proceeds along the template towards its point of attachment to the support;
(b) identifying one or more nucleotides of the polynucleotide; and
(c) repeating steps (a) and (b) until the sequence of nucleotides is determined.

15. The method of claim 14, wherein each extension probe has a non-extendable moiety at one terminus.

16. The method of claim 14, wherein the step of identifying includes detecting a label attached to the most recently ligated extension probe.

17. A method for identifying a sequence of nucleotides in a template polynucleotide, the method comprising the steps of:
(a) providing a template polynucleotide attached to a microparticle that is immobilized in or on a semi-solid support;
(b) extending an initializing oligonucleotide along the template polynucleotide by ligating an oligonucleotide probe thereto to form an extended duplex, wherein the oligonucleotide probe comprises a scissile linkage and is from one of at least two distinguishably labeled probe families to which the template polynucleotide is exposed prior to the ligating, and wherein each probe family comprises a plurality of oligonucleotide probes having identical labels but different sequences that comprise:
(1) a constrained portion of least two constrained nucleosides, wherein the constrained nucleosides: (i) are at least 2-fold degenerate among the probes in the probe family, (ii) need not be located contiguously, and (iii) are not selected independently of each other, such that
(2) knowing the label of a probe eliminates one or more combinations of nucleotides nucleosides as possibilities for the sequence of the constrained portion, and
(3) knowing the identity of a constrained residue nucleoside in that probe further eliminates at least one possible identity for another constrained residue nucleoside in the probe;
(c) identifying one or more nucleotides of the polynucleotide; and
(d) repeating steps (b) and (c) until the sequence of nucleotides is determined.

18. The method of claim 17, wherein the extending step is performed in the semi-solid support.

19. The method of claim 17, wherein the template is attached to a microparticle that is attached to a substantially planar, rigid substrate.

20. The method of claim 1 comprising the steps of:
(a) providing a probe-template duplex comprising an oligonucleotide probe from one of the at least two distinguishably labeled probe families hybridized to a template polynucleotide, the probe having an extendable terminus, the probe-template duplex being attached to a microparticle that is embedded in or on a semi-solid support;
(b) ligating an extension oligonucleotide probe from one of the at least two distinguishably labeled probe families to said extendable terminus, to form an extended duplex containing an extended oligonucleotide probe, wherein the extension probe comprises a phosphorothiolate linkage;
(c) identifying, in the extended duplex, at least one nucleotide in the template polynucleotide that is either (1) complementary to the just-ligated extension probe or (2) a nucleotide residue in the template polynucleotide which is immediately downstream of the extended oligonucleotide probe;

(d) generating an extendable terminus on the extended oligonucleotide probe, if an extendable terminus is not already present, such that the terminus generated is different from the terminus to which the last extension probe was ligated; and (e) repeating steps (b), (c) and (d) until a sequence of nucleotides in the template polynucleotide is determined.

21. The method of claim 17 wherein step (a) comprises amplifying a template polynucleotide molecule in a compartment of an emulsion in the presence of microparticle so that a microparticle having a clonal population of template polynucleotides attached thereto is produced, recovering the microparticle from the emulsion, and embedding the microparticle in or on a semi-solid support.

22. The method of claim 21, wherein
(i) a plurality of template polynucleotide molecules comprising different sequences are amplified in individual compartments of the emulsion;
(ii) a plurality of microparticles, each having attached thereto a clonal populations of template polynucleotides, wherein the clonal populations have different sequences, is recovered from the emulsion and embedded in or on the support, and
(iii) steps (b), (c), and (d) are performed in parallel on the clonal populations attached to the embedded microparticles so as to determine a plurality of sequences in parallel.

23. The method of claim 14, wherein the oligonucleotide probe is from one of at least two distinguishably labeled probe families to which the template polynucleotide is exposed prior to the ligating.

24. The method of claim 14, wherein the oligonucleotide probe is fluorescently labeled and the identifying comprises detecting the fluorescently labeled probe.

25. The method of claim 1, wherein the method is performed in parallel on a plurality of templates attached to one or more solid supports and/or immobilized in or on a semi-solid support during the extending step.

26. The method of claim 23, comprising the steps of:
(a) providing a probe-template duplex comprising an oligonucleotide probe from one of the at least two distinguishably labeled probe families hybridized to a template polynucleotide, the primer having an extendable terminus;

(b) ligating an extension oligonucleotide probe from one of the at least two distinguishably labeled probe families to said extendable terminus, to form an extended duplex containing an extended oligonucleotide probe;

(c) identifying, in the extended duplex, at least one nucleotide in the template polynucleotide that is either (1) complementary to the just-ligated extension probe or (2) a nucleotide residue in the template polynucleotide which is immediately downstream of the extended oligonucleotide probe;

(d) generating an extendable terminus on the extended oligonucleotide probe, if an extendable terminus is not already present, such that the terminus generated is different from the terminus to which the last extension probe was ligated; and (e) repeating steps (b), (c) and (d) until a sequence of nucleotides in the template polynucleotide is determined.

27. The method of claim 26, wherein the step of identifying includes removing said non-extendable moiety and extending said extended oligonucleotide probe with a nucleic acid polymerase in the presence of one or more labeled chain-terminating nucleoside triphosphates.

28. The method of claim 26, further including a step of capping an extended oligonucleotide probe whenever no extension probe has ligated to the extendable terminus in the ligation step.

29. The method of claim 26, wherein the oligonucleotide probe contains a phosphorothiolate linkage, and wherein the generating step comprises cleaving the phosphorothiolate linkage with a cleavage agent comprising an atom selected from the group consisting of: Ag, Hg, Cu, Mn, Zn and Cd.

30. The method of claim 26, further comprising the steps of:
(f) removing the ligated probes and the initializing oligonucleotide from the template;
(g) repeating step (a) using a second oligonucleotide that is bound to a different sequence of the template polynucleotide; and (h) repeating steps (b) to (e).

31. The method of claim 26, wherein the ligating and generating steps are performed in or on a semi-solid support.

* * * * *

SEQUENCE LISTING

```
<160> NUMBER OF SEQ ID NOS: 46

<210> SEQ ID NO 1
<211> LENGTH: 18
<212> TYPE: DNA
<213> ORGANISM: Artificial sequence
<220> FEATURE:
<223> OTHER INFORMATION: Synthetic

<400> SEQUENCE: 1
cagacgacaa gtataatg                                                 18

<210> SEQ ID NO 2
<211> LENGTH: 18
<212> TYPE: DNA
<213> ORGANISM: Artificial sequence
<220> FEATURE:
<223> OTHER INFORMATION: Synthetic

<400> SEQUENCE: 2
cagacgagaa gtataatg                                                 18

<210> SEQ ID NO 3
<211> LENGTH: 18
<212> TYPE: DNA
<213> ORGANISM: Artificial sequence
<220> FEATURE:
<223> OTHER INFORMATION: Synthetic

<400> SEQUENCE: 3
```
cagacgagtt catattac					18

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
ctaaggtagc gactgtccta					20

<210> SEQ ID NO 5
<211> LENGTH: 35
<212> TYPE: DNA
<213> ORGANISM: Artificial sequence
<220> FEATURE:
<223> OTHER INFORMATION: Synthetic

<400> SEQUENCE: 5
ttaggaccgt tatagttagg tgatgcatta ccctg					35

<210> SEQ ID NO 6
<211> LENGTH: 17
<212> TYPE: DNA
<213> ORGANISM: Artificial sequence
<220> FEATURE:
<223> OTHER INFORMATION: Synthetic

<400> SEQUENCE: 6
ggtgatgcat taccctg					17

<210> SEQ ID NO 7
<211> LENGTH: 54
<212> TYPE: DNA
<213> ORGANISM: Artificial sequence
<220> FEATURE:
<223> OTHER INFORMATION: Synthetic - template in Figure 3B

<400> SEQUENCE: 7
accaaatggc acccaatttt gcatcccagg ggcattaccg aatggagccg tatc					54

<210> SEQ ID NO 8
<211> LENGTH: 26
<212> TYPE: DNA
<213> ORGANISM: Artificial sequence
<220> FEATURE:
<223> OTHER INFORMATION: Synthetic - extended strand in Figure 6D
<220> FEATURE:
<221> NAME/KEY: misc_feature
<222> LOCATION: (1)..(2)
<223> OTHER INFORMATION: N= inosine
<220> FEATURE:
<221> NAME/KEY: misc_feature
<222> LOCATION: (2)..(3)
<223> OTHER INFORMATION: phosphorothiolate linkage
<220> FEATURE:
<221> NAME/KEY: misc_feature
<222> LOCATION: (3)..(3)
<223> OTHER INFORMATION: N= A, C, T, or G
<220> FEATURE:
<221> NAME/KEY: misc_feature
<222> LOCATION: (4)..(4)
<223> OTHER INFORMATION: N= inosine
<220> FEATURE:
<221> NAME/KEY: misc_feature
<222> LOCATION: (5)..(5)
<223> OTHER INFORMATION: N= A, C, T, or G
<220> FEATURE:
<221> NAME/KEY: misc_feature

```
<222> LOCATION: (6)..(6)
<223> OTHER INFORMATION: N= inosine
<220> FEATURE:
<221> NAME/KEY: misc_feature
<222> LOCATION: (7)..(7)
<223> OTHER INFORMATION: N= A, C, T, or G
<220> FEATURE:
<221> NAME/KEY: misc_feature
<222> LOCATION: (9)..(9)
<223> OTHER INFORMATION: N= A, C, T, or G
<220> FEATURE:
<221> NAME/KEY: misc_feature
<222> LOCATION: (10)..(10)
<223> OTHER INFORMATION: N= inosine
<220> FEATURE:
<221> NAME/KEY: misc_feature
<222> LOCATION: (11)..(11)
<223> OTHER INFORMATION: N= A, C, T, or G
<220> FEATURE:
<221> NAME/KEY: misc_feature
<222> LOCATION: (12)..(12)
<223> OTHER INFORMATION: N= inosine
<220> FEATURE:
<221> NAME/KEY: misc_feature
<222> LOCATION: (13)..(13)
<223> OTHER INFORMATION: N= A, C, T, or G
<220> FEATURE:
<221> NAME/KEY: misc_feature
<222> LOCATION: (15)..(15)
<223> OTHER INFORMATION: N= A, C, T, or G
<220> FEATURE:
<221> NAME/KEY: misc_feature
<222> LOCATION: (16)..(16)
<223> OTHER INFORMATION: N= inosine
<220> FEATURE:
<221> NAME/KEY: misc_feature
<222> LOCATION: (17)..(17)
<223> OTHER INFORMATION: N= A, C, T, or G
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: N= A, C, T, or G
<220> FEATURE:
<221> NAME/KEY: misc_feature
<222> LOCATION: (21)..(21)
<223> OTHER INFORMATION: N= A, C, T, or G
<220> FEATURE:
<221> NAME/KEY: misc_feature
<222> LOCATION: (22)..(22)
<223> OTHER INFORMATION: N= inosine
<220> FEATURE:
<221> NAME/KEY: misc_feature
<222> LOCATION: (23)..(23)
<223> OTHER INFORMATION: N= A, C, T, or G
<220> FEATURE:
<221> NAME/KEY: misc_feature
<222> LOCATION: (24)..(24)
<223> OTHER INFORMATION: N= inosine
<220> FEATURE:
<221> NAME/KEY: misc_feature
<222> LOCATION: (25)..(25)
<223> OTHER INFORMATION: N= A, C, T, or G

<400> SEQUENCE: 8
nnnnnnntnn nnncnnnnnt nnnnna                                26

<210> SEQ ID NO 9
<211> LENGTH: 18
<212> TYPE: DNA
<213> ORGANISM: Artificial sequence
<220> FEATURE:
<223> OTHER INFORMATION: Synthetic - extended strand in Figure 6E
<220> FEATURE:
```

```
<221> NAME/KEY: misc_feature
<222> LOCATION: (1)..(1)
<223> OTHER INFORMATION: N= A, C, T, or G
<220> FEATURE:
<221> NAME/KEY: misc_feature
<222> LOCATION: (2)..(2)
<223> OTHER INFORMATION: N= inosine
<220> FEATURE:
<221> NAME/KEY: misc_feature
<222> LOCATION: (3)..(3)
<223> OTHER INFORMATION: N= A, C, T, or G
<220> FEATURE:
<221> NAME/KEY: misc_feature
<222> LOCATION: (4)..(4)
<223> OTHER INFORMATION: N= inosine
<220> FEATURE:
<221> NAME/KEY: misc_feature
<222> LOCATION: (5)..(5)
<223> OTHER INFORMATION: N= A, C, T, or G
<220> FEATURE:
<221> NAME/KEY: misc_feature
<222> LOCATION: (7)..(7)
<223> OTHER INFORMATION: N= A, C, T, or G
<220> FEATURE:
<221> NAME/KEY: misc_feature
<222> LOCATION: (8)..(8)
<223> OTHER INFORMATION: N= inosine
<220> FEATURE:
<221> NAME/KEY: misc_feature
<222> LOCATION: (9)..(9)
<223> OTHER INFORMATION: N= A, C, T, or G
<220> FEATURE:
<221> NAME/KEY: misc_feature
<222> LOCATION: (10)..(10)
<223> OTHER INFORMATION: N= inosine
<220> FEATURE:
<221> NAME/KEY: misc_feature
<222> LOCATION: (11)..(11)
<223> OTHER INFORMATION: N= A, C, T, or G
<220> FEATURE:
<221> NAME/KEY: misc_feature
<222> LOCATION: (13)..(13)
<223> OTHER INFORMATION: N= A, C, T, or G
<220> FEATURE:
<221> NAME/KEY: misc_feature
<222> LOCATION: (14)..(14)
<223> OTHER INFORMATION: N= inosine
<220> FEATURE:
<221> NAME/KEY: misc_feature
<222> LOCATION: (15)..(15)
<223> OTHER INFORMATION: N= A, C, T, or G
<220> FEATURE:
<221> NAME/KEY: misc_feature
<222> LOCATION: (16)..(16)
<223> OTHER INFORMATION: N= inosine
<220> FEATURE:
<221> NAME/KEY: misc_feature
<222> LOCATION: (17)..(17)
<223> OTHER INFORMATION: N= A, C, T, or G

<400> SEQUENCE: 9
nnnnngnnnn ncnnnnnt                                                18

<210> SEQ ID NO 10
<211> LENGTH: 20
<212> TYPE: DNA
<213> ORGANISM: Artificial sequence
<220> FEATURE:
<223> OTHER INFORMATION: Synthetic - extended strand in Figure 6F
<220> FEATURE:
<221> NAME/KEY: misc_feature
<222> LOCATION: (1)..(2)
<223> OTHER INFORMATION: N = inosine
<220> FEATURE:
<221> NAME/KEY: misc_feature
<222> LOCATION: (2)..(3)
<223> OTHER INFORMATION: phosphorothiolate linkage
```

```
<220> FEATURE:
<221> NAME/KEY: misc_feature
<222> LOCATION: (3)..(3)
<223> OTHER INFORMATION: N= A, C, T, or G
<220> FEATURE:
<221> NAME/KEY: misc_feature
<222> LOCATION: (4)..(4)
<223> OTHER INFORMATION: N= inosine
<220> FEATURE:
<221> NAME/KEY: misc_feature
<222> LOCATION: (5)..(5)
<223> OTHER INFORMATION: N= A, C, T, or G
<220> FEATURE:
<221> NAME/KEY: misc_feature
<222> LOCATION: (6)..(6)
<223> OTHER INFORMATION: N= inosine
<220> FEATURE:
<221> NAME/KEY: misc_feature
<222> LOCATION: (7)..(7)
<223> OTHER INFORMATION: N= A, C, T, or G
<220> FEATURE:
<221> NAME/KEY: misc_feature
<222> LOCATION: (9)..(9)
<223> OTHER INFORMATION: N= A, C, T, or G
<220> FEATURE:
<221> NAME/KEY: misc_feature
<222> LOCATION: (10)..(10)
<223> OTHER INFORMATION: N= inosine
<220> FEATURE:
<221> NAME/KEY: misc_feature
<222> LOCATION: (11)..(11)
<223> OTHER INFORMATION: N= A, C, T, or G
<220> FEATURE:
<221> NAME/KEY: misc_feature
<222> LOCATION: (12)..(12)
<223> OTHER INFORMATION: N= inosine
<220> FEATURE:
<221> NAME/KEY: misc_feature
<222> LOCATION: (13)..(13)
<223> OTHER INFORMATION: N= A, C, T, or G
<220> FEATURE:
<221> NAME/KEY: misc_feature
<222> LOCATION: (15)..(15)
<223> OTHER INFORMATION: N= A, C, T, or G
<220> FEATURE:
<221> NAME/KEY: misc_feature
<222> LOCATION: (16)..(16)
<223> OTHER INFORMATION: N= inosine
<220> FEATURE:
<221> NAME/KEY: misc_feature
<222> LOCATION: (17)..(17)
<223> OTHER INFORMATION: N= A, C, T, or G
<220> FEATURE:
<221> NAME/KEY: misc_feature
<222> LOCATION: (18)..(18)
<223> OTHER INFORMATION: N= inosine
<220> FEATURE:
<221> NAME/KEY: misc_feature
<222> LOCATION: (19)..(19)
<223> OTHER INFORMATION: N= A, C, T, or G

<400> SEQUENCE: 10
nnnnnnngnn nnnannnnnc                                              20

<210> SEQ ID NO 11
<211> LENGTH: 24
<212> TYPE: DNA
<213> ORGANISM: Artificial sequence
<220> FEATURE:
<223> OTHER INFORMATION: Synthetic - template in Figure 6F

<400> SEQUENCE: 11
gcagatttta gaccagtcgt atgc                                         24

<210> SEQ ID NO 12
```

```
<211> LENGTH: 23
<212> TYPE: DNA
<213> ORGANISM: Artificial sequence
<220> FEATURE:
<223> OTHER INFORMATION: Synthetic - initializing oligo in Figure 8

<400> SEQUENCE: 12
ctgccccggg ttcctcattc tct                                            23

<210> SEQ ID NO 13
<211> LENGTH: 53
<212> TYPE: DNA
<213> ORGANISM: Artificial sequence
<220> FEATURE:
<223> OTHER INFORMATION: Synthetic - template LST7 in Figure 8

<400> SEQUENCE: 13
agagaatgag gaacccgggg cagacgaaca gagtgatata tgaactcaag gat           53

<210> SEQ ID NO 14
<211> LENGTH: 13
<212> TYPE: DNA
<213> ORGANISM: Artificial sequence
<220> FEATURE:
<223> OTHER INFORMATION: Synthetic - ligation product in Figure 8
<220> FEATURE:
<221> NAME/KEY: misc_feature
<222> LOCATION: (5)..(6)
<223> OTHER INFORMATION: phosphorothiolate linkage

<400> SEQUENCE: 14
tcactctgtt cgt                                                       13

<210> SEQ ID NO 15
<211> LENGTH: 23
<212> TYPE: DNA
<213> ORGANISM: Artificial sequence
<220> FEATURE:
<223> OTHER INFORMATION: Synthetic - primer in Figures 9, 12, 13 and 16

<400> SEQUENCE: 15
ctgccccggg ttcctcattc tct                                            23

<210> SEQ ID NO 16
<211> LENGTH: 31
<212> TYPE: DNA
<213> ORGANISM: Artificial sequence
<220> FEATURE:
<223> OTHER INFORMATION: Synthetic - template LST1 in Figure 9

<400> SEQUENCE: 16
agagaatgag gaacccgggg cagtcacgag t                                   31

<210> SEQ ID NO 17
<211> LENGTH: 23
<212> TYPE: DNA
<213> ORGANISM: Artificial sequence
<220> FEATURE:
<223> OTHER INFORMATION: Synthetic - primer in Figure 11

<400> SEQUENCE: 17
ctgccccggg ttcctattcc tct                                            23

<210> SEQ ID NO 18
<211> LENGTH: 53
<212> TYPE: DNA
<213> ORGANISM: Artificial sequence
```

```
<220> FEATURE:
<223> OTHER INFORMATION: Synthetic - template LST1 in Figure 11

<400> SEQUENCE: 18
agagaatgag gaacccgggg cagtcacgag tgtgtgcact gcgtacgtcg acg          53

<210> SEQ ID NO 19
<211> LENGTH: 32
<212> TYPE: DNA
<213> ORGANISM: Artificial sequence
<220> FEATURE:
<223> OTHER INFORMATION: Synthetic - template LST6 in Figure 12

<400> SEQUENCE: 19
agagaatgag gaacccgggg cagacgacaa gt                                 32

<210> SEQ ID NO 20
<211> LENGTH: 26
<212> TYPE: DNA
<213> ORGANISM: Artificial sequence
<220> FEATURE:
<223> OTHER INFORMATION: Synthetic - primer region in Figure 12B

<400> SEQUENCE: 20
agagagaatg aggaacccgg ggcaga                                        26

<210> SEQ ID NO 21
<211> LENGTH: 35
<212> TYPE: DNA
<213> ORGANISM: Artificial sequence
<220> FEATURE:
<223> OTHER INFORMATION: Synthetic - figure 12B

<400> SEQUENCE: 21
agagagaatg aggaacccgg ggcagacgac aagta                              35

<210> SEQ ID NO 22
<211> LENGTH: 34
<212> TYPE: DNA
<213> ORGANISM: Artificial sequence
<220> FEATURE:
<223> OTHER INFORMATION: Synthetic - Figure 12B

<400> SEQUENCE: 22
agagagaatg aggaacccgg ggcagacgac cgca                               34

<210> SEQ ID NO 23
<211> LENGTH: 34
<212> TYPE: DNA
<213> ORGANISM: Artificial sequence
<220> FEATURE:
<223> OTHER INFORMATION: Synthetic - Figure 12B

<400> SEQUENCE: 23
agagagaatg aggaacccgg ggcagacgac ccca                               34

<210> SEQ ID NO 24
<211> LENGTH: 34
<212> TYPE: DNA
<213> ORGANISM: Artificial sequence
<220> FEATURE:
<223> OTHER INFORMATION: Synthetic - Figure 12B

<400> SEQUENCE: 24
agagagaatg aggaacccgg ggcagacgcc acca                               34
```

```
<210> SEQ ID NO 25
<211> LENGTH: 34
<212> TYPE: DNA
<213> ORGANISM: Artificial sequence
<220> FEATURE:
<223> OTHER INFORMATION: Synthetic - Figure 12B

<400> SEQUENCE: 25
agagagaatg aggaacccgg ggcagacgcc acca                                34

<210> SEQ ID NO 26
<211> LENGTH: 75
<212> TYPE: DNA
<213> ORGANISM: Artificial sequence
<220> FEATURE:
<223> OTHER INFORMATION: Synthetic - template LST1 in figures 13, 16,
      17, and 19

<400> SEQUENCE: 26
cgagccccct ctgagtcagg acagagaatg aggaacccgg ggcagtcacg agtgtgtgca    60
ctgcgtacgt cgacg                                                    75

<210> SEQ ID NO 27
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figures 16 and 17

<400> SEQUENCE: 27
actcgtgact gccccgggtt cctcattctc t                                  31

<210> SEQ ID NO 28
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 16

<400> SEQUENCE: 28
aagcaccgct gccccgggtt cctcattctc t                                  31

<210> SEQ ID NO 29
<211> LENGTH: 75
<212> TYPE: DNA
<213> ORGANISM: Artificial sequence
<220> FEATURE:
<223> OTHER INFORMATION: Synthetic - template LST2 in Figure 16

<400> SEQUENCE: 29
cgagccccct ctgagtcagg acagagaatg aggaacccgg ggcagcggtg cttgctggct    60
cacatgatcg cagta                                                    75

<210> SEQ ID NO 30
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 16

<400> SEQUENCE: 30
tatacaccct gccccgggtt cctcattctc t                                  31
```

```
<210> SEQ ID NO 31
<211> LENGTH: 75
<212> TYPE: DNA
<213> ORGANISM: Artificial sequence
<220> FEATURE:
<223> OTHER INFORMATION: Synthetic - template LST3 in Figure 16

<400> SEQUENCE: 31
cgagccccct ctgagtcagg acagagaatg aggaacccgg ggcagggtgt atatgcaata      60
gtatctacgc gtgct                                                       75

<210> SEQ ID NO 32
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 16

<400> SEQUENCE: 32
tcgagaatct gccccgggtt cctcattctc t                                     31

<210> SEQ ID NO 33
<211> LENGTH: 75
<212> TYPE: DNA
<213> ORGANISM: Artificial sequence
<220> FEATURE:
<223> OTHER INFORMATION: Synthetic - template LST4 in Figure 16

<400> SEQUENCE: 33
cgagccccct ctgagtcagg acagagaatg aggaacccgg ggcagattct cgataagtac      60
agtgatacgc tagcg                                                       75

<210> SEQ ID NO 34
<211> LENGTH: 31
<212> TYPE: DNA
<213> ORGANISM: Artificial sequence
<220> FEATURE:
<223> OTHER INFORMATION: Synthetic - primer with probe in Figure 18

<400> SEQUENCE: 34
actcgtgtct gccccgggtt cctcattctc t                                     31

<210> SEQ ID NO 35
<211> LENGTH: 75
<212> TYPE: DNA
<213> ORGANISM: Artificial sequence
<220> FEATURE:
<223> OTHER INFORMATION: Synthetic - template LST1.A in Figure 18

<400> SEQUENCE: 35
cgagccccct ctgagtcagg acagagaatg aggaacccgg ggcagacacg agtgtgtgca      60
ctgcgtacgt cgacg                                                       75

<210> SEQ ID NO 36
<211> LENGTH: 31
<212> TYPE: DNA
<213> ORGANISM: Artificial sequence
<220> FEATURE:
<223> OTHER INFORMATION: Synthetic - primer with probe in Figure 18

<400> SEQUENCE: 36
actcgtgcct gccccgggtt cctcattctc t                                     31
```

<210> SEQ ID NO 37
<211> LENGTH: 75
<212> TYPE: DNA
<213> ORGANISM: Artificial sequence
<220> FEATURE:
<223> OTHER INFORMATION: Synthetic - template LST1.G in Figure 18

<400> SEQUENCE: 37 cgagcccect ctgagtcagg acagagaatg aggaacccgg ggcaggcacg agtgtgtgca    60
ctgcgtacgt cgacg    75

<210> SEQ ID NO 38
<211> LENGTH: 31
<212> TYPE: DNA
<213> ORGANISM: Artificial sequence
<220> FEATURE:
<223> OTHER INFORMATION: Synthetic - primer with probe in Figure 18

<400> SEQUENCE: 38
actcgtggct gccccgggtt cctcattctc t    31

<210> SEQ ID NO 39
<211> LENGTH: 75
<212> TYPE: DNA
<213> ORGANISM: Artificial sequence
<220> FEATURE:
<223> OTHER INFORMATION: Synthetic - template LST1.C in Figure 18

<400> SEQUENCE: 39 cgagcccect ctgagtcagg acagagaatg aggaacccgg ggcagccacg agtgtgtgca    60
ctgcgtacgt cgacg    75

<210> SEQ ID NO 40
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 19
<220> FEATURE:
<221> NAME/KEY: misc_feature
<222> LOCATION: (1)..(1)
<223> OTHER INFORMATION: N= inosine
<220> FEATURE:
<221> NAME/KEY: misc_feature
<222> LOCATION: (2)..(2)
<223> OTHER INFORMATION: N = A, C, T, or G
<220> FEATURE:
<221> NAME/KEY: misc_feature
<222> LOCATION: (3)..(3)
<223> OTHER INFORMATION: N= inosine
<220> FEATURE:
<221> NAME/KEY: misc_feature
<222> LOCATION: (4)..(7)
<223> OTHER INFORMATION: N = A, C, T, or G

<400> SEQUENCE: 40
nnnnnnnact gccccgggtt cctcattctc t    31

<210> SEQ ID NO 41
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 19
<220> FEATURE:

```
<221> NAME/KEY: misc_feature
<222> LOCATION: (1)..(1)
<223> OTHER INFORMATION: N= inosine
<220> FEATURE:
<221> NAME/KEY: misc_feature
<222> LOCATION: (2)..(2)
<223> OTHER INFORMATION: N= A, C, T, or G
<220> FEATURE:
<221> NAME/KEY: misc_feature
<222> LOCATION: (3)..(3)
<223> OTHER INFORMATION: N= inosine
<220> FEATURE:
<221> NAME/KEY: misc_feature
<222> LOCATION: (4)..(7)
<223> OTHER INFORMATION: N= A, C, T, or G

<400> SEQUENCE: 41
nnnnnnngct gcccccggtt cctcattctc t                               31

<210> SEQ ID NO 42
<211> LENGTH: 75
<212> TYPE: DNA
<213> ORGANISM: Artificial sequence
<220> FEATURE:
<223> OTHER INFORMATION: Synthetic - template LST2 Figure 19

<400> SEQUENCE: 42 cgagcccct ctgagtcagg acagagaatg aggaacccgg ggcagcggtg cttgctggct   60
cacatgatcg cagta                                                  75

<210> SEQ ID NO 43
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 19
<220> FEATURE:
<221> NAME/KEY: misc_feature
<222> LOCATION: (1)..(1)
<223> OTHER INFORMATION: N= inosine
<220> FEATURE:
<221> NAME/KEY: misc_feature
<222> LOCATION: (2)..(2)
<223> OTHER INFORMATION: N= A, C, T, or G
<220> FEATURE:
<221> NAME/KEY: misc_feature
<222> LOCATION: (3)..(3)
<223> OTHER INFORMATION: N= inosine
<220> FEATURE:
<221> NAME/KEY: misc_feature
<222> LOCATION: (4)..(7)
<223> OTHER INFORMATION: N= A, C, T, or G

<400> SEQUENCE: 43
nnnnnnncct gcccccggtt cctcattctc t                               31

<210> SEQ ID NO 44
<211> LENGTH: 75
<212> TYPE: DNA
<213> ORGANISM: Artificial sequence
<220> FEATURE:
<223> OTHER INFORMATION: Synthetic - template LST3 in Figure 19

<400> SEQUENCE: 44 cgagcccct ctgagtcagg acagagaatg aggaacccgg ggcagggtgt atatgcaata   60
gtatctacgc gtgct                                                  75

<210> SEQ ID NO 45
```

```
<211> LENGTH: 31
<212> TYPE: DNA
<213> ORGANISM: Artificial sequence
<220> FEATURE:
<223> OTHER INFORMATION: Synthetic - initializing oligonucleotide with
      probe in Figure 19
<220> FEATURE:
<221> NAME/KEY: misc_feature
<222> LOCATION: (1)..(1)
<223> OTHER INFORMATION: N= inosine
<220> FEATURE:
<221> NAME/KEY: misc_feature
<222> LOCATION: (2)..(2)
<223> OTHER INFORMATION: N= A, C, T, or G
<220> FEATURE:
<221> NAME/KEY: misc_feature
<222> LOCATION: (3)..(3)
<223> OTHER INFORMATION: N= inosine
<220> FEATURE:
<221> NAME/KEY: misc_feature
<222> LOCATION: (4)..(7)
<223> OTHER INFORMATION: N= A, C, T, or G

<400> SEQUENCE: 45
nnnnnnntct gcccccggtt cctcattctc t                                31

<210> SEQ ID NO 46
<211> LENGTH: 75
<212> TYPE: DNA
<213> ORGANISM: Artificial sequence
<220> FEATURE:
<223> OTHER INFORMATION: Synthetic - template LST4 in Figure 19

<400> SEQUENCE: 46 cgagcccct ctgagtcagg acagagaatg aggaacccgg ggcagattct cgataagtac  60
agtgatacgc tagcg                                                  75
```